US010294286B2

(12) United States Patent
Garred et al.

(10) Patent No.: US 10,294,286 B2
(45) **Date of Patent: *May 21, 2019**

(54) CHIMERIC INHIBITOR MOLECULES OF COMPLEMENT ACTIVATION

(71) Applicants: Rigshospitalet, Copenhagen O (DK); Kobenhavns Universitet, Copenhagen K (DK); Syddansk Universitet, Odense M (DK)

(72) Inventors: Peter Garred, Charlottelund (DK); Tina Hummelshoj Glue, Soborg (DK); Mikkel-Ole Skjodt, Frederiksberg C (DK)

(73) Assignee: OMEROS CORPORATION, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,412

(22) Filed: Jan. 6, 2017

(65) Prior Publication Data

US 2017/0166616 A1 Jun. 15, 2017

Related U.S. Application Data

(63) Continuation of application No. 14/585,369, filed on Dec. 30, 2014, now Pat. No. 9,573,984, which is a continuation-in-part of application No. 13/582,814, filed as application No. PCT/EP2011/053309 on Mar. 4, 2011, now Pat. No. 9,815,876.

(60) Provisional application No. 61/311,024, filed on Mar. 5, 2010.

(30) Foreign Application Priority Data

Mar. 5, 2010 (EP) .................................... 10155621

(51) Int. Cl.

| | |
|---|---|
| ***A61K 38/36*** | (2006.01) |
| ***A61K 38/00*** | (2006.01) |
| ***A61P 7/08*** | (2006.01) |
| ***A61K 38/14*** | (2006.01) |
| ***A61K 35/14*** | (2015.01) |
| ***A61K 38/16*** | (2006.01) |
| ***C07K 1/00*** | (2006.01) |
| ***C07K 14/00*** | (2006.01) |
| ***C07K 16/00*** | (2006.01) |
| ***C07K 17/00*** | (2006.01) |
| ***C12P 21/08*** | (2006.01) |
| ***C07K 14/47*** | (2006.01) |
| ***A61K 38/17*** | (2006.01) |
| ***A61K 45/06*** | (2006.01) |
| ***C07K 14/705*** | (2006.01) |
| ***C07K 14/81*** | (2006.01) |

(52) U.S. Cl.

CPC .......... *C07K 14/47* (2013.01); *A61K 38/1725* (2013.01); *A61K 45/06* (2013.01); *C07K 14/472* (2013.01); *C07K 14/4726* (2013.01); *C07K 14/70596* (2013.01); *C07K 14/8121* (2013.01); *H05K 999/99* (2013.01); *A61K 38/00* (2013.01); *C07K 2319/01* (2013.01); *C07K 2319/02* (2013.01); *C07K 2319/30* (2013.01); *C07K 2319/70* (2013.01); *Y02A 50/385* (2018.01); *Y02A 50/411* (2018.01)

(58) Field of Classification Search

None

See application file for complete search history.

(56) References Cited

U.S. PATENT DOCUMENTS

| | | | |
|---|---|---|---|
| 9,573,984 B2 * | 2/2017 | Garred ................ | C07K 14/472 |
| 2008/0221011 A1 | 9/2008 | Gilkeson et al. | |
| 2008/0267980 A1 | 10/2008 | Tomlinson et al. | |

FOREIGN PATENT DOCUMENTS

| | | | | |
|---|---|---|---|---|
| EP | 1539964 B1 | 12/2006 | | |
| JP | 2004-504027 A | 12/2004 | | |
| WO | WO 2002/006460 A2 | 1/2002 | | |
| WO | WO 2002/006460 A3 | 1/2002 | | |
| WO | WO 2004/050907 A2 | 6/2004 | | |
| WO | WO 2007/047995 A2 | 4/2007 | | |
| WO | WO-2007047995 A2 * | 4/2007 | .......... | A61K 38/482 |
| WO | WO 2007/117996 A2 | 10/2007 | | |
| WO | WO 2007/149567 A2 | 12/2007 | | |

OTHER PUBLICATIONS

Beinrohr et al. "C1, MBL-MASPs and C1 Inhibitor: novel approaches for targeting complement-mediated inflammation" Trends in Molecular Medicine 14:511-521. (Year: 2008).*

UniprotKB-P48740 (MASP1_HUMAN) http://www.uniprot.org/uniprot/P48740#P48740-3. (Year: 2008).*

Skjoedt et al. "A Novel Mannose-binding Lectin/Ficolin-associated Protein is Highly Expressed in Heart and Skeletal Muscle Tissues and Inhibits Complement Activation" J. Biol. Chem. 285:8234-8243. (Year: 2010).*

Harris et al. "Coupling complement regulators to immunoglobulin domains generates effective anti-complement reagents with extended half-life in vivo" Clin. Exp. Immunol. 129:198-207. (Year: 2002).*

Banda, N.K., et al., "Targeted Inhibition of the Complement Alternative Pathway with Complement Receptor 2 and Factor H Attenuates Collagen Antibody-Induced Arthritis in Mice," *The Journal of Immunology*, 2009, vol. 183: 5928-5937, The American Association of Immunologists, Inc.

(Continued)

*Primary Examiner* — Zachary J Miknis

(74) *Attorney, Agent, or Firm* — Womble Bond Dickinson (US) LLP

(57) ABSTRACT

The present invention relates to novel chimeric molecules of ficolin-associated polypeptides, such as fusion polypeptides for the use in the treatment of conditions associated with inflammation, apoptosis, autoimmunity, coagulation, thrombotic or coagulopathic related diseases. The present invention further relates to nucleic acid molecules encoding such fusion polypeptides, vectors and host cells used in the production of the fusion polypeptides.

10 Claims, 45 Drawing Sheets

Figure 1:
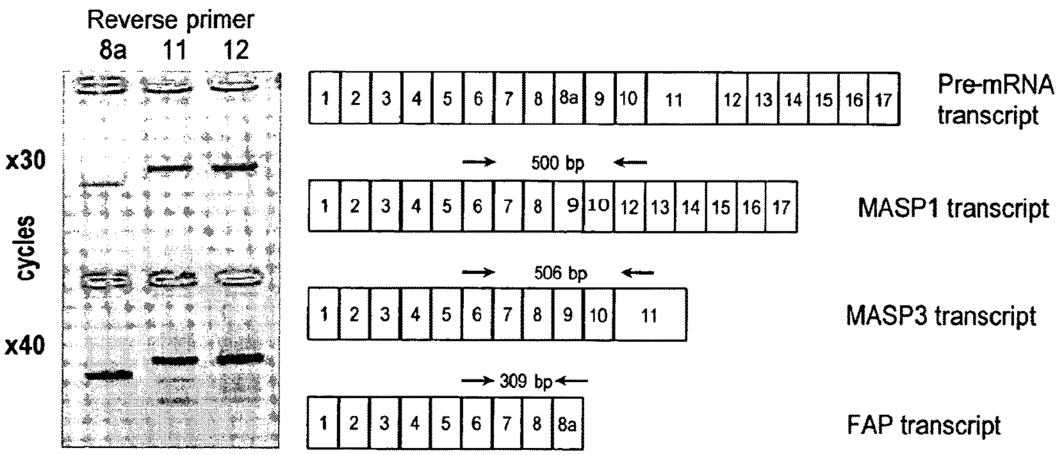

Specification includes a Sequence Listing.

(56) References Cited

OTHER PUBLICATIONS

Beinrohr, L., et al., "C1, MBL-MASPs and C1-inhibitor: novel approaches for targeting complement-mediated inflammation," *Trends in Molecular Medicine*, 2008, vol. 14(12): 511-521, Institute of Enzymology, Budapest, Hungary.
EMBL Database Report for Accession No. ASQ27368, Sep. 18, 2008 (XP002637579).
European Examination Report for European Patent Application No. 10737833.3, dated May 12, 2015.
Fujita, T., "Evolution of the Lectin-Complement Pathway and its Role in Innate Immunity," *Nature Reviews | Immunology*, May 2002, 2: 346-353, Nature Publishing Group.
International Search Report for PCT/US2007/065274 dated Oct. 11, 2007.
International Search Report for PCT/US2007/014602 dated Mar. 6, 2008.
Japanese Application No. 2012-555437, Non-Final Rejection dated Apr. 21, 2015.
Lambris, J.D., et al., "Complement evasion by human pathogens," *Nature Reviews | Microbiology*, Feb. 2008, 6: 132-142, Nature Publishing Group.
Larsen, et al., "Disease-associated Mutations in Human Mannose-binding Lectin Compromise Oligomerization and Activity of the Final Protein," *J. Biol Chem.*, vol. 279: 21302-21311. Published online Feb. 5, 2004.
Makrides, S., "Therapeutic Inhibition of the Complement System," *Pharmacological Reviews*, 1998, vol. 50, pp. 59-88.
Ratovitski, et al., "Variation in the biochemical/biophysical properties of mutant superoxide dismutase 1 enzymes and the rate of disease progression in familial amyotrophic lateral sclerosis kindreds," *Human Molecular Genetics*, vol. 8, pp. 1451-1460. Published 1999.
Skjoedt, et al., "A Novel Mannose-binding Lectin/Ficolin-associated Protein is Highly Expressed in Heart and Skeletal Muscle Tissues and Inhibits Complement Activation." *J. Biol. Chem.*, vol. 285:8234-8243. Published online Jan. 6, 2010.
Teillet, F., et al., "Crystal Structure of the CUB1-EGF-CUB2 Domain of Human MASP-1/3 and Identification of it Interaction Sites with Mannan-binding lectin and Ficolins," *The Journal of Biological Chemistry*, 2008, vol. 283(37), pp. 25715-25724.
UniprotKB—P48740 (MASP1_HUMAN), http://www.uniprot.or/uniprot/P487040#P48740-3.
Wallis, R., "Interactions Between Mannose-Binding Lectin and Masps During Complement Activation by the Lectin Pathway," *Immunobiology*, 2007, vol. 212, pp. 289-299.

* cited by examiner

```
               10        20        30        40        50        60        70        80        90       100       110
       ....|....|....|....|....|....|....|....|....|....|....|....|....|....|....|....|....|....|....|....|....|....|
MASP1  MRWLLLYYALCFSLSKASAHTVELNNMFGQIQSPGYPDSYPSDSEVTWNITVPDGFRIKLYFMHFNLESSYLCEYDYVKVETEDQVLATFCGRETTDTEQTPGQEVVLSP
MASP3  ..............................................................................................................
FAP    ..............................................................................................................

              120       130       140       150       160       170       180       190       200       210       220
       ....|....|....|....|....|....|....|....|....|....|....|....|....|....|....|....|....|....|....|....|....|....|
MASP1  GSFMSITFRSDFSNEERFTGFDAHYMAVDVDECKEREDEELSCDHYCHNYIGGYYCSCRFGYILHTDNRTCRVECSDNLFTQRTGVITSPDFPNPYPKSSECLYTIELEE
MASP3  ..............................................................................................................
FAP    ..............................................................................................................

              230       240       250       260       270       280       290       300       310       320       330
       ....|....|....|....|....|....|....|....|....|....|....|....|....|....|....|....|....|....|....|....|....|....|
MASP1  GFMVNLQFEDIFDIEDHPEVPCPYDYIKIKVGPKVLGPFCGEKAPEPISTQSHSVLILFHSDNSGENRGWRLSYRAAGNECPELQPPVHGKIEPSQAKYFFKDQVLVSCD
MASP3  ..............................................................................................................
FAP    ..............................................................................................................

              340       350       360       370       380       390       400       410       420       430       440
       ....|....|....|....|....|....|....|....|....|....|....|....|....|....|....|....|....|....|....|....|....|....|
MASP1  TGYKVLKDNVEMDTFQIECLKDGTWSNKIPTCKIVDCRAPGELEHGLITFSTRNNLTTYKSEIKYSCQEPYYKMLNNNTGIYTCSAQGVWMNKVLGRSLPTCLPVCGLPK
MASP3  ........................................................................................................E..Q.S
FAP    .................................KNEIDLES..KSEQV.E

              450       460       470       480       490       500       510       520       530       540       550
       ....|....|....|....|....|....|....|....|....|....|....|....|....|....|....|....|....|....|....|....|....|....|
MASP1  FSR-KLMARIFNGRPAQKGTTPWIAMLSHLNGQPFCGGSLLGSSWIVTAAHCLHQSLDPEDPTLRDSDLLSPSDFKIILGKHWRLRSDENEQHLGVKHTTLHPQYDPNTF
MASP3  R.LPS.VK..IG..N.EP.LF..Q.LIVVEDTSRVPNDKWF..GALLS.SWI.TAAHVLRS--Q.RDTTVI.VSKEHVTVYLGLHDVRDKSGAVNSSAARVVLHP.F.IQ
FAP

              560       570       580       590       600       610       620       630       640       650       660
       ....|....|....|....|....|....|....|....|....|....|....|....|....|....|....|....|....|....|....|....|....|....|
MASP1  ENDVALVELLESPVLNAFVMPICLPEGPQQEGAMVIVSGWGKQFLQRFPETLMEIEIPIVDHSTCQKAYAPLKKKVTRDMICAGEKEGGKDACAGDSGGPMVTLNRERGQ
MASP3  NYNHDIALVQLQEPVPLGPHVMPVCLPRLEPEGPAPHMLGLVAGWGISNPNVTVD..ISSGTR.LSDVLQYV.LP.VPHAE.KTSY.SRSGNYSVTENMFCAGYYEGGKD
FAP

              670       680       690       700       710       720       730
       ....|....|....|....|....|....|....|....|....|....|....|....|....|....|
MASP1  WYLVGTVSWGDDCGKKDRYGVYSYIHHNKDWIQRVTGVRN
MASP3  TC.GDSGGAFVIFDDLSQRW.VQGLVSWGGPEECGSKQVYGVYTKVSNYVDWVWEQMGLPQSVVEPQVER
FAP
```

Figure 4

Figure 11

| **Immobilized ligand** | **Soluble analyte** | **$K_{on}$ ($M^{-1}$ $s^{-1}$)** | **$K_{off}$ ($s^{-1}$)** | **$K_D$ (nM)** |
| --- | --- | --- | --- | --- |
| rFicolin-2 | MASP-1 | $8.9 \times 10^4$ | $4.4 \times 10^{-4}$ | 5.0 |
| rFicolin-2 | MASP-3 | $1.0 \times 10^5$ | $3.0 \times 10^{-4}$ | 2.9 |

```
              10        20        30        40        50        60        70        80        90       100       110       120
         ....|....|....|....|....|....|....|....|....|....|....|....|....|....|....|....|....|....|....|....|....|....|....|....|
GULF     ETENMELKNKVQDLENQLRITQVSAPPAGSMTPKSPSTDIFDMIPFSPISHQSSMPTRNGTQPPPVPSRSTEIKRDLFGAEPFDPFNCGAADFPPDIQSKLDEMQVTILIDWPINDLFHF
FAP      -------..EI-...SE.KSE..TE-----------------------------------------------------------------------------------------------

             130       140
         ....|....|....|....|....|.
GULF     DMGQRECYVPKLWFPSIIFAIKTRLK
FAP      --------------------------
```

Figure 12

MAP-1/C4bp expression vector:

| Vector | K | SP | MAP-1 | L | C4bp | S | Vector | or

| Vector | K | SP | C4bp | L | MAP-1 | S | Vector |

MAP-1/C4bp protein:

| MAP-1 | L | C4bp | or

| C4bp | L | MAP-1 |

MAP-1/C4bp protein with signal peptide:

| SP | MAP-1 | L | C4bp | or

| SP | C4bp | L | MAP-1 |

C4bp constructs:

| C4bpA | or | C4bpB | or | C4bpA | C4bpB | or | C4bpB | C4bpA |

MAP-1/C1-inh expression vector:

| Vector | K | SP | MAP-1 | L | C1-inh | S | Vector | or

| Vector | K | SP | C1-inh | L | MAP-1 | S | Vector |

MAP-1/C1-inh protein:

| MAP-1 | L | C1-inh | or

| C1-inh | L | MAP-1 |

MAP-1/C1-inh protein with signal peptide:

| SP | MAP-1 | L | C1-inh | or

| SP | C1-inh | L | MAP-1 |

SEQUENCE LISTING

<160> NUMBER OF SEQ ID NOS: 75

<210> SEQ ID NO 1
<211> LENGTH: 380
<212> TYPE: PRT
<213> ORGANISM: Homo sapiens

<400> SEQUENCE: 1

```
Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160
```

-continued

```
Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Lys Asn Glu Ile Asp
        355                 360                 365

Leu Glu Ser Glu Leu Lys Ser Glu Gln Val Thr Glu
    370                 375                 380
```

<210> SEQ ID NO 2
<211> LENGTH: 1143
<212> TYPE: DNA
<213> ORGANISM: Homo sapiens

<400> SEQUENCE: 2

```
atgaggtggc tgcttctcta ttatgctctg tgcttctccc tgtcaaaggc ttcagcccac      60

accgtggagc taaacaatat gtttggccag atccagtcgc ctggttatcc agactcctat     120

cccagtgatt cagaggtgac ttggaatatc actgtcccag atgggtttcg gatcaagctt     180

tacttcatgc acttcaactt ggaatcctcc tacctttgtg aatatgacta tgtgaaggta     240

gaaactgagg accaggtgct ggcaaccttc tgtggcaggg agaccacaga cacagagcag     300

actcccggcc aggaggtggt cctctcccct ggctccttca tgtccatcac tttccggtca     360

gatttctcca atgaggagcg tttcacaggc tttgatgccc actacatggc tgtggatgtg     420

gacgagtgca aggagaggga ggacgaggag ctgtcctgtg accactactg ccacaactac     480

attggcggct actactgctc ctgccgcttc ggctacatcc tccacacaga caacaggacc     540

tgccgagtgg agtgcagtga caacctcttc actcaaagga ctggggtgat caccagccct     600

gacttcccaa acccttaccc caagagctct gaatgcctgt ataccatcga gctggaggag     660

ggtttcatgg tcaacctgca gtttgaggac atatttgaca ttgaggacca tcctgaggtg     720

ccctgcccct atgactacat caagatcaaa gttggtccaa aagttttggg gcctttctgt     780

ggagagaaag ccccagaacc catcagcacc cagagccaca gtgtcctgat cctgttccat     840

agtgacaact cgggagagaa ccggggctgg aggctctcat acagggctgc aggaaatgag     900
```

```
tgcccagagc tacagcctcc tgtccatggg aaaatcgagc cctcccaagc caagtatttc    960

ttcaaagacc aagtgctcgt cagctgtgac acaggctaca aagtgctgaa ggataatgtg   1020

gagatggaca cattccagat tgagtgtctg aaggatggga cgtggagtaa caagattccc   1080

acctgtaaaa aaaatgaaat cgatctggag agcgaactca agtcagagca agtgacagag   1140

tga                                                                 1143


<210> SEQ ID NO 3
<211> LENGTH: 297
<212> TYPE: PRT
<213> ORGANISM: Homo sapiens

<400> SEQUENCE: 3

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala
    290                 295


<210> SEQ ID NO 4
<211> LENGTH: 17
```

<212> TYPE: PRT
<213> ORGANISM: Homo sapiens

<400> SEQUENCE: 4

Lys Asn Glu Ile Asp Leu Glu Ser Glu Leu Lys Ser Glu Gln Val Thr
1               5                   10                  15

Glu

<210> SEQ ID NO 5
<211> LENGTH: 699
<212> TYPE: PRT
<213> ORGANISM: Homo sapiens

<400> SEQUENCE: 5

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu

```
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Ile Thr Phe Ser Thr Arg Asn
    370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Val Cys Gly Leu Pro Lys Phe Ser Arg Lys Leu Met Ala Arg
        435                 440                 445

Ile Phe Asn Gly Arg Pro Ala Gln Lys Gly Thr Thr Pro Trp Ile Ala
    450                 455                 460

Met Leu Ser His Leu Asn Gly Gln Pro Phe Cys Gly Gly Ser Leu Leu
465                 470                 475                 480

Gly Ser Ser Trp Ile Val Thr Ala Ala His Cys Leu His Gln Ser Leu
                485                 490                 495

Asp Pro Glu Asp Pro Thr Leu Arg Asp Ser Asp Leu Leu Ser Pro Ser
            500                 505                 510

Asp Phe Lys Ile Ile Leu Gly Lys His Trp Arg Leu Arg Ser Asp Glu
        515                 520                 525

Asn Glu Gln His Leu Gly Val Lys His Thr Thr Leu His Pro Gln Tyr
    530                 535                 540

Asp Pro Asn Thr Phe Glu Asn Asp Val Ala Leu Val Glu Leu Leu Glu
545                 550                 555                 560

Ser Pro Val Leu Asn Ala Phe Val Met Pro Ile Cys Leu Pro Glu Gly
                565                 570                 575

Pro Gln Gln Glu Gly Ala Met Val Ile Val Ser Gly Trp Gly Lys Gln
            580                 585                 590

Phe Leu Gln Arg Phe Pro Glu Thr Leu Met Glu Ile Glu Ile Pro Ile
        595                 600                 605

Val Asp His Ser Thr Cys Gln Lys Ala Tyr Ala Pro Leu Lys Lys Lys
    610                 615                 620

Val Thr Arg Asp Met Ile Cys Ala Gly Glu Lys Glu Gly Gly Lys Asp
625                 630                 635                 640

Ala Cys Ala Gly Asp Ser Gly Gly Pro Met Val Thr Leu Asn Arg Glu
                645                 650                 655

Arg Gly Gln Trp Tyr Leu Val Gly Thr Val Ser Trp Gly Asp Asp Cys
            660                 665                 670

Gly Lys Lys Asp Arg Tyr Gly Val Tyr Ser Tyr Ile His His Asn Lys
        675                 680                 685

Asp Trp Ile Gln Arg Val Thr Gly Val Arg Asn
    690                 695
```

<210> SEQ ID NO 6
<211> LENGTH: 4353
<212> TYPE: DNA
<213> ORGANISM: Homo sapiens

<400> SEQUENCE: 6

-continued

```
gaagtcagcc acacaggata aaggagggaa gggaaggagc agatcttttc ggtaggaaga     60
cagattttgt tgtcaggttc ctgggagtgc aagagcaagt caaaggagag agagaggaga    120
gaggaaaagc cagagggaga gagggggaga ggggatctgt tgcaggcagg ggaaggcgtg    180
acctgaatgg agaatgccag ccaattccag agacacacag ggacctcaga acaaagataa    240
ggcatcacgg acaccacacc gggcacgagc tcacaggcaa gtcaagctgg gaggaccaag    300
gccgggcagc cgggagcacc caaggcagga aaatgaggtg gctgcttctc tattatgctc    360
tgtgcttctc cctgtcaaag gcttcagccc acaccgtgga gctaaacaat atgtttggcc    420
agatccagtc gcctggttat ccagactcct atcccagtga ttcagaggtg acttggaata    480
tcactgtccc agatgggttt cggatcaagc tttacttcat gcacttcaac ttggaatcct    540
cctacctttg tgaatatgac tatgtgaagg tagaaactga ggaccaggtg ctggcaacct    600
tctgtggcag ggagaccaca gacacagagc agactcccgg ccaggaggtg gtcctctccc    660
ctggctcctt catgtccatc actttccggt cagatttctc caatgaggag cgtttcacag    720
gctttgatgc ccactacatg gctgtggatg tggacgagtg caaggagagg gaggacgagg    780
agctgtcctg tgaccactac tgccacaact acattggcgg ctactactgc tcctgccgct    840
tcggctacat cctccacaca gacaacagga cctgccgagt ggagtgcagt gacaacctct    900
tcactcaaag gactggggtg atcaccagcc ctgacttccc aaacccttac cccaagagct    960
ctgaatgcct gtataccatc gagctggagg agggtttcat ggtcaacctg cagtttgagg   1020
acatatttga cattgaggac catcctgagg tgccctgccc ctatgactac atcaagatca   1080
aagttggtcc aaaagttttg ggcctttct gtggagagaa agccccagaa cccatcagca    1140
cccagagcca cagtgtcctg atcctgttcc atagtgacaa ctcgggagag aaccggggct   1200
ggaggctctc atacagggct gcaggaaatg agtgcccaga gctacagcct cctgtccatg   1260
ggaaaatcga gccctcccaa gccaagtatt tcttcaaaga ccaagtgctc gtcagctgtg   1320
acacaggcta caaagtgctg aaggataatg tggagatgga cacattccag attgagtgtc   1380
tgaaggatgg gacgtggagt aacaagattc ccacctgtaa aattgtagac tgtagagccc   1440
caggagagct ggaacacggg ctgatcacct tctctacaag gaacaacctc accacataca   1500
agtctgagat caaatactcc tgtcaggagc cctattacaa gatgctcaac aataacacag   1560
gtatatatac ctgttctgcc caaggagtct ggatgaataa agtattgggg agaagcctac   1620
ccacctgcct tccagtgtgt gggctcccca agttctcccg gaagctgatg gccaggatct   1680
tcaatggacg cccagcccag aaaggcacca ctccctggat tgccatgctg tcacacctga   1740
atgggcagcc cttctgcgga ggctcccttc taggctccag ctggatcgtg accgccgcac   1800
actgcctcca ccagtcactc gatccggaag atccgaccct acgtgattca gacttgctca   1860
gcccttctga cttcaaaatc atcctgggca agcattggag gctccggtca gatgaaaatg   1920
aacagcatct cggcgtcaaa cacaccactc tccaccccca gtatgatccc aacacattcg   1980
agaatgacgt ggctctggtg gagctgttgg agagcccagt gctgaatgcc ttcgtgatgc   2040
ccatctgtct gcctgaggga ccccagcagg aaggagccat ggtcatcgtc agcggctggg   2100
ggaagcagtt cttgcaaagg ttcccagaga ccctgatgga gattgaaatc ccgattgttg   2160
accacagcac ctgccagaag gcttatgccc cgctgaagaa gaaagtgacc agggacatga   2220
tctgtgctgg ggagaaggaa gggggaaagg acgcctgtgc gggtgactct ggaggcccca   2280
tggtgaccct gaatagagaa agaggccagt ggtacctggt gggcactgtg tcctggggtg   2340
atgactgtgg gaagaaggac cgctacggag tatactctta catccaccac aacaaggact   2400
```

```
ggatccagag ggtcaccgga gtgaggaact gaatttggct cctcagcccc agcaccacca   2460
gctgtgggca gtcagtagca gaggacgatc ctccgatgaa agcagccatt tctcctttcc   2520
ttcctcccat cccccctcct tcggcctatc cattactggg caatagagca ggtatcttca   2580
ccccctttc actctcttta aagagatgga gcaagagagt ggtcagaaca caggccgaat   2640
ccaggctcta tcacttacta gtttgcagtg ctgggcaggt gacttcatct cttcgaactt   2700
cagtttcttc ataagatgga aatgctatac cttacctacc tcgtaaaagt ctgatgagga   2760
aaagattaac taatagatgc atagcactta acagagtgca tagcatacac tgttttcaat   2820
aaatgcacct tagcagaagg tcgatgtgtc taccaggcag acgaagctct cttacaaacc   2880
cctgcctggg tcttagcatt gatcagtgac acacctctcc cctcaacctt gaccatctcc   2940
atctgccctt aaatgctgta tgcttttttg ccaccgtgca acttgcccaa catcaatctt   3000
caccctcatc cctaaaaaag taaaacagac aaggttctga gtcctgtggt atgtccccta   3060
gcaaatgtaa ctaggaacat gcactagatg acagattgcg ggagggcctg agagaagcag   3120
ggacaggagg gagcctgggg attgtggttt gggaaggcag acacctggtt ctagaactag   3180
ctctgccctt agcccccctgt atgaccctat gcaagtcctc ctccctcatc tcaaagggtc   3240
ctcaaagctc tgacgatcta agatacaatg aagccatttt ccccctgata agatgaggta   3300
aagccaatgt aaccaaaagg caaaaattac aatcggttca aaggaacttt gatgcagaca   3360
aaatgctgct gctgctgctc ctgaaatacc caccccttttc cactacgggt gggttcccaa   3420
ggacatggga caggcaaagt gtgagccaaa ggatccttcc ttattcctaa gcagagcatc   3480
tgctctgggc cctggcctcc ttcccttctt gggaaactgg gctgcatgag gtgggccctg   3540
gtagtttgta ccccaggccc ctatactctt ccttcctatg tccacagctg accccaagca   3600
gccgttcccc gactcctcac ccctgagcct caccctgaac tccctcatct tgcaaggcca   3660
taagtgtttt ccaagcaaaa tgcctctccc atcctctctc aggaagcttc tagagacttt   3720
atgccctcca gagctccaag atataagccc tccaagggat cagaagctcc aagttcctgt   3780
cttctgtttt atagaaattg atcttccctg ggggacttta actcttgacc tgtatgcagc   3840
tgttggagta attccaggtc tcttgaaaaa aaagaggaag ataatggaga atgagaacat   3900
atatatatat atattaagcc ccaggctgaa tactcaggga cagcaattca cagcctgcct   3960
ctggttctat aaacaagtca ttctacctct ttgtgccctg ctgtttattc tgtaagggga   4020
aggtggcaat gggacccagc tccatcagac acttgtcaag ctagcagaaa ctccattttc   4080
aatgccaaag aagaactgta atgctgtttt ggaatcatcc caaggcatcc caagacacca   4140
tatcttccca tttcaagcac tgcctgggca caccccaaca tcccaggctg tggtggctcc   4200
tgtgggaact acctagatga agagagtatc atttatacct tctaggagct cctattggga   4260
gacatgaaac atatgtaatt gactaccatg taatagaaca aaccctgcca agtgctgctt   4320
tggaaagtca tggaggtaaa agaaagacca ttc                              4353
```

```
<210> SEQ ID NO 7
<211> LENGTH: 728
<212> TYPE: PRT
<213> ORGANISM: Homo sapiens

<400> SEQUENCE: 7

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
```

-continued

```
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Ile Thr Phe Ser Thr Arg Asn
    370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Glu Cys Gly Gln Pro Ser Arg Ser Leu Pro Ser Leu Val Lys
        435                 440                 445
```

```
Arg Ile Ile Gly Gly Arg Asn Ala Glu Pro Gly Leu Phe Pro Trp Gln
    450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Ala Ser Trp Ile Leu Thr Ala Ala
                485                 490                 495

His Val Leu Arg Ser Gln Arg Arg Asp Thr Thr Val Ile Pro Val Ser
            500                 505                 510

Lys Glu His Val Thr Val Tyr Leu Gly Leu His Asp Val Arg Asp Lys
        515                 520                 525

Ser Gly Ala Val Asn Ser Ser Ala Ala Arg Val Val Leu His Pro Asp
    530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Val Cys Leu Pro Arg
                565                 570                 575

Leu Glu Pro Glu Gly Pro Ala Pro His Met Leu Gly Leu Val Ala Gly
            580                 585                 590

Trp Gly Ile Ser Asn Pro Asn Val Thr Val Asp Glu Ile Ile Ser Ser
        595                 600                 605

Gly Thr Arg Thr Leu Ser Asp Val Leu Gln Tyr Val Lys Leu Pro Val
    610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
                645                 650                 655

Lys Asp Thr Cys Leu Gly Asp Ser Gly Gly Ala Phe Val Ile Phe Asp
            660                 665                 670

Asp Leu Ser Gln Arg Trp Val Val Gln Gly Leu Val Ser Trp Gly Gly
        675                 680                 685

Pro Glu Glu Cys Gly Ser Lys Gln Val Tyr Gly Val Tyr Thr Lys Val
    690                 695                 700

Ser Asn Tyr Val Asp Trp Val Trp Glu Gln Met Gly Leu Pro Gln Ser
705                 710                 715                 720

Val Val Glu Pro Gln Val Glu Arg
                725
```

<210> SEQ ID NO 8
<211> LENGTH: 4137
<212> TYPE: DNA
<213> ORGANISM: Homo sapiens

<400> SEQUENCE: 8

```
gaagtcagcc acacaggata aaggagggaa gggaaggagc agatcttttc ggtaggaaga     60

cagattttgt tgtcaggttc ctgggagtgc aagagcaagt caaaggagag agagaggaga    120

gaggaaaagc cagagggaga gagggggaga ggggatctgt tgcaggcagg ggaaggcgtg    180

acctgaatgg agaatgccag ccaattccag agacacacag ggacctcaga acaaagataa    240

ggcatcacgg acaccacacc gggcacgagc tcacaggcaa gtcaagctgg gaggaccaag    300

gccgggcagc cgggagcacc caaggcagga aaatgaggtg gctgcttctc tattatgctc    360

tgtgcttctc cctgtcaaag gcttcagccc acaccgtgga gctaaacaat atgtttggcc    420

agatccagtc gcctggttat ccagactcct atcccagtga ttcagaggtg acttggaata    480
```

-continued

```
tcactgtccc agatgggttt cggatcaagc tttacttcat gcacttcaac ttggaatcct    540
cctacctttg tgaatatgac tatgtgaagg tagaaactga ggaccaggtg ctggcaacct    600
tctgtggcag ggagaccaca gacacagagc agactcccgg ccaggaggtg gtcctctccc    660
ctggctcctt catgtccatc actttccggt cagatttctc caatgaggag cgtttcacag    720
gctttgatgc ccactacatg gctgtggatg tggacgagtg caaggagagg gaggacgagg    780
agctgtcctg tgaccactac tgccacaact acattggcgg ctactactgc tcctgccgct    840
tcggctacat cctccacaca gacaacagga cctgccgagt ggagtgcagt gacaacctct    900
tcactcaaag gactggggtg atcaccagcc ctgacttccc aaacccttac cccaagagct    960
ctgaatgcct gtataccatc gagctggagg agggtttcat ggtcaacctg cagtttgagg   1020
acatatttga cattgaggac catcctgagg tgccctgccc ctatgactac atcaagatca   1080
aagttggtcc aaaagttttg gggcctttct gtggagagaa agccccagaa cccatcagca   1140
cccagagcca cagtgtcctg atcctgttcc atagtgacaa ctcgggagag aaccggggct   1200
ggaggctctc atacagggct gcaggaaatg agtgcccaga gctacagcct cctgtccatg   1260
ggaaaatcga gccctcccaa gccaagtatt tcttcaaaga ccaagtgctc gtcagctgtg   1320
acacaggcta caaagtgctg aaggataatg tggagatgga cacattccag attgagtgtc   1380
tgaaggatgg gacgtggagt aacaagattc ccacctgtaa aattgtagac tgtagagccc   1440
caggagagct ggaacacggg ctgatcacct tctctacaag gaacaacctc accacataca   1500
agtctgagat caaatactcc tgtcaggagc cctattacaa gatgctcaac aataacacag   1560
gtatatatac ctgttctgcc caaggagtct ggatgaataa agtattgggg agaagcctac   1620
ccacctgcct tccagagtgt ggtcagccct cccgctccct gccaagcctg gtcaagagga   1680
tcattggggg ccgaaatgct gagcctggcc tcttcccgtg gcaggccctg atagtggtgg   1740
aggacacttc gagagtgcca aatgacaagt ggtttgggag tggggccctg ctctctgcgt   1800
cctggatcct cacagcagct catgtgctgc gctcccagcg tagagacacc acggtgatac   1860
cagtctccaa ggagcatgtc accgtctacc tgggcttgca tgatgtgcga gacaaatcgg   1920
gggcagtcaa cagctcagct gcccgagtgg tgctccaccc agacttcaac atccaaaact   1980
acaaccacga tatagctctg gtgcagctgc aggagcctgt gcccctggga ccccacgtta   2040
tgcctgtctg cctgccaagg cttgagcctg aaggcccggc cccccacatg ctgggcctgg   2100
tggccggctg ggggcatctcc aatcccaatg tgacagtgga tgagatcatc agcagtggca   2160
cacggacctt gtcagatgtc ctgcagtatg tcaagttacc cgtggtgcct cacgctgagt   2220
gcaaaactag ctatgagtcc cgctcgggca attacagcgt cacggagaac atgttctgtg   2280
ctggctacta cgagggcggc aaagacacgt gccttggaga tagcggtggg gcctttgtca   2340
tctttgatga cttgagccag cgctgggtgg tgcaaggcct ggtgtcctgg gggggacctg   2400
aagaatgcgg cagcaagcag gtctatggag tctacacaaa ggtctccaat tacgtggact   2460
gggtgtggga gcagatgggc ttaccacaaa gtgttgtgga gccccaggtg gaacggtgag   2520
ctgacttact tcctcggggc ctgcctcccc tgagcgaagc tacaccgcac ttccgacagc   2580
acactccaca ttacttatca gaccatatgg aatggaacac actgacctag cggtggcttc   2640
tcctaccgag acagccccca ggaccctgag aggcagagtg tggtataggg aaaaggctcc   2700
aggcaggaga cctgtgttcc tgagcttgtc caagtctctt tccctgtctg ggcctcactc   2760
taccgagtaa tacaatgcag gagctcaacc aaggcctctg tgccaatccc agcactcctt   2820
tccaggccat gcttcttacc ccagtggcct ttattcactc ctgaccactt atcaaaccca   2880
```

-continued

```
tcggtcctac tgttggtata actgagcttg gacctgacta ttagaaaatg gtttctaaca   2940

ttgaactgaa tgccgcatct gtatattttc ctgctctgcc ttctgggact agccttggcc   3000

taatccttcc tctaggagaa gagcattcag gttttgggag atggctcata gccaagcccc   3060

tctctcttag tgtgatccct tggagcacct tcatgcctgg ggtttctctc ccaaaagctt   3120

cttgcagtct aagccttatc ccttatgttc cccattaaag gaatttcaaa agacatggag   3180

aaagttggga aggtttgtgc tgactgctgg gagcagaata gccgtgggag gcccaccaag   3240

cccttaaatt cccattgtca actcagaaca catttgggcc catatgccac cctggaacac   3300

cagctgacac catgggcgtc cacacctgct gctccagaca agcacaaagc aatctttcag   3360

ccttgaaatg tattatctga aaggctacct gaagcccagg cccgaatatg gggacttagt   3420

cgattacctg gaaaaagaaa agacccacac tgtgtcctgc tgtgcttttg ggcaggaaaa   3480

tggaagaaag agtggggtgg gcacattaga agtcacccaa atcctgccag gctgcctggc   3540

atccctgggg catgagctgg gcggagaatc caccccgcag gatgttcaga gggacccact   3600

ccttcatttt tcagagtcaa aggaatcaga ggctcaccca tggcaggcag tgaaaagagc   3660

caggagtcct gggttctagt ccctgctctg cccccaactg gctgtataac ctttgaaaaa   3720

tcattttctt tgtctgagtc tctggttctc cgtcagcaac aggctggcat aaggtcccct   3780

gcaggttcct tctagctgga gcactcagag cttccctgac tgctagcagc ctctctggcc   3840

ctcacagggc tgattgttct ccttctccct ggagctctct ctcctgaaaa tctccatcag   3900

agcaaggcag ccagagaagc ccctgagagg gaatgattgg gaagtgtcca ctttctcaac   3960

cggctcatca aacacactcc tttgtctatg aatggcacat gtaaatgatg ttatattttg   4020

tatcttttat atcatatgct tcaccattct gtaaagggcc tctgcattgt tgctcccatc   4080

aggggtctca agtggaaata aaccctcgtg gataaccaaa aaaaaaaaaa aaaaaaa      4137
```

```
<210> SEQ ID NO 9
<211> LENGTH: 686
<212> TYPE: PRT
<213> ORGANISM: Homo sapiens

<400> SEQUENCE: 9

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
```

-continued

```
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
        195                 200                 205

Ser Ser Cys Thr Tyr Ser Ile Ser Leu Glu Glu Gly Phe Ser Val Ile
    210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
        275                 280                 285

Trp Lys Ile His Tyr Thr Ser Thr Ala Gln Pro Cys Pro Tyr Pro Met
    290                 295                 300

Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
                325                 330                 335

Gly His Leu Pro Leu Lys Ser Phe Thr Ala Val Cys Gln Lys Asp Gly
            340                 345                 350

Ser Trp Asp Arg Pro Met Pro Ala Cys Ser Ile Val Asp Cys Gly Pro
        355                 360                 365

Pro Asp Asp Leu Pro Ser Gly Arg Val Glu Tyr Ile Thr Gly Pro Gly
    370                 375                 380

Val Thr Thr Tyr Lys Ala Val Ile Gln Tyr Ser Cys Glu Glu Thr Phe
385                 390                 395                 400

Tyr Thr Met Lys Val Asn Asp Gly Lys Tyr Val Cys Glu Ala Asp Gly
                405                 410                 415

Phe Trp Thr Ser Ser Lys Gly Glu Lys Ser Leu Pro Val Cys Glu Pro
            420                 425                 430

Val Cys Gly Leu Ser Ala Arg Thr Thr Gly Gly Arg Ile Tyr Gly Gly
        435                 440                 445

Gln Lys Ala Lys Pro Gly Asp Phe Pro Trp Gln Val Leu Ile Leu Gly
    450                 455                 460

Gly Thr Thr Ala Ala Gly Ala Leu Leu Tyr Asp Asn Trp Val Leu Thr
465                 470                 475                 480

Ala Ala His Ala Val Tyr Glu Gln Lys His Asp Ala Ser Ala Leu Asp
                485                 490                 495

Ile Arg Met Gly Thr Leu Lys Arg Leu Ser Pro His Tyr Thr Gln Ala
            500                 505                 510

Trp Ser Glu Ala Val Phe Ile His Glu Gly Tyr Thr His Asp Ala Gly
        515                 520                 525

Phe Asp Asn Asp Ile Ala Leu Ile Lys Leu Asn Asn Lys Val Val Ile
    530                 535                 540

Asn Ser Asn Ile Thr Pro Ile Cys Leu Pro Arg Lys Glu Ala Glu Ser
545                 550                 555                 560

Phe Met Arg Thr Asp Asp Ile Gly Thr Ala Ser Gly Trp Gly Leu Thr
                565                 570                 575
```

```
Gln Arg Gly Phe Leu Ala Arg Asn Leu Met Tyr Val Asp Ile Pro Ile
            580                 585                 590

Val Asp His Gln Lys Cys Thr Ala Ala Tyr Glu Lys Pro Pro Tyr Pro
        595                 600                 605

Arg Gly Ser Val Thr Ala Asn Met Leu Cys Ala Gly Leu Glu Ser Gly
    610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
            660                 665                 670

Ile Asn Tyr Ile Pro Trp Ile Glu Asn Ile Ile Ser Asp Phe
        675                 680                 685


<210> SEQ ID NO 10
<211> LENGTH: 2460
<212> TYPE: DNA
<213> ORGANISM: Homo sapiens

<400> SEQUENCE: 10

ggccagctgg acgggcacac catgaggctg ctgaccctcc tgggccttct gtgtggctcg      60

gtggccaccc ccttgggccc gaagtggcct gaacctgtgt tcgggcgcct ggcatccccc     120

ggctttccag gggagtatgc caatgaccag gagcggcgct ggaccctgac tgcacccccc     180

ggctaccgcc tgcgcctcta cttcacccac ttcgacctgg agctctccca cctctgcgag     240

tacgacttcg tcaagctgag ctcgggggcc aaggtgctgg ccacgctgtg cgggcaggag     300

agcacagaca cggagcgggc ccctggcaag gacactttct actcgctggg ctccagcctg     360

gacattacct tccgctccga ctactccaac gagaagccgt tcacggggtt cgaggccttc     420

tatgcagccg aggacattga cgagtgccag gtggccccgg gagaggcgcc cacctgcgac     480

caccactgcc acaaccacct gggcggtttc tactgctcct gccgcgcagg ctacgtcctg     540

caccgtaaca agcgcacctg ctcagccctg tgctccggcc aggtcttcac ccagaggtct     600

ggggagctca gcagccctga atacccacgg ccgtatccca aactctccag ttgcacttac     660

agcatcagcc tggaggaggg gttcagtgtc attctggact ttgtggagtc cttcgatgtg     720

gagacacacc ctgaaaccct gtgtccctac gactttctca agattcaaac agacagagaa     780

gaacatggcc cattctgtgg gaagacattg ccccacagga ttgaaacaaa aagcaacacg     840

gtgaccatca cctttgtcac agatgaatca ggagaccaca caggctggaa gatccactac     900

acgagcacag cgcagccttg cccttatccg atggcgccac ctaatggcca cgtttcacct     960

gtgcaagcca aatacatcct gaaagacagc ttctccatct tttgcgagac tggctatgag    1020

cttctgcaag gtcacttgcc cctgaaatcc tttactgcag tttgtcagaa agatggatct    1080

tgggaccggc caatgcccgc gtgcagcatt gttgactgtg gccctcctga tgatctaccc    1140

agtggccgag tggagtacat cacaggtcct ggagtgacca cctacaaagc tgtgattcag    1200

tacagctgtg aagagacctt ctacacaatg aaagtgaatg atggtaaata tgtgtgtgag    1260

gctgatggat tctggacgag ctccaaagga gaaaaatcac tcccagtctg tgagcctgtt    1320

tgtggactat cagcccgcac aacaggaggg cgtatatatg gagggcaaaa ggcaaaacct    1380

ggtgattttc cttggcaagt cctgatatta ggtggaacca cagcagcagg tgcactttta    1440

tatgacaact gggtcctaac agctgctcat gccgtctatg agcaaaaaca tgatgcatcc    1500
```

```
gccctggaca ttcgaatggg caccctgaaa agactatcac ctcattatac acaagcctgg   1560

tctgaagctg tttttataca tgaaggttat actcatgatg ctggctttga caatgacata   1620

gcactgatta aattgaataa caaagttgta atcaatagca acatcacgcc tatttgtctg   1680

ccaagaaaag aagctgaatc ctttatgagg acagatgaca ttggaactgc atctggatgg   1740

ggattaaccc aaaggggttt tcttgctaga aatctaatgt atgtcgacat accgattgtt   1800

gaccatcaaa aatgtactgc tgcatatgaa aagccaccct atccaagggg aagtgtaact   1860

gctaacatgc tttgtgctgg cttagaaagt gggggcaagg acagctgcag aggtgacagc   1920

ggagggggcac tggtgtttct agatagtgaa acagagaggt ggtttgtggg aggaatagtg   1980

tcctggggtt ccatgaattg tggggaagca ggtcagtatg gagtctacac aaaagttatt   2040

aactatattc cctggatcga gaacataatt agtgattttt aacttgcgtg tctgcagtca   2100

aggattcttc atttttagaa atgcctgtga agaccttggc agcgacgtgg ctcgagaagc   2160

attcatcatt actgtggaca tggcagttgt tgctccaccc aaaaaaacag actccaggtg   2220

aggctgctgt catttctcca cttgccagtt taattccagc cttacccatt gactcaaggg   2280

gacataaacc acgagagtga cagtcatctt tgcccaccca gtgtaatgtc actgctcaaa   2340

ttacatttca ttaccttaaa aagccagtct cttttcatac tggctgttgg catttctgta   2400

aactgcctgt ccatgctctt tgtttttaaa cttgttctta ttgaaaaaaa aaaaaaaaaa   2460
```

<210> SEQ ID NO 11
<211> LENGTH: 185
<212> TYPE: PRT
<213> ORGANISM: Homo sapiens

<400> SEQUENCE: 11

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Glu Gln Ser Leu
            180                 185
```

<210> SEQ ID NO 12

<211> LENGTH: 738
<212> TYPE: DNA
<213> ORGANISM: Homo sapiens

<400> SEQUENCE: 12

```
ggccagctgg acgggcacac catgaggctg ctgaccctcc tgggccttct gtgtggctcg      60

gtggccaccc ccttgggccc gaagtggcct gaacctgtgt tcgggcgcct ggcatccccc     120

ggctttccag gggagtatgc caatgaccag gagcggcgct ggaccctgac tgcacccccc     180

ggctaccgcc tgcgcctcta cttcacccac ttcgacctgg agctctccca cctctgcgag     240

tacgacttcg tcaagctgag ctcgggggcc aaggtgctgg ccacgctgtg cgggcaggag     300

agcacagaca cggagcgggc ccctggcaag gacactttct actcgctggg ctccagcctg     360

gacattacct tccgctccga ctactccaac gagaagccgt tcacggggtt cgaggccttc     420

tatgcagccg aggacattga cgagtgccag gtggccccgg gagaggcgcc cacctgcgac     480

caccactgcc acaaccacct gggcggtttc tactgctcct gccgcgcagg ctacgtcctg     540

caccgtaaca agcgcacctg ctcagagcag agcctctagc ctcccctgga gctccggcct     600

gcccagcagg tcagaagcca gagccagcct gctggcctca gctccgggtt gggctgagat     660

ggctgtgccc caactcccat tcacccacca tggacccaat aataaacctg gccccacccc     720

aaaaaaaaaa aaaaaaaa                                                   738
```

<210> SEQ ID NO 13
<211> LENGTH: 18
<212> TYPE: DNA
<213> ORGANISM: Artificial Sequence
<220> FEATURE:
<223> OTHER INFORMATION: DNA primer

<400> SEQUENCE: 13

```
gcacccagag ccacagtg                                                    18
```

<210> SEQ ID NO 14
<211> LENGTH: 18
<212> TYPE: DNA
<213> ORGANISM: Artificial Sequence
<220> FEATURE:
<223> OTHER INFORMATION: DNA Primer

<400> SEQUENCE: 14

```
gccttccagt gtgtgggc                                                    18
```

<210> SEQ ID NO 15
<211> LENGTH: 19
<212> TYPE: DNA
<213> ORGANISM: Artificial Sequence
<220> FEATURE:
<223> OTHER INFORMATION: DNA Primer

<400> SEQUENCE: 15

```
gccttccaga gtgtggtca                                                   19
```

<210> SEQ ID NO 16
<211> LENGTH: 19
<212> TYPE: DNA
<213> ORGANISM: Artificial Sequence
<220> FEATURE:
<223> OTHER INFORMATION: DNA Primer

<400> SEQUENCE: 16

```
cgatctggag agcgaactc                                                   19
```

-continued

<210> SEQ ID NO 17
<211> LENGTH: 19
<212> TYPE: DNA
<213> ORGANISM: Artificial Sequence
<220> FEATURE:
<223> OTHER INFORMATION: DNA Primer

<400> SEQUENCE: 17
ctgttcttca cactggctg 19

<210> SEQ ID NO 18
<211> LENGTH: 20
<212> TYPE: DNA
<213> ORGANISM: Artificial Sequence
<220> FEATURE:
<223> OTHER INFORMATION: DNA Primer

<400> SEQUENCE: 18
ctgctgagat catgttgttc 20

<210> SEQ ID NO 19
<211> LENGTH: 15
<212> TYPE: DNA
<213> ORGANISM: Artificial Sequence
<220> FEATURE:
<223> OTHER INFORMATION: DNA Primer

<400> SEQUENCE: 19
ttatacgact cacta 15

<210> SEQ ID NO 20
<211> LENGTH: 1231
<212> TYPE: PRT
<213> ORGANISM: homo sapiens

<400> SEQUENCE: 20

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
```

-continued

```
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn His Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Arg Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605
```

-continued

```
Val Gln Cys Tyr His Phe Gly Leu Ser Pro Asp Leu Pro Ile Cys Lys
    610                 615                 620

Glu Gln Val Gln Ser Cys Gly Pro Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
    850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro  Met Gly Glu Lys Lys  Asp Val Tyr
        995                 1000                 1005

Lys Ala  Gly Glu Gln Val Thr  Tyr Thr Cys Ala Thr  Tyr Tyr Lys
    1010                 1015                 1020
```

```
Met Asp  Gly Ala Ser Asn Val  Thr Cys Ile Asn Ser  Arg Trp Thr
1025                 1030                 1035

Gly Arg  Pro Thr Cys Arg Asp  Thr Ser Cys Val Asn  Pro Pro Thr
1040                 1045                 1050

Val Gln  Asn Ala Tyr Ile Val  Ser Arg Gln Met Ser  Lys Tyr Pro
1055                 1060                 1065

Ser Gly  Glu Arg Val Arg Tyr  Gln Cys Arg Ser Pro  Tyr Glu Met
1070                 1075                 1080

Phe Gly  Asp Glu Glu Val Met  Cys Leu Asn Gly Asn  Trp Thr Glu
1085                 1090                 1095

Pro Pro  Gln Cys Lys Asp Ser  Thr Gly Lys Cys Gly  Pro Pro Pro
1100                 1105                 1110

Pro Ile  Asp Asn Gly Asp Ile  Thr Ser Phe Pro Leu  Ser Val Tyr
1115                 1120                 1125

Ala Pro  Ala Ser Ser Val Glu  Tyr Gln Cys Gln Asn  Leu Tyr Gln
1130                 1135                 1140

Leu Glu  Gly Asn Lys Arg Ile  Thr Cys Arg Asn Gly  Gln Trp Ser
1145                 1150                 1155

Glu Pro  Pro Lys Cys Leu His  Pro Cys Val Ile Ser  Arg Glu Ile
1160                 1165                 1170

Met Glu  Asn Tyr Asn Ile Ala  Leu Arg Trp Thr Ala  Lys Gln Lys
1175                 1180                 1185

Leu Tyr  Ser Arg Thr Gly Glu  Ser Val Glu Phe Val  Cys Lys Arg
1190                 1195                 1200

Gly Tyr  Arg Leu Ser Ser Arg  Ser His Thr Leu Arg  Thr Thr Cys
1205                 1210                 1215

Trp Asp  Gly Lys Leu Glu Tyr  Pro Thr Cys Ala Lys  Arg
1220                 1225                 1230


<210> SEQ ID NO 21
<211> LENGTH: 597
<212> TYPE: PRT
<213> ORGANISM: homo sapiens

<400> SEQUENCE: 21

Met His Pro Pro Lys Thr Pro Ser Gly Ala Leu His Arg Lys Arg Lys
1               5                   10                  15

Met Ala Ala Trp Pro Phe Ser Arg Leu Trp Lys Val Ser Asp Pro Ile
            20                  25                  30

Leu Phe Gln Met Thr Leu Ile Ala Ala Leu Leu Pro Ala Val Leu Gly
        35                  40                  45

Asn Cys Gly Pro Pro Pro Thr Leu Ser Phe Ala Ala Pro Met Asp Ile
    50                  55                  60

Thr Leu Thr Glu Thr Arg Phe Lys Thr Gly Thr Thr Leu Lys Tyr Thr
65                  70                  75                  80

Cys Leu Pro Gly Tyr Val Arg Ser His Ser Thr Gln Thr Leu Thr Cys
                85                  90                  95

Asn Ser Asp Gly Glu Trp Val Tyr Asn Thr Phe Cys Ile Tyr Lys Arg
            100                 105                 110

Cys Arg His Pro Gly Glu Leu Arg Asn Gly Gln Val Glu Ile Lys Thr
        115                 120                 125

Asp Leu Ser Phe Gly Ser Gln Ile Glu Phe Ser Cys Ser Glu Gly Phe
    130                 135                 140

Phe Leu Ile Gly Ser Thr Thr Ser Arg Cys Glu Val Gln Asp Arg Gly
145                 150                 155                 160
```

-continued

```
Val Gly Trp Ser His Pro Leu Pro Gln Cys Glu Ile Val Lys Cys Lys
                165                 170                 175

Pro Pro Pro Asp Ile Arg Asn Gly Arg His Ser Gly Glu Glu Asn Phe
            180                 185                 190

Tyr Ala Tyr Gly Phe Ser Val Thr Tyr Ser Cys Asp Pro Arg Phe Ser
        195                 200                 205

Leu Leu Gly His Ala Ser Ile Ser Cys Thr Val Glu Asn Glu Thr Ile
    210                 215                 220

Gly Val Trp Arg Pro Ser Pro Pro Thr Cys Glu Lys Ile Thr Cys Arg
225                 230                 235                 240

Lys Pro Asp Val Ser His Gly Glu Met Val Ser Gly Phe Gly Pro Ile
                245                 250                 255

Tyr Asn Tyr Lys Asp Thr Ile Val Phe Lys Cys Gln Lys Gly Phe Val
            260                 265                 270

Leu Arg Gly Ser Ser Val Ile His Cys Asp Ala Asp Ser Lys Trp Asn
        275                 280                 285

Pro Ser Pro Pro Ala Cys Glu Pro Asn Ser Cys Ile Asn Leu Pro Asp
    290                 295                 300

Ile Pro His Ala Ser Trp Glu Thr Tyr Pro Arg Pro Thr Lys Glu Asp
305                 310                 315                 320

Val Tyr Val Val Gly Thr Val Leu Arg Tyr Arg Cys His Pro Gly Tyr
                325                 330                 335

Lys Pro Thr Thr Asp Glu Pro Thr Thr Val Ile Cys Gln Lys Asn Leu
            340                 345                 350

Arg Trp Thr Pro Tyr Gln Gly Cys Glu Ala Leu Cys Cys Pro Glu Pro
        355                 360                 365

Lys Leu Asn Asn Gly Glu Ile Thr Gln His Arg Lys Ser Arg Pro Ala
    370                 375                 380

Asn His Cys Val Tyr Phe Tyr Gly Asp Glu Ile Ser Phe Ser Cys His
385                 390                 395                 400

Glu Thr Ser Arg Phe Ser Ala Ile Cys Gln Gly Asp Gly Thr Trp Ser
                405                 410                 415

Pro Arg Thr Pro Ser Cys Gly Asp Ile Cys Asn Phe Pro Pro Lys Ile
            420                 425                 430

Ala His Gly His Tyr Lys Gln Ser Ser Ser Tyr Ser Phe Phe Lys Glu
        435                 440                 445

Glu Ile Ile Tyr Glu Cys Asp Lys Gly Tyr Ile Leu Val Gly Gln Ala
    450                 455                 460

Lys Leu Ser Cys Ser Tyr Ser His Trp Ser Ala Pro Ala Pro Gln Cys
465                 470                 475                 480

Lys Ala Leu Cys Arg Lys Pro Glu Leu Val Asn Gly Arg Leu Ser Val
                485                 490                 495

Asp Lys Asp Gln Tyr Val Glu Pro Glu Asn Val Thr Ile Gln Cys Asp
            500                 505                 510

Ser Gly Tyr Gly Val Val Gly Pro Gln Ser Ile Thr Cys Ser Gly Asn
        515                 520                 525

Arg Thr Trp Tyr Pro Glu Val Pro Lys Cys Glu Trp Glu Thr Pro Glu
    530                 535                 540

Gly Cys Glu Gln Val Leu Thr Gly Lys Arg Leu Met Gln Cys Leu Pro
545                 550                 555                 560

Asn Pro Glu Asp Val Lys Met Ala Leu Glu Val Tyr Lys Leu Ser Leu
                565                 570                 575
```

Glu Ile Glu Gln Leu Glu Leu Gln Arg Asp Ser Ala Arg Gln Ser Thr
580 585 590

Leu Asp Lys Glu Leu
595

<210> SEQ ID NO 22
<211> LENGTH: 252
<212> TYPE: PRT
<213> ORGANISM: homo sapiens

<400> SEQUENCE: 22

Met Phe Phe Trp Cys Ala Cys Cys Leu Met Val Ala Trp Arg Val Ser
1 5 10 15

Ala Ser Asp Ala Glu His Cys Pro Glu Leu Pro Pro Val Asp Asn Ser
20 25 30

Ile Phe Val Ala Lys Glu Val Glu Gly Gln Ile Leu Gly Thr Tyr Val
35 40 45

Cys Ile Lys Gly Tyr His Leu Val Gly Lys Lys Thr Leu Phe Cys Asn
50 55 60

Ala Ser Lys Glu Trp Asp Asn Thr Thr Thr Glu Cys Arg Leu Gly His
65 70 75 80

Cys Pro Asp Pro Val Leu Val Asn Gly Glu Phe Ser Ser Ser Gly Pro
85 90 95

Val Asn Val Ser Asp Lys Ile Thr Phe Met Cys Asn Asp His Tyr Ile
100 105 110

Leu Lys Gly Ser Asn Arg Ser Gln Cys Leu Glu Asp His Thr Trp Ala
115 120 125

Pro Pro Phe Pro Ile Cys Lys Ser Arg Asp Cys Asp Pro Pro Gly Asn
130 135 140

Pro Val His Gly Tyr Phe Glu Gly Asn Asn Phe Thr Leu Gly Ser Thr
145 150 155 160

Ile Ser Tyr Tyr Cys Glu Asp Arg Tyr Tyr Leu Val Gly Val Gln Glu
165 170 175

Gln Gln Cys Val Asp Gly Glu Trp Ser Ser Ala Leu Pro Val Cys Lys
180 185 190

Leu Ile Gln Glu Ala Pro Lys Pro Glu Cys Glu Lys Ala Leu Leu Ala
195 200 205

Phe Gln Glu Ser Lys Asn Leu Cys Glu Ala Met Glu Asn Phe Met Gln
210 215 220

Gln Leu Lys Glu Ser Gly Met Thr Met Glu Glu Leu Lys Tyr Ser Leu
225 230 235 240

Glu Leu Lys Lys Ala Glu Leu Lys Ala Lys Leu Leu
245 250

<210> SEQ ID NO 23
<211> LENGTH: 583
<212> TYPE: PRT
<213> ORGANISM: homo sapiens

<400> SEQUENCE: 23

Met Lys Leu Leu His Val Phe Leu Leu Phe Leu Cys Phe His Leu Arg
1 5 10 15

Phe Cys Lys Val Thr Tyr Thr Ser Gln Glu Asp Leu Val Glu Lys Lys
20 25 30

Cys Leu Ala Lys Lys Tyr Thr His Leu Ser Cys Asp Lys Val Phe Cys
35 40 45

-continued

```
Gln Pro Trp Gln Arg Cys Ile Glu Gly Thr Cys Val Cys Lys Leu Pro
    50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
        115                 120                 125

Val Lys Leu Val Asp Gln Asp Lys Thr Met Phe Ile Cys Lys Ser Ser
    130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
        195                 200                 205

Phe Ala Asp Val Val Cys Tyr Thr Gln Lys Ala Asp Ser Pro Met Asp
    210                 215                 220

Asp Phe Phe Gln Cys Val Asn Gly Lys Tyr Ile Ser Gln Met Lys Ala
225                 230                 235                 240

Cys Asp Gly Ile Asn Asp Cys Gly Asp Gln Ser Asp Glu Leu Cys Cys
                245                 250                 255

Lys Ala Cys Gln Gly Lys Gly Phe His Cys Lys Ser Gly Val Cys Ile
            260                 265                 270

Pro Ser Gln Tyr Gln Cys Asn Gly Glu Val Asp Cys Ile Thr Gly Glu
        275                 280                 285

Asp Glu Val Gly Cys Ala Gly Phe Ala Ser Val Ala Gln Glu Glu Thr
    290                 295                 300

Glu Ile Leu Thr Ala Asp Met Asp Ala Glu Arg Arg Arg Ile Lys Ser
305                 310                 315                 320

Leu Leu Pro Lys Leu Ser Cys Gly Val Lys Asn Arg Met His Ile Arg
                325                 330                 335

Arg Lys Arg Ile Val Gly Gly Lys Arg Ala Gln Leu Gly Asp Leu Pro
            340                 345                 350

Trp Gln Val Ala Ile Lys Asp Ala Ser Gly Ile Thr Cys Gly Gly Ile
        355                 360                 365

Tyr Ile Gly Gly Cys Trp Ile Leu Thr Ala Ala His Cys Leu Arg Ala
    370                 375                 380

Ser Lys Thr His Arg Tyr Gln Ile Trp Thr Thr Val Val Asp Trp Ile
385                 390                 395                 400

His Pro Asp Leu Lys Arg Ile Val Ile Glu Tyr Val Asp Arg Ile Ile
                405                 410                 415

Phe His Glu Asn Tyr Asn Ala Gly Thr Tyr Gln Asn Asp Ile Ala Leu
            420                 425                 430

Ile Glu Met Lys Lys Asp Gly Asn Lys Lys Asp Cys Glu Leu Pro Arg
        435                 440                 445

Ser Ile Pro Ala Cys Val Pro Trp Ser Pro Tyr Leu Phe Gln Pro Asn
    450                 455                 460

Asp Thr Cys Ile Val Ser Gly Trp Gly Arg Glu Lys Asp Asn Glu Arg
```

```
465                 470                 475                 480

Val Phe Ser Leu Gln Trp Gly Glu Val Lys Leu Ile Ser Asn Cys Ser
                485                 490                 495

Lys Phe Tyr Gly Asn Arg Phe Tyr Glu Lys Glu Met Glu Cys Ala Gly
            500                 505                 510

Thr Tyr Asp Gly Ser Ile Asp Ala Cys Lys Gly Asp Ser Gly Gly Pro
        515                 520                 525

Leu Val Cys Met Asp Ala Asn Asn Val Thr Tyr Val Trp Gly Val Val
    530                 535                 540

Ser Trp Gly Glu Asn Cys Gly Lys Pro Glu Phe Pro Gly Val Tyr Thr
545                 550                 555                 560

Lys Val Ala Asn Tyr Phe Asp Trp Ile Ser Tyr His Val Gly Arg Pro
                565                 570                 575

Phe Ile Ser Gln Tyr Asn Val
            580


<210> SEQ ID NO 24
<211> LENGTH: 500
<212> TYPE: PRT
<213> ORGANISM: homo sapiens

<400> SEQUENCE: 24

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Ser Pro Arg Val Leu Ser Asn Asn Ser Asp
                245                 250                 255
```

```
Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
    290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ala Ser Ala Ile Ser Val
    450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500
```

<210> SEQ ID NO 25
<211> LENGTH: 680
<212> TYPE: PRT
<213> ORGANISM: homo sapiens

<400> SEQUENCE: 25

```
His Thr Val Glu Leu Asn Asn Met Phe Gly Gln Ile Gln Ser Pro Gly
1               5                   10                  15

Tyr Pro Asp Ser Tyr Pro Ser Asp Ser Glu Val Thr Trp Asn Ile Thr
            20                  25                  30

Val Pro Asp Gly Phe Arg Ile Lys Leu Tyr Phe Met His Phe Asn Leu
        35                  40                  45

Glu Ser Ser Tyr Leu Cys Glu Tyr Asp Tyr Val Lys Val Glu Thr Glu
    50                  55                  60

Asp Gln Val Leu Ala Thr Phe Cys Gly Arg Glu Thr Thr Asp Thr Glu
65                  70                  75                  80

Gln Thr Pro Gly Gln Glu Val Val Leu Ser Pro Gly Ser Phe Met Ser
                85                  90                  95

Ile Thr Phe Arg Ser Asp Phe Ser Asn Glu Glu Arg Phe Thr Gly Phe
            100                 105                 110

Asp Ala His Tyr Met Ala Val Asp Val Asp Glu Cys Lys Glu Arg Glu
        115                 120                 125
```

```
Asp Glu Glu Leu Ser Cys Asp His Tyr Cys His Asn Tyr Ile Gly Gly
    130                 135                 140

Tyr Tyr Cys Ser Cys Arg Phe Gly Tyr Ile Leu His Thr Asp Asn Arg
145                 150                 155                 160

Thr Cys Arg Val Glu Cys Ser Asp Asn Leu Phe Thr Gln Arg Thr Gly
                165                 170                 175

Val Ile Thr Ser Pro Asp Phe Pro Asn Pro Tyr Pro Lys Ser Ser Glu
            180                 185                 190

Cys Leu Tyr Thr Ile Glu Leu Glu Glu Gly Phe Met Val Asn Leu Gln
        195                 200                 205

Phe Glu Asp Ile Phe Asp Ile Glu Asp His Pro Glu Val Pro Cys Pro
    210                 215                 220

Tyr Asp Tyr Ile Lys Ile Lys Val Gly Pro Lys Val Leu Gly Pro Phe
225                 230                 235                 240

Cys Gly Glu Lys Ala Pro Glu Pro Ile Ser Thr Gln Ser His Ser Val
                245                 250                 255

Leu Ile Leu Phe His Ser Asp Asn Ser Gly Glu Asn Arg Gly Trp Arg
            260                 265                 270

Leu Ser Tyr Arg Ala Ala Gly Asn Glu Cys Pro Glu Leu Gln Pro Pro
        275                 280                 285

Val His Gly Lys Ile Glu Pro Ser Gln Ala Lys Tyr Phe Phe Lys Asp
    290                 295                 300

Gln Val Leu Val Ser Cys Asp Thr Gly Tyr Lys Val Leu Lys Asp Asn
305                 310                 315                 320

Val Glu Met Asp Thr Phe Gln Ile Glu Cys Leu Lys Asp Gly Thr Trp
                325                 330                 335

Ser Asn Lys Ile Pro Thr Cys Lys Lys Asn Glu Ile Asp Leu Glu Ser
            340                 345                 350

Glu Leu Lys Ser Glu Gln Val Thr Glu Gly Gly Gly Gly Ser Gly Gly
        355                 360                 365

Gly Gly Ser Cys Val Ala Glu Asp Cys Asn Glu Leu Pro Pro Arg Arg
    370                 375                 380

Asn Thr Glu Ile Leu Thr Gly Ser Trp Ser Asp Gln Thr Tyr Pro Glu
385                 390                 395                 400

Gly Thr Gln Ala Ile Tyr Lys Cys Arg Pro Gly Tyr Arg Ser Leu Gly
                405                 410                 415

Asn Val Ile Met Val Cys Arg Lys Gly Glu Trp Val Ala Leu Asn Pro
            420                 425                 430

Leu Arg Lys Cys Gln Lys Arg Pro Cys Gly His Pro Gly Asp Thr Pro
        435                 440                 445

Phe Gly Thr Phe Thr Leu Thr Gly Gly Asn Val Phe Glu Tyr Gly Val
    450                 455                 460

Lys Ala Val Tyr Thr Cys Asn Glu Gly Tyr Gln Leu Leu Gly Glu Ile
465                 470                 475                 480

Asn Tyr Arg Glu Cys Asp Thr Asp Gly Trp Thr Asn Asp Ile Pro Ile
                485                 490                 495

Cys Glu Val Val Lys Cys Leu Pro Val Thr Ala Pro Glu Asn Gly Lys
            500                 505                 510

Ile Val Ser Ser Ala Met Glu Pro Asp Arg Glu Tyr His Phe Gly Gln
        515                 520                 525

Ala Val Arg Phe Val Cys Asn Ser Gly Tyr Lys Ile Glu Gly Asp Glu
    530                 535                 540
```

-continued

```
Glu Met His Cys Ser Asp Asp Gly Phe Trp Ser Lys Glu Lys Pro Lys
545                 550                 555                 560

Cys Val Glu Ile Ser Cys Lys Ser Pro Asp Val Ile Asn Gly Ser Pro
                565                 570                 575

Ile Ser Gln Lys Ile Ile Tyr Lys Glu Asn Glu Arg Phe Gln Tyr Lys
            580                 585                 590

Cys Asn Met Gly Tyr Glu Tyr Ser Glu Arg Gly Asp Ala Val Cys Thr
        595                 600                 605

Glu Ser Gly Trp Arg Pro Leu Pro Ser Cys Glu Glu Lys Ser Cys Asp
    610                 615                 620

Asn Pro Tyr Ile Pro Asn Gly Asp Tyr Ser Pro Leu Arg Ile Lys His
625                 630                 635                 640

Arg Thr Gly Asp Glu Ile Thr Tyr Gln Cys Arg Asn Gly Phe Tyr Pro
                645                 650                 655

Ala Thr Arg Gly Asn Thr Ala Lys Cys Thr Ser Thr Gly Trp Ile Pro
            660                 665                 670

Ala Pro Arg Cys Thr Leu Lys Pro
        675                 680
```

<210> SEQ ID NO 26
<211> LENGTH: 2032
<212> TYPE: DNA
<213> ORGANISM: homo sapiens

<400> SEQUENCE: 26

```
cacaccgtgg agctaaacaa tatgtttggc cagatccagt cgcctggtta tccagactcc     60

tatcccagtg attcagaggt gacttggaat atcactgtcc cagatgggtt tcggatcaag    120

ctttacttca tgcacttcaa cttggaatcc tcctaccttt gtgaatatga ctatgtgaag    180

gtagaaactg aggaccaggt gctggcaacc ttctgtggca gggagaccac agacacagag    240

cagactcccg gccaggaggt ggtcctctcc cctggctcct tcatgtccat cactttccgg    300

tcagatttct ccaatgagga gcgtttcaca ggctttgatg cccactacat ggctgtggat    360

gtggacgagt gcaaggagag ggaggacgag gagctgtcct gtgaccacta ctgccacaac    420

tacattggcg gctactactg ctcctgccgc ttcggctaca tcctccacac agacaacagg    480

acctgccgag tggagtgcag tgacaacctc ttcactcaaa ggactggggt gatcaccagc    540

cctgacttcc caaaccctta ccccaagagc tctgaatgcc tgtataccat cgagctggag    600

gagggtttca tggtcaacct gcagtttgag gacatatttg acattgagga ccatcctgag    660

gtgccctgcc cctatgacta catcaagatc aaagttggtc caaaagtttt ggggcctttc    720

tgtggagaga aagccccaga acccatcagc acccagagcc acagtgtcct gatcctgttc    780

catagtgaca actcgggaga gaaccggggc tggaggctct catacagggc tgcaggaaat    840

gagtgcccag agctacagcc tcctgtccat gggaaaatcg agccctccca agccaagtat    900

ttcttcaaag accaagtgct cgtcagctgt gacacaggct acaaagtgct gaaggataat    960

gtggagatgg acacattcca gattgagtgt ctgaaggatg ggacgtggag taacaagatt   1020

cccacctgta aaaaaaatga aatcgatctg gagagcgaac tcaagtcaga gcaagtgaca   1080

gagggcggag gtgggtcggg tggcggcgga tcttgtgtag cagaagattg caatgaactt   1140

cctccaagaa gaaatacaga aattctgaca ggttcctggt ctgaccaaac atatccagaa   1200

ggcacccagg ctatctataa atgccgccct ggatatagat ctcttggaaa tgtaataatg   1260

gtatgcagga agggagaatg ggttgctctt aatccattaa ggaaatgtca gaaaaggccc   1320
```

```
tgtggacatc ctggagatac tccttttggt acttttaccc ttacaggagg aaatgtgttt   1380

gaatatggtg taaaagctgt gtatacatgt aatgaggggt atcaattgct aggtgagatt   1440

aattaccgtg aatgtgacac agatggatgg accaatgata ttcctatatg tgaagttgtg   1500

aagtgtttac cagtgacagc accagagaat ggaaaaattg tcagtagtgc aatggaacca   1560

gatcgggaat accattttgg acaagcagta cggtttgtat gtaactcagg ctacaagatt   1620

gaaggagatg aagaaatgca ttgttcagac gatggttttt ggagtaaaga gaaaccaaag   1680

tgtgtggaaa tttcatgcaa atccccagat gttataaatg gatctcctat atctcagaag   1740

attatttata aggagaatga acgatttcaa tataaatgta acatgggtta tgaatacagt   1800

gaaagaggag atgctgtatg cactgaatct ggatggcgtc cgttgccttc atgtgaagaa   1860

aaatcatgtg ataatcctta tattccaaat ggtgactact cacctttaag gattaaacac   1920

agaactggag atgaaatcac gtaccagtgt agaaatggtt tttatcctgc aacccgggga   1980

aatacagcaa aatgcacaag tactggctgg atacctgctc cgagatgtac ct           2032
```

<210> SEQ ID NO 27
<211> LENGTH: 680
<212> TYPE: PRT
<213> ORGANISM: homo sapiens

<400> SEQUENCE: 27

```
Cys Val Ala Glu Asp Cys Asn Glu Leu Pro Pro Arg Arg Asn Thr Glu
1               5                   10                  15

Ile Leu Thr Gly Ser Trp Ser Asp Gln Thr Tyr Pro Glu Gly Thr Gln
            20                  25                  30

Ala Ile Tyr Lys Cys Arg Pro Gly Tyr Arg Ser Leu Gly Asn Val Ile
        35                  40                  45

Met Val Cys Arg Lys Gly Glu Trp Val Ala Leu Asn Pro Leu Arg Lys
    50                  55                  60

Cys Gln Lys Arg Pro Cys Gly His Pro Gly Asp Thr Pro Phe Gly Thr
65                  70                  75                  80

Phe Thr Leu Thr Gly Gly Asn Val Phe Glu Tyr Gly Val Lys Ala Val
                85                  90                  95

Tyr Thr Cys Asn Glu Gly Tyr Gln Leu Leu Gly Glu Ile Asn Tyr Arg
            100                 105                 110

Glu Cys Asp Thr Asp Gly Trp Thr Asn Asp Ile Pro Ile Cys Glu Val
        115                 120                 125

Val Lys Cys Leu Pro Val Thr Ala Pro Glu Asn Gly Lys Ile Val Ser
    130                 135                 140

Ser Ala Met Glu Pro Asp Arg Glu Tyr His Phe Gly Gln Ala Val Arg
145                 150                 155                 160

Phe Val Cys Asn Ser Gly Tyr Lys Ile Glu Gly Asp Glu Glu Met His
                165                 170                 175

Cys Ser Asp Asp Gly Phe Trp Ser Lys Glu Lys Pro Lys Cys Val Glu
            180                 185                 190

Ile Ser Cys Lys Ser Pro Asp Val Ile Asn Gly Ser Pro Ile Ser Gln
        195                 200                 205

Lys Ile Ile Tyr Lys Glu Asn Glu Arg Phe Gln Tyr Lys Cys Asn Met
    210                 215                 220

Gly Tyr Glu Tyr Ser Glu Arg Gly Asp Ala Val Cys Thr Glu Ser Gly
225                 230                 235                 240

Trp Arg Pro Leu Pro Ser Cys Glu Glu Lys Ser Cys Asp Asn Pro Tyr
                245                 250                 255
```

```
Ile Pro Asn Gly Asp Tyr Ser Pro Leu Arg Ile Lys His Arg Thr Gly
            260                 265                 270

Asp Glu Ile Thr Tyr Gln Cys Arg Asn Gly Phe Tyr Pro Ala Thr Arg
        275                 280                 285

Gly Asn Thr Ala Lys Cys Thr Ser Thr Gly Trp Ile Pro Ala Pro Arg
    290                 295                 300

Cys Thr Leu Lys Pro Gly Gly Gly Gly Ser Gly Gly Gly Gly Ser His
305                 310                 315                 320

Thr Val Glu Leu Asn Asn Met Phe Gly Gln Ile Gln Ser Pro Gly Tyr
                325                 330                 335

Pro Asp Ser Tyr Pro Ser Asp Ser Glu Val Thr Trp Asn Ile Thr Val
            340                 345                 350

Pro Asp Gly Phe Arg Ile Lys Leu Tyr Phe Met His Phe Asn Leu Glu
        355                 360                 365

Ser Ser Tyr Leu Cys Glu Tyr Asp Tyr Val Lys Val Glu Thr Glu Asp
    370                 375                 380

Gln Val Leu Ala Thr Phe Cys Gly Arg Glu Thr Thr Asp Thr Glu Gln
385                 390                 395                 400

Thr Pro Gly Gln Glu Val Val Leu Ser Pro Gly Ser Phe Met Ser Ile
                405                 410                 415

Thr Phe Arg Ser Asp Phe Ser Asn Glu Glu Arg Phe Thr Gly Phe Asp
            420                 425                 430

Ala His Tyr Met Ala Val Asp Val Asp Glu Cys Lys Glu Arg Glu Asp
        435                 440                 445

Glu Glu Leu Ser Cys Asp His Tyr Cys His Asn Tyr Ile Gly Gly Tyr
    450                 455                 460

Tyr Cys Ser Cys Arg Phe Gly Tyr Ile Leu His Thr Asp Asn Arg Thr
465                 470                 475                 480

Cys Arg Val Glu Cys Ser Asp Asn Leu Phe Thr Gln Arg Thr Gly Val
                485                 490                 495

Ile Thr Ser Pro Asp Phe Pro Asn Pro Tyr Pro Lys Ser Ser Glu Cys
            500                 505                 510

Leu Tyr Thr Ile Glu Leu Glu Glu Gly Phe Met Val Asn Leu Gln Phe
        515                 520                 525

Glu Asp Ile Phe Asp Ile Glu Asp His Pro Glu Val Pro Cys Pro Tyr
    530                 535                 540

Asp Tyr Ile Lys Ile Lys Val Gly Pro Lys Val Leu Gly Pro Phe Cys
545                 550                 555                 560

Gly Glu Lys Ala Pro Glu Pro Ile Ser Thr Gln Ser His Ser Val Leu
                565                 570                 575

Ile Leu Phe His Ser Asp Asn Ser Gly Glu Asn Arg Gly Trp Arg Leu
            580                 585                 590

Ser Tyr Arg Ala Ala Gly Asn Glu Cys Pro Glu Leu Gln Pro Pro Val
        595                 600                 605

His Gly Lys Ile Glu Pro Ser Gln Ala Lys Tyr Phe Phe Lys Asp Gln
    610                 615                 620

Val Leu Val Ser Cys Asp Thr Gly Tyr Lys Val Leu Lys Asp Asn Val
625                 630                 635                 640

Glu Met Asp Thr Phe Gln Ile Glu Cys Leu Lys Asp Gly Thr Trp Ser
                645                 650                 655

Asn Lys Ile Pro Thr Cys Lys Lys Asn Glu Ile Asp Leu Glu Ser Glu
            660                 665                 670
```

```
Leu Lys Ser Glu Gln Val Thr Glu
        675                 680


<210> SEQ ID NO 28
<211> LENGTH: 2032
<212> TYPE: DNA
<213> ORGANISM: homo sapiens

<400> SEQUENCE: 28

tgtgtagcag aagattgcaa tgaacttcct ccaagaagaa atacagaaat tctgacaggt     60

tcctggtctg accaaacata tccagaaggc acccaggcta tctataaatg ccgccctgga    120

tatagatctc ttggaaatgt aataatggta tgcaggaagg gagaatgggt tgctcttaat    180

ccattaagga aatgtcagaa aaggccctgt ggacatcctg gagatactcc ttttggtact    240

tttaccctta caggaggaaa tgtgtttgaa tatggtgtaa aagctgtgta tacatgtaat    300

gaggggtatc aattgctagg tgagattaat taccgtgaat gtgacacaga tggatggacc    360

aatgatattc ctatatgtga agttgtgaag tgtttaccag tgacagcacc agagaatgga    420

aaaattgtca gtagtgcaat ggaaccagat cgggaatacc attttggaca agcagtacgg    480

tttgtatgta actcaggcta caagattgaa ggagatgaag aaatgcattg ttcagacgat    540

ggtttttgga gtaaagagaa accaaagtgt gtggaaattt catgcaaatc cccagatgtt    600

ataaatggat ctcctatatc tcagaagatt atttataagg agaatgaacg atttcaatat    660

aaatgtaaca tgggttatga atacagtgaa agaggagatg ctgtatgcac tgaatctgga    720

tggcgtccgt tgccttcatg tgaagaaaaa tcatgtgata atccttatat tccaaatggt    780

gactactcac ctttaaggat taaacacaga actggagatg aaatcacgta ccagtgtaga    840

aatggttttt atcctgcaac ccggggaaat acagcaaaat gcacaagtac tggctggata    900

cctgctccga gatgtacctg gcggaggtgg gtcgggtggc ggcggatctc acaccgtgga    960

gctaaacaat atgtttggcc agatccagtc gcctggttat ccagactcct atcccagtga   1020

ttcagaggtg acttggaata tcactgtccc agatgggttt cggatcaagc tttacttcat   1080

gcacttcaac ttggaatcct cctacctttg tgaatatgac tatgtgaagg tagaaactga   1140

ggaccaggtg ctggcaacct tctgtggcag ggagaccaca gacacagagc agactcccgg   1200

ccaggaggtg gtcctctccc ctggctcctt catgtccatc actttccggt cagatttctc   1260

caatgaggag cgtttcacag gctttgatgc ccactacatg gctgtggatg tggacgagtg   1320

caaggagagg gaggacgagg agctgtcctg tgaccactac tgccacaact acattggcgg   1380

ctactactgc tcctgccgct tcggctacat cctccacaca gacaacagga cctgccgagt   1440

ggagtgcagt gacaacctct tcactcaaag gactggggtg atcaccagcc ctgacttccc   1500

aaacccttac cccaagagct ctgaatgcct gtataccatc gagctggagg agggtttcat   1560

ggtcaacctg cagtttgagg acatatttga cattgaggac catcctgagg tgccctgccc   1620

ctatgactac atcaagatca aagttggtcc aaaagttttg ggcctttctt gtggagagaa   1680

agccccagaa cccatcagca cccagagcca cagtgtcctg atcctgttcc atagtgacaa   1740

ctcgggagag aaccggggct ggaggctctc atacagggct gcaggaaatg agtgcccaga   1800

gctacagcct cctgtccatg ggaaaatcga gccctcccaa gccaagtatt tcttcaaaga   1860

ccaagtgctc gtcagctgtg acacaggcta caaagtgctg aaggataatg tggagatgga   1920

cacattccag attgagtgtc tgaaggatgg gacgtggagt aacaagattc ccacctgtaa   1980

aaaaaatgaa atcgatctgg agagcgaact caagtcagag caagtgacag ag           2032
```

<210> SEQ ID NO 29
<211> LENGTH: 363
<212> TYPE: PRT
<213> ORGANISM: homo sapiens

<400> SEQUENCE: 29

```
Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys
        355                 360
```

<210> SEQ ID NO 30

<211> LENGTH: 295
<212> TYPE: PRT
<213> ORGANISM: homo sapiens

<400> SEQUENCE: 30

```
Trp Leu Leu Leu Tyr Tyr Ala Leu Cys Phe Ser Leu Ser Lys Ala Ser
1               5                   10                  15

Ala His Thr Val Glu Leu Asn Asn Met Phe Gly Gln Ile Gln Ser Pro
            20                  25                  30

Gly Tyr Pro Asp Ser Tyr Pro Ser Asp Ser Glu Val Thr Trp Asn Ile
        35                  40                  45

Thr Val Pro Asp Gly Phe Arg Ile Lys Leu Tyr Phe Met His Phe Asn
    50                  55                  60

Leu Glu Ser Ser Tyr Leu Cys Glu Tyr Asp Tyr Val Lys Val Glu Thr
65                  70                  75                  80

Glu Asp Gln Val Leu Ala Thr Phe Cys Gly Arg Glu Thr Thr Asp Thr
                85                  90                  95

Glu Gln Thr Pro Gly Gln Glu Val Val Leu Ser Pro Gly Ser Phe Met
            100                 105                 110

Ser Ile Thr Phe Arg Ser Asp Phe Ser Asn Glu Glu Arg Phe Thr Gly
        115                 120                 125

Phe Asp Ala His Tyr Met Ala Val Asp Val Asp Glu Cys Lys Glu Arg
    130                 135                 140

Glu Asp Glu Glu Leu Ser Cys Asp His Tyr Cys His Asn Tyr Ile Gly
145                 150                 155                 160

Gly Tyr Tyr Cys Ser Cys Arg Phe Gly Tyr Ile Leu His Thr Asp Asn
                165                 170                 175

Arg Thr Cys Arg Val Glu Cys Ser Asp Asn Leu Phe Thr Gln Arg Thr
            180                 185                 190

Gly Val Ile Thr Ser Pro Asp Phe Pro Asn Pro Tyr Pro Lys Ser Ser
        195                 200                 205

Glu Cys Leu Tyr Thr Ile Glu Leu Glu Glu Gly Phe Met Val Asn Leu
    210                 215                 220

Gln Phe Glu Asp Ile Phe Asp Ile Glu Asp His Pro Glu Val Pro Cys
225                 230                 235                 240

Pro Tyr Asp Tyr Ile Lys Ile Lys Val Gly Pro Lys Val Leu Gly Pro
                245                 250                 255

Phe Cys Gly Glu Lys Ala Pro Glu Pro Ile Ser Thr Gln Ser His Ser
            260                 265                 270

Val Leu Ile Leu Phe His Ser Asp Asn Ser Gly Glu Asn Arg Gly Trp
        275                 280                 285

Arg Leu Ser Tyr Arg Ala Ala
    290                 295
```

<210> SEQ ID NO 31
<211> LENGTH: 198
<212> TYPE: PRT
<213> ORGANISM: homo sapiens

<400> SEQUENCE: 31

```
Val Glu Cys Ser Asp Asn Leu Phe Thr Gln Arg Thr Gly Val Ile Thr
1               5                   10                  15

Ser Pro Asp Phe Pro Asn Pro Tyr Pro Lys Ser Ser Glu Cys Leu Tyr
            20                  25                  30

Thr Ile Glu Leu Glu Glu Gly Phe Met Val Asn Leu Gln Phe Glu Asp
        35                  40                  45
```

```
Ile Phe Asp Ile Glu Asp His Pro Glu Val Pro Cys Pro Tyr Asp Tyr
    50                  55                  60

Ile Lys Ile Lys Val Gly Pro Lys Val Leu Gly Pro Phe Cys Gly Glu
65                  70                  75                  80

Lys Ala Pro Glu Pro Ile Ser Thr Gln Ser His Ser Val Leu Ile Leu
                85                  90                  95

Phe His Ser Asp Asn Ser Gly Glu Asn Arg Gly Trp Arg Leu Ser Tyr
            100                 105                 110

Arg Ala Ala Gly Asn Glu Cys Pro Glu Leu Gln Pro Pro Val His Gly
        115                 120                 125

Lys Ile Glu Pro Ser Gln Ala Lys Tyr Phe Phe Lys Asp Gln Val Leu
    130                 135                 140

Val Ser Cys Asp Thr Gly Tyr Lys Val Leu Lys Asp Asn Val Glu Met
145                 150                 155                 160

Asp Thr Phe Gln Ile Glu Cys Leu Lys Asp Gly Thr Trp Ser Asn Lys
                165                 170                 175

Ile Pro Thr Cys Lys Lys Asn Glu Ile Asp Leu Glu Ser Glu Leu Lys
            180                 185                 190

Ser Glu Gln Val Thr Glu
        195


<210> SEQ ID NO 32
<211> LENGTH: 264
<212> TYPE: PRT
<213> ORGANISM: homo sapiens

<400> SEQUENCE: 32

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
```

```
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu
            260


<210> SEQ ID NO 33
<211> LENGTH: 845
<212> TYPE: PRT
<213> ORGANISM: homo sapiens

<400> SEQUENCE: 33

Arg Lys Cys Tyr Phe Pro Tyr Leu Glu Asn Gly Tyr Asn Gln Asn His
1               5                   10                  15

Gly Arg Lys Phe Val Gln Gly Lys Ser Ile Asp Val Ala Cys His Pro
            20                  25                  30

Gly Tyr Ala Leu Pro Lys Ala Gln Thr Thr Val Thr Cys Met Glu Asn
        35                  40                  45

Gly Trp Ser Pro Thr Pro Arg Cys Ile Arg Val Lys Thr Cys Ser Lys
    50                  55                  60

Ser Ser Ile Asp Ile Glu Asn Gly Phe Ile Ser Glu Ser Gln Tyr Thr
65                  70                  75                  80

Tyr Ala Leu Lys Glu Lys Ala Lys Tyr Gln Cys Lys Leu Gly Tyr Val
                85                  90                  95

Thr Ala Asp Gly Glu Thr Ser Gly Ser Ile Arg Cys Gly Lys Asp Gly
            100                 105                 110

Trp Ser Ala Gln Pro Thr Cys Ile Lys Ser Cys Asp Ile Pro Val Phe
        115                 120                 125

Met Asn Ala Arg Thr Lys Asn Asp Phe Thr Trp Phe Lys Leu Asn Asp
    130                 135                 140

Thr Leu Asp Tyr Glu Cys His Asp Gly Tyr Glu Ser Asn Thr Gly Ser
145                 150                 155                 160

Thr Thr Gly Ser Ile Val Cys Gly Tyr Asn Gly Trp Ser Asp Leu Pro
                165                 170                 175

Ile Cys Tyr Glu Arg Glu Cys Glu Leu Pro Lys Ile Asp Val His Leu
            180                 185                 190

Val Pro Asp Arg Lys Lys Asp Gln Tyr Lys Val Gly Glu Val Leu Lys
        195                 200                 205

Phe Ser Cys Lys Pro Gly Phe Thr Ile Val Gly Pro Asn Ser Val Gln
    210                 215                 220

Cys Tyr His Phe Gly Leu Ser Pro Asp Leu Pro Ile Cys Lys Glu Gln
225                 230                 235                 240

Val Gln Ser Cys Gly Pro Pro Pro Glu Leu Leu Asn Gly Asn Val Lys
                245                 250                 255

Glu Lys Thr Lys Glu Glu Tyr Gly His Ser Glu Val Val Glu Tyr Tyr
            260                 265                 270

Cys Asn Pro Arg Phe Leu Met Lys Gly Pro Asn Lys Ile Gln Cys Val
        275                 280                 285

Asp Gly Glu Trp Thr Thr Leu Pro Val Cys Ile Val Glu Glu Ser Thr
    290                 295                 300

Cys Gly Asp Ile Pro Glu Leu Glu His Gly Trp Ala Gln Leu Ser Ser
305                 310                 315                 320
```

-continued

```
Pro Pro Tyr Tyr Tyr Gly Asp Ser Val Glu Phe Asn Cys Ser Glu Ser
                325                 330                 335

Phe Thr Met Ile Gly His Arg Ser Ile Thr Cys Ile His Gly Val Trp
            340                 345                 350

Thr Gln Leu Pro Gln Cys Val Ala Ile Asp Lys Leu Lys Lys Cys Lys
        355                 360                 365

Ser Ser Asn Leu Ile Ile Leu Glu Glu His Leu Lys Asn Lys Lys Glu
    370                 375                 380

Phe Asp His Asn Ser Asn Ile Arg Tyr Arg Cys Arg Gly Lys Glu Gly
385                 390                 395                 400

Trp Ile His Thr Val Cys Ile Asn Gly Arg Trp Asp Pro Glu Val Asn
                405                 410                 415

Cys Ser Met Ala Gln Ile Gln Leu Cys Pro Pro Pro Pro Gln Ile Pro
            420                 425                 430

Asn Ser His Asn Met Thr Thr Thr Leu Asn Tyr Arg Asp Gly Glu Lys
        435                 440                 445

Val Ser Val Leu Cys Gln Glu Asn Tyr Leu Ile Gln Glu Gly Glu Glu
    450                 455                 460

Ile Thr Cys Lys Asp Gly Arg Trp Gln Ser Ile Pro Leu Cys Val Glu
465                 470                 475                 480

Lys Ile Pro Cys Ser Gln Pro Pro Gln Ile Glu His Gly Thr Ile Asn
                485                 490                 495

Ser Ser Arg Ser Ser Gln Glu Ser Tyr Ala His Gly Thr Lys Leu Ser
            500                 505                 510

Tyr Thr Cys Glu Gly Gly Phe Arg Ile Ser Glu Glu Asn Glu Thr Thr
        515                 520                 525

Cys Tyr Met Gly Lys Trp Ser Ser Pro Pro Gln Cys Glu Gly Leu Pro
    530                 535                 540

Cys Lys Ser Pro Pro Glu Ile Ser His Gly Val Val Ala His Met Ser
545                 550                 555                 560

Asp Ser Tyr Gln Tyr Gly Glu Glu Val Thr Tyr Lys Cys Phe Glu Gly
                565                 570                 575

Phe Gly Ile Asp Gly Pro Ala Ile Ala Lys Cys Leu Gly Glu Lys Trp
            580                 585                 590

Ser His Pro Pro Ser Cys Ile Lys Thr Asp Cys Leu Ser Leu Pro Ser
        595                 600                 605

Phe Glu Asn Ala Ile Pro Met Gly Glu Lys Lys Asp Val Tyr Lys Ala
    610                 615                 620

Gly Glu Gln Val Thr Tyr Thr Cys Ala Thr Tyr Tyr Lys Met Asp Gly
625                 630                 635                 640

Ala Ser Asn Val Thr Cys Ile Asn Ser Arg Trp Thr Gly Arg Pro Thr
                645                 650                 655

Cys Arg Asp Thr Ser Cys Val Asn Pro Pro Thr Val Gln Asn Ala Tyr
            660                 665                 670

Ile Val Ser Arg Gln Met Ser Lys Tyr Pro Ser Gly Glu Arg Val Arg
        675                 680                 685

Tyr Gln Cys Arg Ser Pro Tyr Glu Met Phe Gly Asp Glu Glu Val Met
    690                 695                 700

Cys Leu Asn Gly Asn Trp Thr Glu Pro Pro Gln Cys Lys Asp Ser Thr
705                 710                 715                 720

Gly Lys Cys Gly Pro Pro Pro Pro Ile Asp Asn Gly Asp Ile Thr Ser
                725                 730                 735

Phe Pro Leu Ser Val Tyr Ala Pro Ala Ser Ser Val Glu Tyr Gln Cys
```

```
            740                 745                 750

Gln Asn Leu Tyr Gln Leu Glu Gly Asn Lys Arg Ile Thr Cys Arg Asn
        755                 760                 765

Gly Gln Trp Ser Glu Pro Pro Lys Cys Leu His Pro Cys Val Ile Ser
    770                 775                 780

Arg Glu Ile Met Glu Asn Tyr Asn Ile Ala Leu Arg Trp Thr Ala Lys
785                 790                 795                 800

Gln Lys Leu Tyr Ser Arg Thr Gly Glu Ser Val Glu Phe Val Cys Lys
                805                 810                 815

Arg Gly Tyr Arg Leu Ser Ser Arg Ser His Thr Leu Arg Thr Thr Cys
            820                 825                 830

Trp Asp Gly Lys Leu Glu Tyr Pro Thr Cys Ala Lys Arg
        835                 840                 845


<210> SEQ ID NO 34
<211> LENGTH: 483
<212> TYPE: PRT
<213> ORGANISM: homo sapiens

<400> SEQUENCE: 34

Lys Thr Cys Ser Lys Ser Ser Ile Asp Ile Glu Asn Gly Phe Ile Ser
1               5                   10                  15

Glu Ser Gln Tyr Thr Tyr Ala Leu Lys Glu Lys Ala Lys Tyr Gln Cys
            20                  25                  30

Lys Leu Gly Tyr Val Thr Ala Asp Gly Glu Thr Ser Gly Ser Ile Arg
        35                  40                  45

Cys Gly Lys Asp Gly Trp Ser Ala Gln Pro Thr Cys Ile Lys Ser Cys
    50                  55                  60

Asp Ile Pro Val Phe Met Asn Ala Arg Thr Lys Asn Asp Phe Thr Trp
65                  70                  75                  80

Phe Lys Leu Asn Asp Thr Leu Asp Tyr Glu Cys His Asp Gly Tyr Glu
                85                  90                  95

Ser Asn Thr Gly Ser Thr Thr Gly Ser Ile Val Cys Gly Tyr Asn Gly
            100                 105                 110

Trp Ser Asp Leu Pro Ile Cys Tyr Glu Arg Glu Cys Glu Leu Pro Lys
        115                 120                 125

Ile Asp Val His Leu Val Pro Asp Arg Lys Lys Asp Gln Tyr Lys Val
    130                 135                 140

Gly Glu Val Leu Lys Phe Ser Cys Lys Pro Gly Phe Thr Ile Val Gly
145                 150                 155                 160

Pro Asn Ser Val Gln Cys Tyr His Phe Gly Leu Ser Pro Asp Leu Pro
                165                 170                 175

Ile Cys Lys Glu Gln Val Gln Ser Cys Gly Pro Pro Pro Glu Leu Leu
            180                 185                 190

Asn Gly Asn Val Lys Glu Lys Thr Lys Glu Glu Tyr Gly His Ser Glu
        195                 200                 205

Val Val Glu Tyr Tyr Cys Asn Pro Arg Phe Leu Met Lys Gly Pro Asn
    210                 215                 220

Lys Ile Gln Cys Val Asp Gly Glu Trp Thr Thr Leu Pro Val Cys Ile
225                 230                 235                 240

Val Glu Glu Ser Thr Cys Gly Asp Ile Pro Glu Leu Glu His Gly Trp
                245                 250                 255

Ala Gln Leu Ser Ser Pro Pro Tyr Tyr Tyr Gly Asp Ser Val Glu Phe
            260                 265                 270
```

```
Asn Cys Ser Glu Ser Phe Thr Met Ile Gly His Arg Ser Ile Thr Cys
        275                 280                 285

Ile His Gly Val Trp Thr Gln Leu Pro Gln Cys Val Ala Ile Asp Lys
    290                 295                 300

Leu Lys Lys Cys Lys Ser Ser Asn Leu Ile Ile Leu Glu Glu His Leu
305                 310                 315                 320

Lys Asn Lys Lys Glu Phe Asp His Asn Ser Asn Ile Arg Tyr Arg Cys
                325                 330                 335

Arg Gly Lys Glu Gly Trp Ile His Thr Val Cys Ile Asn Gly Arg Trp
            340                 345                 350

Asp Pro Glu Val Asn Cys Ser Met Ala Gln Ile Gln Leu Cys Pro Pro
        355                 360                 365

Pro Pro Gln Ile Pro Asn Ser His Asn Met Thr Thr Thr Leu Asn Tyr
    370                 375                 380

Arg Asp Gly Glu Lys Val Ser Val Leu Cys Gln Glu Asn Tyr Leu Ile
385                 390                 395                 400

Gln Glu Gly Glu Glu Ile Thr Cys Lys Asp Gly Arg Trp Gln Ser Ile
                405                 410                 415

Pro Leu Cys Val Glu Lys Ile Pro Cys Ser Gln Pro Pro Gln Ile Glu
            420                 425                 430

His Gly Thr Ile Asn Ser Ser Arg Ser Ser Gln Glu Ser Tyr Ala His
        435                 440                 445

Gly Thr Lys Leu Ser Tyr Thr Cys Glu Gly Gly Phe Arg Ile Ser Glu
    450                 455                 460

Glu Asn Glu Thr Thr Cys Tyr Met Gly Lys Trp Ser Ser Pro Pro Gln
465                 470                 475                 480

Cys Glu Gly


<210> SEQ ID NO 35
<211> LENGTH: 180
<212> TYPE: PRT
<213> ORGANISM: homo sapiens

<400> SEQUENCE: 35

Glu Ser Thr Cys Gly Asp Ile Pro Glu Leu Glu His Gly Trp Ala Gln
1               5                   10                  15

Leu Ser Ser Pro Pro Tyr Tyr Tyr Gly Asp Ser Val Glu Phe Asn Cys
            20                  25                  30

Ser Glu Ser Phe Thr Met Ile Gly His Arg Ser Ile Thr Cys Ile His
        35                  40                  45

Gly Val Trp Thr Gln Leu Pro Gln Cys Val Ala Ile Asp Lys Leu Lys
    50                  55                  60

Lys Cys Lys Ser Ser Asn Leu Ile Ile Leu Glu Glu His Leu Lys Asn
65                  70                  75                  80

Lys Lys Glu Phe Asp His Asn Ser Asn Ile Arg Tyr Arg Cys Arg Gly
                85                  90                  95

Lys Glu Gly Trp Ile His Thr Val Cys Ile Asn Gly Arg Trp Asp Pro
            100                 105                 110

Glu Val Asn Cys Ser Met Ala Gln Ile Gln Leu Cys Pro Pro Pro Pro
        115                 120                 125

Gln Ile Pro Asn Ser His Asn Met Thr Thr Thr Leu Asn Tyr Arg Asp
    130                 135                 140

Gly Glu Lys Val Ser Val Leu Cys Gln Glu Asn Tyr Leu Ile Gln Glu
145                 150                 155                 160
```

```
Gly Glu Glu Ile Thr Cys Lys Asp Gly Arg Trp Gln Ser Ile Pro Leu
                165                 170                 175

Cys Val Glu Lys
            180


<210> SEQ ID NO 36
<211> LENGTH: 126
<212> TYPE: PRT
<213> ORGANISM: homo sapiens

<400> SEQUENCE: 36

Thr Gly Lys Cys Gly Pro Pro Pro Pro Ile Asp Asn Gly Asp Ile Thr
1               5                   10                  15

Ser Phe Pro Leu Ser Val Tyr Ala Pro Ala Ser Ser Val Glu Tyr Gln
            20                  25                  30

Cys Gln Asn Leu Tyr Gln Leu Glu Gly Asn Lys Arg Ile Thr Cys Arg
        35                  40                  45

Asn Gly Gln Trp Ser Glu Pro Pro Lys Cys Leu His Pro Cys Val Ile
    50                  55                  60

Ser Arg Glu Ile Met Glu Asn Tyr Asn Ile Ala Leu Arg Trp Thr Ala
65                  70                  75                  80

Lys Gln Lys Leu Tyr Ser Arg Thr Gly Glu Ser Val Glu Phe Val Cys
                85                  90                  95

Lys Arg Gly Tyr Arg Leu Ser Ser Arg Ser His Thr Leu Arg Thr Thr
            100                 105                 110

Cys Trp Asp Gly Lys Leu Glu Tyr Pro Thr Cys Ala Lys Arg
        115                 120                 125


<210> SEQ ID NO 37
<211> LENGTH: 188
<212> TYPE: PRT
<213> ORGANISM: homo sapiens

<400> SEQUENCE: 37

Asn Cys Gly Pro Pro Pro Thr Leu Ser Phe Ala Ala Pro Met Asp Ile
1               5                   10                  15

Thr Leu Thr Glu Thr Arg Phe Lys Thr Gly Thr Thr Leu Lys Tyr Thr
            20                  25                  30

Cys Leu Pro Gly Tyr Val Arg Ser His Ser Thr Gln Thr Leu Thr Cys
        35                  40                  45

Asn Ser Asp Gly Glu Trp Val Tyr Asn Thr Phe Cys Ile Tyr Lys Arg
    50                  55                  60

Cys Arg His Pro Gly Glu Leu Arg Asn Gly Gln Val Glu Ile Lys Thr
65                  70                  75                  80

Asp Leu Ser Phe Gly Ser Gln Ile Glu Phe Ser Cys Ser Glu Gly Phe
                85                  90                  95

Phe Leu Ile Gly Ser Thr Thr Ser Arg Cys Glu Val Gln Asp Arg Gly
            100                 105                 110

Val Gly Trp Ser His Pro Leu Pro Gln Cys Glu Ile Val Lys Cys Lys
        115                 120                 125

Pro Pro Pro Asp Ile Arg Asn Gly Arg His Ser Gly Glu Glu Asn Phe
    130                 135                 140

Tyr Ala Tyr Gly Phe Ser Val Thr Tyr Ser Cys Asp Pro Arg Phe Ser
145                 150                 155                 160

Leu Leu Gly His Ala Ser Ile Ser Cys Thr Val Glu Asn Glu Thr Ile
                165                 170                 175
```

```
Gly Val Trp Arg Pro Ser Pro Pro Thr Cys Glu Lys
            180                 185


<210> SEQ ID NO 38
<211> LENGTH: 246
<212> TYPE: PRT
<213> ORGANISM: homo sapiens

<400> SEQUENCE: 38

Asn Cys Gly Pro Pro Pro Thr Leu Ser Phe Ala Ala Pro Met Asp Ile
1               5                   10                  15

Thr Leu Thr Glu Thr Arg Phe Lys Thr Gly Thr Thr Leu Lys Tyr Thr
            20                  25                  30

Cys Leu Pro Gly Tyr Val Arg Ser His Ser Thr Gln Thr Leu Thr Cys
        35                  40                  45

Asn Ser Asp Gly Glu Trp Val Tyr Asn Thr Phe Cys Ile Tyr Lys Arg
    50                  55                  60

Cys Arg His Pro Gly Glu Leu Arg Asn Gly Gln Val Glu Ile Lys Thr
65                  70                  75                  80

Asp Leu Ser Phe Gly Ser Gln Ile Glu Phe Ser Cys Ser Glu Gly Phe
                85                  90                  95

Phe Leu Ile Gly Ser Thr Thr Ser Arg Cys Glu Val Gln Asp Arg Gly
            100                 105                 110

Val Gly Trp Ser His Pro Leu Pro Gln Cys Glu Ile Val Lys Cys Lys
        115                 120                 125

Pro Pro Pro Asp Ile Arg Asn Gly Arg His Ser Gly Glu Glu Asn Phe
    130                 135                 140

Tyr Ala Tyr Gly Phe Ser Val Thr Tyr Ser Cys Asp Pro Arg Phe Ser
145                 150                 155                 160

Leu Leu Gly His Ala Ser Ile Ser Cys Thr Val Glu Asn Glu Thr Ile
                165                 170                 175

Gly Val Trp Arg Pro Ser Pro Pro Thr Cys Glu Lys Gly His Cys Pro
            180                 185                 190

Asp Pro Val Leu Val Asn Gly Glu Phe Ser Ser Ser Gly Pro Val Asn
        195                 200                 205

Val Ser Asp Lys Ile Thr Phe Met Cys Asn Asp His Tyr Ile Leu Lys
    210                 215                 220

Gly Ser Asn Arg Ser Gln Cys Leu Glu Asp His Thr Trp Ala Pro Pro
225                 230                 235                 240

Phe Pro Ile Cys Lys Ser
                245


<210> SEQ ID NO 39
<211> LENGTH: 304
<212> TYPE: PRT
<213> ORGANISM: homo sapiens

<400> SEQUENCE: 39

Asn Cys Gly Pro Pro Pro Thr Leu Ser Phe Ala Ala Pro Met Asp Ile
1               5                   10                  15

Thr Leu Thr Glu Thr Arg Phe Lys Thr Gly Thr Thr Leu Lys Tyr Thr
            20                  25                  30

Cys Leu Pro Gly Tyr Val Arg Ser His Ser Thr Gln Thr Leu Thr Cys
        35                  40                  45

Asn Ser Asp Gly Glu Trp Val Tyr Asn Thr Phe Cys Ile Tyr Lys Arg
    50                  55                  60
```

Cys Arg His Pro Gly Glu Leu Arg Asn Gly Gln Val Glu Ile Lys Thr
65 70 75 80

Asp Leu Ser Phe Gly Ser Gln Ile Glu Phe Ser Cys Ser Glu Gly Phe
85 90 95

Phe Leu Ile Gly Ser Thr Thr Ser Arg Cys Glu Val Gln Asp Arg Gly
100 105 110

Val Gly Trp Ser His Pro Leu Pro Gln Cys Glu Ile Val Lys Cys Lys
115 120 125

Pro Pro Pro Asp Ile Arg Asn Gly Arg His Ser Gly Glu Glu Asn Phe
130 135 140

Tyr Ala Tyr Gly Phe Ser Val Thr Tyr Ser Cys Asp Pro Arg Phe Ser
145 150 155 160

Leu Leu Gly His Ala Ser Ile Ser Cys Thr Val Glu Asn Glu Thr Ile
165 170 175

Gly Val Trp Arg Pro Ser Pro Pro Thr Cys Glu Lys Glu His Cys Pro
180 185 190

Glu Leu Pro Pro Val Asp Asn Ser Ile Phe Val Ala Lys Glu Val Glu
195 200 205

Gly Gln Ile Leu Gly Thr Tyr Val Cys Ile Lys Gly Tyr His Leu Val
210 215 220

Gly Lys Lys Thr Leu Phe Cys Asn Ala Ser Lys Glu Trp Asp Asn Thr
225 230 235 240

Thr Thr Glu Cys Arg Leu Gly His Cys Pro Asp Pro Val Leu Val Asn
245 250 255

Gly Glu Phe Ser Ser Ser Gly Pro Val Asn Val Ser Asp Lys Ile Thr
260 265 270

Phe Met Cys Asn Asp His Tyr Ile Leu Lys Gly Ser Asn Arg Ser Gln
275 280 285

Cys Leu Glu Asp His Thr Trp Ala Pro Pro Phe Pro Ile Cys Lys Ser
290 295 300

<210> SEQ ID NO 40
<211> LENGTH: 665
<212> TYPE: PRT
<213> ORGANISM: homo sapiens

<400> SEQUENCE: 40

Asn Cys Gly Pro Pro Pro Thr Leu Ser Phe Ala Ala Pro Met Asp Ile
1 5 10 15

Thr Leu Thr Glu Thr Arg Phe Lys Thr Gly Thr Thr Leu Lys Tyr Thr
20 25 30

Cys Leu Pro Gly Tyr Val Arg Ser His Ser Thr Gln Thr Leu Thr Cys
35 40 45

Asn Ser Asp Gly Glu Trp Val Tyr Asn Thr Phe Cys Ile Tyr Lys Arg
50 55 60

Cys Arg His Pro Gly Glu Leu Arg Asn Gly Gln Val Glu Ile Lys Thr
65 70 75 80

Asp Leu Ser Phe Gly Ser Gln Ile Glu Phe Ser Cys Ser Glu Gly Phe
85 90 95

Phe Leu Ile Gly Ser Thr Thr Ser Arg Cys Glu Val Gln Asp Arg Gly
100 105 110

Val Gly Trp Ser His Pro Leu Pro Gln Cys Glu Ile Val Lys Cys Lys
115 120 125

Pro Pro Pro Asp Ile Arg Asn Gly Arg His Ser Gly Glu Glu Asn Phe
130 135 140

```
Tyr Ala Tyr Gly Phe Ser Val Thr Tyr Ser Cys Asp Pro Arg Phe Ser
145                 150                 155                 160

Leu Leu Gly His Ala Ser Ile Ser Cys Thr Val Glu Asn Glu Thr Ile
                165                 170                 175

Gly Val Trp Arg Pro Ser Pro Pro Thr Cys Glu Lys Ile Thr Cys Arg
            180                 185                 190

Lys Pro Asp Val Ser His Gly Glu Met Val Ser Gly Phe Gly Pro Ile
        195                 200                 205

Tyr Asn Tyr Lys Asp Thr Ile Val Phe Lys Cys Gln Lys Gly Phe Val
    210                 215                 220

Leu Arg Gly Ser Ser Val Ile His Cys Asp Ala Asp Ser Lys Trp Asn
225                 230                 235                 240

Pro Ser Pro Pro Ala Cys Glu Pro Asn Ser Cys Ile Asn Leu Pro Asp
                245                 250                 255

Ile Pro His Ala Ser Trp Glu Thr Tyr Pro Arg Pro Thr Lys Glu Asp
            260                 265                 270

Val Tyr Val Val Gly Thr Val Leu Arg Tyr Arg Cys His Pro Gly Tyr
        275                 280                 285

Lys Pro Thr Thr Asp Glu Pro Thr Thr Val Ile Cys Gln Lys Asn Leu
    290                 295                 300

Arg Trp Thr Pro Tyr Gln Gly Cys Glu Ala Leu Cys Cys Pro Glu Pro
305                 310                 315                 320

Lys Leu Asn Asn Gly Glu Ile Thr Gln His Arg Lys Ser Arg Pro Ala
                325                 330                 335

Asn His Cys Val Tyr Phe Tyr Gly Asp Glu Ile Ser Phe Ser Cys His
            340                 345                 350

Glu Thr Ser Arg Phe Ser Ala Ile Cys Gln Gly Asp Gly Thr Trp Ser
        355                 360                 365

Pro Arg Thr Pro Ser Cys Gly Asp Ile Cys Asn Phe Pro Pro Lys Ile
    370                 375                 380

Ala His Gly His Tyr Lys Gln Ser Ser Ser Tyr Ser Phe Phe Lys Glu
385                 390                 395                 400

Glu Ile Ile Tyr Glu Cys Asp Lys Gly Tyr Ile Leu Val Gly Gln Ala
                405                 410                 415

Lys Leu Ser Cys Ser Tyr Ser His Trp Ser Ala Pro Ala Pro Gln Cys
            420                 425                 430

Lys Ala Leu Cys Arg Lys Pro Glu Leu Val Asn Gly Arg Leu Ser Val
        435                 440                 445

Asp Lys Asp Gln Tyr Val Glu Pro Glu Asn Val Thr Ile Gln Cys Asp
    450                 455                 460

Ser Gly Tyr Gly Val Val Gly Pro Gln Ser Ile Thr Cys Ser Gly Asn
465                 470                 475                 480

Arg Thr Trp Tyr Pro Glu Val Pro Lys Cys Glu Trp Glu His Cys Pro
                485                 490                 495

Glu Leu Pro Pro Val Asp Asn Ser Ile Phe Val Ala Lys Glu Val Glu
            500                 505                 510

Gly Gln Ile Leu Gly Thr Tyr Val Cys Ile Lys Gly Tyr His Leu Val
        515                 520                 525

Gly Lys Lys Thr Leu Phe Cys Asn Ala Ser Lys Glu Trp Asp Asn Thr
    530                 535                 540

Thr Thr Glu Cys Arg Leu Gly His Cys Pro Asp Pro Val Leu Val Asn
545                 550                 555                 560
```

-continued

```
Gly Glu Phe Ser Ser Ser Gly Pro Val Asn Val Ser Asp Lys Ile Thr
            565                 570                 575

Phe Met Cys Asn Asp His Tyr Ile Leu Lys Gly Ser Asn Arg Ser Gln
            580                 585                 590

Cys Leu Glu Asp His Thr Trp Ala Pro Pro Phe Pro Ile Cys Lys Ser
        595                 600                 605

Arg Asp Cys Asp Pro Pro Gly Asn Pro Val His Gly Tyr Phe Glu Gly
    610                 615                 620

Asn Asn Phe Thr Leu Gly Ser Thr Ile Ser Tyr Tyr Cys Glu Asp Arg
625                 630                 635                 640

Tyr Tyr Leu Val Gly Val Gln Glu Gln Gln Cys Val Asp Gly Glu Trp
            645                 650                 655

Ser Ser Ala Leu Pro Val Cys Lys Leu
            660                 665


<210> SEQ ID NO 41
<211> LENGTH: 473
<212> TYPE: PRT
<213> ORGANISM: homo sapiens

<400> SEQUENCE: 41

Lys Phe Ser Val Ser Leu Lys His Gly Asn Thr Asp Ser Glu Gly Ile
1               5                   10                  15

Val Glu Val Lys Leu Val Asp Gln Asp Lys Thr Met Phe Ile Cys Lys
            20                  25                  30

Ser Ser Trp Ser Met Arg Glu Ala Asn Val Ala Cys Leu Asp Leu Gly
        35                  40                  45

Phe Gln Gln Gly Ala Asp Thr Gln Arg Arg Phe Lys Leu Ser Asp Leu
    50                  55                  60

Ser Ile Asn Ser Thr Glu Cys Leu His Val His Cys Arg Gly Leu Glu
65                  70                  75                  80

Thr Ser Leu Ala Glu Cys Thr Phe Thr Lys Arg Arg Thr Met Gly Tyr
                85                  90                  95

Gln Asp Phe Ala Asp Val Val Cys Tyr Thr Gln Lys Ala Asp Ser Pro
            100                 105                 110

Met Asp Asp Phe Phe Gln Cys Val Asn Gly Lys Tyr Ile Ser Gln Met
        115                 120                 125

Lys Ala Cys Asp Gly Ile Asn Asp Cys Gly Asp Gln Ser Asp Glu Leu
    130                 135                 140

Cys Cys Lys Ala Cys Gln Gly Lys Gly Phe His Cys Lys Ser Gly Val
145                 150                 155                 160

Cys Ile Pro Ser Gln Tyr Gln Cys Asn Gly Glu Val Asp Cys Ile Thr
                165                 170                 175

Gly Glu Asp Glu Val Gly Cys Ala Gly Phe Ala Ser Val Ala Gln Glu
            180                 185                 190

Glu Thr Glu Ile Leu Thr Ala Asp Met Asp Ala Glu Arg Arg Arg Ile
        195                 200                 205

Lys Ser Leu Leu Pro Lys Leu Ser Cys Gly Val Lys Asn Arg Met His
    210                 215                 220

Ile Arg Arg Lys Arg Ile Val Gly Gly Lys Arg Ala Gln Leu Gly Asp
225                 230                 235                 240

Leu Pro Trp Gln Val Ala Ile Lys Asp Ala Ser Gly Ile Thr Cys Gly
                245                 250                 255

Gly Ile Tyr Ile Gly Gly Cys Trp Ile Leu Thr Ala Ala His Cys Leu
            260                 265                 270
```

```
Arg Ala Ser Lys Thr His Arg Tyr Gln Ile Trp Thr Thr Val Val Asp
        275                 280                 285

Trp Ile His Pro Asp Leu Lys Arg Ile Val Ile Glu Tyr Val Asp Arg
    290                 295                 300

Ile Ile Phe His Glu Asn Tyr Asn Ala Gly Thr Tyr Gln Asn Asp Ile
305                 310                 315                 320

Ala Leu Ile Glu Met Lys Lys Asp Gly Asn Lys Lys Asp Cys Glu Leu
                325                 330                 335

Pro Arg Ser Ile Pro Ala Cys Val Pro Trp Ser Pro Tyr Leu Phe Gln
            340                 345                 350

Pro Asn Asp Thr Cys Ile Val Ser Gly Trp Gly Arg Glu Lys Asp Asn
        355                 360                 365

Glu Arg Val Phe Ser Leu Gln Trp Gly Glu Val Lys Leu Ile Ser Asn
    370                 375                 380

Cys Ser Lys Phe Tyr Gly Asn Arg Phe Tyr Glu Lys Glu Met Glu Cys
385                 390                 395                 400

Ala Gly Thr Tyr Asp Gly Ser Ile Asp Ala Cys Lys Gly Asp Ser Gly
                405                 410                 415

Gly Pro Leu Val Cys Met Asp Ala Asn Asn Val Thr Tyr Val Trp Gly
            420                 425                 430

Val Val Ser Trp Gly Glu Asn Cys Gly Lys Pro Glu Phe Pro Gly Val
        435                 440                 445

Tyr Thr Lys Val Ala Asn Tyr Phe Asp Trp Ile Ser Tyr His Val Gly
    450                 455                 460

Arg Pro Phe Ile Ser Gln Tyr Asn Val
465                 470


<210> SEQ ID NO 42
<211> LENGTH: 366
<212> TYPE: PRT
<213> ORGANISM: homo sapiens

<400> SEQUENCE: 42

Lys Ala Asp Ser Pro Met Asp Asp Phe Phe Gln Cys Val Asn Gly Lys
1               5                   10                  15

Tyr Ile Ser Gln Met Lys Ala Cys Asp Gly Ile Asn Asp Cys Gly Asp
            20                  25                  30

Gln Ser Asp Glu Leu Cys Cys Lys Ala Cys Gln Gly Lys Gly Phe His
        35                  40                  45

Cys Lys Ser Gly Val Cys Ile Pro Ser Gln Tyr Gln Cys Asn Gly Glu
    50                  55                  60

Val Asp Cys Ile Thr Gly Glu Asp Glu Val Gly Cys Ala Gly Phe Ala
65                  70                  75                  80

Ser Val Ala Gln Glu Glu Thr Glu Ile Leu Thr Ala Asp Met Asp Ala
                85                  90                  95

Glu Arg Arg Arg Ile Lys Ser Leu Leu Pro Lys Leu Ser Cys Gly Val
            100                 105                 110

Lys Asn Arg Met His Ile Arg Arg Lys Arg Ile Val Gly Gly Lys Arg
        115                 120                 125

Ala Gln Leu Gly Asp Leu Pro Trp Gln Val Ala Ile Lys Asp Ala Ser
    130                 135                 140

Gly Ile Thr Cys Gly Gly Ile Tyr Ile Gly Gly Cys Trp Ile Leu Thr
145                 150                 155                 160

Ala Ala His Cys Leu Arg Ala Ser Lys Thr His Arg Tyr Gln Ile Trp
```

```
                165                 170                 175

Thr Thr Val Val Asp Trp Ile His Pro Asp Leu Lys Arg Ile Val Ile
            180                 185                 190

Glu Tyr Val Asp Arg Ile Ile Phe His Glu Asn Tyr Asn Ala Gly Thr
        195                 200                 205

Tyr Gln Asn Asp Ile Ala Leu Ile Glu Met Lys Lys Asp Gly Asn Lys
    210                 215                 220

Lys Asp Cys Glu Leu Pro Arg Ser Ile Pro Ala Cys Val Pro Trp Ser
225                 230                 235                 240

Pro Tyr Leu Phe Gln Pro Asn Asp Thr Cys Ile Val Ser Gly Trp Gly
                245                 250                 255

Arg Glu Lys Asp Asn Glu Arg Val Phe Ser Leu Gln Trp Gly Glu Val
            260                 265                 270

Lys Leu Ile Ser Asn Cys Ser Lys Phe Tyr Gly Asn Arg Phe Tyr Glu
        275                 280                 285

Lys Glu Met Glu Cys Ala Gly Thr Tyr Asp Gly Ser Ile Asp Ala Cys
    290                 295                 300

Lys Gly Asp Ser Gly Gly Pro Leu Val Cys Met Asp Ala Asn Asn Val
305                 310                 315                 320

Thr Tyr Val Trp Gly Val Val Ser Trp Gly Glu Asn Cys Gly Lys Pro
                325                 330                 335

Glu Phe Pro Gly Val Tyr Thr Lys Val Ala Asn Tyr Phe Asp Trp Ile
            340                 345                 350

Ser Tyr His Val Gly Arg Pro Phe Ile Ser Gln Tyr Asn Val
        355                 360                 365


<210> SEQ ID NO 43
<211> LENGTH: 327
<212> TYPE: PRT
<213> ORGANISM: homo sapiens

<400> SEQUENCE: 43

Lys Ala Cys Gln Gly Lys Gly Phe His Cys Lys Ser Gly Val Cys Ile
1               5                   10                  15

Pro Ser Gln Tyr Gln Cys Asn Gly Glu Val Asp Cys Ile Thr Gly Glu
            20                  25                  30

Asp Glu Val Gly Cys Ala Gly Phe Ala Ser Val Ala Gln Glu Glu Thr
        35                  40                  45

Glu Ile Leu Thr Ala Asp Met Asp Ala Glu Arg Arg Arg Ile Lys Ser
    50                  55                  60

Leu Leu Pro Lys Leu Ser Cys Gly Val Lys Asn Arg Met His Ile Arg
65                  70                  75                  80

Arg Lys Arg Ile Val Gly Gly Lys Arg Ala Gln Leu Gly Asp Leu Pro
                85                  90                  95

Trp Gln Val Ala Ile Lys Asp Ala Ser Gly Ile Thr Cys Gly Gly Ile
            100                 105                 110

Tyr Ile Gly Gly Cys Trp Ile Leu Thr Ala Ala His Cys Leu Arg Ala
        115                 120                 125

Ser Lys Thr His Arg Tyr Gln Ile Trp Thr Thr Val Val Asp Trp Ile
    130                 135                 140

His Pro Asp Leu Lys Arg Ile Val Ile Glu Tyr Val Asp Arg Ile Ile
145                 150                 155                 160

Phe His Glu Asn Tyr Asn Ala Gly Thr Tyr Gln Asn Asp Ile Ala Leu
                165                 170                 175
```

-continued

```
Ile Glu Met Lys Lys Asp Gly Asn Lys Lys Asp Cys Glu Leu Pro Arg
            180                 185                 190

Ser Ile Pro Ala Cys Val Pro Trp Ser Pro Tyr Leu Phe Gln Pro Asn
        195                 200                 205

Asp Thr Cys Ile Val Ser Gly Trp Gly Arg Glu Lys Asp Asn Glu Arg
    210                 215                 220

Val Phe Ser Leu Gln Trp Gly Glu Val Lys Leu Ile Ser Asn Cys Ser
225                 230                 235                 240

Lys Phe Tyr Gly Asn Arg Phe Tyr Glu Lys Glu Met Glu Cys Ala Gly
                245                 250                 255

Thr Tyr Asp Gly Ser Ile Asp Ala Cys Lys Gly Asp Ser Gly Gly Pro
            260                 265                 270

Leu Val Cys Met Asp Ala Asn Asn Val Thr Tyr Val Trp Gly Val Val
        275                 280                 285

Ser Trp Gly Glu Asn Cys Gly Lys Pro Glu Phe Pro Gly Val Tyr Thr
    290                 295                 300

Lys Val Ala Asn Tyr Phe Asp Trp Ile Ser Tyr His Val Gly Arg Pro
305                 310                 315                 320

Phe Ile Ser Gln Tyr Asn Val
                325


<210> SEQ ID NO 44
<211> LENGTH: 285
<212> TYPE: PRT
<213> ORGANISM: homo sapiens

<400> SEQUENCE: 44

Val Ala Gln Glu Glu Thr Glu Ile Leu Thr Ala Asp Met Asp Ala Glu
1               5                   10                  15

Arg Arg Arg Ile Lys Ser Leu Leu Pro Lys Leu Ser Cys Gly Val Lys
            20                  25                  30

Asn Arg Met His Ile Arg Arg Lys Arg Ile Val Gly Gly Lys Arg Ala
        35                  40                  45

Gln Leu Gly Asp Leu Pro Trp Gln Val Ala Ile Lys Asp Ala Ser Gly
    50                  55                  60

Ile Thr Cys Gly Gly Ile Tyr Ile Gly Gly Cys Trp Ile Leu Thr Ala
65                  70                  75                  80

Ala His Cys Leu Arg Ala Ser Lys Thr His Arg Tyr Gln Ile Trp Thr
                85                  90                  95

Thr Val Val Asp Trp Ile His Pro Asp Leu Lys Arg Ile Val Ile Glu
            100                 105                 110

Tyr Val Asp Arg Ile Ile Phe His Glu Asn Tyr Asn Ala Gly Thr Tyr
        115                 120                 125

Gln Asn Asp Ile Ala Leu Ile Glu Met Lys Lys Asp Gly Asn Lys Lys
    130                 135                 140

Asp Cys Glu Leu Pro Arg Ser Ile Pro Ala Cys Val Pro Trp Ser Pro
145                 150                 155                 160

Tyr Leu Phe Gln Pro Asn Asp Thr Cys Ile Val Ser Gly Trp Gly Arg
                165                 170                 175

Glu Lys Asp Asn Glu Arg Val Phe Ser Leu Gln Trp Gly Glu Val Lys
            180                 185                 190

Leu Ile Ser Asn Cys Ser Lys Phe Tyr Gly Asn Arg Phe Tyr Glu Lys
        195                 200                 205

Glu Met Glu Cys Ala Gly Thr Tyr Asp Gly Ser Ile Asp Ala Cys Lys
    210                 215                 220
```

```
Gly Asp Ser Gly Gly Pro Leu Val Cys Met Asp Ala Asn Asn Val Thr
225                 230                 235                 240

Tyr Val Trp Gly Val Val Ser Trp Gly Glu Asn Cys Gly Lys Pro Glu
                245                 250                 255

Phe Pro Gly Val Tyr Thr Lys Val Ala Asn Tyr Phe Asp Trp Ile Ser
            260                 265                 270

Tyr His Val Gly Arg Pro Phe Ile Ser Gln Tyr Asn Val
        275                 280                 285


<210> SEQ ID NO 45
<211> LENGTH: 365
<212> TYPE: PRT
<213> ORGANISM: homo sapiens

<400> SEQUENCE: 45

His Ser Thr Glu Ala Val Leu Gly Asp Ala Leu Val Asp Phe Ser Leu
1               5                   10                  15

Lys Leu Tyr His Ala Phe Ser Ala Met Lys Lys Val Glu Thr Asn Met
            20                  25                  30

Ala Phe Ser Pro Phe Ser Ile Ala Ser Leu Leu Thr Gln Val Leu Leu
        35                  40                  45

Gly Ala Gly Glu Asn Thr Lys Thr Asn Leu Glu Ser Ile Leu Ser Tyr
    50                  55                  60

Pro Lys Asp Phe Thr Cys Val His Gln Ala Leu Lys Gly Phe Thr Thr
65                  70                  75                  80

Lys Gly Val Thr Ser Val Ser Gln Ile Phe His Ser Pro Asp Leu Ala
                85                  90                  95

Ile Arg Asp Thr Phe Val Asn Ala Ser Arg Thr Leu Tyr Ser Ser Ser
            100                 105                 110

Pro Arg Val Leu Ser Asn Asn Ser Asp Ala Asn Leu Glu Leu Ile Asn
        115                 120                 125

Thr Trp Val Ala Lys Asn Thr Asn Asn Lys Ile Ser Arg Leu Leu Asp
    130                 135                 140

Ser Leu Pro Ser Asp Thr Arg Leu Val Leu Leu Asn Ala Ile Tyr Leu
145                 150                 155                 160

Ser Ala Lys Trp Lys Thr Thr Phe Asp Pro Lys Lys Thr Arg Met Glu
                165                 170                 175

Pro Phe His Phe Lys Asn Ser Val Ile Lys Val Pro Met Met Asn Ser
            180                 185                 190

Lys Lys Tyr Pro Val Ala His Phe Ile Asp Gln Thr Leu Lys Ala Lys
        195                 200                 205

Val Gly Gln Leu Gln Leu Ser His Asn Leu Ser Leu Val Ile Leu Val
    210                 215                 220

Pro Gln Asn Leu Lys His Arg Leu Glu Asp Met Glu Gln Ala Leu Ser
225                 230                 235                 240

Pro Ser Val Phe Lys Ala Ile Met Glu Lys Leu Glu Met Ser Lys Phe
                245                 250                 255

Gln Pro Thr Leu Leu Thr Leu Pro Arg Ile Lys Val Thr Thr Ser Gln
            260                 265                 270

Asp Met Leu Ser Ile Met Glu Lys Leu Glu Phe Phe Asp Phe Ser Tyr
        275                 280                 285

Asp Leu Asn Leu Cys Gly Leu Thr Glu Asp Pro Asp Leu Gln Val Ser
    290                 295                 300

Ala Met Gln His Gln Thr Val Leu Glu Leu Thr Glu Thr Gly Val Glu
```

-continued

```
305                 310                 315                 320

Ala Ala Ala Ala Ser Ala Ile Ser Val Ala Arg Thr Leu Leu Val Phe
                325                 330                 335

Glu Val Gln Gln Pro Phe Leu Phe Val Leu Trp Asp Gln Gln His Lys
            340                 345                 350

Phe Pro Val Phe Met Gly Arg Val Tyr Asp Pro Arg Ala
        355                 360                 365


<210> SEQ ID NO 46
<211> LENGTH: 678
<212> TYPE: PRT
<213> ORGANISM: homo sapiens

<400> SEQUENCE: 46

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala Ala Leu
            20                  25                  30

Leu Pro Ala Arg Glu Ala Thr Gln Phe Leu Arg Pro Arg Gln Arg Arg
        35                  40                  45

Ala Phe Gln Val Phe Glu Glu Ala Lys Gln Gly His Leu Glu Arg Glu
    50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp Cys Ile
                85                  90                  95

Asn Lys Tyr Gly Ser Pro Tyr Thr Lys Asn Ser Gly Phe Ala Thr Cys
            100                 105                 110

Val Gln Asn Leu Pro Asp Gln Cys Thr Pro Asn Pro Cys Asp Arg Lys
        115                 120                 125

Gly Thr Gln Ala Cys Gln Asp Leu Met Gly Asn Phe Phe Cys Leu Cys
    130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
        195                 200                 205

Glu Ala Arg Cys Lys Asn Leu Pro Gly Ser Tyr Ser Cys Leu Cys Asp
    210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu Asp Ile Leu Pro Cys Val Pro Phe Ser Val
        275                 280                 285

Ala Lys Ser Val Lys Ser Leu Tyr Leu Gly Arg Met Phe Ser Gly Thr
    290                 295                 300

Pro Val Ile Arg Leu Arg Phe Lys Arg Leu Gln Pro Thr Arg Leu Val
305                 310                 315                 320
```

-continued

```
Ala Glu Phe Asp Phe Arg Thr Phe Asp Pro Glu Gly Ile Leu Leu Phe
                325                 330                 335

Ala Gly Gly His Gln Asp Ser Thr Trp Ile Val Leu Ala Leu Arg Ala
            340                 345                 350

Gly Arg Leu Glu Leu Gln Leu Arg Tyr Asn Gly Val Gly Arg Val Thr
        355                 360                 365

Ser Ser Gly Pro Val Ile Asn His Gly Met Trp Gln Thr Ile Ser Val
    370                 375                 380

Glu Glu Leu Ala Arg Asn Leu Val Ile Lys Val Asn Arg Asp Ala Val
385                 390                 395                 400

Met Lys Ile Ala Val Ala Gly Asp Leu Phe Gln Pro Glu Arg Gly Leu
                405                 410                 415

Tyr His Leu Asn Leu Thr Val Gly Gly Ile Pro Phe His Glu Lys Asp
            420                 425                 430

Leu Val Gln Pro Ile Asn Pro Arg Leu Asp Gly Cys Met Arg Ser Trp
        435                 440                 445

Asn Trp Leu Asn Gly Glu Asp Thr Thr Ile Gln Glu Thr Val Lys Val
    450                 455                 460

Asn Thr Arg Met Gln Cys Phe Ser Val Thr Glu Arg Gly Ser Phe Tyr
465                 470                 475                 480

Pro Gly Ser Gly Phe Ala Phe Tyr Ser Leu Asp Tyr Met Arg Thr Pro
                485                 490                 495

Leu Asp Val Gly Thr Glu Ser Thr Trp Glu Val Glu Val Val Ala His
            500                 505                 510

Ile Arg Pro Ala Ala Asp Thr Gly Val Leu Phe Ala Leu Trp Ala Pro
        515                 520                 525

Asp Leu Arg Ala Val Pro Leu Ser Val Ala Leu Val Asp Tyr His Ser
    530                 535                 540

Thr Lys Lys Leu Lys Lys Gln Leu Val Val Leu Ala Val Glu His Thr
545                 550                 555                 560

Ala Leu Ala Leu Met Glu Ile Lys Val Cys Asp Gly Gln Glu His Val
                565                 570                 575

Val Thr Val Ser Leu Arg Asp Gly Glu Ala Thr Leu Glu Val Asp Gly
            580                 585                 590

Thr Arg Gly Gln Ser Glu Val Ser Ala Ala Gln Leu Gln Glu Arg Leu
        595                 600                 605

Ala Val Leu Glu Arg His Leu Arg Ser Pro Val Leu Thr Phe Ala Gly
    610                 615                 620

Gly Leu Pro Asp Val Pro Val Thr Ser Ala Pro Val Thr Ala Phe Tyr
625                 630                 635                 640

Arg Gly Cys Met Thr Leu Glu Val Asn Arg Arg Leu Leu Asp Leu Asp
                645                 650                 655

Glu Ala Ala Tyr Lys His Ser Asp Ile Thr Ala His Ser Cys Pro Pro
            660                 665                 670

Val Glu Pro Ala Ala Ala
        675
```

<210> SEQ ID NO 47
<211> LENGTH: 2041
<212> TYPE: DNA
<213> ORGANISM: homo sapiens

<400> SEQUENCE: 47
gccacctgcg tgcaaaacct gcctgaccag tgcacgccca acccctgcga taggaagggg     60

-continued

```
acccaagcct gccaggacct catgggcaac ttcttctgcc tgtgtaaagc tggctggggg    120
ggccggctct gcgacaaaga tgtcaacgaa tgcagccagg agaacggggg ctgcctccag    180
atctgccaca acaagccggg tagcttccac tgttcctgcc acagcggctt cgagctctcc    240
tctgatggca ggacctgcca agacatagac gagtgcgcag actcggaggc ctgcggggag    300
gcgcgctgca agaacctgcc cggctcctac tcctgcctct gtgacgaggg ctttgcgtac    360
agctcccagg agaaggcttg ccgagatgtg gacgagtgtc tgcagggccg ctgtgagcag    420
gtctgcgtga actccccagg gagctacacc tgccactgtg acgggcgtgg gggcctcaag    480
ctgtcccagg acatggacac ctgtgaggac atcttgccgt gcgtgccctt cagcgtggcc    540
aagagtgtga agtccttgta cctgggccgg atgttcagtg ggacccccgt gatccgactg    600
cgcttcaaga ggctgcagcc caccaggctg gtagctgagt ttgacttccg gacctttgac    660
cccgagggca tcctcctctt tgccggaggc caccaggaca gcacctggat cgtgctggcc    720
ctgagagccg gccggctgga gctgcagctg cgctacaacg gtgtcggccg tgtcaccagc    780
agcggcccgg tcatcaacca tggcatgtgg cagacaatct ctgttgagga gctggcgcgg    840
aatctggtca tcaaggtcaa cagggatgct gtcatgaaaa tcgcggtggc cggggacttg    900
ttccaaccgg agcgaggact gtatcatctg aacctgaccg tgggaggtat tcccttccat    960
gagaaggacc tcgtgcagcc tataaaccct cgtctggatg gctgcatgag gagctggaac   1020
tggctgaacg gagaagacac caccatccag gaaacggtga aagtgaacac gaggatgcag   1080
tgcttctcgg tgacggagag aggctctttc taccccggga gcggcttcgc cttctacagc   1140
ctggactaca tgcggacccc tctggacgtc gggactgaat caacctggga agtagaagtc   1200
gtggctcaca tccgcccagc cgcagacaca ggcgtgctgt ttgcgctctg ggcccccgac   1260
ctccgtgccg tgcctctctc tgtggcactg gtagactatc actccacgaa gaaactcaag   1320
aagcagctgg tggtcctggc cgtggagcat acggccttgg ccctaatgga gatcaaggtc   1380
tgcgacggcc aagagcacgt ggtcaccgtc tcgctgaggg acggtgaggc caccctggag   1440
gtggacggca ccaggggcca gagcgaggtg agcgccgcgc agctgcagga gaggctggcc   1500
gtgctcgaga ggcacctgcg gagccccgtg ctcacctttg ctggcggcct gccagatgtg   1560
ccggtgactt cagcgccagt caccgcgttc taccgcggct gcatgacact ggaggtcaac   1620
cggaggctgc tggacctgga cgaggcggcg tacaagcaca gcgacatcac ggcccactcc   1680
tgcccccccg tggagcccgc cgcagcctag gcccccacgg gacgcggcag gcttctcagt   1740
ctctgtccga gacagccggg aggagcctgg gggctcctca ccacgtgggg ccatgctgag   1800
agctgggctt tcctctgtga ccatcccggc ctgtaacata tctgtaaata gtgagatgga   1860
cttggggcct ctgacgccgc gcactcagcc gtgggcccgg gcgcggggag gccggcgcag   1920
cgcagagcgg gctcgaagaa aataattctc tattattttt attaccaagc gcttctttct   1980
gactctaaaa tatggaaaat aaaatattta cagaaagctt tgtaaaaaaa aaaaaaaaaa   2040
a                                                                   2041
```

<210> SEQ ID NO 48
<211> LENGTH: 405
<212> TYPE: PRT
<213> ORGANISM: homo sapiens

<400> SEQUENCE: 48

```
Met Asp Thr Cys Glu Asp Ile Leu Pro Cys Val Pro Phe Ser Val Ala
1               5                   10                  15
```

-continued

```
Lys Ser Val Lys Ser Leu Tyr Leu Gly Arg Met Phe Ser Gly Thr Pro
            20                  25                  30

Val Ile Arg Leu Arg Phe Lys Arg Leu Gln Pro Thr Arg Leu Val Ala
        35                  40                  45

Glu Phe Asp Phe Arg Thr Phe Asp Pro Glu Gly Ile Leu Leu Phe Ala
    50                  55                  60

Gly Gly His Gln Asp Ser Thr Trp Ile Val Leu Ala Leu Arg Ala Gly
65                  70                  75                  80

Arg Leu Glu Leu Gln Leu Arg Tyr Asn Gly Val Gly Arg Val Thr Ser
                85                  90                  95

Ser Gly Pro Val Ile Asn His Gly Met Trp Gln Thr Ile Ser Val Glu
            100                 105                 110

Glu Leu Ala Arg Asn Leu Val Ile Lys Val Asn Arg Asp Ala Val Met
        115                 120                 125

Lys Ile Ala Val Ala Gly Asp Leu Phe Gln Pro Glu Arg Gly Leu Tyr
    130                 135                 140

His Leu Asn Leu Thr Val Gly Gly Ile Pro Phe His Glu Lys Asp Leu
145                 150                 155                 160

Val Gln Pro Ile Asn Pro Arg Leu Asp Gly Cys Met Arg Ser Trp Asn
                165                 170                 175

Trp Leu Asn Gly Glu Asp Thr Thr Ile Gln Glu Thr Val Lys Val Asn
            180                 185                 190

Thr Arg Met Gln Cys Phe Ser Val Thr Glu Arg Gly Ser Phe Tyr Pro
        195                 200                 205

Gly Ser Gly Phe Ala Phe Tyr Ser Leu Asp Tyr Met Arg Thr Pro Leu
    210                 215                 220

Asp Val Gly Thr Glu Ser Thr Trp Glu Val Glu Val Val Ala His Ile
225                 230                 235                 240

Arg Pro Ala Ala Asp Thr Gly Val Leu Phe Ala Leu Trp Ala Pro Asp
                245                 250                 255

Leu Arg Ala Val Pro Leu Ser Val Ala Leu Val Asp Tyr His Ser Thr
            260                 265                 270

Lys Lys Leu Lys Lys Gln Leu Val Val Leu Ala Val Glu His Thr Ala
        275                 280                 285

Leu Ala Leu Met Glu Ile Lys Val Cys Asp Gly Gln Glu His Val Val
    290                 295                 300

Thr Val Ser Leu Arg Asp Gly Glu Ala Thr Leu Glu Val Asp Gly Thr
305                 310                 315                 320

Arg Gly Gln Ser Glu Val Ser Ala Ala Gln Leu Gln Glu Arg Leu Ala
                325                 330                 335

Val Leu Glu Arg His Leu Arg Ser Pro Val Leu Thr Phe Ala Gly Gly
            340                 345                 350

Leu Pro Asp Val Pro Val Thr Ser Ala Pro Val Thr Ala Phe Tyr Arg
        355                 360                 365

Gly Cys Met Thr Leu Glu Val Asn Arg Arg Leu Leu Asp Leu Asp Glu
    370                 375                 380

Ala Ala Tyr Lys His Ser Asp Ile Thr Ala His Ser Cys Pro Pro Val
385                 390                 395                 400

Glu Pro Ala Ala Ala
                405
```

<210> SEQ ID NO 49
<211> LENGTH: 2188
<212> TYPE: DNA

<213> ORGANISM: homo sapiens

<400> SEQUENCE: 49

```
ttgattgaaa ccagtaaatg cttctctttg ggttggggt tttagtttca aatgcccccg     60
gggggttact ttttacggcc ccgtgtcctg tagcaccgtc atttaaatgg aacagcacag    120
cgtgcaccgc cgccccccac ccctccacca agcagggccc ttcccagctc tccacctgct    180
gggctgaagt cagccttccc agccgggcct tgatcagaag cgtgcaccaa caccccggga    240
gctgcccggt caggggagga gggcagggaa atggggccag ggcgcgctgg ccccacagag    300
tctggatgcg acctctgggt ggtgccctgg ccagtccctg cagccgcctg ccccagcccc    360
gtctgagatg ccgctgtgct gcggttggcc ggtttttttt tgcttgcaga catagacgag    420
tgcgcagact cggaggcctg cggggaggcg cgctgcaaga acctgcccgg ctcctactcc    480
tgcctctgtg acgagggctt tgcgtacagc tcccaggaga aggcttgccg agatgtggac    540
gagtgtctgc agggccgctg tgagcaggtc tgcgtgaact ccccagggag ctacacctgc    600
cactgtgacg ggcgtggggg cctcaagctg tcccaggaca tggacacctg tgaggacatc    660
ttgccgtgcg tgcccttcag cgtggccaag agtgtgaagt ccttgtacct gggccggatg    720
ttcagtggga cccccgtgat ccgactgcgc ttcaagaggc tgcagcccac caggctggta    780
gctgagtttg acttccggac ctttgacccc gagggcatcc tcctctttgc cggaggccac    840
caggacagca cctggatcgt gctggccctg agagccggcc ggctggagct gcagctgcgc    900
tacaacggtg tcggccgtgt caccagcagc ggcccggtca tcaaccatgg catgtggcag    960
acaatctctg ttgaggagct ggcgcggaat ctggtcatca aggtcaacag ggatgctgtc   1020
atgaaaatcg cggtggccgg ggacttgttc caaccggagc gaggactgta tcatctgaac   1080
ctgaccgtgg gaggtattcc cttccatgag aaggacctcg tgcagcctat aaaccctcgt   1140
ctggatggct gcatgaggag ctggaactgg ctgaacggag aagacaccac catccaggaa   1200
acggtgaaag tgaacacgag gatgcagtgc ttctcggtga cggagagagg ctctttctac   1260
cccgggagcg gcttcgcctt ctacagcctg gactacatgc ggacccctct ggacgtcggg   1320
actgaatcaa cctgggaagt agaagtcgtg gctcacatcc gcccagccgc agacacaggc   1380
gtgctgtttg cgctctgggc ccccgacctc cgtgccgtgc ctctctctgt ggcactggta   1440
gactatcact ccacgaagaa actcaagaag cagctggtgg tcctggccgt ggagcatacg   1500
gccttggccc taatggagat caaggtctgc gacggccaag agcacgtggt caccgtctcg   1560
ctgagggacg gtgaggccac cctggaggtg gacggcacca ggggccagag cgaggtgagc   1620
gccgcgcagc tgcaggagag gctggccgtg ctcgagaggc acctgcggag ccccgtgctc   1680
acctttgctg gcggcctgcc agatgtgccg gtgacttcag cgccagtcac cgcgttctac   1740
cgcggctgca tgacactgga ggtcaaccgg aggctgctgg acctggacga ggcggcgtac   1800
aagcacagcg acatcacggc ccactcctgc ccccccgtgg agcccgccgc agcctaggcc   1860
cccacgggac gcggcaggct tctcagtctc tgtccgagac agccgggagg agcctggggg   1920
ctcctcacca cgtggggcca tgctgagagc tgggctttcc tctgtgacca tcccggcctg   1980
taacatatct gtaaatagtg agatggactt ggggcctctg acgccgcgca ctcagccgtg   2040
ggcccgggcg cggggaggcc ggcgcagcgc agagcgggct cgaagaaaat aattctctat   2100
tatttttatt accaagcgct tctttctgac tctaaaatat ggaaaataaa atatttacag   2160
aaagctttgt aaaaaaaaaa aaaaaaaa                                      2188
```

-continued

```
<210> SEQ ID NO 50
<211> LENGTH: 379
<212> TYPE: PRT
<213> ORGANISM: homo sapiens

<400> SEQUENCE: 50

Met Phe Ser Gly Thr Pro Val Ile Arg Leu Arg Phe Lys Arg Leu Gln
1               5                   10                  15

Pro Thr Arg Leu Val Ala Glu Phe Asp Phe Arg Thr Phe Asp Pro Glu
            20                  25                  30

Gly Ile Leu Leu Phe Ala Gly Gly His Gln Asp Ser Thr Trp Ile Val
        35                  40                  45

Leu Ala Leu Arg Ala Gly Arg Leu Glu Leu Gln Leu Arg Tyr Asn Gly
    50                  55                  60

Val Gly Arg Val Thr Ser Ser Gly Pro Val Ile Asn His Gly Met Trp
65                  70                  75                  80

Gln Thr Ile Ser Val Glu Glu Leu Ala Arg Asn Leu Val Ile Lys Val
                85                  90                  95

Asn Arg Asp Ala Val Met Lys Ile Ala Val Ala Gly Asp Leu Phe Gln
            100                 105                 110

Pro Glu Arg Gly Leu Tyr His Leu Asn Leu Thr Val Gly Gly Ile Pro
        115                 120                 125

Phe His Glu Lys Asp Leu Val Gln Pro Ile Asn Pro Arg Leu Asp Gly
    130                 135                 140

Cys Met Arg Ser Trp Asn Trp Leu Asn Gly Glu Asp Thr Thr Ile Gln
145                 150                 155                 160

Glu Thr Val Lys Val Asn Thr Arg Met Gln Cys Phe Ser Val Thr Glu
                165                 170                 175

Arg Gly Ser Phe Tyr Pro Gly Ser Gly Phe Ala Phe Tyr Ser Leu Asp
            180                 185                 190

Tyr Met Arg Thr Pro Leu Asp Val Gly Thr Glu Ser Thr Trp Glu Val
        195                 200                 205

Glu Val Val Ala His Ile Arg Pro Ala Ala Asp Thr Gly Val Leu Phe
    210                 215                 220

Ala Leu Trp Ala Pro Asp Leu Arg Ala Val Pro Leu Ser Val Ala Leu
225                 230                 235                 240

Val Asp Tyr His Ser Thr Lys Lys Leu Lys Lys Gln Leu Val Val Leu
                245                 250                 255

Ala Val Glu His Thr Ala Leu Ala Leu Met Glu Ile Lys Val Cys Asp
            260                 265                 270

Gly Gln Glu His Val Val Thr Val Ser Leu Arg Asp Gly Glu Ala Thr
        275                 280                 285

Leu Glu Val Asp Gly Thr Arg Gly Gln Ser Glu Val Ser Ala Ala Gln
    290                 295                 300

Leu Gln Glu Arg Leu Ala Val Leu Glu Arg His Leu Arg Ser Pro Val
305                 310                 315                 320

Leu Thr Phe Ala Gly Gly Leu Pro Asp Val Pro Val Thr Ser Ala Pro
                325                 330                 335

Val Thr Ala Phe Tyr Arg Gly Cys Met Thr Leu Glu Val Asn Arg Arg
            340                 345                 350

Leu Leu Asp Leu Asp Glu Ala Ala Tyr Lys His Ser Asp Ile Thr Ala
        355                 360                 365

His Ser Cys Pro Pro Val Glu Pro Ala Ala Ala
    370                 375
```

<210> SEQ ID NO 51
<211> LENGTH: 2523
<212> TYPE: DNA
<213> ORGANISM: homo sapiens

<400> SEQUENCE: 51
cacaccgacc tgtcacaccg gtgcctgtca caccactgcc tgtcacactg acttgtcacc 60
ggtgtctgtc acaccgacct gtcacactgg tgcctgtcac actggtgcct gtcacaccga 120
cctgtcacac cggtgcctgt cacaccgacc tgtcacactg acctgtcaca ccggtaggaa 180
tgcagtaccc acatgtggac gtttctgggc agggcggctc ttgtctttcc tcttcagcct 240
gggcctgtgc ctgggggttg atgagagtga gcatttattt aaaaagcaaa accacaggtg 300
gaaagagtca ccaggacagc ttctcggagt cgcagacctg ggatgcagcc gtggggctct 360
tgggtctggg ctgcgacgtt cagggcttcc agccagccct cgccttgagg ttctttgcct 420
cgctgcctca tgtactcatg cagagggtgt cggacccctg cgagatgtcc agctcaccct 480
ggctgcccac ggtgggcagg gcaggcctgg ctcagcccca gcccctccat cttccagggg 540
tgtcagctca caccggcttt ggttctgtcc cccttcgggc agcgtggaga aaccacagcc 600
cagaacaggg aactttccag gacagccatc ttcaaggcat ccatatctat ttcataatag 660
tgtatacttt ttaatgattc tctgtaattt ttgtatgctt gaaatatttc ataatttaaa 720
aataaagggt caagggaaat gagcagggaa ggagatgacg gggacccccg agaagccctg 780
tgggaagcgg ctgctgcaag cccgcccttc acctgggagt cccagtgggg caggtgtgac 840
agcctctggg gtctcagcag ctagaggcgg ggtggccact cccgaggcac aggagggaca 900
gtggacccgc tgcgcggccg gggcgtgggg ctcaggggag caggagtgaa ggccacatcc 960
ccgaccggcg tggcccccgt ccgtggcagg acatcttgcc gtgcgtgccc ttcagcgtgg 1020
ccaagagtgt gaagtccttg tacctgggcc ggatgttcag tggacccccc gtgatccgac 1080
tgcgcttcaa gaggctgcag cccaccaggc tggtagctga gtttgacttc cggacctttg 1140
accccgaggg catcctcctc tttgccggag gccaccagga cagcacctgg atcgtgctgg 1200
ccctgagagc cggccggctg gagctgcagc tgcgctacaa cggtgtcggc cgtgtcacca 1260
gcagcggccc ggtcatcaac catggcatgt ggcagacaat ctctgttgag gagctggcgc 1320
ggaatctggt catcaaggtc aacagggatg ctgtcatgaa aatcgcggtg gccggggact 1380
tgttccaacc ggagcgagga ctgtatcatc tgaacctgac cgtgggaggt attcccttcc 1440
atgagaagga cctcgtgcag cctataaacc ctcgtctgga tggctgcatg aggagctgga 1500
actggctgaa cggagaagac accaccatcc aggaaacggt gaaagtgaac acgaggatgc 1560
agtgcttctc ggtgacggag agaggctctt tctaccccgg gagcggcttc gccttctaca 1620
gcctggacta catgcggacc cctctggacg tcgggactga atcaacctgg gaagtagaag 1680
tcgtggctca catccgccca gccgcagaca caggcgtgct gtttgcgctc tgggcccccg 1740
acctccgtgc cgtgcctctc tctgtggcac tggtagacta tcactccacg aagaaactca 1800
agaagcagct ggtggtcctg gccgtggagc atacggcctt ggccctaatg gagatcaagg 1860
tctgcgacgg ccaagagcac gtggtcaccg tctcgctgag ggacggtgag gccaccctgg 1920
aggtggacgg caccaggggc cagagcgagg tgagcgccgc gcagctgcag gagaggctgg 1980
ccgtgctcga gaggcacctg cggagccccg tgctcacctt tgctggcggc ctgccagatg 2040
tgccggtgac ttcagcgcca gtcaccgcgt tctaccgcgg ctgcatgaca ctggaggtca 2100
accggaggct gctggacctg gacgaggcgg cgtacaagca cagcgacatc acggcccact 2160
cctgcccccc cgtggagccc gccgcagcct aggcccccac gggacgcggc aggcttctca 2220
gtctctgtcc gagacagccg ggaggagcct gggggctcct caccacgtgg ggccatgctg 2280
agagctgggc tttcctctgt gaccatcccg gcctgtaaca tatctgtaaa tagtgagatg 2340
gacttggggc ctctgacgcc gcgcactcag ccgtgggccc gggcgcgggg aggccggcgc 2400
agcgcagagc gggctcgaag aaaataattc tctattattt ttattaccaa gcgcttcttt 2460
ctgactctaa aatatggaaa ataaaatatt tacagaaagc tttgtaaaaa aaaaaaaaaa 2520
aaa 2523

<210> SEQ ID NO 52
<211> LENGTH: 676
<212> TYPE: PRT
<213> ORGANISM: homo sapiens

<400> SEQUENCE: 52

Met Arg Val Leu Gly Gly Arg Cys Gly Ala Leu Leu Ala Cys Leu Leu
1 5 10 15

Leu Val Leu Pro Val Ser Glu Ala Asn Phe Leu Ser Lys Gln Gln Ala
20 25 30

Ser Gln Val Leu Val Arg Lys Arg Arg Ala Asn Ser Leu Leu Glu Glu
35 40 45

Thr Lys Gln Gly Asn Leu Glu Arg Glu Cys Ile Glu Glu Leu Cys Asn
50 55 60

Lys Glu Glu Ala Arg Glu Val Phe Glu Asn Asp Pro Glu Thr Asp Tyr
65 70 75 80

Phe Tyr Pro Lys Tyr Leu Val Cys Leu Arg Ser Phe Gln Thr Gly Leu
85 90 95

Phe Thr Ala Ala Arg Gln Ser Thr Asn Ala Tyr Pro Asp Leu Arg Ser
100 105 110

Cys Val Asn Ala Ile Pro Asp Gln Cys Ser Pro Leu Pro Cys Asn Glu
115 120 125

Asp Gly Tyr Met Ser Cys Lys Asp Gly Lys Ala Ser Phe Thr Cys Thr
130 135 140

Cys Lys Pro Gly Trp Gln Gly Glu Lys Cys Glu Phe Asp Ile Asn Glu
145 150 155 160

Cys Lys Asp Pro Ser Asn Ile Asn Gly Gly Cys Ser Gln Ile Cys Asp
165 170 175

Asn Thr Pro Gly Ser Tyr His Cys Ser Cys Lys Asn Gly Phe Val Met
180 185 190

Leu Ser Asn Lys Lys Asp Cys Lys Asp Val Asp Glu Cys Ser Leu Lys
195 200 205

Pro Ser Ile Cys Gly Thr Ala Val Cys Lys Asn Ile Pro Gly Asp Phe
210 215 220

Glu Cys Glu Cys Pro Glu Gly Tyr Arg Tyr Asn Leu Lys Ser Lys Ser
225 230 235 240

Cys Glu Asp Ile Asp Glu Cys Ser Glu Asn Met Cys Ala Gln Leu Cys
245 250 255

Val Asn Tyr Pro Gly Gly Tyr Thr Cys Tyr Cys Asp Gly Lys Lys Gly
260 265 270

Phe Lys Leu Ala Gln Asp Gln Lys Ser Cys Glu Val Val Ser Val Cys
275 280 285

Leu Pro Leu Asn Leu Asp Thr Lys Tyr Glu Leu Leu Tyr Leu Ala Glu
290 295 300

```
Gln Phe Ala Gly Val Val Leu Tyr Leu Lys Phe Arg Leu Pro Glu Ile
305                 310                 315                 320

Ser Arg Phe Ser Ala Glu Phe Asp Phe Arg Thr Tyr Asp Ser Glu Gly
                325                 330                 335

Val Ile Leu Tyr Ala Glu Ser Ile Asp His Ser Ala Trp Leu Leu Ile
            340                 345                 350

Ala Leu Arg Gly Gly Lys Ile Glu Val Gln Leu Lys Asn Glu His Thr
        355                 360                 365

Ser Lys Ile Thr Thr Gly Gly Asp Val Ile Asn Asn Gly Leu Trp Asn
    370                 375                 380

Met Val Ser Val Glu Glu Leu Glu His Ser Ile Ser Ile Lys Ile Ala
385                 390                 395                 400

Lys Glu Ala Val Met Asp Ile Asn Lys Pro Gly Pro Leu Phe Lys Pro
                405                 410                 415

Glu Asn Gly Leu Leu Glu Thr Lys Val Tyr Phe Ala Gly Phe Pro Arg
            420                 425                 430

Lys Val Glu Ser Glu Leu Ile Lys Pro Ile Asn Pro Arg Leu Asp Gly
        435                 440                 445

Cys Ile Arg Ser Trp Asn Leu Met Lys Gln Gly Ala Ser Gly Ile Lys
    450                 455                 460

Glu Ile Ile Gln Glu Lys Gln Asn Lys His Cys Leu Val Thr Val Glu
465                 470                 475                 480

Lys Gly Ser Tyr Tyr Pro Gly Ser Gly Ile Ala Gln Phe His Ile Asp
                485                 490                 495

Tyr Asn Asn Val Ser Ser Ala Glu Gly Trp His Val Asn Val Thr Leu
            500                 505                 510

Asn Ile Arg Pro Ser Thr Gly Thr Gly Val Met Leu Ala Leu Val Ser
        515                 520                 525

Gly Asn Asn Thr Val Pro Phe Ala Val Ser Leu Val Asp Ser Thr Ser
    530                 535                 540

Glu Lys Ser Gln Asp Ile Leu Leu Ser Val Glu Asn Thr Val Ile Tyr
545                 550                 555                 560

Arg Ile Gln Ala Leu Ser Leu Cys Ser Asp Gln Gln Ser His Leu Glu
                565                 570                 575

Phe Arg Val Asn Arg Asn Asn Leu Glu Leu Ser Thr Pro Leu Lys Ile
            580                 585                 590

Glu Thr Ile Ser His Glu Asp Leu Gln Arg Gln Leu Ala Val Leu Asp
        595                 600                 605

Lys Ala Met Lys Ala Lys Val Ala Thr Tyr Leu Gly Gly Leu Pro Asp
    610                 615                 620

Val Pro Phe Ser Ala Thr Pro Val Asn Ala Phe Tyr Asn Gly Cys Met
625                 630                 635                 640

Glu Val Asn Ile Asn Gly Val Gln Leu Asp Leu Asp Glu Ala Ile Ser
                645                 650                 655

Lys His Asn Asp Ile Arg Ala His Ser Cys Pro Ser Val Trp Lys Lys
            660                 665                 670

Thr Lys Asn Ser
        675
```

<210> SEQ ID NO 53
<211> LENGTH: 3595
<212> TYPE: DNA
<213> ORGANISM: homo sapiens

<400> SEQUENCE: 53

```
tttggaaacg tcacactgtg gaggaaaagc agcaactagg gagctggtga agaaggatgt     60
ctcagcagtg tttactaggc ctccaacact agagcccatc cccagctcc gaaaagcttc    120
ctggaaatgt ccttgttatc acttcccctc tcgggctggg cgctgggagc gggcggtctc    180
ctccgccccc ggctgttccg ccgaggctcg ctgggtcgct ggcgccgccg cgcagcacgg    240
ctcagaccga ggcgcacagg ctcgcagctc cgcggcgcct agcgctccgg tccccgccgc    300
gacgcgccac cgtccctgcc ggcgcctccg cgcgcttcga aatgagggtc ctgggtgggc    360
gctgcggggc gctgctggcg tgtctcctcc tagtgcttcc cgtctcagag gcaaactttt    420
tgtcaaagca acaggcttca caagtcctgg ttaggaagcg tcgtgcaaat tctttacttg    480
aagaaaccaa acagggtaat cttgaaagag aatgcatcga agaactgtgc aataaagaag    540
aagccaggga ggtctttgaa aatgacccgg aaacggatta tttttatcca aaatacttag    600
tttgtcttcg ctcttttcaa actgggttat tcactgctgc acgtcagtca actaatgctt    660
atcctgacct aagaagctgt gtcaatgcca ttccagacca gtgtagtcct ctgccatgca    720
atgaagatgg atatatgagc tgcaaagatg gaaaagcttc ttttacttgc acttgtaaac    780
caggttggca aggagaaaag tgtgaatttg acataaatga atgcaaagat ccctcaaata    840
taaatggagg ttgcagtcaa atttgtgata atacacctgg aagttaccac tgttcctgta    900
aaaatggttt tgttatgctt tcaaataaga aagattgtaa agatgtggat gaatgctctt    960
tgaagccaag catttgtggc acagctgtgt gcaagaacat cccaggagat tttgaatgtg   1020
aatgccccga aggctacaga tataatctca aatcaaagtc ttgtgaagat atagatgaat   1080
gctctgagaa catgtgtgct cagctttgtg tcaattaccc tggaggttac acttgctatt   1140
gtgatgggaa gaaaggattc aaacttgccc aagatcagaa gagttgtgag gttgtttcag   1200
tgtgccttcc cttgaacctt gacacaaagt atgaattact ttacttggcg gagcagtttg   1260
caggggttgt tttatattta aaatttcgtt tgccagaaat cagcagattt tcagcagaat   1320
ttgatttccg gacatatgat tcagaaggcg tgatactgta cgcagaatct atcgatcact   1380
cagcgtggct cctgattgca cttcgtggtg gaaagattga agttcagctt aagaatgaac   1440
atacatccaa aatcacaact ggaggtgatg ttattaataa tggtctatgg aatatggtgt   1500
ctgtggaaga attagaacat agtattagca ttaaaatagc taaagaagct gtgatggata   1560
taaataaacc tggacccctt tttaagccgg aaaatggatt gctggaaacc aaagtatact   1620
ttgcaggatt ccctcggaaa gtggaaagtg aactcattaa accgattaac cctcgtctag   1680
atggatgtat acgaagctgg aatttgatga agcaaggagc ttctggaata aaggaaatta   1740
ttcaagaaaa acaaaataag cattgcctgg ttactgtgga gaagggctcc tactatcctg   1800
gttctggaat tgctcaattt cacatagatt ataataatgt atccagtgct gagggttggc   1860
atgtaaatgt gaccttgaat attcgtccat ccacgggcac tggtgttatg cttgccttgg   1920
tttctggtaa caacacagtg ccctttgctg tgtccttggt ggactccacc tctgaaaaat   1980
cacaggatat tctgttatct gttgaaaata ctgtaatata tcggatacag gccctaagtc   2040
tatgttccga tcaacaatct catctggaat ttagagtcaa cagaaacaat ctggagttgt   2100
cgacaccact taaaatagaa accatctccc atgaagacct tcaaagacaa cttgccgtct   2160
tggacaaagc aatgaaagca aaagtggcca catacctggg tggccttcca gatgttccat   2220
tcagtgccac accagtgaat gccttttata atggctgcat ggaagtgaat attaatggtg   2280
tacagttgga tctggatgaa gccatttcta aacataatga tattagagct cactcatgtc   2340
```

```
catcagtttg gaaaaagaca aagaattctt aaggcatctt ttctctgctt ataatacctt   2400

ttccttgtgt gtaattatac ttatgtttca ataacagctg aagggtttta tttacaatgt   2460

gcagtctttg attattttgt ggtcctttcc tgggattttt aaaaggtcct ttgtcaagga   2520

aaaaaattct gttgtgatat aaatcacagt aaagaaattc ttacttctct tgctatctaa   2580

gaatagtgaa aaataacaat tttaaatttg aatttttttc ctacaaatga cagtttcaat   2640

ttttgtttgt aaaactaaat tttaatttta tcatcatgaa ctagtgtcta aatacctatg   2700

tttttttcag aaagcaagga agtaaactca aacaaaagtg cgtgtaatta aatactatta   2760

atcataggca gatactattt tgtttatgtt tttgtttttt tcctgatgaa ggcagaagag   2820

atggtggtct attaaatatg aattgaatgg agggtcctaa tgccttattt caaaacaatt   2880

cctcaggggg aacagctttg gcttcatctt tctcttgtgt ggcttcacat ttaaaccagt   2940

atctttattg aattagaaaa caagtgggac atattttcct gagagcagca caggaatctt   3000

cttcttggca gctgcagtct gtcaggatga gatatcagat taggttggat aggtggggaa   3060

atctgaagtg ggtacatttt ttaaattttg ctgtgtgggt cacacaaggt ctacattaca   3120

aaagacagaa ttcagggatg gaaaggagaa tgaacaaatg tgggagttca tagttttcct   3180

tgaatccaac ttttaattac cagagtaagt tgccaaaatg tgattgttga agtacaaaag   3240

gaactatgaa aaccagaaca aattttaaca aaaggacaac cacagaggga tatagtgaat   3300

atcgtatcat tgtaatcaaa gaagtaagga ggtaagattg ccacgtgcct gctggtactg   3360

tgatgcattt caagtggcag ttttatcacg tttgaatcta ccattcatag ccagatgtgt   3420

atcagatgtt tcactgacag tttttaacaa taaattcttt tcactgtatt ttatatcact   3480

tataataaat cggtgtataa ttttaaaatg catgtgaata tctttattat atcaactgtt   3540

tgaataaaac aaaattacat aatagacatt taactcttca aaaaaaaaaa aaaaa        3595
```

<210> SEQ ID NO 54
<211> LENGTH: 1019
<212> TYPE: PRT
<213> ORGANISM: homo sapiens

<400> SEQUENCE: 54

```
His Thr Val Glu Leu Asn Asn Met Phe Gly Gln Ile Gln Ser Pro Gly
1               5                   10                  15

Tyr Pro Asp Ser Tyr Pro Ser Asp Ser Glu Val Thr Trp Asn Ile Thr
            20                  25                  30

Val Pro Asp Gly Phe Arg Ile Lys Leu Tyr Phe Met His Phe Asn Leu
        35                  40                  45

Glu Ser Ser Tyr Leu Cys Glu Tyr Asp Tyr Val Lys Val Glu Thr Glu
    50                  55                  60

Asp Gln Val Leu Ala Thr Phe Cys Gly Arg Glu Thr Thr Asp Thr Glu
65                  70                  75                  80

Gln Thr Pro Gly Gln Glu Val Val Leu Ser Pro Gly Ser Phe Met Ser
                85                  90                  95

Ile Thr Phe Arg Ser Asp Phe Ser Asn Glu Glu Arg Phe Thr Gly Phe
            100                 105                 110

Asp Ala His Tyr Met Ala Val Asp Val Asp Glu Cys Lys Glu Arg Glu
        115                 120                 125

Asp Glu Glu Leu Ser Cys Asp His Tyr Cys His Asn Tyr Ile Gly Gly
    130                 135                 140

Tyr Tyr Cys Ser Cys Arg Phe Gly Tyr Ile Leu His Thr Asp Asn Arg
```

-continued

```
145                 150                 155                 160

Thr Cys Arg Val Glu Cys Ser Asp Asn Leu Phe Thr Gln Arg Thr Gly
                165                 170                 175

Val Ile Thr Ser Pro Asp Phe Pro Asn Pro Tyr Pro Lys Ser Ser Glu
            180                 185                 190

Cys Leu Tyr Thr Ile Glu Leu Glu Glu Gly Phe Met Val Asn Leu Gln
        195                 200                 205

Phe Glu Asp Ile Phe Asp Ile Glu Asp His Pro Glu Val Pro Cys Pro
    210                 215                 220

Tyr Asp Tyr Ile Lys Ile Lys Val Gly Pro Lys Val Leu Gly Pro Phe
225                 230                 235                 240

Cys Gly Glu Lys Ala Pro Glu Pro Ile Ser Thr Gln Ser His Ser Val
                245                 250                 255

Leu Ile Leu Phe His Ser Asp Asn Ser Gly Glu Asn Arg Gly Trp Arg
            260                 265                 270

Leu Ser Tyr Arg Ala Ala Gly Asn Glu Cys Pro Glu Leu Gln Pro Pro
        275                 280                 285

Val His Gly Lys Ile Glu Pro Ser Gln Ala Lys Tyr Phe Phe Lys Asp
    290                 295                 300

Gln Val Leu Val Ser Cys Asp Thr Gly Tyr Lys Val Leu Lys Asp Asn
305                 310                 315                 320

Val Glu Met Asp Thr Phe Gln Ile Glu Cys Leu Lys Asp Gly Thr Trp
                325                 330                 335

Ser Asn Lys Ile Pro Thr Cys Lys Lys Asn Glu Ile Asp Leu Glu Ser
            340                 345                 350

Glu Leu Lys Ser Glu Gln Val Thr Glu Gly Gly Gly Gly Ser Gly Gly
        355                 360                 365

Gly Gly Ser Ala Leu Leu Pro Ala Arg Glu Ala Thr Gln Phe Leu Arg
    370                 375                 380

Pro Arg Gln Arg Arg Ala Phe Gln Val Phe Glu Glu Ala Lys Gln Gly
385                 390                 395                 400

His Leu Glu Arg Glu Cys Val Glu Glu Leu Cys Ser Arg Glu Glu Ala
                405                 410                 415

Arg Glu Val Phe Glu Asn Asp Pro Glu Thr Asp Tyr Phe Tyr Pro Arg
            420                 425                 430

Tyr Leu Asp Cys Ile Asn Lys Tyr Gly Ser Pro Tyr Thr Lys Asn Ser
        435                 440                 445

Gly Phe Ala Thr Cys Val Gln Asn Leu Pro Asp Gln Cys Thr Pro Asn
    450                 455                 460

Pro Cys Asp Arg Lys Gly Thr Gln Ala Cys Gln Asp Leu Met Gly Asn
465                 470                 475                 480

Phe Phe Cys Leu Cys Lys Ala Gly Trp Gly Gly Arg Leu Cys Asp Lys
                485                 490                 495

Asp Val Asn Glu Cys Ser Gln Glu Asn Gly Gly Cys Leu Gln Ile Cys
            500                 505                 510

His Asn Lys Pro Gly Ser Phe His Cys Ser Cys His Ser Gly Phe Glu
        515                 520                 525

Leu Ser Ser Asp Gly Arg Thr Cys Gln Asp Ile Asp Glu Cys Ala Asp
    530                 535                 540

Ser Glu Ala Cys Gly Glu Ala Arg Cys Lys Asn Leu Pro Gly Ser Tyr
545                 550                 555                 560

Ser Cys Leu Cys Asp Glu Gly Phe Ala Tyr Ser Ser Gln Glu Lys Ala
                565                 570                 575
```

-continued

```
Cys Arg Asp Val Asp Glu Cys Leu Gln Gly Arg Cys Glu Gln Val Cys
            580                 585                 590

Val Asn Ser Pro Gly Ser Tyr Thr Cys His Cys Asp Gly Arg Gly Gly
        595                 600                 605

Leu Lys Leu Ser Gln Asp Met Asp Thr Cys Glu Asp Ile Leu Pro Cys
    610                 615                 620

Val Pro Phe Ser Val Ala Lys Ser Val Lys Ser Leu Tyr Leu Gly Arg
625                 630                 635                 640

Met Phe Ser Gly Thr Pro Val Ile Arg Leu Arg Phe Lys Arg Leu Gln
                645                 650                 655

Pro Thr Arg Leu Val Ala Glu Phe Asp Phe Arg Thr Phe Asp Pro Glu
            660                 665                 670

Gly Ile Leu Leu Phe Ala Gly Gly His Gln Asp Ser Thr Trp Ile Val
        675                 680                 685

Leu Ala Leu Arg Ala Gly Arg Leu Glu Leu Gln Leu Arg Tyr Asn Gly
    690                 695                 700

Val Gly Arg Val Thr Ser Ser Gly Pro Val Ile Asn His Gly Met Trp
705                 710                 715                 720

Gln Thr Ile Ser Val Glu Glu Leu Ala Arg Asn Leu Val Ile Lys Val
                725                 730                 735

Asn Arg Asp Ala Val Met Lys Ile Ala Val Ala Gly Asp Leu Phe Gln
            740                 745                 750

Pro Glu Arg Gly Leu Tyr His Leu Asn Leu Thr Val Gly Gly Ile Pro
        755                 760                 765

Phe His Glu Lys Asp Leu Val Gln Pro Ile Asn Pro Arg Leu Asp Gly
    770                 775                 780

Cys Met Arg Ser Trp Asn Trp Leu Asn Gly Glu Asp Thr Thr Ile Gln
785                 790                 795                 800

Glu Thr Val Lys Val Asn Thr Arg Met Gln Cys Phe Ser Val Thr Glu
                805                 810                 815

Arg Gly Ser Phe Tyr Pro Gly Ser Gly Phe Ala Phe Tyr Ser Leu Asp
            820                 825                 830

Tyr Met Arg Thr Pro Leu Asp Val Gly Thr Glu Ser Thr Trp Glu Val
        835                 840                 845

Glu Val Val Ala His Ile Arg Pro Ala Ala Asp Thr Gly Val Leu Phe
    850                 855                 860

Ala Leu Trp Ala Pro Asp Leu Arg Ala Val Pro Leu Ser Val Ala Leu
865                 870                 875                 880

Val Asp Tyr His Ser Thr Lys Lys Leu Lys Lys Gln Leu Val Val Leu
                885                 890                 895

Ala Val Glu His Thr Ala Leu Ala Leu Met Glu Ile Lys Val Cys Asp
            900                 905                 910

Gly Gln Glu His Val Val Thr Val Ser Leu Arg Asp Gly Glu Ala Thr
        915                 920                 925

Leu Glu Val Asp Gly Thr Arg Gly Gln Ser Glu Val Ser Ala Ala Gln
    930                 935                 940

Leu Gln Glu Arg Leu Ala Val Leu Glu Arg His Leu Arg Ser Pro Val
945                 950                 955                 960

Leu Thr Phe Ala Gly Gly Leu Pro Asp Val Pro Val Thr Ser Ala Pro
                965                 970                 975

Val Thr Ala Phe Tyr Arg Gly Cys Met Thr Leu Glu Val Asn Arg Arg
            980                 985                 990
```

```
Leu Leu Asp Leu Asp Glu Ala Ala  Tyr Lys His Ser Asp  Ile Thr Ala
        995                 1000                1005

His Ser  Cys Pro Pro Val Glu  Pro Ala Ala Ala
    1010                 1015


<210> SEQ ID NO 55
<211> LENGTH: 1019
<212> TYPE: PRT
<213> ORGANISM: homo sapiens

<400> SEQUENCE: 55

Ala Leu Leu Pro Ala Arg Glu Ala Thr Gln Phe Leu Arg Pro Arg Gln
1               5                   10                  15

Arg Arg Ala Phe Gln Val Phe Glu Glu Ala Lys Gln Gly His Leu Glu
            20                  25                  30

Arg Glu Cys Val Glu Glu Leu Cys Ser Arg Glu Glu Ala Arg Glu Val
        35                  40                  45

Phe Glu Asn Asp Pro Glu Thr Asp Tyr Phe Tyr Pro Arg Tyr Leu Asp
    50                  55                  60

Cys Ile Asn Lys Tyr Gly Ser Pro Tyr Thr Lys Asn Ser Gly Phe Ala
65                  70                  75                  80

Thr Cys Val Gln Asn Leu Pro Asp Gln Cys Thr Pro Asn Pro Cys Asp
                85                  90                  95

Arg Lys Gly Thr Gln Ala Cys Gln Asp Leu Met Gly Asn Phe Phe Cys
            100                 105                 110

Leu Cys Lys Ala Gly Trp Gly Gly Arg Leu Cys Asp Lys Asp Val Asn
        115                 120                 125

Glu Cys Ser Gln Glu Asn Gly Gly Cys Leu Gln Ile Cys His Asn Lys
    130                 135                 140

Pro Gly Ser Phe His Cys Ser Cys His Ser Gly Phe Glu Leu Ser Ser
145                 150                 155                 160

Asp Gly Arg Thr Cys Gln Asp Ile Asp Glu Cys Ala Asp Ser Glu Ala
                165                 170                 175

Cys Gly Glu Ala Arg Cys Lys Asn Leu Pro Gly Ser Tyr Ser Cys Leu
            180                 185                 190

Cys Asp Glu Gly Phe Ala Tyr Ser Ser Gln Glu Lys Ala Cys Arg Asp
        195                 200                 205

Val Asp Glu Cys Leu Gln Gly Arg Cys Glu Gln Val Cys Val Asn Ser
    210                 215                 220

Pro Gly Ser Tyr Thr Cys His Cys Asp Gly Arg Gly Gly Leu Lys Leu
225                 230                 235                 240

Ser Gln Asp Met Asp Thr Cys Glu Asp Ile Leu Pro Cys Val Pro Phe
                245                 250                 255

Ser Val Ala Lys Ser Val Lys Ser Leu Tyr Leu Gly Arg Met Phe Ser
            260                 265                 270

Gly Thr Pro Val Ile Arg Leu Arg Phe Lys Arg Leu Gln Pro Thr Arg
        275                 280                 285

Leu Val Ala Glu Phe Asp Phe Arg Thr Phe Asp Pro Glu Gly Ile Leu
    290                 295                 300

Leu Phe Ala Gly Gly His Gln Asp Ser Thr Trp Ile Val Leu Ala Leu
305                 310                 315                 320

Arg Ala Gly Arg Leu Glu Leu Gln Leu Arg Tyr Asn Gly Val Gly Arg
                325                 330                 335

Val Thr Ser Ser Gly Pro Val Ile Asn His Gly Met Trp Gln Thr Ile
            340                 345                 350
```

-continued

```
Ser Val Glu Glu Leu Ala Arg Asn Leu Val Ile Lys Val Asn Arg Asp
        355                 360                 365

Ala Val Met Lys Ile Ala Val Ala Gly Asp Leu Phe Gln Pro Glu Arg
    370                 375                 380

Gly Leu Tyr His Leu Asn Leu Thr Val Gly Gly Ile Pro Phe His Glu
385                 390                 395                 400

Lys Asp Leu Val Gln Pro Ile Asn Pro Arg Leu Asp Gly Cys Met Arg
                405                 410                 415

Ser Trp Asn Trp Leu Asn Gly Glu Asp Thr Thr Ile Gln Glu Thr Val
            420                 425                 430

Lys Val Asn Thr Arg Met Gln Cys Phe Ser Val Thr Glu Arg Gly Ser
        435                 440                 445

Phe Tyr Pro Gly Ser Gly Phe Ala Phe Tyr Ser Leu Asp Tyr Met Arg
    450                 455                 460

Thr Pro Leu Asp Val Gly Thr Glu Ser Thr Trp Glu Val Glu Val Val
465                 470                 475                 480

Ala His Ile Arg Pro Ala Ala Asp Thr Gly Val Leu Phe Ala Leu Trp
                485                 490                 495

Ala Pro Asp Leu Arg Ala Val Pro Leu Ser Val Ala Leu Val Asp Tyr
            500                 505                 510

His Ser Thr Lys Lys Leu Lys Lys Gln Leu Val Val Leu Ala Val Glu
        515                 520                 525

His Thr Ala Leu Ala Leu Met Glu Ile Lys Val Cys Asp Gly Gln Glu
    530                 535                 540

His Val Val Thr Val Ser Leu Arg Asp Gly Glu Ala Thr Leu Glu Val
545                 550                 555                 560

Asp Gly Thr Arg Gly Gln Ser Glu Val Ser Ala Ala Gln Leu Gln Glu
                565                 570                 575

Arg Leu Ala Val Leu Glu Arg His Leu Arg Ser Pro Val Leu Thr Phe
            580                 585                 590

Ala Gly Gly Leu Pro Asp Val Pro Val Thr Ser Ala Pro Val Thr Ala
        595                 600                 605

Phe Tyr Arg Gly Cys Met Thr Leu Glu Val Asn Arg Arg Leu Leu Asp
    610                 615                 620

Leu Asp Glu Ala Ala Tyr Lys His Ser Asp Ile Thr Ala His Ser Cys
625                 630                 635                 640

Pro Pro Val Glu Pro Ala Ala Ala Gly Gly Gly Gly Ser Gly Gly Gly
                645                 650                 655

Gly Ser His Thr Val Glu Leu Asn Asn Met Phe Gly Gln Ile Gln Ser
            660                 665                 670

Pro Gly Tyr Pro Asp Ser Tyr Pro Ser Asp Ser Glu Val Thr Trp Asn
        675                 680                 685

Ile Thr Val Pro Asp Gly Phe Arg Ile Lys Leu Tyr Phe Met His Phe
    690                 695                 700

Asn Leu Glu Ser Ser Tyr Leu Cys Glu Tyr Asp Tyr Val Lys Val Glu
705                 710                 715                 720

Thr Glu Asp Gln Val Leu Ala Thr Phe Cys Gly Arg Glu Thr Thr Asp
                725                 730                 735

Thr Glu Gln Thr Pro Gly Gln Glu Val Val Leu Ser Pro Gly Ser Phe
            740                 745                 750

Met Ser Ile Thr Phe Arg Ser Asp Phe Ser Asn Glu Glu Arg Phe Thr
        755                 760                 765
```

```
Gly Phe Asp Ala His Tyr Met Ala Val Asp Val Asp Glu Cys Lys Glu
    770                 775                 780

Arg Glu Asp Glu Glu Leu Ser Cys Asp His Tyr Cys His Asn Tyr Ile
785                 790                 795                 800

Gly Gly Tyr Tyr Cys Ser Cys Arg Phe Gly Tyr Ile Leu His Thr Asp
                805                 810                 815

Asn Arg Thr Cys Arg Val Glu Cys Ser Asp Asn Leu Phe Thr Gln Arg
            820                 825                 830

Thr Gly Val Ile Thr Ser Pro Asp Phe Pro Asn Pro Tyr Pro Lys Ser
        835                 840                 845

Ser Glu Cys Leu Tyr Thr Ile Glu Leu Glu Glu Gly Phe Met Val Asn
    850                 855                 860

Leu Gln Phe Glu Asp Ile Phe Asp Ile Glu Asp His Pro Glu Val Pro
865                 870                 875                 880

Cys Pro Tyr Asp Tyr Ile Lys Ile Lys Val Gly Pro Lys Val Leu Gly
                885                 890                 895

Pro Phe Cys Gly Glu Lys Ala Pro Glu Pro Ile Ser Thr Gln Ser His
            900                 905                 910

Ser Val Leu Ile Leu Phe His Ser Asp Asn Ser Gly Glu Asn Arg Gly
        915                 920                 925

Trp Arg Leu Ser Tyr Arg Ala Ala Gly Asn Glu Cys Pro Glu Leu Gln
    930                 935                 940

Pro Pro Val His Gly Lys Ile Glu Pro Ser Gln Ala Lys Tyr Phe Phe
945                 950                 955                 960

Lys Asp Gln Val Leu Val Ser Cys Asp Thr Gly Tyr Lys Val Leu Lys
                965                 970                 975

Asp Asn Val Glu Met Asp Thr Phe Gln Ile Glu Cys Leu Lys Asp Gly
            980                 985                 990

Thr Trp Ser Asn Lys Ile Pro Thr  Cys Lys Lys Asn Glu  Ile Asp Leu
        995                 1000                 1005

Glu Ser  Glu Leu Lys Ser Glu  Gln Val Thr Glu
    1010                 1015
```

<210> SEQ ID NO 56
<211> LENGTH: 1030
<212> TYPE: PRT
<213> ORGANISM: homo sapiens

<400> SEQUENCE: 56

```
His Thr Val Glu Leu Asn Asn Met Phe Gly Gln Ile Gln Ser Pro Gly
1               5                   10                  15

Tyr Pro Asp Ser Tyr Pro Ser Asp Ser Glu Val Thr Trp Asn Ile Thr
            20                  25                  30

Val Pro Asp Gly Phe Arg Ile Lys Leu Tyr Phe Met His Phe Asn Leu
        35                  40                  45

Glu Ser Ser Tyr Leu Cys Glu Tyr Asp Tyr Val Lys Val Glu Thr Glu
    50                  55                  60

Asp Gln Val Leu Ala Thr Phe Cys Gly Arg Glu Thr Thr Asp Thr Glu
65                  70                  75                  80

Gln Thr Pro Gly Gln Glu Val Val Leu Ser Pro Gly Ser Phe Met Ser
                85                  90                  95

Ile Thr Phe Arg Ser Asp Phe Ser Asn Glu Glu Arg Phe Thr Gly Phe
            100                 105                 110

Asp Ala His Tyr Met Ala Val Asp Val Asp Glu Cys Lys Glu Arg Glu
        115                 120                 125
```

```
Asp Glu Glu Leu Ser Cys Asp His Tyr Cys His Asn Tyr Ile Gly Gly
    130                 135                 140

Tyr Tyr Cys Ser Cys Arg Phe Gly Tyr Ile Leu His Thr Asp Asn Arg
145                 150                 155                 160

Thr Cys Arg Val Glu Cys Ser Asp Asn Leu Phe Thr Gln Arg Thr Gly
                165                 170                 175

Val Ile Thr Ser Pro Asp Phe Pro Asn Pro Tyr Pro Lys Ser Ser Glu
            180                 185                 190

Cys Leu Tyr Thr Ile Glu Leu Glu Glu Gly Phe Met Val Asn Leu Gln
        195                 200                 205

Phe Glu Asp Ile Phe Asp Ile Glu Asp His Pro Glu Val Pro Cys Pro
    210                 215                 220

Tyr Asp Tyr Ile Lys Ile Lys Val Gly Pro Lys Val Leu Gly Pro Phe
225                 230                 235                 240

Cys Gly Glu Lys Ala Pro Glu Pro Ile Ser Thr Gln Ser His Ser Val
                245                 250                 255

Leu Ile Leu Phe His Ser Asp Asn Ser Gly Glu Asn Arg Gly Trp Arg
            260                 265                 270

Leu Ser Tyr Arg Ala Ala Gly Asn Glu Cys Pro Glu Leu Gln Pro Pro
        275                 280                 285

Val His Gly Lys Ile Glu Pro Ser Gln Ala Lys Tyr Phe Phe Lys Asp
    290                 295                 300

Gln Val Leu Val Ser Cys Asp Thr Gly Tyr Lys Val Leu Lys Asp Asn
305                 310                 315                 320

Val Glu Met Asp Thr Phe Gln Ile Glu Cys Leu Lys Asp Gly Thr Trp
                325                 330                 335

Ser Asn Lys Ile Pro Thr Cys Lys Lys Asn Glu Ile Asp Leu Glu Ser
            340                 345                 350

Glu Leu Lys Ser Glu Gln Val Thr Glu Gly Gly Gly Gly Ser Gly Gly
        355                 360                 365

Gly Gly Ser Gly Ser Gly Gly Gly Gly Ser Asn Phe Leu Ser Lys Gln
    370                 375                 380

Gln Ala Ser Gln Val Leu Val Arg Lys Arg Arg Ala Asn Ser Leu Leu
385                 390                 395                 400

Glu Glu Thr Lys Gln Gly Asn Leu Glu Arg Glu Cys Ile Glu Glu Leu
                405                 410                 415

Cys Asn Lys Glu Glu Ala Arg Glu Val Phe Glu Asn Asp Pro Glu Thr
            420                 425                 430

Asp Tyr Phe Tyr Pro Lys Tyr Leu Val Cys Leu Arg Ser Phe Gln Thr
        435                 440                 445

Gly Leu Phe Thr Ala Ala Arg Gln Ser Thr Asn Ala Tyr Pro Asp Leu
    450                 455                 460

Arg Ser Cys Val Asn Ala Ile Pro Asp Gln Cys Ser Pro Leu Pro Cys
465                 470                 475                 480

Asn Glu Asp Gly Tyr Met Ser Cys Lys Asp Gly Lys Ala Ser Phe Thr
                485                 490                 495

Cys Thr Cys Lys Pro Gly Trp Gln Gly Glu Lys Cys Glu Phe Asp Ile
            500                 505                 510

Asn Glu Cys Lys Asp Pro Ser Asn Ile Asn Gly Gly Cys Ser Gln Ile
        515                 520                 525

Cys Asp Asn Thr Pro Gly Ser Tyr His Cys Ser Cys Lys Asn Gly Phe
    530                 535                 540
```

-continued

```
Val Met Leu Ser Asn Lys Lys Asp Cys Lys Asp Val Asp Glu Cys Ser
545                 550                 555                 560

Leu Lys Pro Ser Ile Cys Gly Thr Ala Val Cys Lys Asn Ile Pro Gly
                565                 570                 575

Asp Phe Glu Cys Glu Cys Pro Glu Gly Tyr Arg Tyr Asn Leu Lys Ser
            580                 585                 590

Lys Ser Cys Glu Asp Ile Asp Glu Cys Ser Glu Asn Met Cys Ala Gln
        595                 600                 605

Leu Cys Val Asn Tyr Pro Gly Gly Tyr Thr Cys Tyr Cys Asp Gly Lys
    610                 615                 620

Lys Gly Phe Lys Leu Ala Gln Asp Gln Lys Ser Cys Glu Val Val Ser
625                 630                 635                 640

Val Cys Leu Pro Leu Asn Leu Asp Thr Lys Tyr Glu Leu Leu Tyr Leu
                645                 650                 655

Ala Glu Gln Phe Ala Gly Val Val Leu Tyr Leu Lys Phe Arg Leu Pro
            660                 665                 670

Glu Ile Ser Arg Phe Ser Ala Glu Phe Asp Phe Arg Thr Tyr Asp Ser
        675                 680                 685

Glu Gly Val Ile Leu Tyr Ala Glu Ser Ile Asp His Ser Ala Trp Leu
    690                 695                 700

Leu Ile Ala Leu Arg Gly Gly Lys Ile Glu Val Gln Leu Lys Asn Glu
705                 710                 715                 720

His Thr Ser Lys Ile Thr Thr Gly Gly Asp Val Ile Asn Asn Gly Leu
                725                 730                 735

Trp Asn Met Val Ser Val Glu Glu Leu Glu His Ser Ile Ser Ile Lys
            740                 745                 750

Ile Ala Lys Glu Ala Val Met Asp Ile Asn Lys Pro Gly Pro Leu Phe
        755                 760                 765

Lys Pro Glu Asn Gly Leu Leu Glu Thr Lys Val Tyr Phe Ala Gly Phe
    770                 775                 780

Pro Arg Lys Val Glu Ser Glu Leu Ile Lys Pro Ile Asn Pro Arg Leu
785                 790                 795                 800

Asp Gly Cys Ile Arg Ser Trp Asn Leu Met Lys Gln Gly Ala Ser Gly
                805                 810                 815

Ile Lys Glu Ile Ile Gln Glu Lys Gln Asn Lys His Cys Leu Val Thr
            820                 825                 830

Val Glu Lys Gly Ser Tyr Tyr Pro Gly Ser Gly Ile Ala Gln Phe His
        835                 840                 845

Ile Asp Tyr Asn Asn Val Ser Ser Ala Glu Gly Trp His Val Asn Val
    850                 855                 860

Thr Leu Asn Ile Arg Pro Ser Thr Gly Thr Gly Val Met Leu Ala Leu
865                 870                 875                 880

Val Ser Gly Asn Asn Thr Val Pro Phe Ala Val Ser Leu Val Asp Ser
                885                 890                 895

Thr Ser Glu Lys Ser Gln Asp Ile Leu Leu Ser Val Glu Asn Thr Val
            900                 905                 910

Ile Tyr Arg Ile Gln Ala Leu Ser Leu Cys Ser Asp Gln Gln Ser His
        915                 920                 925

Leu Glu Phe Arg Val Asn Arg Asn Asn Leu Glu Leu Ser Thr Pro Leu
    930                 935                 940

Lys Ile Glu Thr Ile Ser His Glu Asp Leu Gln Arg Gln Leu Ala Val
945                 950                 955                 960

Leu Asp Lys Ala Met Lys Ala Lys Val Ala Thr Tyr Leu Gly Gly Leu
```

```
                965                 970                 975

Pro Asp Val Pro Phe Ser Ala Thr Pro Val Asn Ala Phe Tyr Asn Gly
            980                 985                 990

Cys Met Glu Val Asn Ile Asn Gly  Val Gln Leu Asp Leu  Asp Glu Ala
        995                 1000                1005

Ile Ser  Lys His Asn Asp Ile  Arg Ala His Ser Cys  Pro Ser Val
    1010                1015                1020

Trp Lys  Lys Thr Lys Asn Ser
1025                1030


<210> SEQ ID NO 57
<211> LENGTH: 1020
<212> TYPE: PRT
<213> ORGANISM: homo sapiens

<400> SEQUENCE: 57

Asn Phe Leu Ser Lys Gln Gln Ala Ser Gln Val Leu Val Arg Lys Arg
1               5                   10                  15

Arg Ala Asn Ser Leu Leu Glu Glu Thr Lys Gln Gly Asn Leu Glu Arg
            20                  25                  30

Glu Cys Ile Glu Glu Leu Cys Asn Lys Glu Glu Ala Arg Glu Val Phe
        35                  40                  45

Glu Asn Asp Pro Glu Thr Asp Tyr Phe Tyr Pro Lys Tyr Leu Val Cys
    50                  55                  60

Leu Arg Ser Phe Gln Thr Gly Leu Phe Thr Ala Ala Arg Gln Ser Thr
65                  70                  75                  80

Asn Ala Tyr Pro Asp Leu Arg Ser Cys Val Asn Ala Ile Pro Asp Gln
                85                  90                  95

Cys Ser Pro Leu Pro Cys Asn Glu Asp Gly Tyr Met Ser Cys Lys Asp
            100                 105                 110

Gly Lys Ala Ser Phe Thr Cys Thr Cys Lys Pro Gly Trp Gln Gly Glu
        115                 120                 125

Lys Cys Glu Phe Asp Ile Asn Glu Cys Lys Asp Pro Ser Asn Ile Asn
    130                 135                 140

Gly Gly Cys Ser Gln Ile Cys Asp Asn Thr Pro Gly Ser Tyr His Cys
145                 150                 155                 160

Ser Cys Lys Asn Gly Phe Val Met Leu Ser Asn Lys Lys Asp Cys Lys
                165                 170                 175

Asp Val Asp Glu Cys Ser Leu Lys Pro Ser Ile Cys Gly Thr Ala Val
            180                 185                 190

Cys Lys Asn Ile Pro Gly Asp Phe Glu Cys Glu Cys Pro Glu Gly Tyr
        195                 200                 205

Arg Tyr Asn Leu Lys Ser Lys Ser Cys Glu Asp Ile Asp Glu Cys Ser
    210                 215                 220

Glu Asn Met Cys Ala Gln Leu Cys Val Asn Tyr Pro Gly Gly Tyr Thr
225                 230                 235                 240

Cys Tyr Cys Asp Gly Lys Lys Gly Phe Lys Leu Ala Gln Asp Gln Lys
                245                 250                 255

Ser Cys Glu Val Val Ser Val Cys Leu Pro Leu Asn Leu Asp Thr Lys
            260                 265                 270

Tyr Glu Leu Leu Tyr Leu Ala Glu Gln Phe Ala Gly Val Val Leu Tyr
        275                 280                 285

Leu Lys Phe Arg Leu Pro Glu Ile Ser Arg Phe Ser Ala Glu Phe Asp
    290                 295                 300
```

-continued

```
Phe Arg Thr Tyr Asp Ser Glu Gly Val Ile Leu Tyr Ala Glu Ser Ile
305                 310                 315                 320

Asp His Ser Ala Trp Leu Leu Ile Ala Leu Arg Gly Gly Lys Ile Glu
                325                 330                 335

Val Gln Leu Lys Asn Glu His Thr Ser Lys Ile Thr Thr Gly Gly Asp
            340                 345                 350

Val Ile Asn Asn Gly Leu Trp Asn Met Val Ser Val Glu Glu Leu Glu
        355                 360                 365

His Ser Ile Ser Ile Lys Ile Ala Lys Glu Ala Val Met Asp Ile Asn
    370                 375                 380

Lys Pro Gly Pro Leu Phe Lys Pro Glu Asn Gly Leu Leu Glu Thr Lys
385                 390                 395                 400

Val Tyr Phe Ala Gly Phe Pro Arg Lys Val Glu Ser Glu Leu Ile Lys
                405                 410                 415

Pro Ile Asn Pro Arg Leu Asp Gly Cys Ile Arg Ser Trp Asn Leu Met
            420                 425                 430

Lys Gln Gly Ala Ser Gly Ile Lys Glu Ile Ile Gln Glu Lys Gln Asn
        435                 440                 445

Lys His Cys Leu Val Thr Val Glu Lys Gly Ser Tyr Tyr Pro Gly Ser
    450                 455                 460

Gly Ile Ala Gln Phe His Ile Asp Tyr Asn Asn Val Ser Ser Ala Glu
465                 470                 475                 480

Gly Trp His Val Asn Val Thr Leu Asn Ile Arg Pro Ser Thr Gly Thr
                485                 490                 495

Gly Val Met Leu Ala Leu Val Ser Gly Asn Asn Thr Val Pro Phe Ala
            500                 505                 510

Val Ser Leu Val Asp Ser Thr Ser Glu Lys Ser Gln Asp Ile Leu Leu
        515                 520                 525

Ser Val Glu Asn Thr Val Ile Tyr Arg Ile Gln Ala Leu Ser Leu Cys
    530                 535                 540

Ser Asp Gln Gln Ser His Leu Glu Phe Arg Val Asn Arg Asn Asn Leu
545                 550                 555                 560

Glu Leu Ser Thr Pro Leu Lys Ile Glu Thr Ile Ser His Glu Asp Leu
                565                 570                 575

Gln Arg Gln Leu Ala Val Leu Asp Lys Ala Met Lys Ala Lys Val Ala
            580                 585                 590

Thr Tyr Leu Gly Gly Leu Pro Asp Val Pro Phe Ser Ala Thr Pro Val
        595                 600                 605

Asn Ala Phe Tyr Asn Gly Cys Met Glu Val Asn Ile Asn Gly Val Gln
    610                 615                 620

Leu Asp Leu Asp Glu Ala Ile Ser Lys His Asn Asp Ile Arg Ala His
625                 630                 635                 640

Ser Cys Pro Ser Val Trp Lys Lys Thr Lys Asn Ser Gly Ser Gly Gly
                645                 650                 655

Gly Gly Ser His Thr Val Glu Leu Asn Asn Met Phe Gly Gln Ile Gln
            660                 665                 670

Ser Pro Gly Tyr Pro Asp Ser Tyr Pro Ser Asp Ser Glu Val Thr Trp
        675                 680                 685

Asn Ile Thr Val Pro Asp Gly Phe Arg Ile Lys Leu Tyr Phe Met His
    690                 695                 700

Phe Asn Leu Glu Ser Ser Tyr Leu Cys Glu Tyr Asp Tyr Val Lys Val
705                 710                 715                 720

Glu Thr Glu Asp Gln Val Leu Ala Thr Phe Cys Gly Arg Glu Thr Thr
```

```
                725                 730                 735

Asp Thr Glu Gln Thr Pro Gly Gln Glu Val Val Leu Ser Pro Gly Ser
            740                 745                 750

Phe Met Ser Ile Thr Phe Arg Ser Asp Phe Ser Asn Glu Glu Arg Phe
        755                 760                 765

Thr Gly Phe Asp Ala His Tyr Met Ala Val Asp Val Asp Glu Cys Lys
    770                 775                 780

Glu Arg Glu Asp Glu Glu Leu Ser Cys Asp His Tyr Cys His Asn Tyr
785                 790                 795                 800

Ile Gly Gly Tyr Tyr Cys Ser Cys Arg Phe Gly Tyr Ile Leu His Thr
                805                 810                 815

Asp Asn Arg Thr Cys Arg Val Glu Cys Ser Asp Asn Leu Phe Thr Gln
            820                 825                 830

Arg Thr Gly Val Ile Thr Ser Pro Asp Phe Pro Asn Pro Tyr Pro Lys
        835                 840                 845

Ser Ser Glu Cys Leu Tyr Thr Ile Glu Leu Glu Glu Gly Phe Met Val
    850                 855                 860

Asn Leu Gln Phe Glu Asp Ile Phe Asp Ile Glu Asp His Pro Glu Val
865                 870                 875                 880

Pro Cys Pro Tyr Asp Tyr Ile Lys Ile Lys Val Gly Pro Lys Val Leu
                885                 890                 895

Gly Pro Phe Cys Gly Glu Lys Ala Pro Glu Pro Ile Ser Thr Gln Ser
            900                 905                 910

His Ser Val Leu Ile Leu Phe His Ser Asp Asn Ser Gly Glu Asn Arg
        915                 920                 925

Gly Trp Arg Leu Ser Tyr Arg Ala Ala Gly Asn Glu Cys Pro Glu Leu
    930                 935                 940

Gln Pro Pro Val His Gly Lys Ile Glu Pro Ser Gln Ala Lys Tyr Phe
945                 950                 955                 960

Phe Lys Asp Gln Val Leu Val Ser Cys Asp Thr Gly Tyr Lys Val Leu
                965                 970                 975

Lys Asp Asn Val Glu Met Asp Thr Phe Gln Ile Glu Cys Leu Lys Asp
            980                 985                 990

Gly Thr Trp Ser Asn Lys Ile Pro  Thr Cys Lys Lys Asn  Glu Ile Asp
        995                 1000                1005

Leu Glu  Ser Glu Leu Lys Ser  Glu Gln Val Thr Glu
    1010                 1015                 1020


<210> SEQ ID NO 58
<211> LENGTH: 13
<212> TYPE: PRT
<213> ORGANISM: Homo sapiens

<400> SEQUENCE: 58

Ile Cys Val Val Gln Asp Trp Gly His His Arg Cys Thr
1               5                   10


<210> SEQ ID NO 59
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)...(18)
<223> OTHER INFORMATION: exon 6 forward primer
```

<400> SEQUENCE: 59
gcacccagag ccacagtg 18

<210> SEQ ID NO 60
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)...(18)
<223> OTHER INFORMATION: reverse primer MASP1 in exon 12

<400> SEQUENCE: 60
gccttccagt gtgtgggc 18

<210> SEQ ID NO 61
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)...(19)
<223> OTHER INFORMATION: reverse primer for MASP3 in exon 11

<400> SEQUENCE: 61
gccttccaga gtgtggtca 19

<210> SEQ ID NO 62
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)...(19)
<223> OTHER INFORMATION: reverse primer for FAP in exon 8a

<400> SEQUENCE: 62
cgatctggag agcgaactc 19

<210> SEQ ID NO 63
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)...(19)
<223> OTHER INFORMATION: forward primer for exon 8a

<400> SEQUENCE: 63
cgatctggag agcgaactc 19

<210> SEQ ID NO 64
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)...(20)
<223> OTHER INFORMATION: reverse primer for exon 8a

<400> SEQUENCE: 64
ctgctgagat catgttgttc 20

<210> SEQ ID NO 65
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)...(15)
<223> OTHER INFORMATION: T7 sequence

<400> SEQUENCE: 65
ttatacgact cacta 15

<210> SEQ ID NO 66
<211> LENGTH: 7
<212> TYPE: PRT
<213> ORGANISM: Artificial Sequence
<220> FEATURE:
<223> OTHER INFORMATION: synthetic

<400> SEQUENCE: 66

Val Ser Val Phe Pro Leu Glu
1 5

<210> SEQ ID NO 67
<211> LENGTH: 5
<212> TYPE: PRT
<213> ORGANISM: Artificial
<220> FEATURE:
<223> OTHER INFORMATION: synthetic

<400> SEQUENCE: 67

Gly Gly Gly Gly Ser
1 5

<210> SEQ ID NO 68
<211> LENGTH: 10
<212> TYPE: PRT
<213> ORGANISM: Artificial
<220> FEATURE:
<223> OTHER INFORMATION: Synthetic

<400> SEQUENCE: 68

Gly Gly Gly Gly Ser Gly Gly Gly Gly Ser
1 5 10

<210> SEQ ID NO 69
<211> LENGTH: 15
<212> TYPE: PRT
<213> ORGANISM: Artificial
<220> FEATURE:
<223> OTHER INFORMATION: Synthetic

<400> SEQUENCE: 69

Gly Gly Gly Gly Ser Gly Gly Gly Gly Ser Gly Gly Gly Gly Ser
1 5 10 15

<210> SEQ ID NO 70
<211> LENGTH: 16
<212> TYPE: PRT
<213> ORGANISM: Artificial
<220> FEATURE:

<223> OTHER INFORMATION: Synthetic

<400> SEQUENCE: 70

```
Gly Gly Gly Ser Gly Gly Gly Ser Gly Gly Gly Ser Gly Gly Gly Ser
1               5                   10                  15
```

<210> SEQ ID NO 71
<211> LENGTH: 5
<212> TYPE: PRT
<213> ORGANISM: Artificial
<220> FEATURE:
<223> OTHER INFORMATION: Synthetic

<400> SEQUENCE: 71

```
Ser Gly Gly Gly Gly
1               5
```

<210> SEQ ID NO 72
<211> LENGTH: 10
<212> TYPE: PRT
<213> ORGANISM: Artificial
<220> FEATURE:
<223> OTHER INFORMATION: synthetic

<400> SEQUENCE: 72

```
Ser Gly Gly Gly Gly Ser Gly Gly Gly Gly
1               5                   10
```

<210> SEQ ID NO 73
<211> LENGTH: 15
<212> TYPE: PRT
<213> ORGANISM: artificial
<220> FEATURE:
<223> OTHER INFORMATION: synthetic

<400> SEQUENCE: 73

```
Ser Gly Gly Gly Gly Ser Gly Gly Gly Gly Ser Gly Gly Gly Gly
1               5                   10                  15
```

<210> SEQ ID NO 74
<211> LENGTH: 20
<212> TYPE: PRT
<213> ORGANISM: Artificial
<220> FEATURE:
<223> OTHER INFORMATION: Synthetic

<400> SEQUENCE: 74

```
Ser Gly Gly Gly Gly Ser Gly Gly Gly Gly Ser Gly Gly Gly Gly Ser
1               5                   10                  15

Gly Gly Gly Gly
            20
```

<210> SEQ ID NO 75
<211> LENGTH: 146
<212> TYPE: PRT
<213> ORGANISM: Homo sapiens
<220> FEATURE:
<221> NAME/KEY: human GULP
<222> LOCATION: (1)..(146)
<223> OTHER INFORMATION: engulfment adaptor PTB domain containing 1
      variant

<400> SEQUENCE: 75

```
Glu Thr Glu Asn Met Glu Leu Lys Asn Lys Val Gln Asp Leu Glu Asn
1               5                   10                  15

Gln Leu Arg Ile Thr Gln Val Ser Ala Pro Pro Ala Gly Ser Met Thr
```

-continued

```
            20                  25                  30

Pro Lys Ser Pro Ser Thr Asp Ile Phe Asp Met Ile Pro Phe Ser Pro
        35                  40                  45

Ile Ser His Gln Ser Ser Met Pro Thr Arg Asn Gly Thr Gln Pro Pro
    50                  55                  60

Pro Val Pro Ser Arg Ser Thr Glu Ile Lys Arg Asp Leu Phe Gly Ala
65                  70                  75                  80

Glu Pro Phe Asp Pro Phe Asn Cys Gly Ala Ala Asp Phe Pro Pro Asp
                85                  90                  95

Ile Gln Ser Lys Leu Asp Glu Met Gln Val Thr Ile Leu Ile Asp Trp
            100                 105                 110

Pro Ile Asn Asp Leu Phe His Phe Asp Met Gly Gln Arg Glu Cys Tyr
        115                 120                 125

Val Pro Lys Leu Trp Phe Pro Ser Ile Ile Phe Ala Ile Lys Thr Arg
    130                 135                 140

Leu Lys
145
```

CHIMERIC INHIBITOR MOLECULES OF COMPLEMENT ACTIVATION

CROSS-REFERENCE TO RELATED APPLICATIONS

This application is a continuation of U.S. patent application Ser. No. 14/585,369, filed Dec. 30, 2014 which is a continuation-in-part of U.S. patent application Ser. No. 13/582,814, filed Nov. 15, 2012 which was a national stage filing under 35 U.S.C. 371 of PCT/EP2011/053309, filed Mar. 4, 2011, which International application was published by the International Bureau in English on Sep. 9, 2011, and which claims the benefit of U.S. Provisional Application No. 61/311,024, filed Mar. 5, 2010 and European Application No. 10155621.5, filed Mar. 5, 2010.

FIELD OF THE INVENTION

The present invention relates to novel chimeric molecules of ficolin-associated polypeptides, such as fusion polypeptides for the use in the treatment of conditions associated with inflammation, apoptosis, autoimmunity, coagulation, thrombotic or coagulopathic related diseases. The present invention further relates to nucleic acid molecules encoding such fusion polypeptides, vectors and host cells used in the production of the fusion polypeptides.

BACKGROUND OF THE INVENTION

Activation of the complement system (C) is accomplished via three different initiation pathways: The alternative (AP), the classical (CP), or the lectin pathway (LCP).

AP activation occurs on foreign surfaces and is caused by a slow, spontaneous hydrolysis of C3 and the activity of the factors properdin, factor B and factor D to form the functional C3 convertase C3bBb. AP also functions as an amplification pathway (the amplification loop) of the two other pathways. Recently it has been shown that the alternative convertase assembly may also be initiated by non-covalent attachment of properdin to some target surfaces. CP activation on the other hand is initiated when C1q binds to immunoglobulins in complex with antigens, which triggers the activation of the C1q-associated serine proteases C1r and C1s. C1s cleaves and activates C4 and C2 to form the CP C3 convertase C4b2a. The LCP is activated when mannose-binding lectin (MBL) or ficolins binds to restricted patterns of carbohydrates or acetylated compounds e.g. on the surface of microorganisms or when exposed on dying host cells. Upon binding to the ligand the associated serine protease MASP-2 activates and cleaves C4 and C2 to form the LCP C3 convertase C4b2a. The function of MASP-1 has been suggested to involve a stabilization of MASP-2 cleavage of C2 and also direct low grade cleavage of C3. Yet other studies relate the function and activity of MASP-1 and MASP-2 to a coagulation system cross-talk involving prothrombin, fibrinogen and factor XIII. Using MASP1/3 knockout mice it was recently demonstrated that MASP-1 in fact contributes to the complement activity. The exact function of the most recently discovered MBL associated serine protease MASP-3 has yet to be elucidated. Studies indicating that MASP-3 associates with a limited range of MBL oligomers and that MASP-3 and the small MBL-associated protein (sMAP) are involved in regulation or inhibition of MBL dependent LCP complement activation have been reported.

MASP-1 and -3 are derived from the same MASP1/3 gene (present on chromosome 3q27-q28) through differential splicing. They contain an identical A-chain except for 15 C-terminal residues. The A chain is comprised of two CUB (C1r/C1s, Urchin-EGF, Bone morphogenetic protein) domains separated by an EGF (Epidermal Growth Factor) domain and followed by two CCP domains (complement control protein). The B-chain including the serine protease domain is different for MASP-1 and MASP-3. The MASP-2 and sMAP are also derived from the same gene (present on chromosome 1p36-p36.2) where sMAP is a truncated form lacking the serine protease domain and a major part of the A-chain. The MASP1/3 gene has been shown to be polymorphic, but the functional importance of this is still poorly understood. However, there is some evidence that polymorphisms in the MASP2/sMAP gene are associated with increased risk of infections. Expression of the MASPs is localized to liver hepatocytes, but a recent study described that human MASP-3 mRNA (as the only MASP-mRNA) was expressed in a broad range of tissues.

OBJECT OF THE INVENTION

It is an object of embodiments of the invention to provide chimeric molecules suitable for the treatment of conditions associated with inflammation, apoptosis, autoimmunity, coagulation, and/or thrombotic or coagulopathic related diseases. The chimeric molecules of the invention may further be suitable as biomarkers for the diagnosis and/or prognosis of these indications as well as for malignant diseases, such as cancers.

SUMMARY OF THE INVENTION

It has been found by the present inventor(s) that novel chimeric molecules that associate with the recognition molecules of the lectin complement pathway may be used in the treatment of specific medical conditions associated with inflammation, apoptosis, autoimmunity, coagulation, and/or thrombotic or coagulopathic related diseases.

So, in a first aspect the present invention relates to a chimeric molecule of a ficolin-associated polypeptide comprising:

a) a ficolin-associated polypeptide; and b) a second modulator of complement activity;

which chimeric molecule is capable of inhibiting complement activation.

In a second aspect the present invention relates to an isolated nucleic acid molecule encoding a chimeric molecule, wherein the ficolin-associated polypeptide and the second modulator of complement activity are directly or indirectly fused to each other in the form of a fusion protein.

In a third aspect the present invention relates to vector comprising an isolated nucleic acid molecule encoding a chimeric molecule, wherein the ficolin-associated polypeptide and the second modulator of complement activity are directly or indirectly fused to each other in the form of a fusion protein.

In a fourth aspect the present invention relates to a host cell comprising a vector comprising an isolated nucleic acid molecule encoding a chimeric molecule, wherein the ficolin-associated polypeptide and the second modulator of complement activity are directly or indirectly fused to each other in the form of a fusion protein.

In a further aspect the present invention relates to a method for producing the chimeric molecule according to the invention, the method comprising cultivating a cell according to the invention in an appropriate growth medium under conditions allowing expression of the polynucleotide construct and recovering the resulting polypeptide from the culture medium.

In a further aspect the present invention relates to a composition comprising the chimeric molecule according to the invention.

In a further aspect the present invention relates to a pharmaceutical composition comprising the chimeric molecule according to the invention.

In a further aspect the present invention relates to a chimeric molecule according to the invention for use as a medicament.

In a further aspect the present invention relates to the use of a chimeric molecule according to the invention; for the preparation of a medicament.

In a further aspect the present invention relates to a chimeric molecule according to the invention as well as pharmaceutical composition comprising a chimeric molecule according to the invention for the treatment of any indications associated with inflammation, apoptosis and/or autoimmunity.

In a further aspect the present invention relates to a chimeric molecule according to the invention for the treatment of any indications associated with coagulation, thrombotic or coagulopathic related diseases.

In a further aspect the present invention relates to a method for the treatment of any indication associated with inflammation, apoptosis and/or autoimmunity, coagulation, thrombotic or coagulopathic related diseases, for preventing the occurrence of thromboembolic complications in identified high risk patients, treatment of a medical condition associated with the heart, or a medical condition associated with a deficiency in a ficolin-associated polypeptide; the method comprising administering a therapeutically or prophylactically effective amount of a chimeric molecule according to the invention to a subject in need thereof.

In a further aspect the present invention relates to the use of a composition according to the invention; for the preparation of a medicament.

In a further aspect the present invention relates to a method for the treatment of any indication described herein, the method comprising simultaneously or sequentially administering a therapeutically or prophylactically effective amount of a chimeric molecule according to the invention and one or more proteins selected from Ficolin-1, 2, 3, and mannose-binding lectin (MBL), C1q, lung surfactant proteins SP-A and/or SP-D, and intracellular collagen-like defence molecules, such as CL-L1.

LEGENDS TO THE FIGURES

FIG. 1: Alternative transcription of the MASP-1 gene. Alternative transcription of the MASP1 gene was detected in liver cDNA. The MASP1, MASP3, and FAP transcripts were amplified using a common forward primer located in exon 6 and specific reverse primers located in exon 12 (MASP1), exon 11 (MASP3), and exon 8a (FAP). Exon 8a as referred to herein may alternatively be referred to as exon 9 with a shift up in numbers of the following exons from 9-17 to 10-18 of the primary transcript. MASP1 generates a fragment of 500 bp, MASP3 generates a fragment of 506 bp and FAP generates a fragment of 309 bp.

Figure 2:
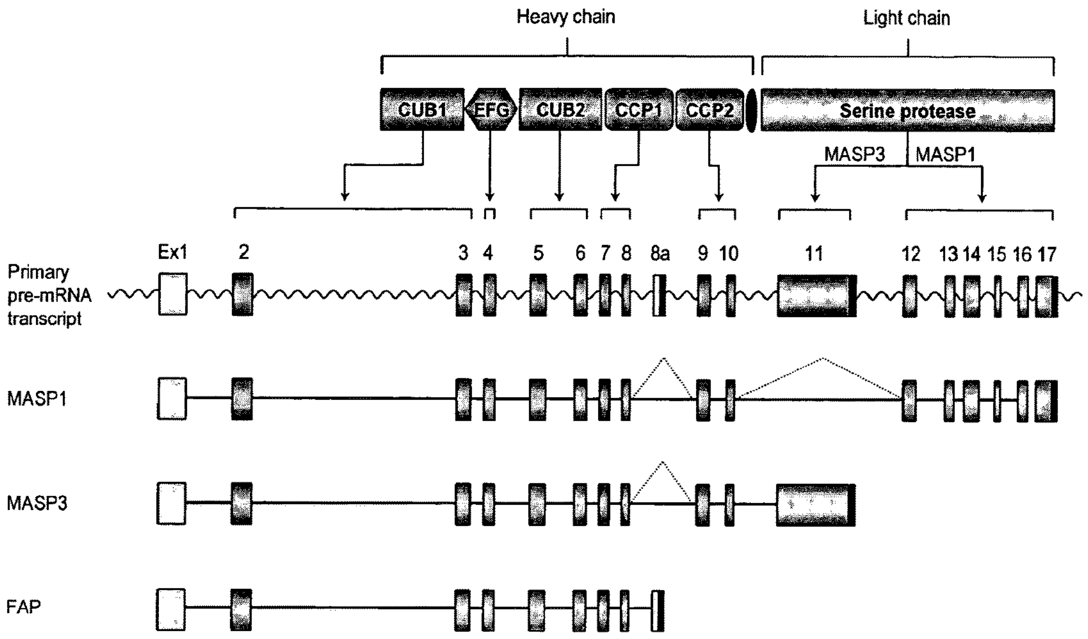

FIG. 2: Alternative splicing of the MASP1 gene. MASP1 is generated by splicing out of 8a and exon 11, which both contain a stop codon sequence (marked with black boxes). The MASP1 sequence contains a stop codon in exon 17. MASP3 is generated by splicing out of exon 8a and FAP is generated if no splicing out of exon 8a occurs. The FAP protein contains the two CUB domains, the EGF domain and the first CCP1 domain.

Figure 3:
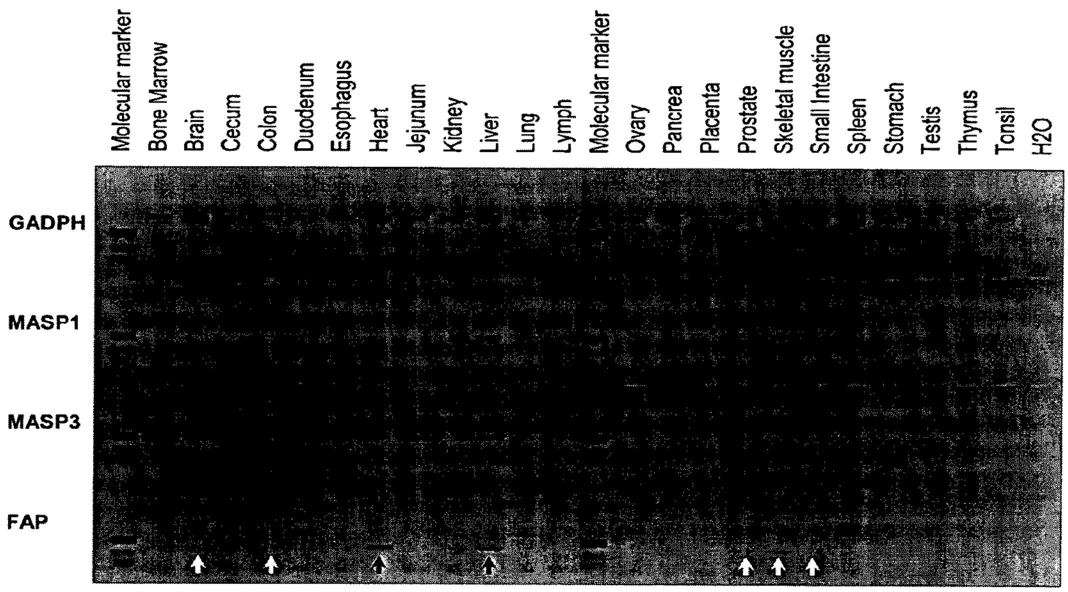

FIG. 3: Tissue expression of the FAP fragment. The tissue distributions of the MASP-1, MASP3, and FAP genes were investigated in cDNA panels from Clontech. MASP-1, MASP-3, and FAP transcripts were amplified using a common forward primer and specific reverse primers. GADPH was used as reference gene. All three genes were highly expressed in the liver, and additionally, FAP was strongly expressed in heart tissue (marked with black arrows). Minor expression of the FAP gene was detected in brain, colon, prostate, skeletal muscle, and small intestine (marked with white arrows).

FIG. 4: Alignment of MASP-1, MASP-3, and FAP (SEQ ID NO: 1). The protein sequences of MASP-1 (SEQ ID NO: 5), MASP-3 (SEQ ID NO: 7), and FAP were aligned using the BioEdit Software. MASP-1 and MASP-3 contain different C-terminal serine protease domains whereas FAP does not contain any serine protease domain. Instead the protein contains 17 new amino acids in the C-terminal region.

Figure 5:
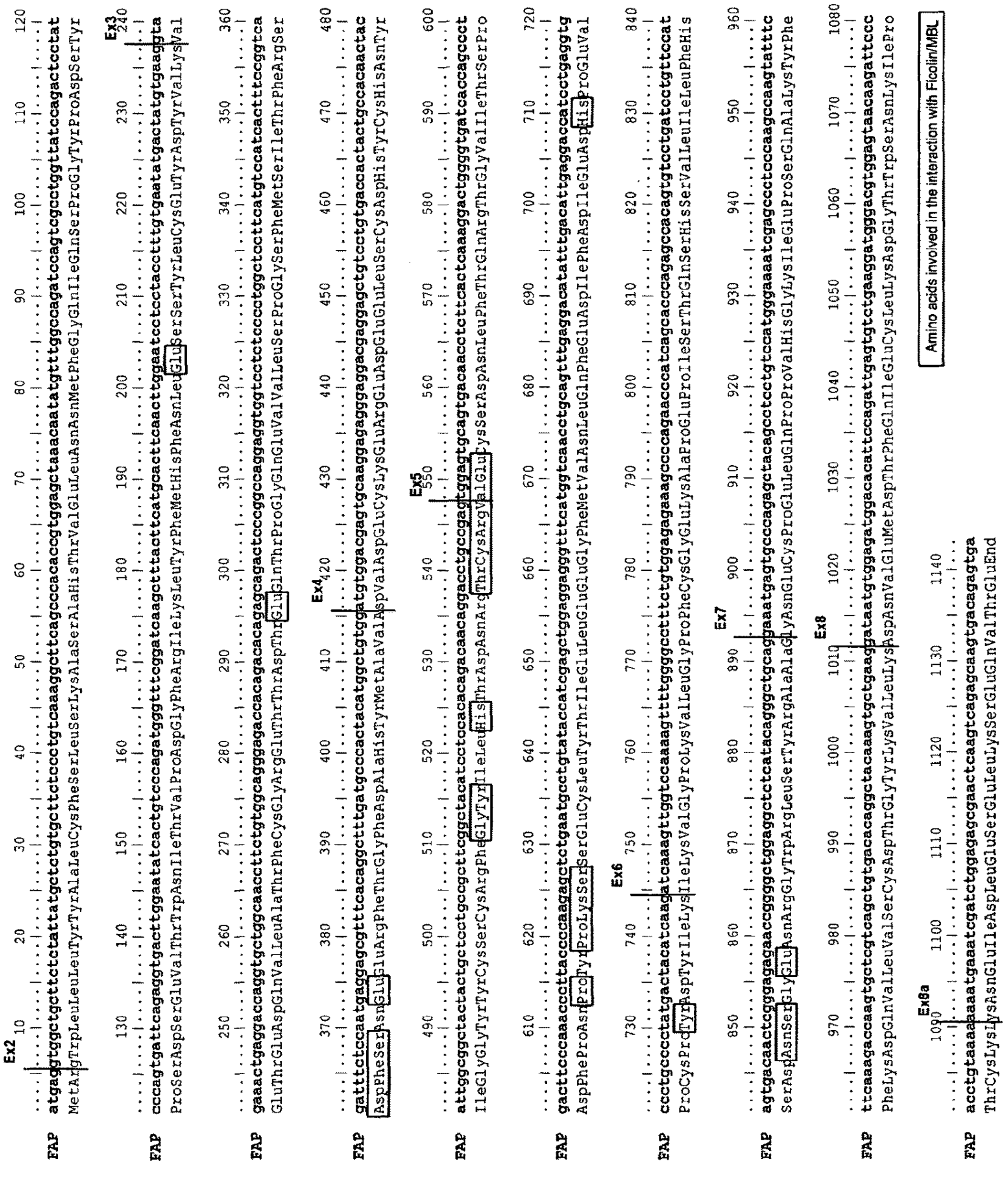

FIG. 5: cDNA sequence and corresponding protein sequence of FAP (amino acid SEQ ID NO: 1; DNA SEQ ID NO: 2). The cDNA sequence is shown in the upper row and the corresponding protein sequence is shown below. Exons regions are divided by black vertical lines. Amino acids believed to be involved in the binding to MBL/ficolins are marked with light-yellow boxes.

Figure 6:
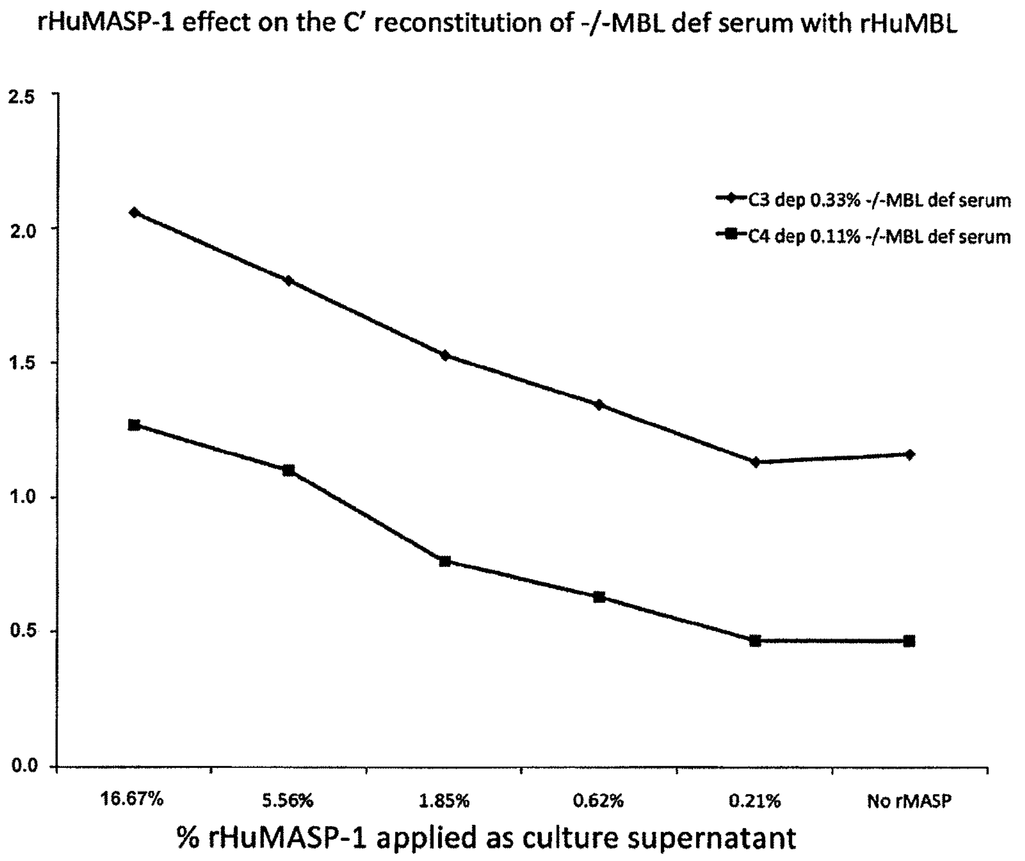

FIG. 6: MASP-1 complement activation. Human MBL were incubated with increased amount of MASP-1. MASP-1 were able to activate both the C3 and C4 complement proteins.

Figure 7:
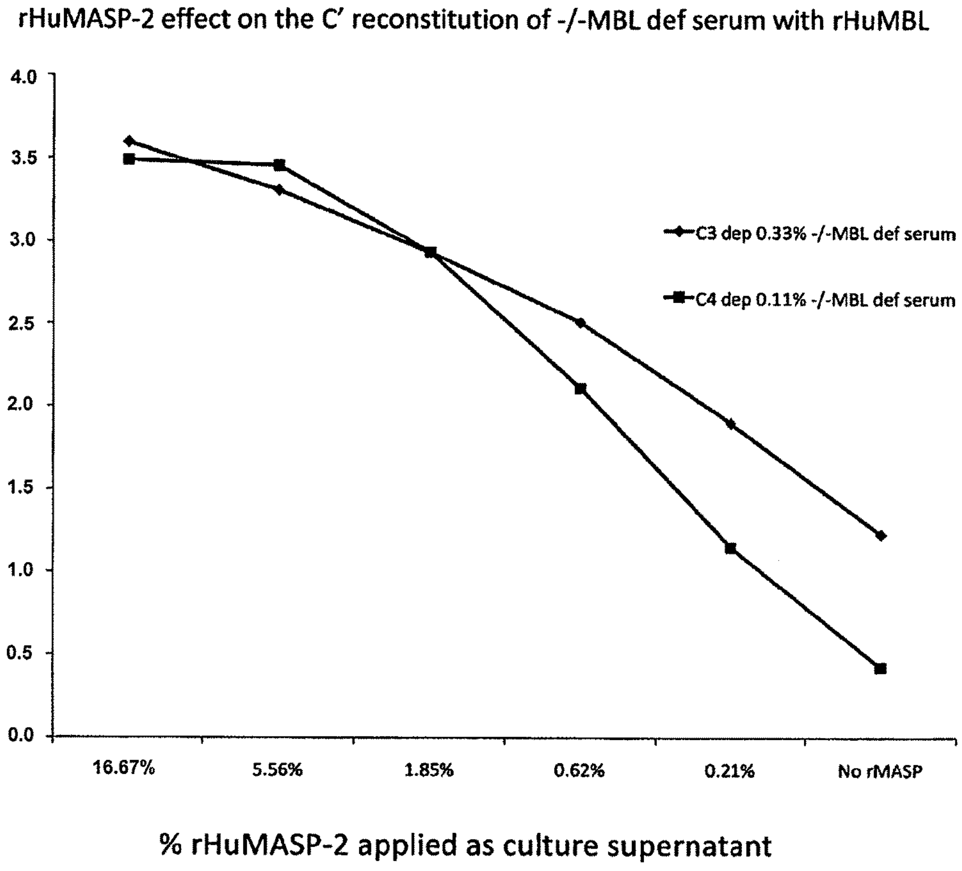

FIG. 7: MASP-2 complement activation. Human MBL were incubated with increased amount of MASP-2. MASP-2 were able to strongly activate both the C3 and C4 complement proteins.

Figure 8:
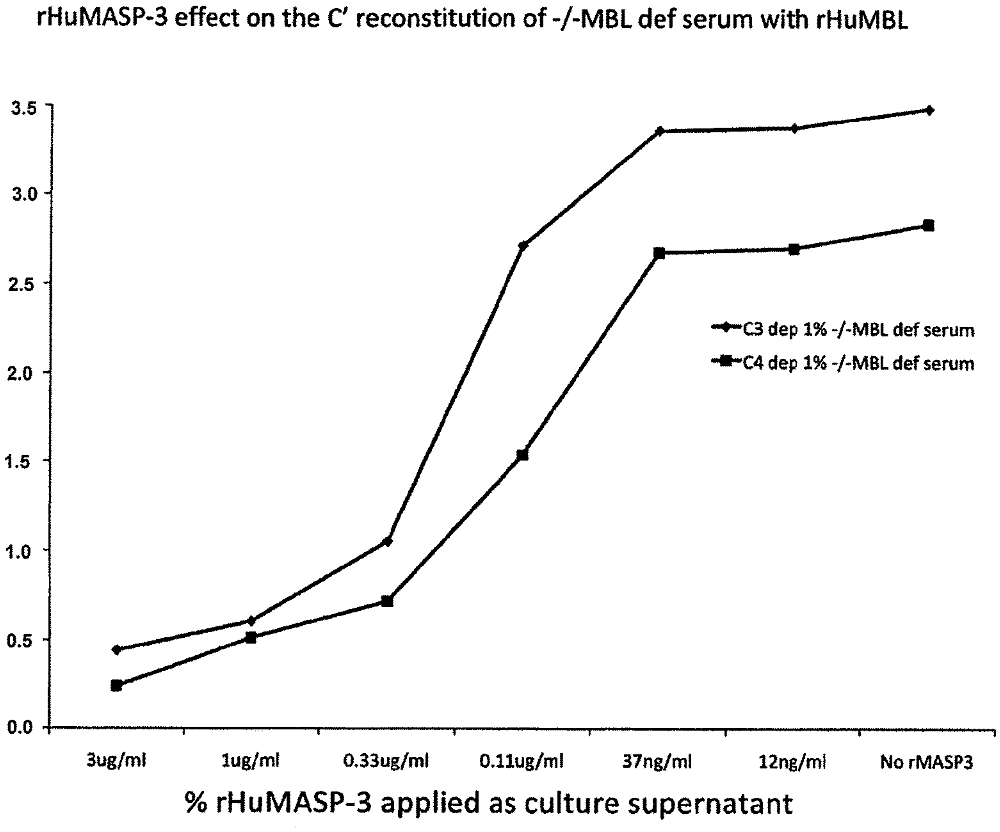

FIG. 8: MASP-3 inhibition of the complement. Human MBL were incubated with increased amount of MASP-3. MASP-3 were able to inhibit the activation of both the C3 and C4 complement proteins.

Figure 9:
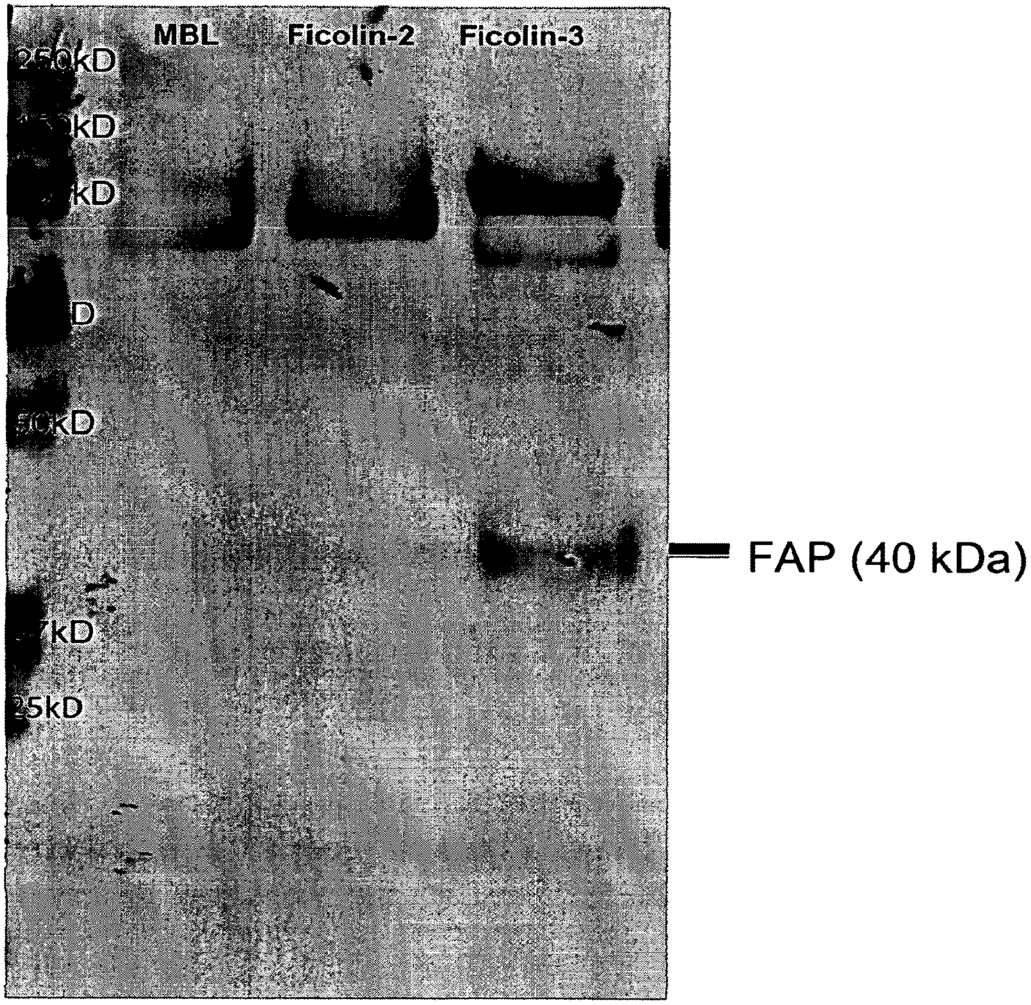

FIG. 9: Immunoprecipitation. Immunoprecipitation of serum Ficolin/MBL with mAb anti-MBL 131-11, anti-Ficolin-2 clone 219, and anti-Ficolin-3 clone 334. Followed by Dynal magnetic bead separation, SDS-PAGE, Western blot and biotin labeled anti-MASP-1/MASP-3 clone 8B3 as signal antibody.

Figure 10:
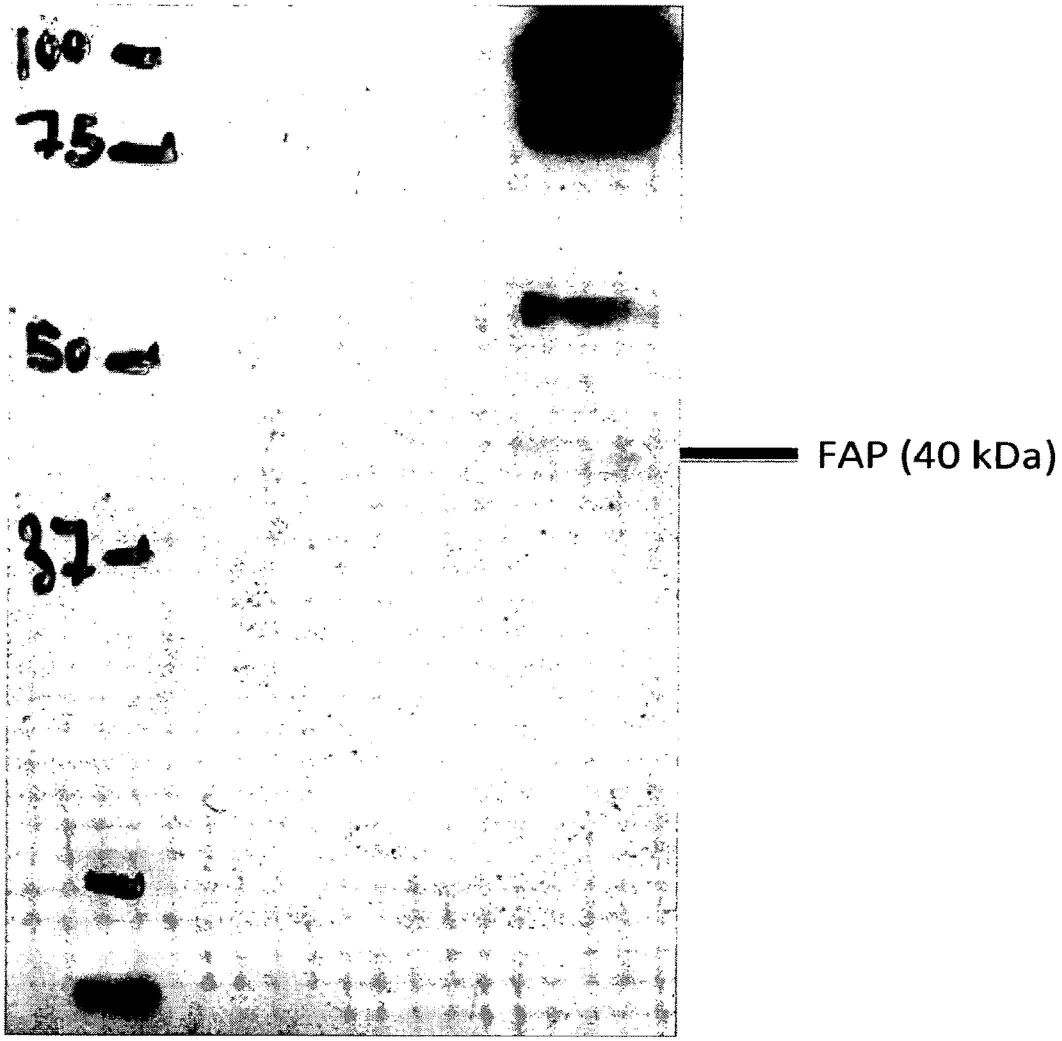

FIG. 10: FAP interact with Ficolin when bound to acetylated human serum albumin (AcHSA). Eluted serum Ficolin binding to AcHSA. Western blot with biotin labelled anti-MASP-1/MASP-3 clone 8B3 as signal antibody.

FIG. 11: Kinetics and dissociation constants for interaction between MASP-1 and MASP-3 and rFicolin-2 (Hummelshøj T et al., Mol. Immunol., 2007).

FIG. 12: Alignment of GULFGULP (SEQ ID NO: 75) and the 17 unique amino acids of FAP (SEQ ID NO: 4).

Figure 13:
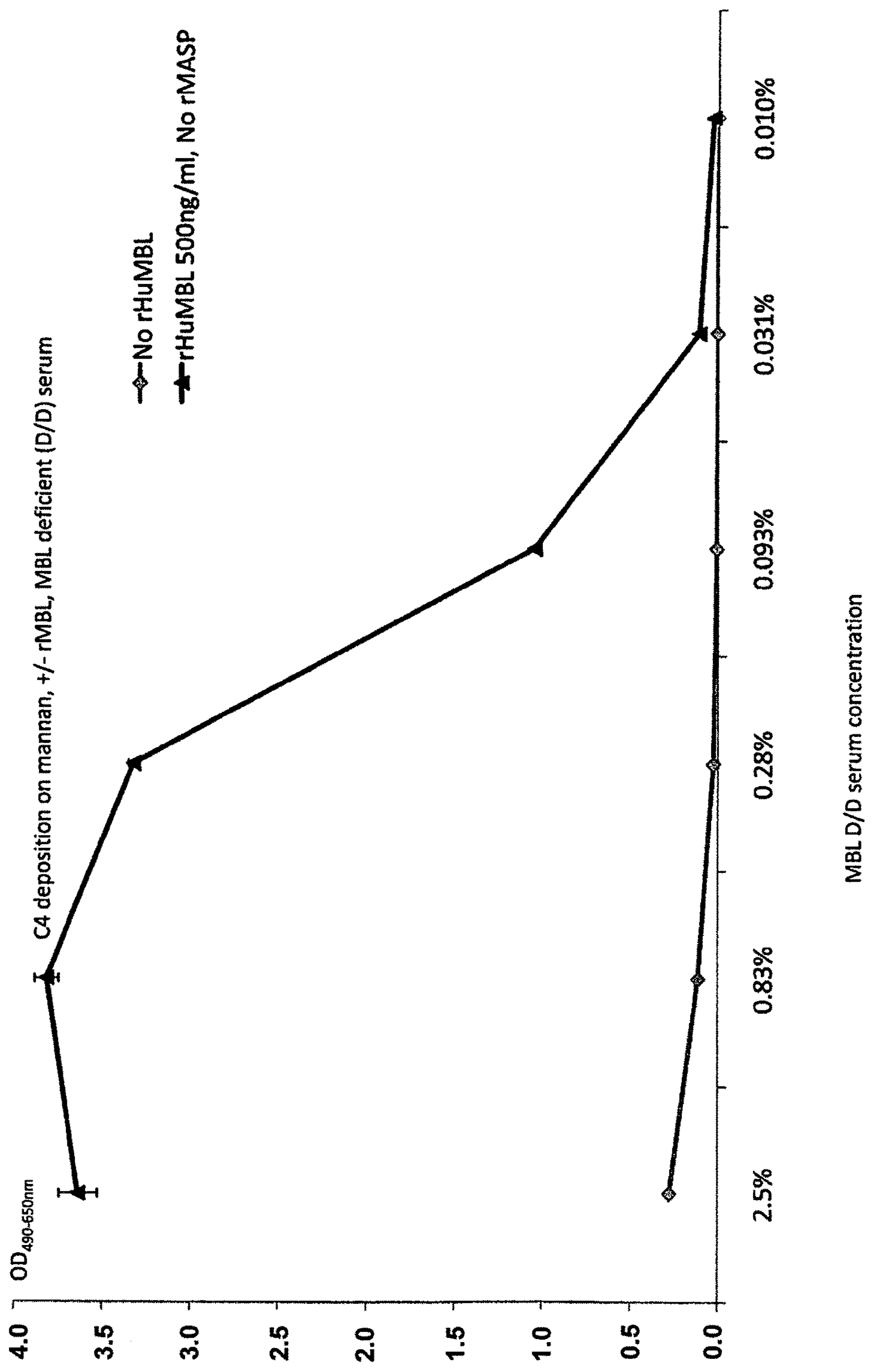

FIG. 13: Complement activation of C4 in a mannan/MBL ELISA assay. Mannan coated wells were incubated with or without recombinant human MBL followed by incubation with MBL homozygous deficient serum in serial dilutions. The C4 deposition was measured using polyclonal anti C4c antibodies. Error bars indicate two times the standard deviations on double determinations of each point on the curves.

Figure 14:
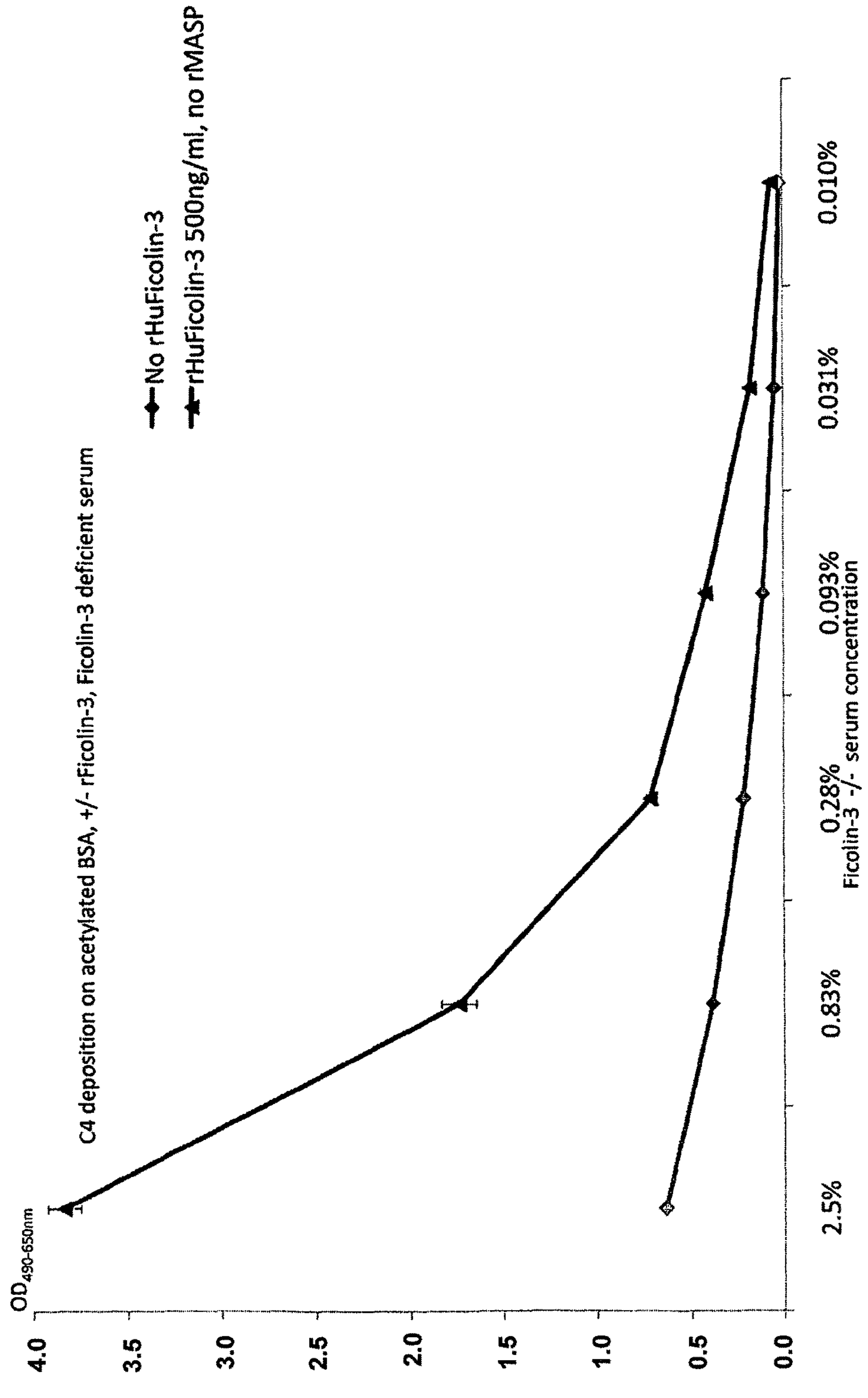

FIG. 14: Complement activation of C4 in an acetylated BSA/Ficolin-3 ELISA assay. AcBSA coated wells were incubated with or without recombinant human Ficolin-3 followed by incubation with Ficolin-3 homozygous deficient serum in serial dilutions. The C4 deposition was measured using polyclonal anti C4c antibodies. Error bars indicate two times the standard deviations on double determinations of each point on the curves.

Figure 15:
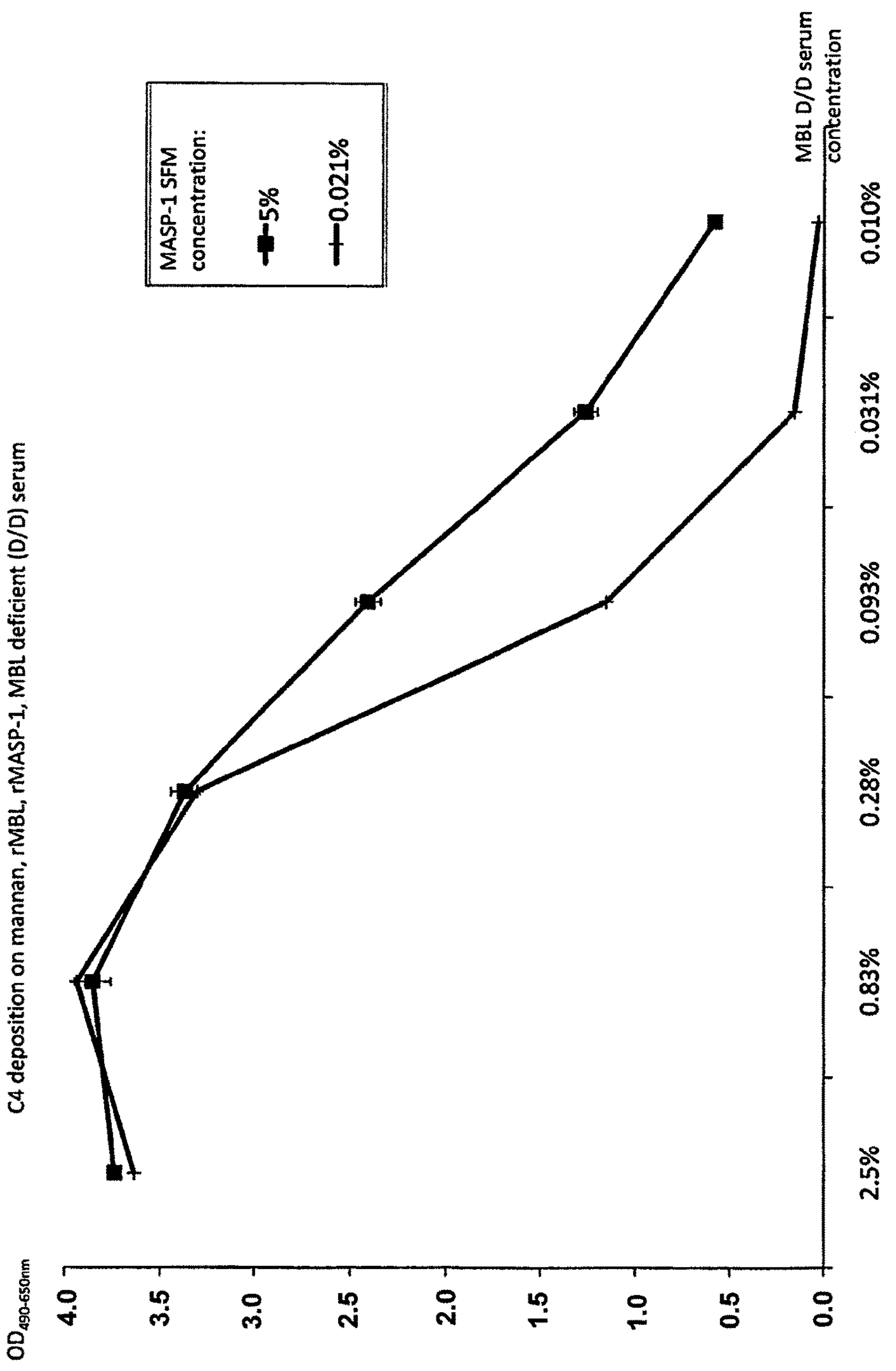

FIG. 15: Complement activation of C4 in a mannan/MBL ELISA assay. Mannan coated wells were incubated with recombinant human MBL followed by incubation with serial dilutions of rMASP-1 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 16:
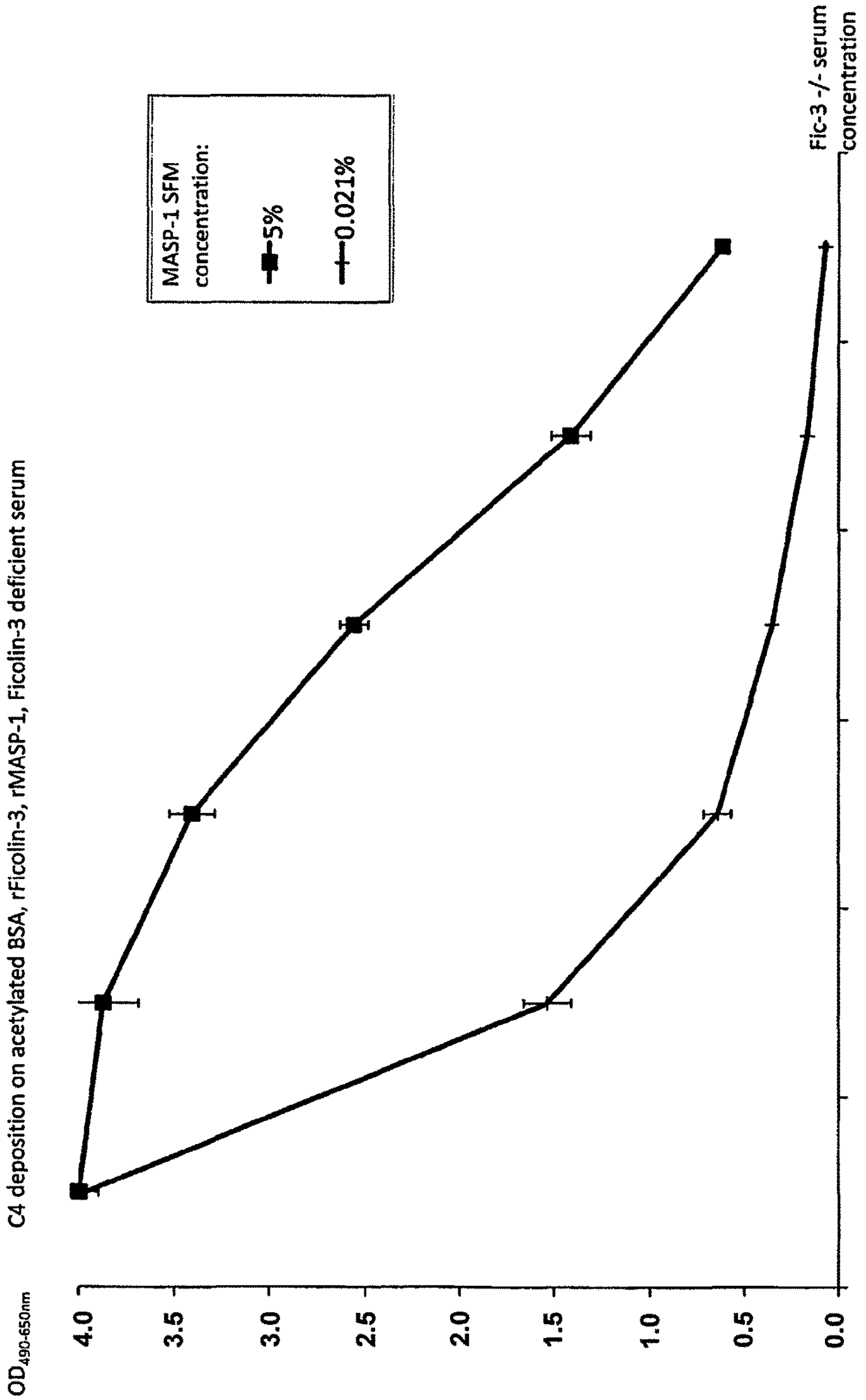

FIG. 16: Complement activation of C4 in an AcBSA/Ficolin-3 ELISA assay. AcBSA coated wells were incubated with recombinant human Ficolin-3 followed by incubation with serial dilutions of rMASP-1 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 17:
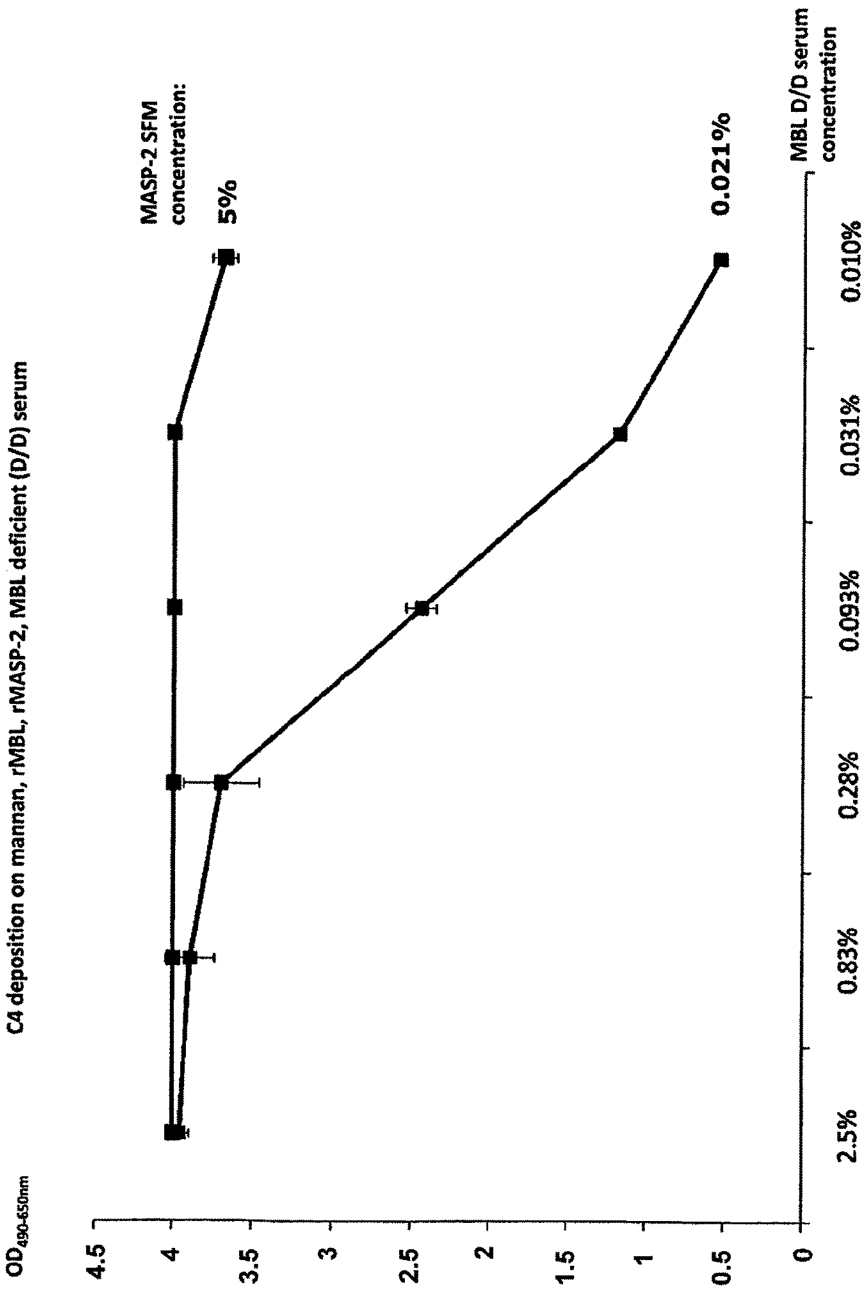

FIG. 17: Complement activation of C4 in a mannan/MBL ELISA. Mannan coated wells were incubated with recombinant human MBL followed by incubation with serial dilutions of rMASP-2 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 18:
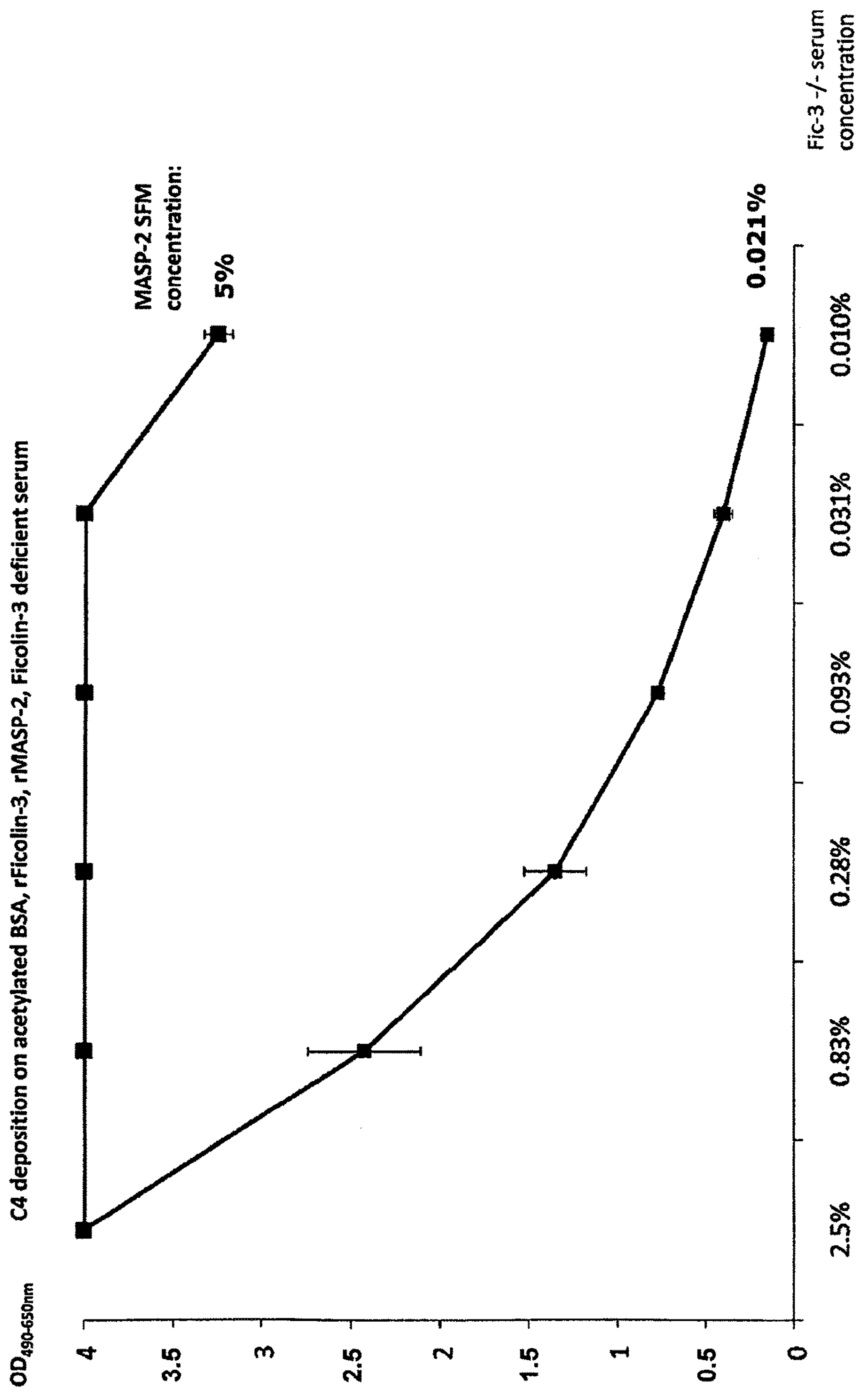

FIG. 18: Complement activation of C4 in an AcBSA/Ficolin-3 ELISA assay. AcBSA coated wells were incubated with recombinant human Ficolin-3 followed by incubation with serial dilutions of rMASP-2 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 19:
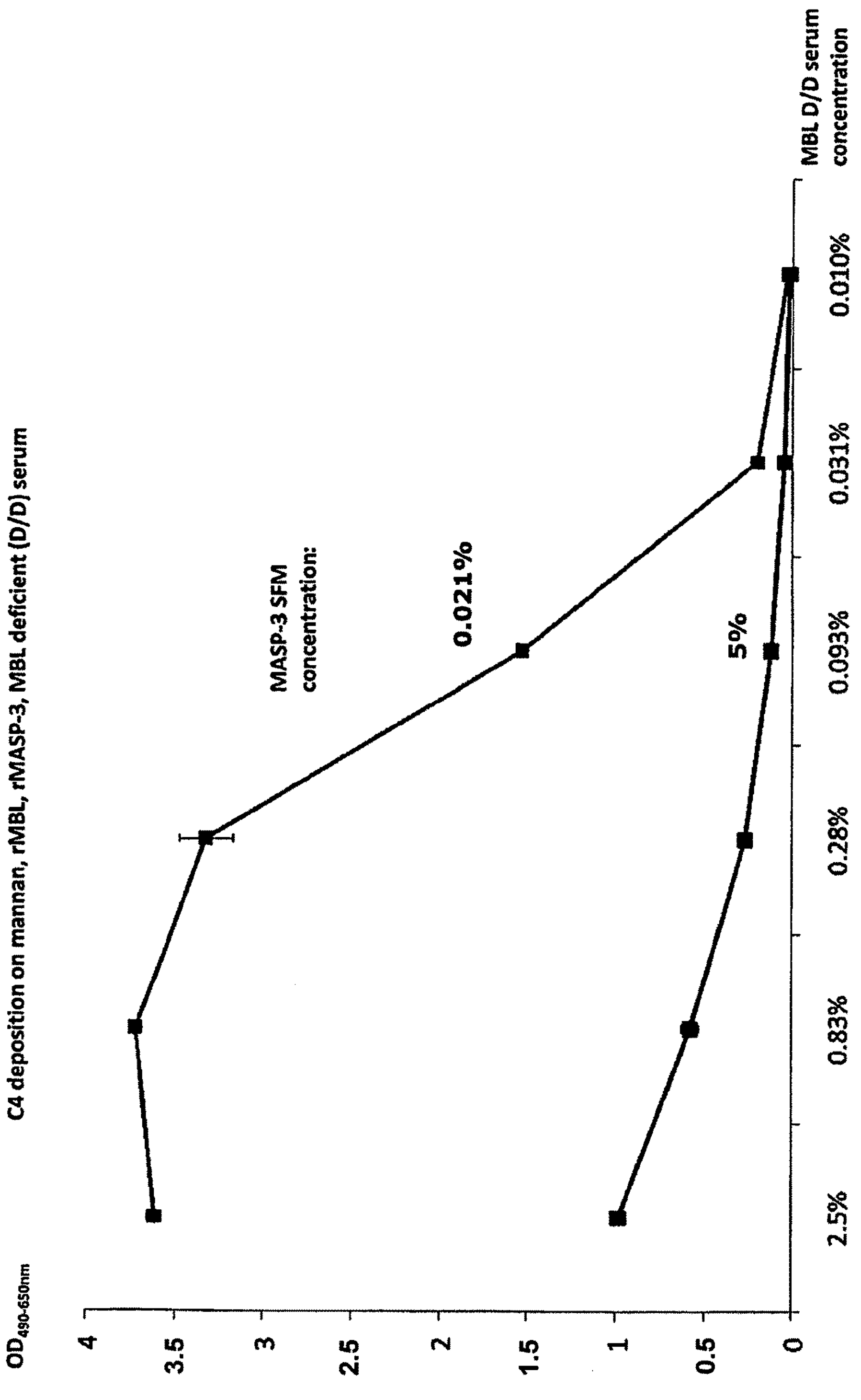

FIG. 19: Complement activation of C4 in a mannan/MBL ELISA assay. Mannan coated wells were incubated with recombinant human MBL followed by incubation with serial dilutions of rMASP-3 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 20:
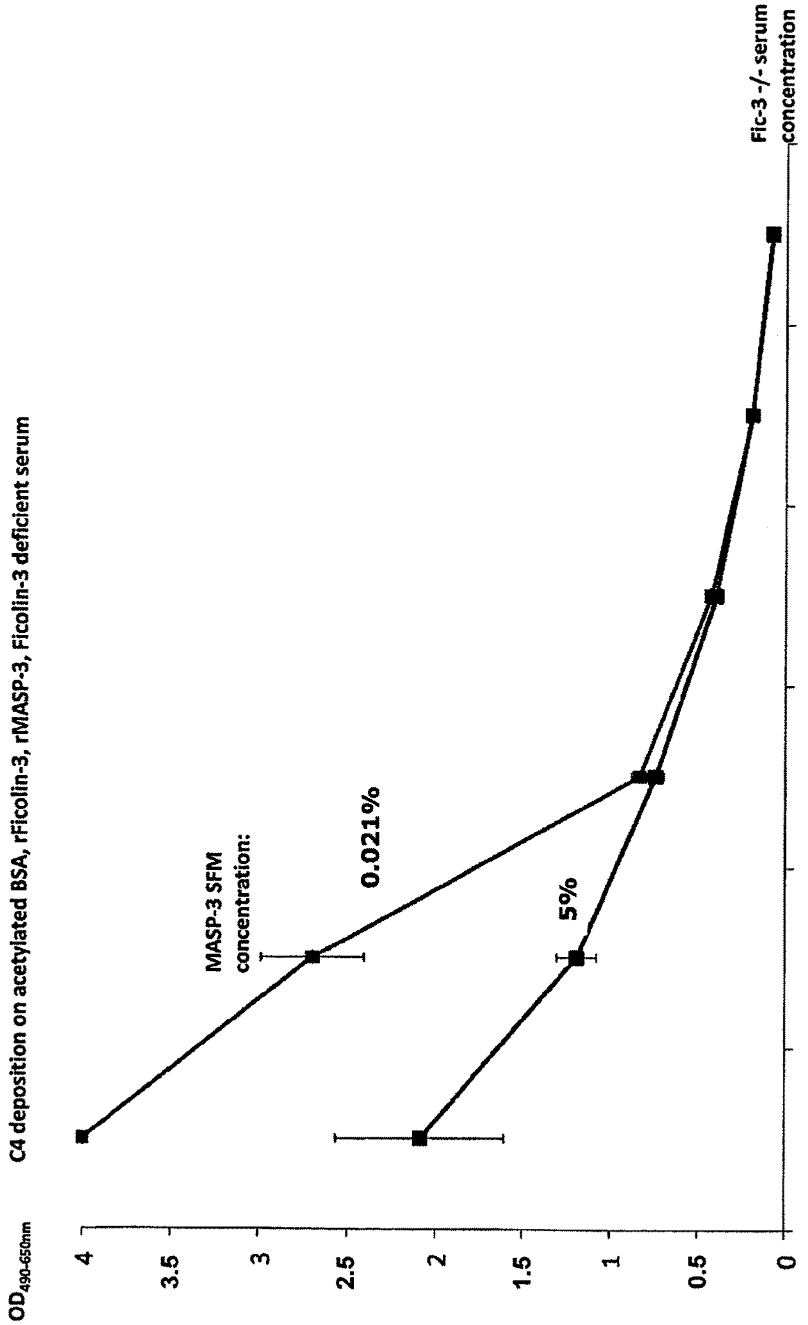

FIG. 20: Complement activation of C4 in an AcBSA/Ficolin-3 ELISA assay. AcBSA coated wells were incubated with recombinant human Ficolin-3 followed by incubation with serial dilutions of rMASP-3 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 21:
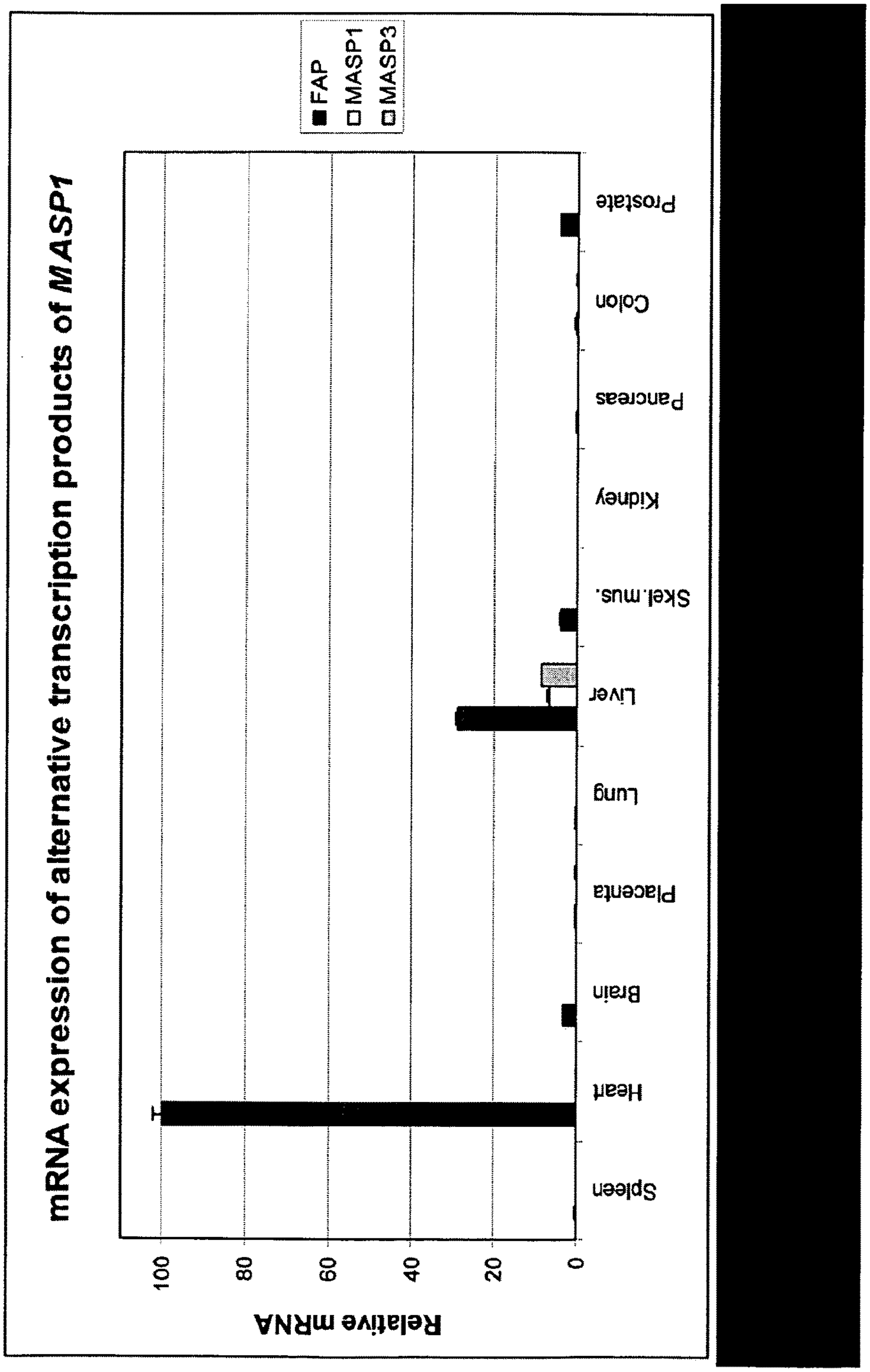

FIG. 21: Tissue distribution of FAP, MASP1 and MASP3. FAP was expressed much higher in the heart tissue compared to MASP1 and MASP3. FAP was expressed three times higher in the heart tissue compared to the FAP expression in liver. Furthermore, a higher FAP expression was observed in the liver compared to the MASP1 and MASP3 expression in the liver. Considerable FAP expression was also detected in brain, skeletal muscle and prostate tissues. The experiment was performed three times in duplicates. Standard error of the mean are indicated.

Figure 22:
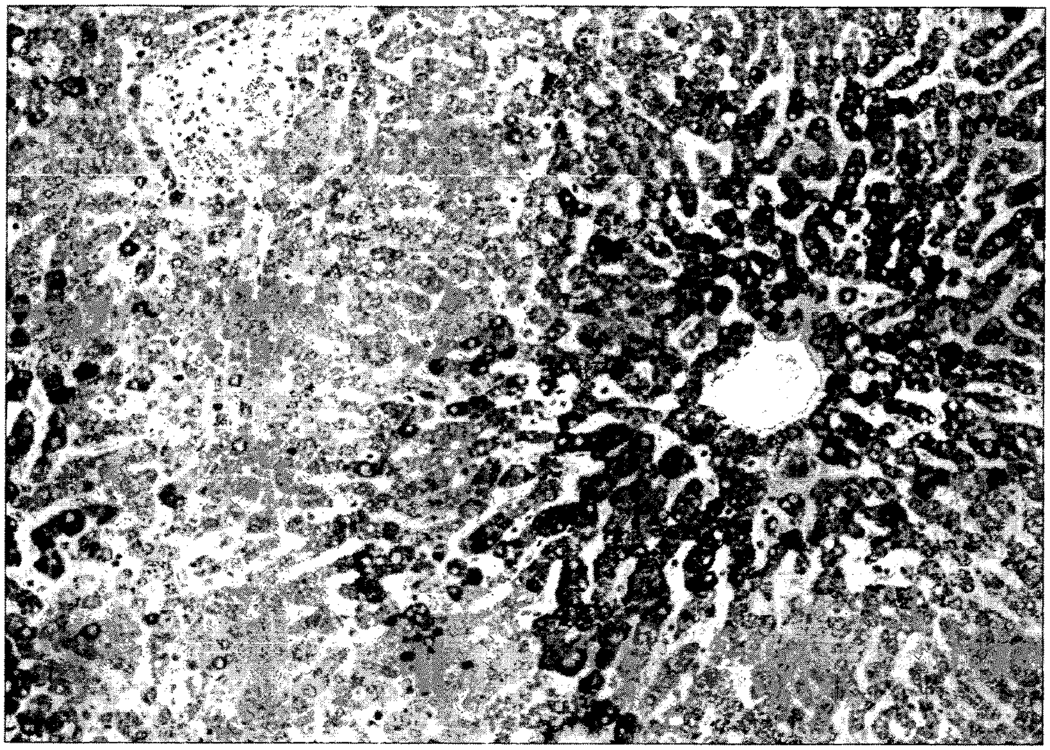

FIG. 22: Immunohistochemical liver localization of MAP-1 using polyclonal mouse antiserum raised against the 17 FAP specific C-terminal residues of the Protein. Control staining was negative. Several different polyclonal antibodies raised against FAP (rabbit and mouse) showed the same pattern staining.

Figure 23:
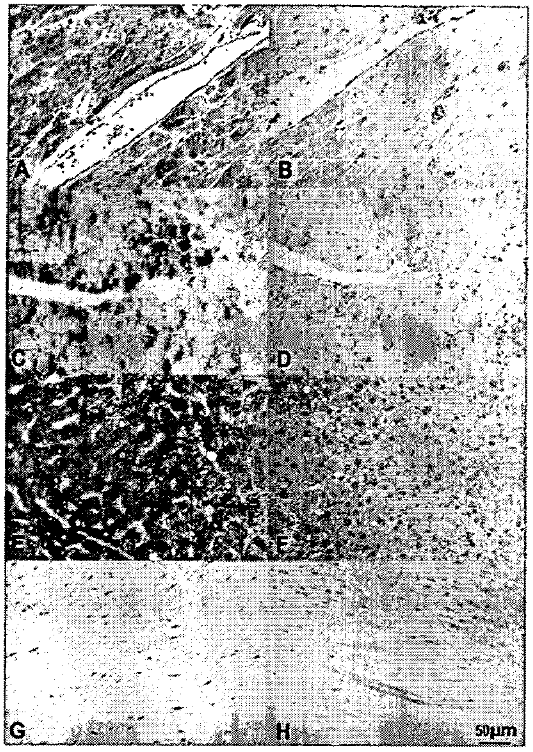

FIG. 23: Immunohistochemical analysis of MAP-1 tissue localization (OM X10). Left panel shows staining with a mAb (12B11) to MAP-1. Right panel shows the isotype control staining with a non-related IgG1k mAb. (A-B): Myocardium, (C-D): Skeletal muscle, (E-F): Liver sample, (G-H): Aortic tissue. Bottom right corner bar indicates 50 μm on all slides.

Figure 24:
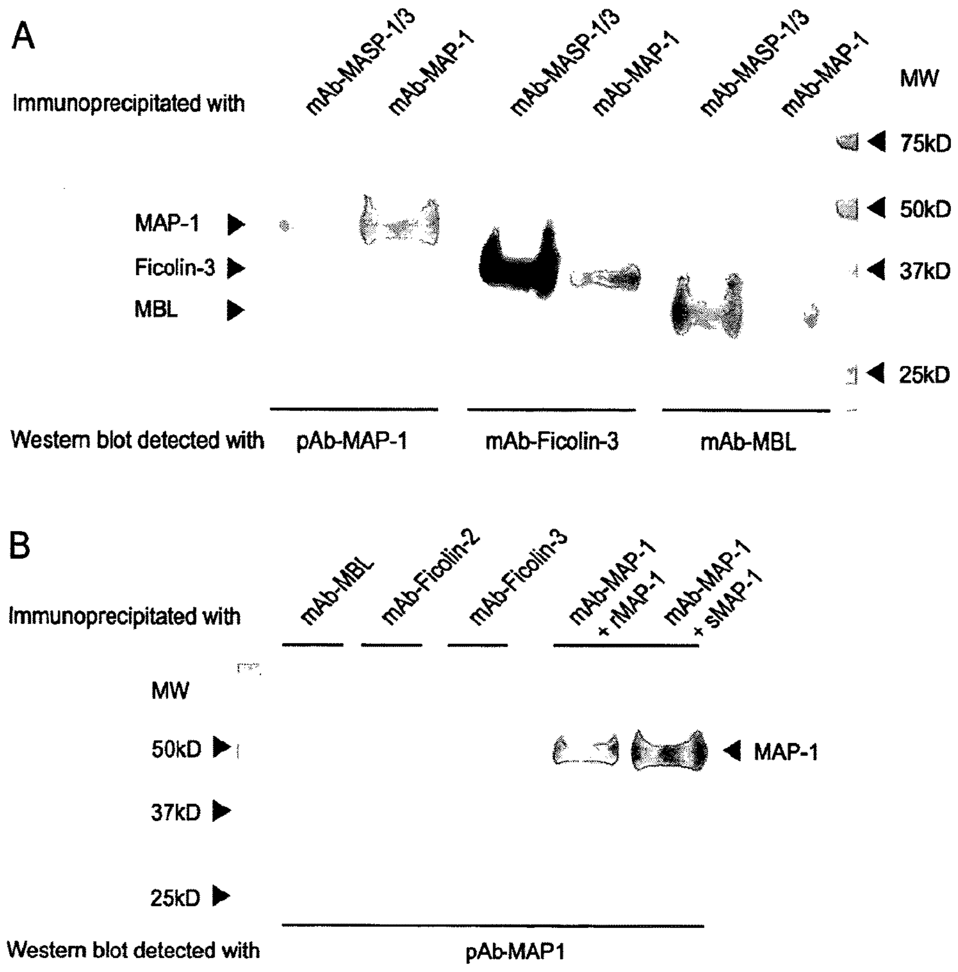

FIG. 24: Immunoprecipitation of MAP-1 and MASP-1/3 serum complexes. (A) MAP-1 and MASP-1/3 was immunoprecipitated from serum using mAb 20C4 (anti MAP-1) and mAb 8B3 (anti MASP-1/3, with an epitope on the common heavy chain). Reduced samples were electro-blotted and developed with pAb to MAP-1 or biotinylated mAbs to Ficolin-3 (FCN334) and MBL (Hyb 131-1). (B) Immunoprecipitation with mAbs to MBL (Hyb 131-11), Ficolin-2 (FCN219) and Ficolin-3 (FCN334) from 1 ml, 300 μl and 100 μl serum, respectively (Left side). Controls were MAP-1 precipitated from serum (sMAP-1) and rMAP-1 from culture supernatant (rMAP-1) using anti MAP-1 mAb 20C4 (right side). The samples were analyzed by western blotting probed with pAb to MAP-1.

Figure 25A:
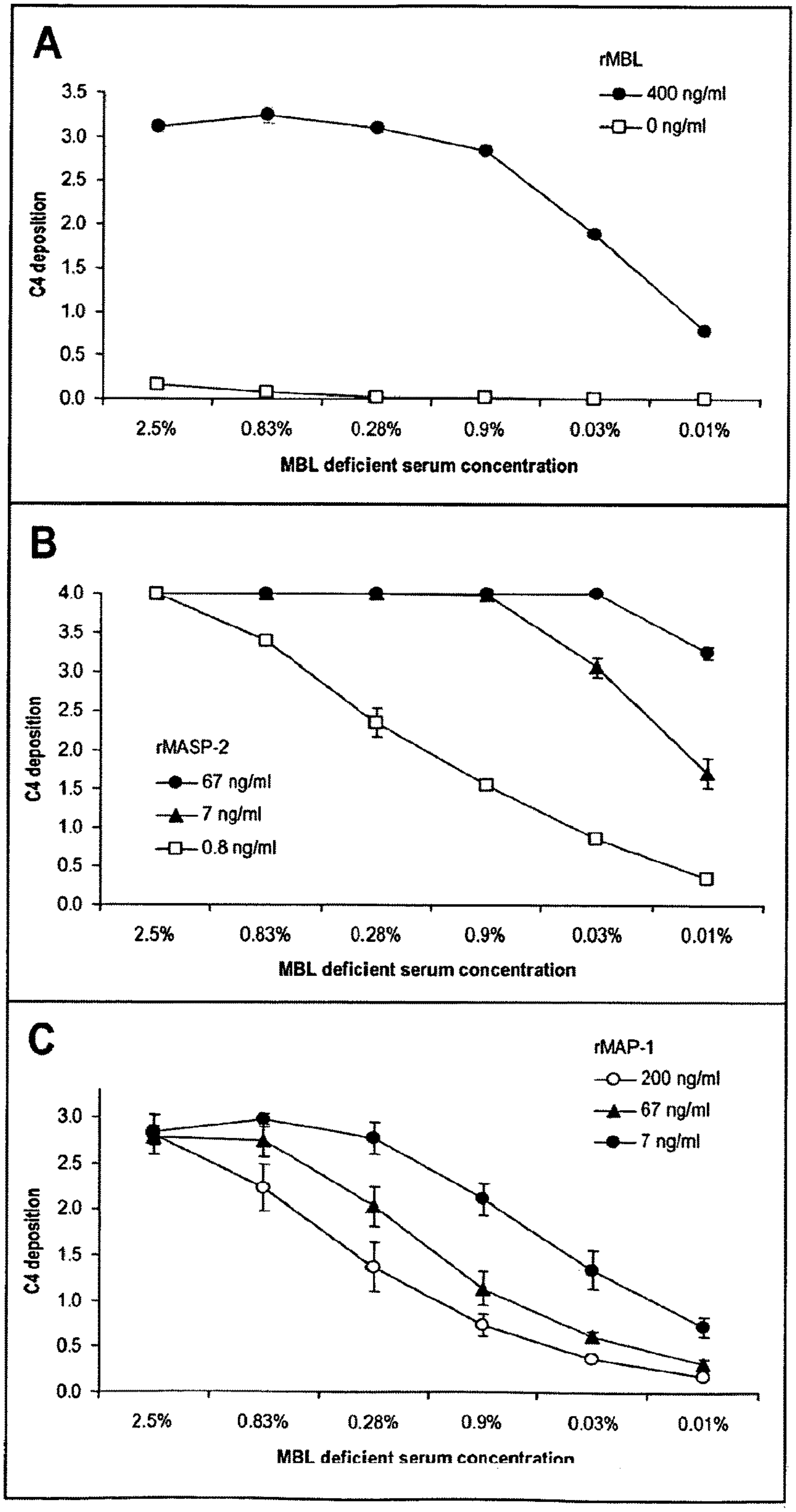
Figure 25B:
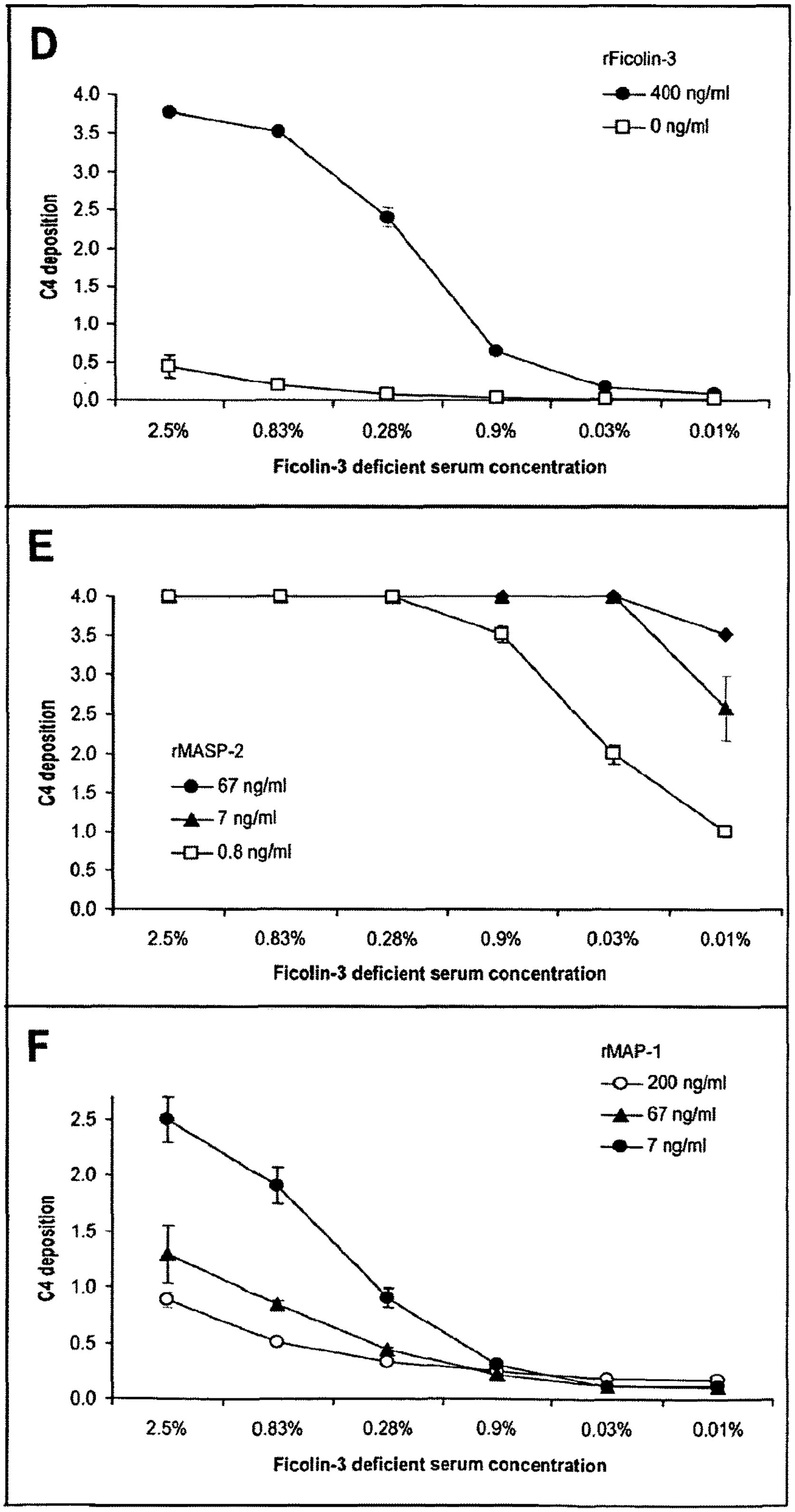

FIGS. 25A and 25B: Influence of MASP-2 and MAP-1 on MBL and Ficolin-3 mediated complement C4 deposition. The C4 depositions were measured using a polyclonal antibody to C4 and are given as $OD_{490\text{-}650\ nm}$ values. Error bars indicate two times the standard deviation of double determinations. Approximated concentrations of rMBL, rFicolin-3. rMAP-1 and rMASP-2 are given in the figure labels. FIG. 25A (A) Reconstitution of the C4 deposition on a mannan coated surface using MBL deficient serum with rMBL at 400 ng/ml. Control was without addition of rMBL. FIG. 25A (B) Dose dependent effect of rMASP-2 on the rMBL mediated C4 deposition. FIG. 25A (C) Dose dependent effect of rMAP-1 on the rMBL mediated C4 deposition. FIG. 25B (D) Reconstitution of the C4 deposition on an AcBSA coated surface using Ficolin-3 deficient serum with rFicolin-3 at 400 ng/ml. Control was without addition of rFicolin-3. FIG. 25B (E) Dose dependent effect of rMASP-2 on the rFicolin-3 mediated C4 deposition. FIG. 25B (F) Dose dependent effect of rMAP-1 on the rFicolin-3 mediated C4 deposition.

Figure 26:
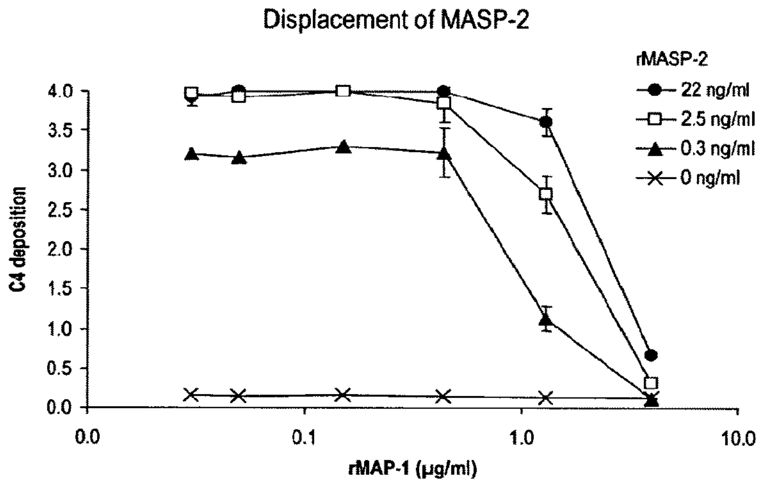

FIG. 26: Influence of MASP-2 and MAP-1 on the complement C4 deposition in a pure system. rMBL on a mannan surface was preincubated with serial dilutions of rMASP-2 in the first dimension. Serial dilutions of rMAP-1 were then applied in the second dimension followed by application of purified C4 at 1 μg/ml. The C4 depositions were measured with a pAb to C4 and are given as $OD_{490\text{-}650\ nm}$ values. Error bars indicate two times the standard deviation of double determinations. Approximated concentrations of rMAP-1 and rMASP-2 are given in the figure labels.

Figure 27:
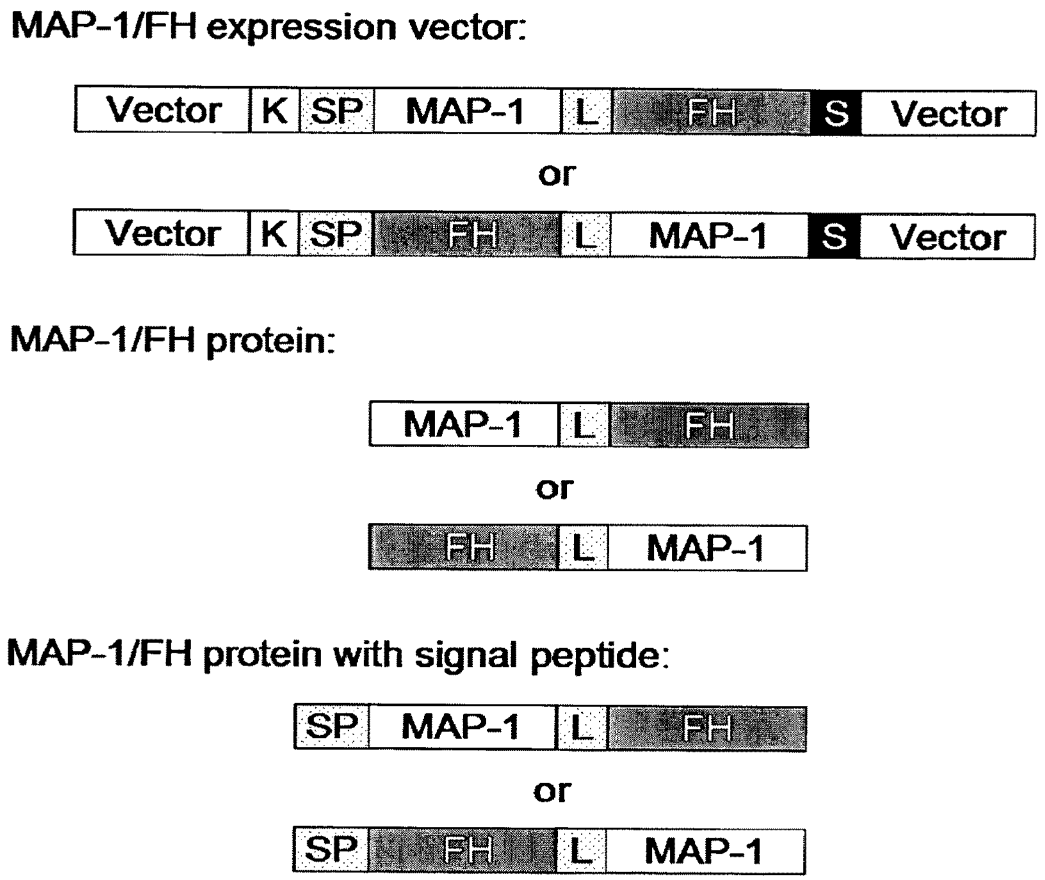

FIG. 27: Schematic diagram of an exemplary MAP-1/FH or FH/MAP-1 expression vector and chimeric constructs of MAP-1/FH or FH/MAP-1 protein. The chimeric expression plasmids contain a Kozak sequence (K), optional linker (L) and a stop codon (S). The vectors may also contain an optional signal peptide (SP).

Figure 28:
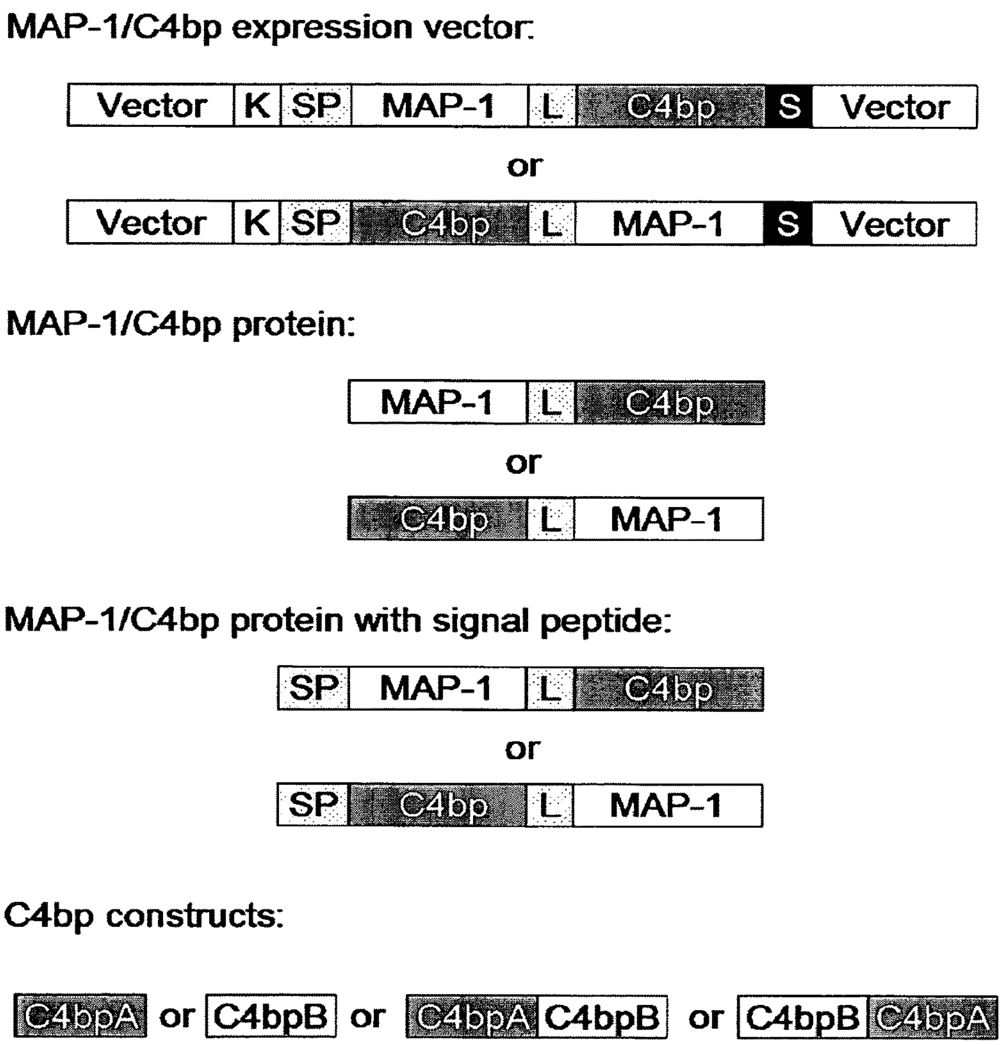

FIG. 28: Schematic diagram of an exemplary MAP-1/C4bp or C4bp/MAP-1 expression vector and chimeric constructs of MAP-1/C4bp or C4bp/MAP-1 protein. The chimeric expression plasmids contain a Kozak sequence (K), optional linker (L) and a stop codon (S). The vectors may also contain an optional signal peptide (SP). C4bp may be composed of either C4bp alfa chain (C4bpA) or C4bp beta chain (C4bpB) alone, or combination of the two chains.

Figure 29:
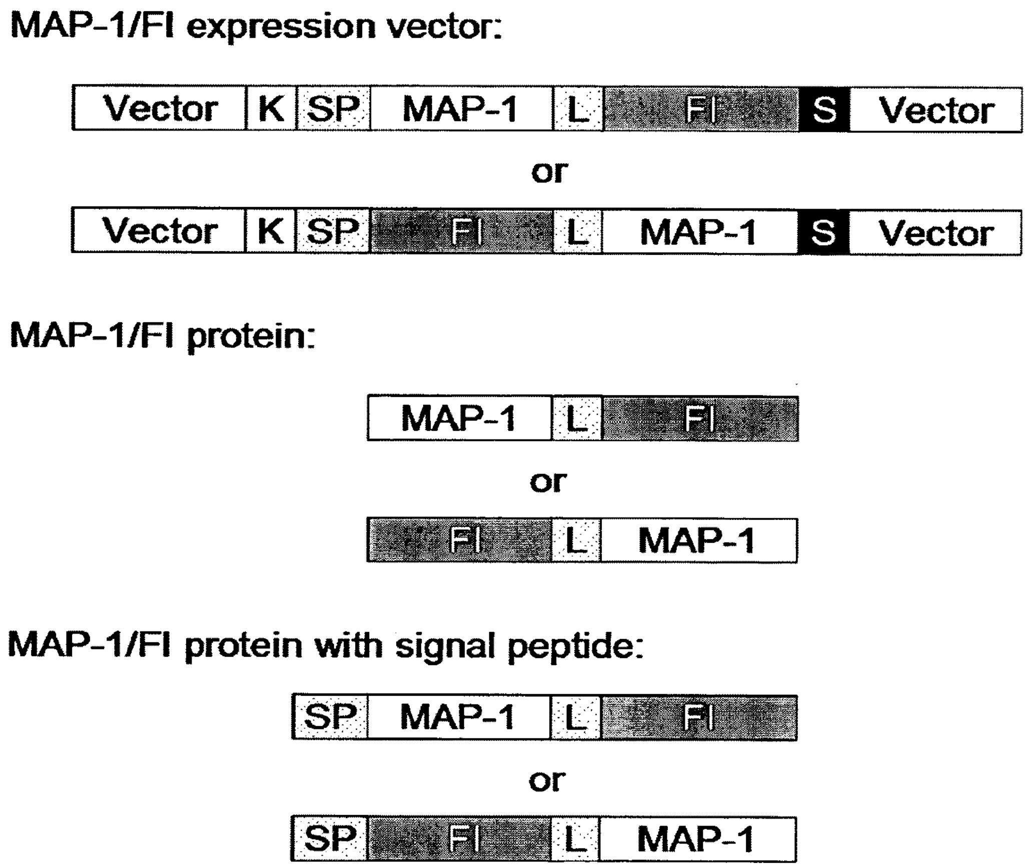

FIG. 29: Schematic diagram of an exemplary MAP-1/FI or FI/MAP-1 expression vector and chimeric constructs of MAP-1/FI or FI/MAP-1 protein. The chimeric expression plasmids contain a Kozak sequence (K), optional linker (L) and a stop codon (S). The vectors may also contain an optional signal peptide (SP).

Figure 30:
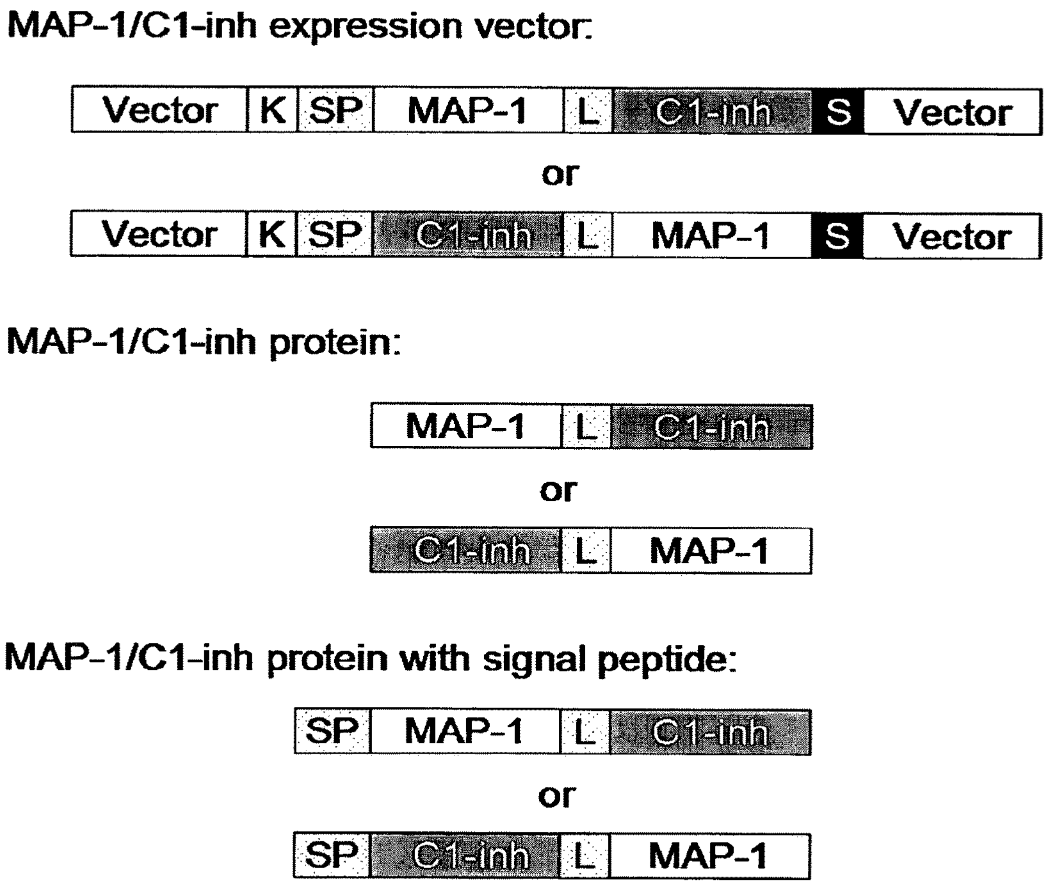

FIG. 30: Schematic diagram of an exemplary MAP-1/C1-inh or C1-inh/MAP-1 expression vector and chimeric constructs of MAP-1/C1-inh or C1-inh/MAP-1 protein. The chimeric expression plasmids contain a Kozak sequence (K), optional linker (L) and a stop codon (S). The vectors may also contain an optional signal peptide (SP).

Figure 31:
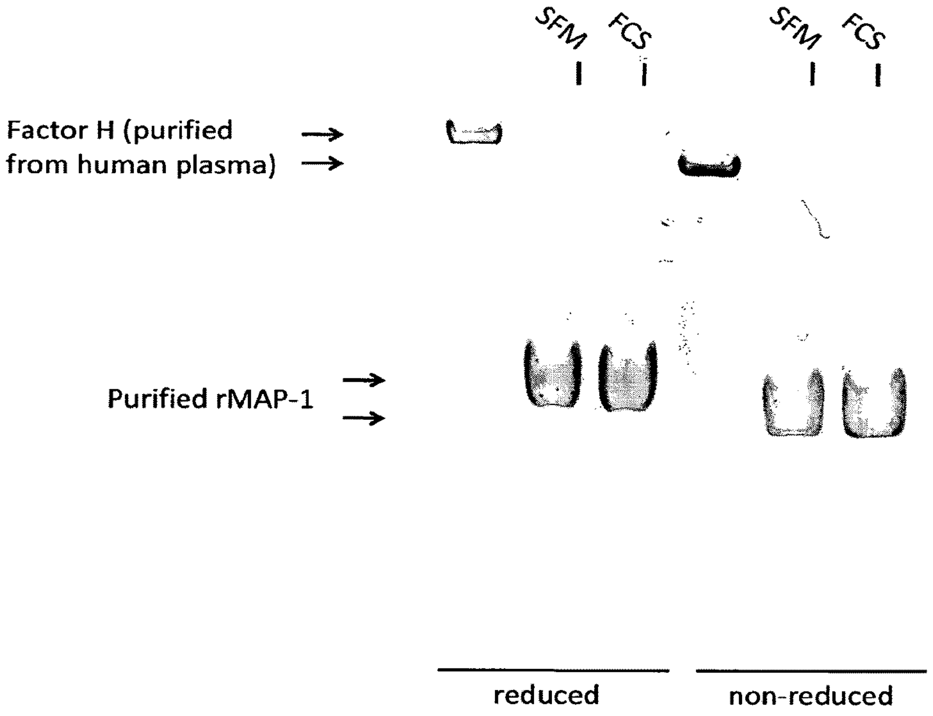

FIG. 31: Purified rMAP-1 and plasma Factor H in 4-12% Bis-Tris SDS-PAGE, Coomassie Brilliant Blue staining analysis of purified plasma Factor H and recombinant MAP-1 (from serum-free medium/SFM or medium with 10% fetal calf serum/FCS).

Figure 32:
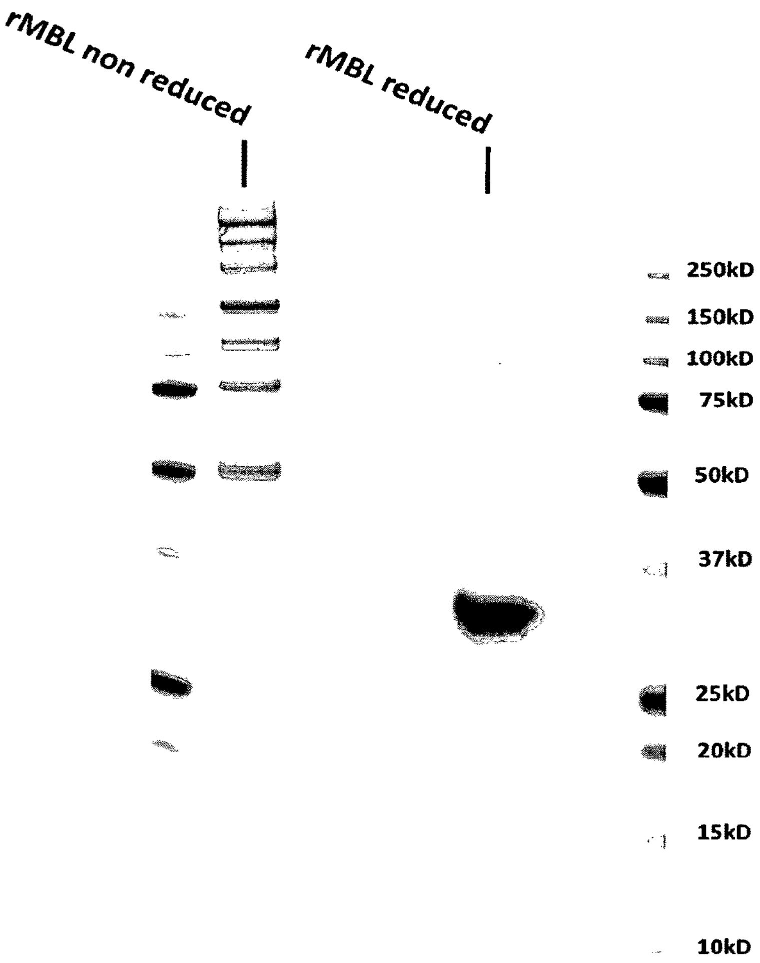

FIG. 32: Purified rMBL (SFM) in 4-12% Bis-Tris SDS-PAGE, Coomassie Brilliant Blue staining analysis of purified recombinant MBL (from serum-free medium/SFM).

Figure 33:
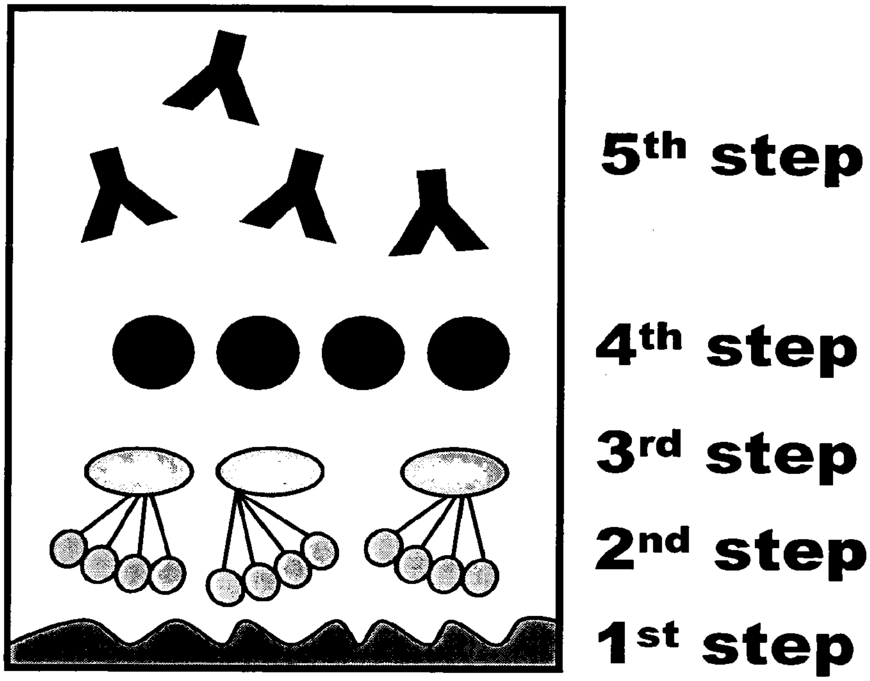

FIG. 33: MBL assay setup overview; Complement assay composition with included steps. Between each step are included three times washing/blocking. 1st step: Coating with Mannan; 2nd step: Application of rMBL, 400 ng/ml; 3rd step: Application of rMAP-1, fH or rMAP-1/fH hybrid in 1st dimension; 4th step: Application of MBL deficient serum (D/D) in 2nd dimension; 5th step: Measurement of C3 or C9 deposition, monoclonal antibodies to C3 or C9.

Figure 34:
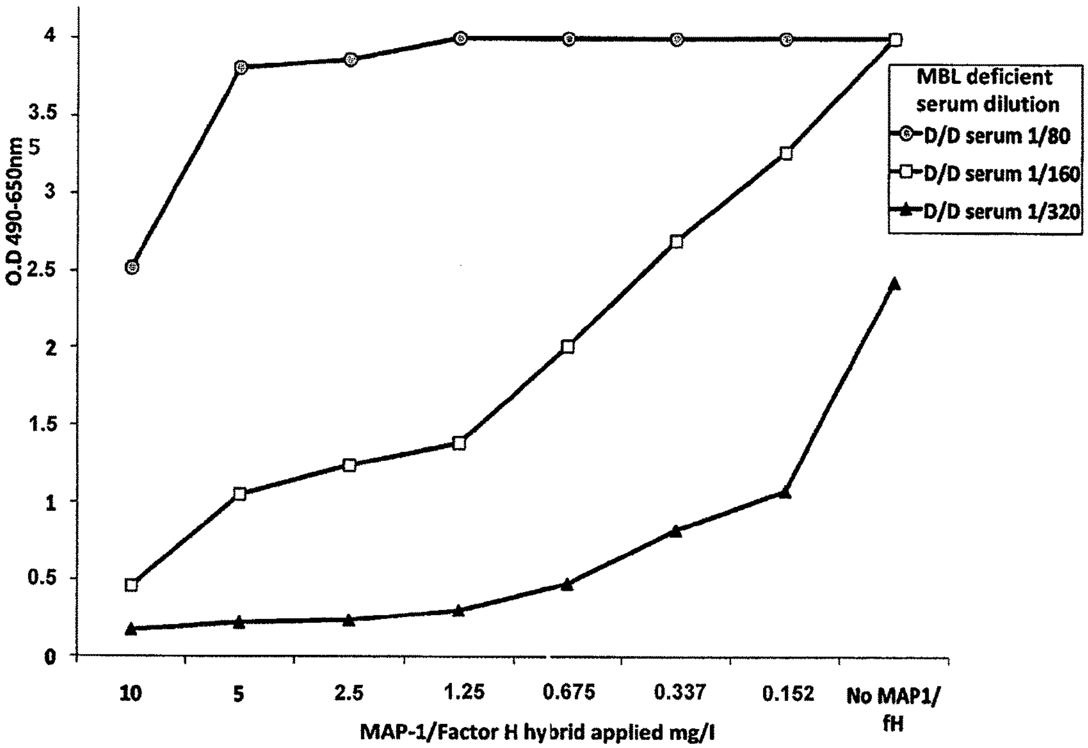

FIG. 34: MAP-1/Factor H hybrid molecule impact on the MBL mediated C3 deposition; Dose-dependent inhibition of complement C3 by a MAP-1/Factor H hybrid molecule.

Figure 35A:
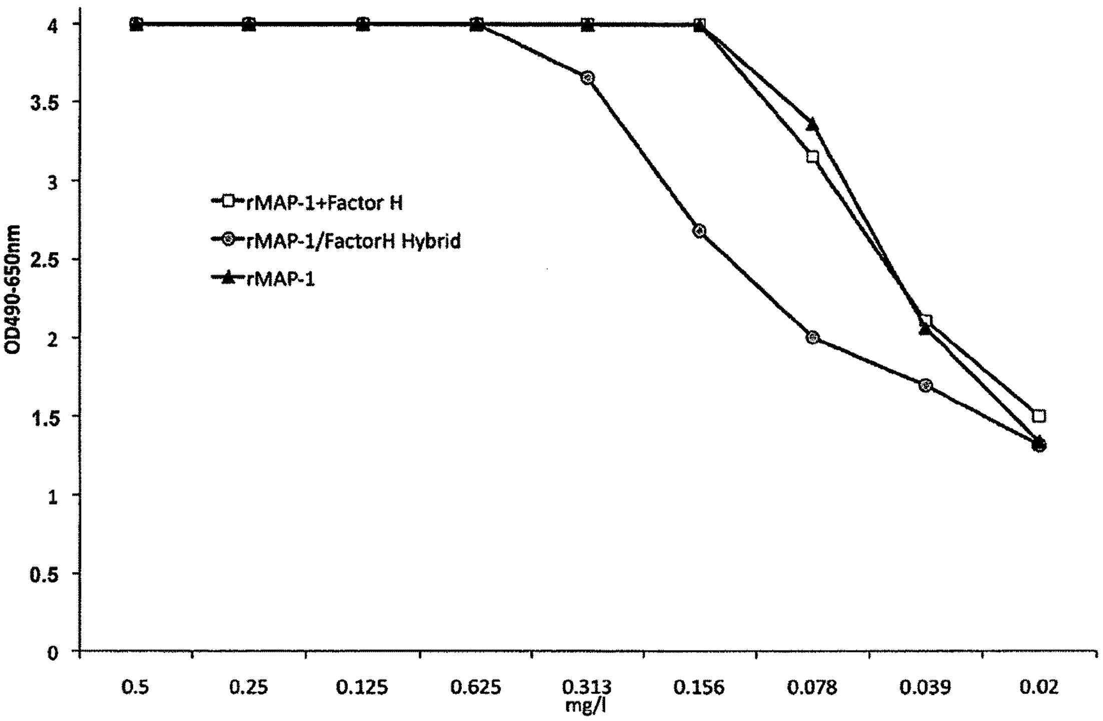

FIG. 35A: rMAP-1 (SFM) association to rMBL bound to mannan; Detection of MAP-1 association with rMBL bound to mannan. Binding of rMAP-1, rMAP-1 with "free" Factor H and rMAP-1/Factor H Hybrid is detected with a monoclonal antibody to MAP-1.

Figure 35B:
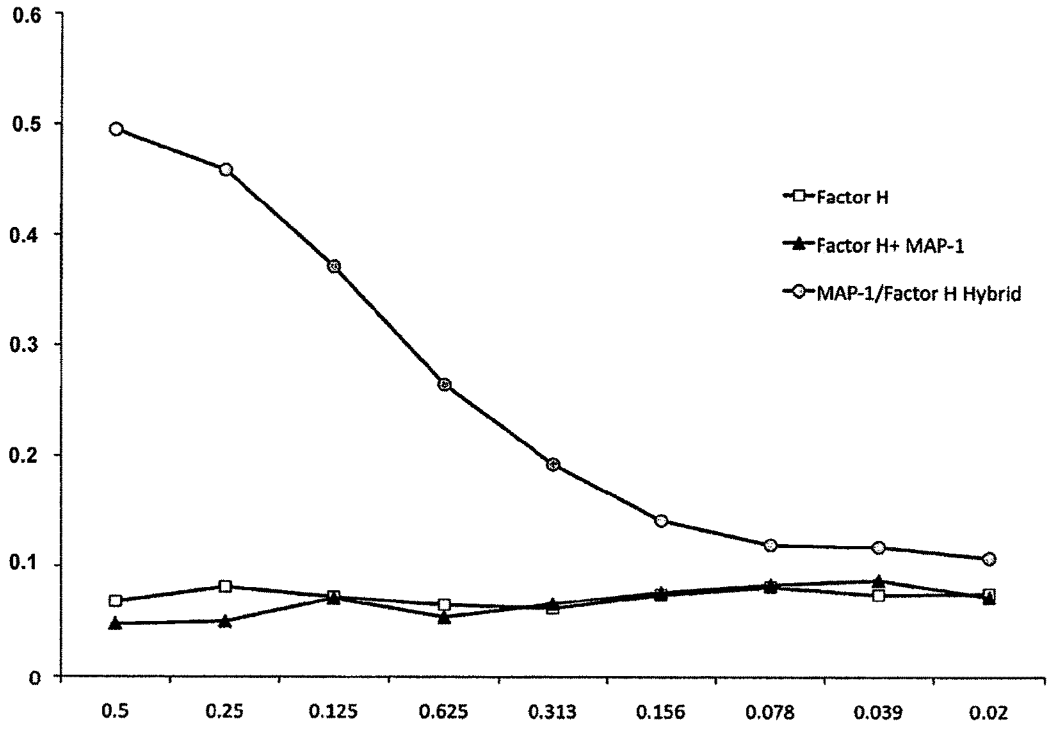

FIG. 35B: Detection of Factor H association with rMBL bound to mannan. Binding of Factor H, rMAP-1 with "free" Factor H and rMAP-1/Factor H Hybrid is detected with a monoclonal antibody to Factor H.

Figure 36A:
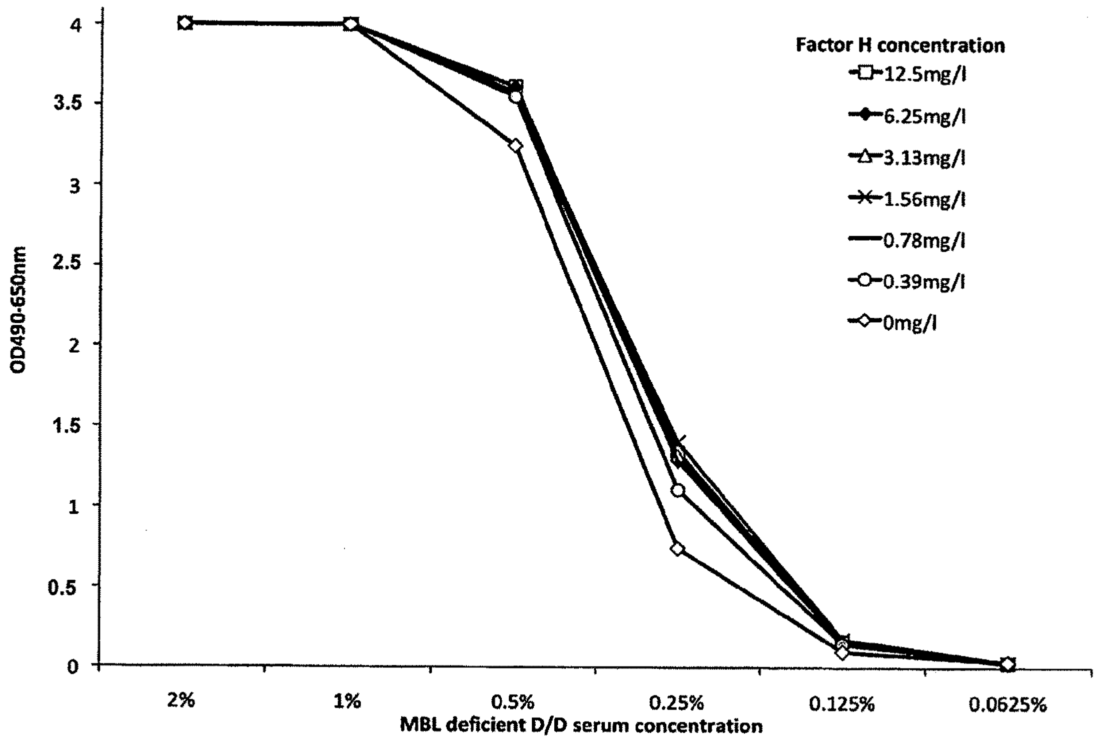

FIG. 36A: Factor H impact on the MBL mediated C3 deposition; Dose-dependent inhibition of the MBL mediated complement C3 by purified "free" Factor H.

Figure 36B:
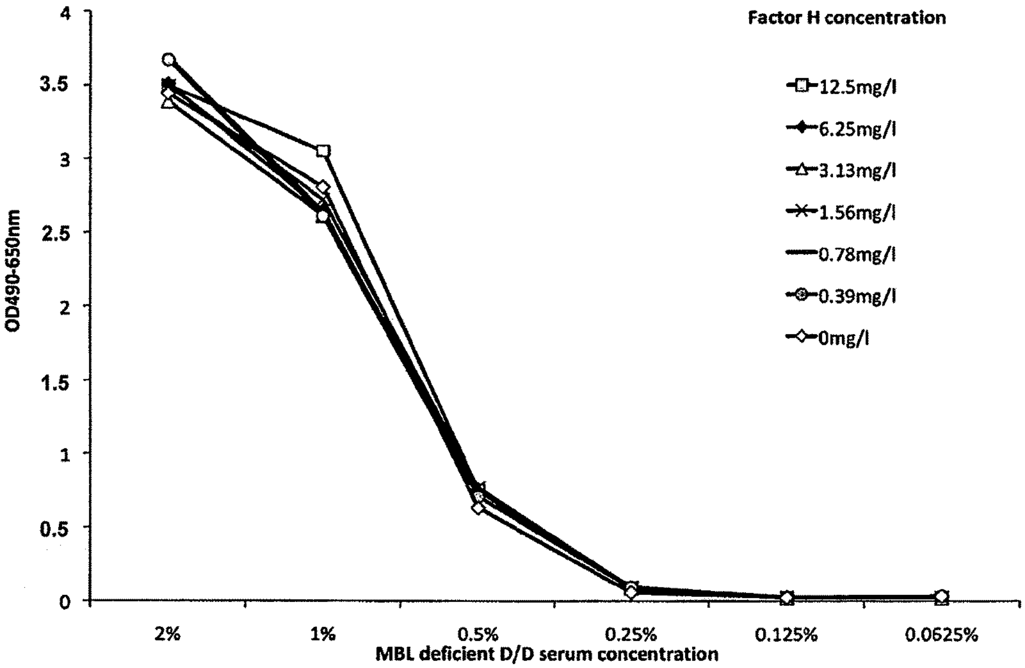

FIG. 36B: Factor H impact on the MBL mediated C9 deposition (TCC); Dose-dependent inhibition of the MBL mediated complement C9 (terminal complement complex/TCC) by purified "free" Factor H.

Figure 37A:
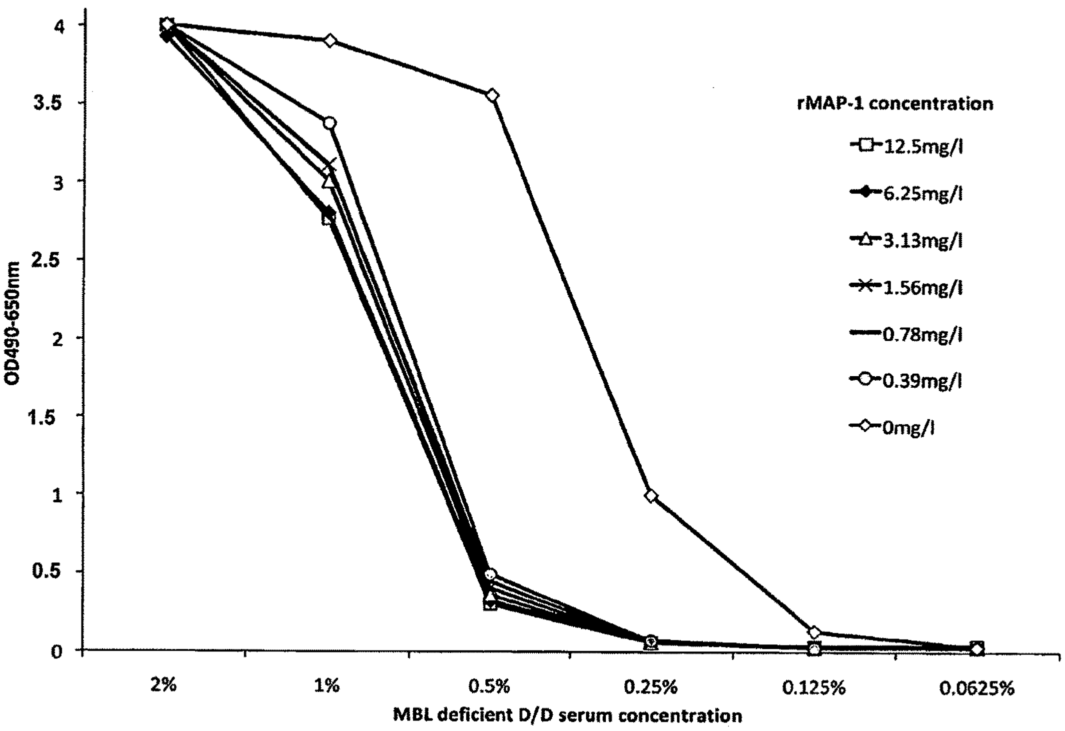

FIG. 37A: rMAP-1 impact on the MBL mediated C3 deposition; Dose-dependent inhibition of the MBL mediated complement C3 by purified recombinant MAP-1.

Figure 37B:
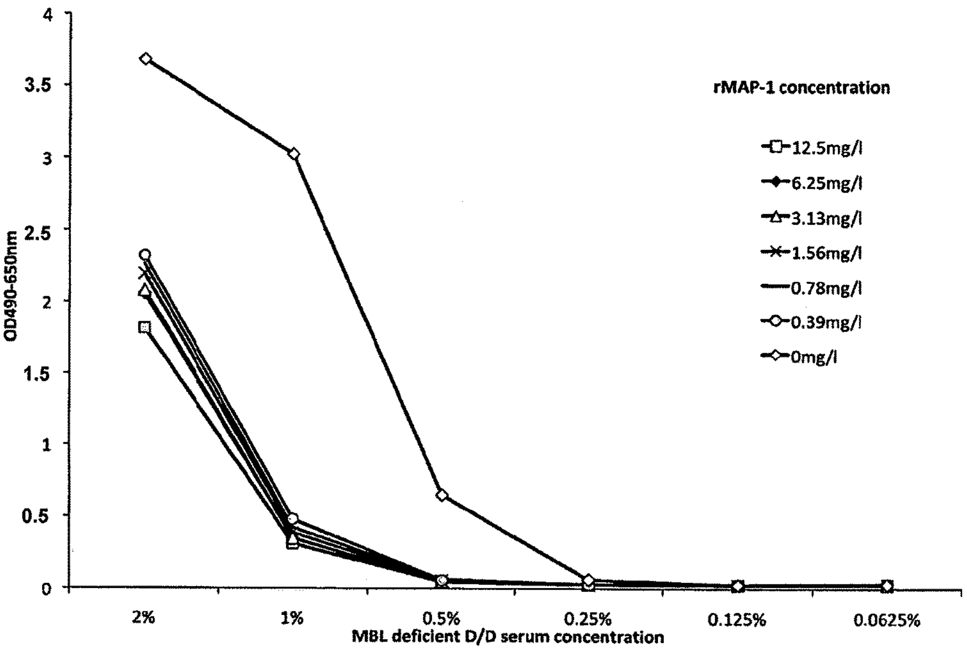

FIG. 37B: rMAP-1 impact on the MBL mediated C9 deposition (TCC); Dose-dependent inhibition of the MBL mediated complement C9 (terminal complement complex/TCC) by purified recombinant MAP-1.

Figure 38A:
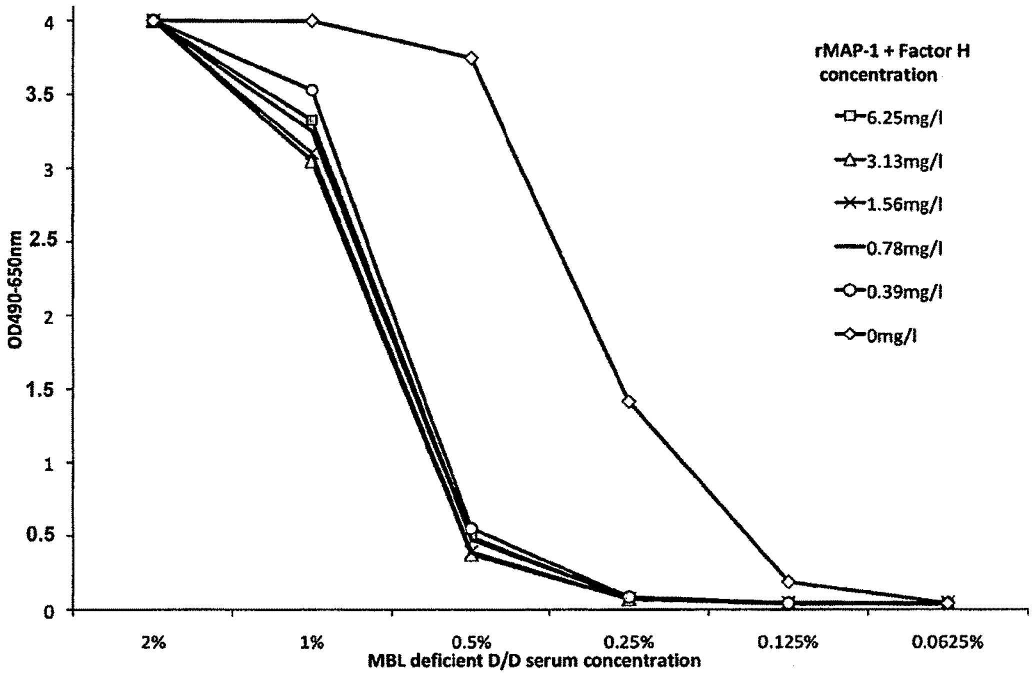

FIG. 38A: rMAP-1+Factor H impact on the MBL mediated C3 deposition; Dose-dependent inhibition of the MBL mediated complement C3 by recombinant MAP-1 and "free" Factor H.

Figure 38B:
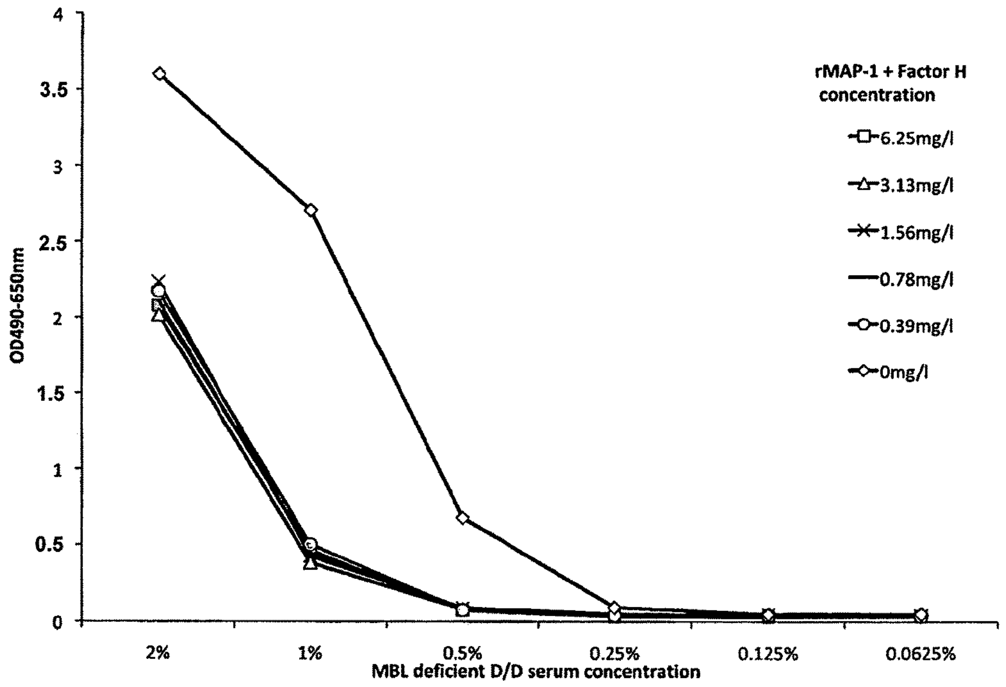

FIG. 38B: rMAP-1+Factor H impact on the MBL mediated C9 deposition (TCC); Dose-dependent inhibition of the MBL mediated complement C9 (terminal complement complex/TCC) by recombinant MAP-1 and "free" Factor H.

Figure 39A:
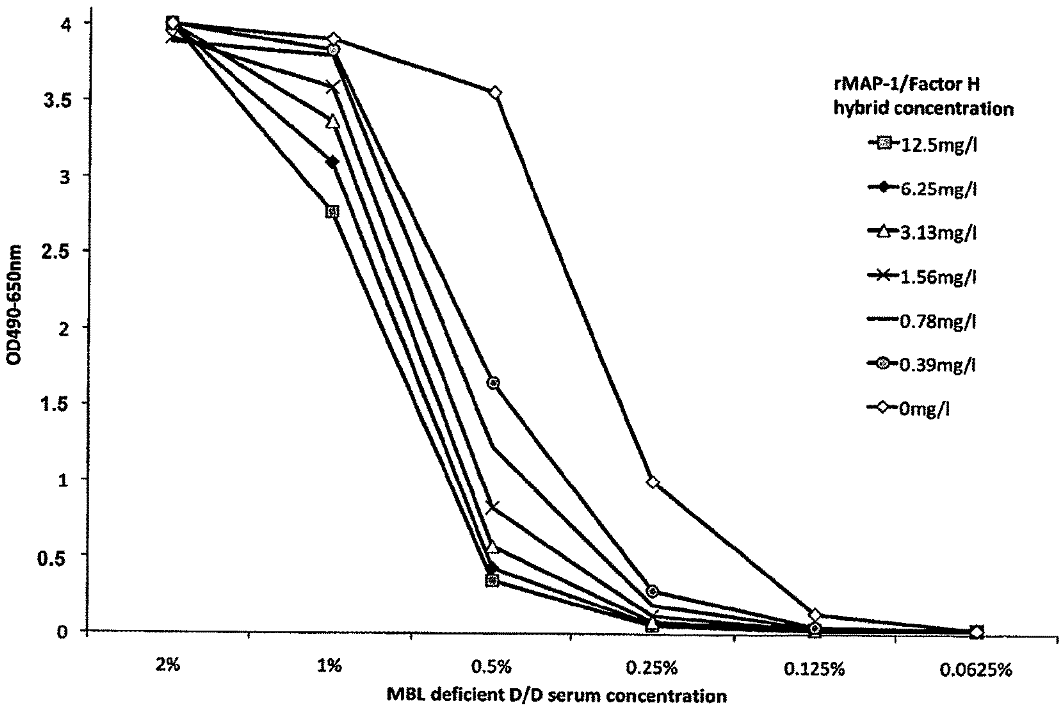

FIG. 39A: rMAP-1/Factor H hybrid impact on the MBL mediated C3 deposition; Dose-dependent inhibition of the MBL mediated complement C3 by rMAP-1/Factor H hybrid molecule.

Figure 39B:
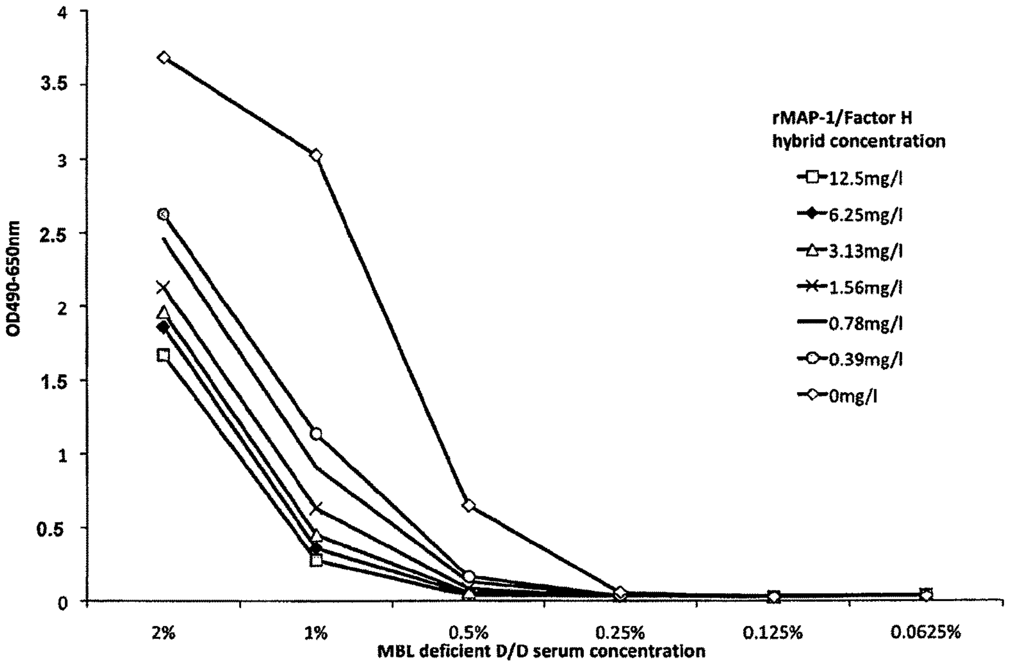

FIG. 39B: rMAP-1/Factor H hybrid impact on the MBL mediated C9 deposition (TCC); Dose-dependent inhibition of the MBL mediated complement C9 (terminal complement complex/TCC) by rMAP-1/Factor H hybrid molecule.

DETAILED DISCLOSURE OF THE INVENTION

The present inventors have discovered a novel plasma protein of 40 kDa associated with the recognition molecules of the lectin complement pathway and identified this as a new alternative transcript variant of MASP-1/MASP-3 that in turn corresponds to the newly discovered plasma protein.

The novel protein (by the inventors named FAP (Ficolin Associated Protein) or MAP-1 (MBL/Ficolin associated protein-1)) has been shown by the present inventors to lack an enzyme domain, but to contain the ficolin/MBL binding domain and is thus expected to be involved in regulation and inhibition of complement and coagulation functions through competitions and displacement of the MASPs or alternatively, but not mutually exclusive as a protein involved in scavenger or signaling functions.

Uncontrolled activation of the complement system and/or the coagulation cascade is strongly associated with fatal severe outcome in variety of diseases ranging from systemic inflammation and sepsis, through myocardial infarction and autoimmunity.

Inhibition of coagulation and complement activation has been shown to be a promising therapeutic tool.

MAP-1 is both a possible novel inhibitor of complement and of coagulation functions. However, the ficolin-associated polypeptides may have other functions, such as a scavenger and/or a signalling function. Moreover, they may be used as a biomarkers in several disease settings, including malignant diseases, autoimmune, metabolic and/or inflammatory conditions.

The inventors of the present invention found the plasma protein present in vivo and named it Ficolin Associated Protein (FAP). It is shown to be primarily associated with the ficolins (FIG. 9), but it may likely also be associated with mannose-binding lectin. By searching nucleotide database of NCBI the inventors of the present invention found a possible transcript variant that corresponds to a truncated of MASP-1. Based on this sequence, primers were designed in order to amplify the putative new gene transcript. Subsequently, using human liver cDNA a new alternative transcript variant of the MASP-1 gene (FIG. 1) was identified. This mRNA strain was sequenced and accordingly the amino acid sequence was determined, which corresponds to the molecular weight of the observed protein in plasma/serum of 40 kDa (FIG. 5). The new protein is partly identical to MASP-1 and MASP-3, but lacks a serine protease domain, but contain a novel exon encoding 17 amino acids followed by a stop codon. This exon is spliced out in the MASP1 and MASP3 transcript (FIG. 2). By using a panel of mRNA expression libraries the present inventors have found evidence that this protein is strongly expressed in the heart, the liver and in the skeletal muscle tissue (FIG. 3). Weak expression was observed in the brain, the digestive tract, prostata and in the spleen (FIG. 3). Taqman analysis confirmed the expression in heart and liver cells. FAP was expressed much higher in the heart tissue compared to MASP1 and MASP3. FAP was expressed three times higher in the heart tissue compared to the FAP expression in liver. Furthermore, a higher FAP expression was observed in the liver compared to the MASP1 and MASP3 expression in the liver. Considerable FAP expression was also detected in brain, skeletal muscle and prostate tissues. The experiment was performed three times in duplicates.

The high expression in the heart is very prominent and has made the present inventors suggest a use of the polypeptides according to the present invention as a very useful protector against tissue damage in autoimmune, metabolic and/or inflammatory conditions, such as medical conditions associated with the heart.

The present inventors have established assays to assess complement activity initiated by ficolins and mannose-binding lectin and the present inventors have thus been able to show a possible functional complement inhibition of FAP.

The present inventors have establishing real time quantitative assays to measure the exact relative expression level in different tissues.

The ficolin-associated polypeptides as well as fusion proteins according to the present invention may be produced by recombinant techniques. Rabbits or mice may be immunized with a unique 17 amino acid long peptide in order to obtain FAP polyclonal and monoclonal specific antibodies, respectively.

Specific FAP antibodies may be used for quantitative measurement of FAP and immunohistochemical detection in different tissues.

Binding constants between FAP and different binding partners as described herein may be determined in ELISA and by using surface plasmon resonance technology (Biacore).

A FAP specific acceptor protein, such as a specific cell surface bound receptor may be identified by standard assays known to the person skilled in the art, such as assays wherein the protein is bound directly to cells.

The novel protein Ficolin Associated Protein (FAP) is an alternative splicing variant of MASP1. The protein lacks the serine protease domain but it still contains the domains that are involved in the binding to the initiators of the lectin pathway of the complement system. Thus, the present inventors expect the protein to be involved in regulation and inhibition of the function of MASP-1 and MASP-3 (complement, coagulation functions and other enzymes substrates) through competitions and displacement of the MASPs. Alternatively, but not mutually exclusive FAP may function as scavenger molecule facilitating removal of FAP/MBL/ficolin complexes bound to endogenous waste material or pathogens.

Uncontrolled activation of the complement system and the coagulation cascade are associated with adverse outcome and functional inhibitors, such as the polypeptides according to the present invention may be very useful for the control of the complement system and the coagulation cascade. In addition the polypeptides according to the present invention may be used in other settings. Another angle could be to use the protein as biomarker in different disease settings.

Chimeric molecules according to the present invention comprising the amino acid sequence of SEQ ID NO:4 or an immunologic fragment or variant thereof may have a specific function associated with this particular sequence of amino acids. It is suggested by the present inventors that such polypeptides may have a function or activity corresponding to the activity of one or more protein selected from DNMT1 DNA (cytosine-5-)-methyltransferase 1 (DNMT1), Golgin subfamily B member 1 (GOLGB1), A-kinase anchor protein 9 (AKAP9), B- and T-lymphocyte-associated protein)(CD272 antigen), PTB domain-containing engulfment adapter protein 1 (GULP), and MACRO domain-containing protein 2.

In some particular interesting embodiments the chimeric molecules according to the present invention have a function or activity corresponding to the activity of PTB domain-containing engulfment adapter protein 1 (GULP).

The ficolin-associated polypeptides are unique and may provide the basis for new drugs and/or new diagnostic tools.

Accordingly, the inventors of the present invention have provided chimeric molecules of a ficolin-associated polypeptide, which chimeric molecule further comprises a second modulator of complement activity.

Ficolin-associated polypeptides are expected to be effective in various clinical settings including indications associated with inflammation, apoptosis and/or autoimmunity. However, chimeric molecules, wherein a second modulator of complement activity, such as a complement inhibitor is fused, added, or conjugated to the ficolin-associated polypeptide are expected to offer significant potential advantages with regard to safety and efficacy.

Definitions

The term “ficolin-associated polypeptide” as used herein means any protein or polypeptide comprising the amino acid sequence 20-380 of native human ficolin-associated protein (FAP) (SEQ ID NO: 1) or amino acid sequence of 16-363 of SEQ ID NO:9, functional variants, functional truncated versions thereof as well as functional derivatives or conjugates, which polypeptide do not have complement activity, but posses the ability to compete with MASP-1, MASP-2, or MASP-3 for binding to ficolin-3, MBL, C1q, lung surfactant proteins SP-A and/or SP-D and/or CL-L1 (and other collectin family members). This includes but is not limited to human ficolin-associated polypeptide (FAP) having SEQ ID NO:1 and variants thereof.

The term “ficolin-associated protein (FAP)” as used herein means proteins that have the amino acid sequence 1-380 (with or without signal peptide, such as the amino acid sequence 20-380) of native human FAP (SEQ ID NO: 1), natural allelic variations and homologous thereof. It also includes proteins with a slightly modified amino acid sequence, for instance, a modified N- or C-terminal end including N- or C-terminal amino acid deletions or additions so long as those proteins substantially retain the activity of FAP. The term “ficolin-associated protein (FAP)” is used interchangeable herein with the terms “MAP-1” or “MBL/Ficolin associated protein-1”. “FAP” within the above definition also includes natural allelic variations that may exist and occur from one individual to another. The term also includes proteins with homologous sequence and similar function derived from other species than human, such as bovine, pig, dog, horse, rat, and mouse. Also, degree and location of glycosylation or other post-translation modifications may vary depending on the chosen host cells and the nature of the host cellular environment.

The term “MBL-Associated Serine Protease-1” or “MASP-1” as used herein means proteins that have the amino acid sequence 1-699 (with or without signal peptide, such as the amino acid sequence 20-699) of native human MASP-1 (SEQ ID NO:5), natural allelic variations and homologous thereof. It is to be understood that the sequence may be in one or more peptide chains, such as in two chains, i.e. the heavy and light chains of the native human protein.

The term "MBL-Associated Serine Protease-3" or "MASP-3" as used herein means proteins that have the amino acid sequence 1-728 (with or without signal peptide, such as the amino acid sequence 20-728) of native human MASP-3 (SEQ ID NO:7), natural allelic variations and homologous thereof. It is to be understood that the sequence may be in one or more peptide chains, such as in two chains, i.e. the heavy and light chains of the native human protein.

The term "MBL-Associated Serine Protease-2" or "MASP-2" as used herein means proteins that have the amino acid sequence 1-686 (with or without signal peptide, such as the amino acid sequence 16-686) of native human MASP-2 (SEQ ID NO:9), natural allelic variations and homologous thereof. It is to be understood that the sequence may be in one or more peptide chains, such as in two chains, i.e. the heavy and light chains of the native human protein.

The terms "small MBL-associated protein", "sMAP", "MBL-associated plasma protein of 19 kD" or, "MAp19" as used herein means proteins that have the amino acid sequence 1-185 (with or without signal peptide, such as the amino acid sequence 16-185) of native human sMAP (SEQ ID NO:11), natural allelic variations and homologous thereof.

The terms "variant" or "variants", as used herein, is intended to designate any protein comprising naturally occurring polypeptide, such as a ficolin-associated polypeptide having the sequence of SEQ ID NO:1 or a polypeptide comprising the amino acid sequence of SEQ ID NO:4, wherein one or more amino acids have been substituted by another amino acid and/or wherein one or more amino acids have been deleted and/or wherein one or more amino acids have been inserted in the polypetide and/or wherein one or more amino acids have been added to the polypeptide. Such addition can take place either at the N-terminal end or at the C-terminal end or both. The "variant" or "variants" within this definition still have functional activity. In some embodiment a variant has 70% sequence identity with the sequence of SEQ ID NO:1. In some embodiments a variant has 80% sequence identity with the sequence of SEQ ID NO:1. In other embodiments a variant has 90% sequence identity with the sequence of SEQ ID NO:1. In a further embodiment a variant has 95% sequence identity with the sequence of SEQ ID NO:1.

In some embodiments a variant has 70% sequence identity with the sequence of SEQ ID NO:4. In some embodiments a variant has 80% sequence identity with the sequence of SEQ ID NO:4. In other embodiments a variant has 90% sequence identity with the sequence of SEQ ID NO:4. In a further embodiment a variant has 95% sequence identity with the sequence of SEQ ID NO:4.

The phrases "functional variant", "functional truncated versions", and "functional derivatives" of a chimeric ficolin-associated polypeptide as used herein refers to variants, truncated versions, as well as derivatives of SEQ ID NO:1, which polypeptides comprises essential sequence parts of SEQ ID NO:1 and at least posses the ability to compete with MASP-1 or MASP-3 for binding to the ficolins or MBL without having the complement activity and/or serine protease activity. It is to be understood that a chimeric molecule of a ficolin-associated polypeptide may have two or three features selected from being a both a variant, and/or truncated and/or a derivative.

A functional variant of a chimeric molecule of a ficolin-associated polypeptide encompass those that exhibit at least about 25%, such as at least about 50%, such as at least about 75%, such as at least about 90% of the specific activity of wild-type FAP that has been produced in the same cell type, when tested in the assays as described herein.

The term "immunologic fragment" as used herein refers to fragment of an amino acid sequence that posses essentially the same functional activities and the same spatial orientation to be recognized by an antibody. Accordingly a specific antibody will bind both the polypeptide and immunologic fragments thereof.

The term "another amino acid" as used herein means one amino acid that is different from that amino acid naturally present at that position. This includes but is not limited to amino acids that can be encoded by a polynucleotide. In some embodiments the different amino acid is in natural L-form and can be encoded by a polynucleotide.

The term "derivative" as used herein, is intended to designate a chimeric molecule of a ficolin-associated polypeptide exhibiting substantially the same or improved biological activity relative to wild-type human FAP, in which one or more of the amino acids of the parent peptide have been chemically modified, e.g. by alkylation, PEGylation, acylation, ester formation or amide formation or the like.

The term "complement activity" as used herein means the ability activate the complement system. The complement activity may be measured with assay as described in the section headed "Assays".

The term "mannose-binding lectin (MBL)" as used herein also means mannan-binding lectin, mannose-binding protein (MBP1), and mannan-binding protein, which terms may be used interchangeably.

The term "capable of associating" as used herein refers to the ability of the proteins according to the present invention to specifically bind in solution one or more of the initiators of the lectin pathway of the complement system or other proteins that may be involved in the effect of the polypeptide.

The term "modulator of complement activity" as used herein refers to any compound that directly or indirectly influences complement activity. The modulator of complement activity may be a direct inhibitor or an indirect inhibitor. Alternatively the modulator may be a homing domain that facilitates the transport and/or uptake at a particular site of complement activity, such as a site of inflammation. Alternatively the modulator may be an immunoglobulin molecule, such as an Fc domain, ligands for adhesion molecules, such as ligands for selectins. In some preferred embodiments, the modulator of complement activity is not a complement activator. The use of the term "second" for a modulator of complement activity simply refers to a modulator of complement activity, which is different from the ficolin-associated polypeptide. Inhibition or modulatory effect of complement activity may be measured according to the assays described herein or any one other assay known to the person skilled in the art.

The term "chimeric molecule" as used herein refers to a molecule comprising at least two domains which are not normally associated, comprising at least (i) a ficolin-associated polypeptide, and (ii) a second modulator of complement activity. The ficolin-associated polypeptide and the second modulator of complement activity may be linked together by any methods known in the art, as long as the desired functionalities of the two portions are maintained.

In some embodiments, the chimeric molecule is a fusion protein. "Fusion protein" used herein refers to two or more peptides, polypeptides, or proteins operably linked to each other. In some embodiments, the two portions are directly fused to each other. In some embodiments, the two portions are linked by an amino acid linker sequence. Examples of linker sequences are known in the art, and include, for example, (Gly4Ser)(SEQ ID NO: 67), (Gly4Ser)2(SEQ ID NO: 68), (Gly4Ser)3(SEQ ID NO: 69), (Gly3Ser)4(SEQ ID NO: 70), (SerGly4) (SEQ ID NO: 71), (SerGly4)2(SEQ ID NO: 72), (SerGly4)3(SEQ ID NO: 73), and (SerGly4)4(SEQ ID NO: 74). Linking sequences can also comprise "natural" linking sequences found between different domains of complement factors. The order of the ficolin-associated polypeptide and the second modulator of complement activity in the fusion protein can vary. For example, in some embodiments, the C-terminus of the ficolin-associated polypeptide is fused (directly or indirectly) to the N-terminus of the second modulator of complement activity. In some embodiments, the N-terminus of the ficolin-associated polypeptide is fused (directly or indirectly) to the C-terminus of the second modulator of complement activity.

In some embodiments, the chimeric molecule comprising the ficolin-associated polypeptide and the second modulator of complement activity is linked via a chemical cross-linker. Linking of the two domains can occur on reactive groups located on the two portions. Reactive groups that can be targeted using a crosslinker include primary amines, sulfhydryls, carbonyls, carbohydrates, and carboxylic acids, or active groups that can be added to proteins. Examples of chemical linkers are well known in the art and include, but are not limited to, bismaleimidohexane, maleimidobenzoyl-N-hydroxysuccinimide ester, NHS-Esters-Maleimide Crosslinkers such as SPDP, carbodiimide, glutaraldehyde, MBS, Sulfo-MBS, SMPB, sulfo-SMPB, GMBS, Sulfo-GMBS, EMCS, Sulfo-EMCS, imidoester crosslinkers such as DMA, DMP, DMS, DTBP, EDC and DTME.

In some embodiments, the ficolin-associated polypeptide and the second modulator of complement activity are non-covalently linked. For example, the two portions may be brought together by two interacting bridging proteins (such as biotin and avidin or streptavidin), each linked to the ficolin-associated polypeptide or to the second modulator of complement activity.

In some embodiments, the chimeric molecules form dimers or multimers.

In some embodiments, the ficolin-associated polypeptide and the modulator of complement activity are directly fused (i.e. linked) to each other as a fusion protein. In some embodiments, the ficolin-associated polypeptide and the modulator of complement activity are indirectly linked via an amino acid linker sequence. In some embodiments, the C-terminus of the ficolin-associated polypeptide is linked (directly or indirectly) to the N-terminus of the modulator of complement activity. In some embodiments, the N-terminus of the ficolin-associated polypeptide is linked (directly or indirectly) to the C-terminus of the modulator of complement activity.

The term "construct" is intended to indicate a polynucleotide segment which may be based on a complete or partial naturally occurring nucleotide sequence encoding the polypeptide of interest. The construct may optionally contain other polynucleotide segments. In a similar way, the term "amino acids which can be encoded by polynucleotide constructs" covers amino acids which can be encoded by the polynucleotide constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln. The term "vector", as used herein, means any nucleic acid entity capable of the amplification in a host cell. Thus, the vector may be an autonomously replicating vector, i.e. a vector, which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e., a gene which encodes a product which is readily detectable or the presence of which is essential for cell growth.

In a further aspect, the invention provides a recombinant host cell comprising the polynucleotide construct or the vector. In some embodiments the recombinant host cell is a eukaryotic cell. In other embodiments the recombinant host cell is of mammalian origin. In a further embodiment the recombinant host cell is selected from the group consisting of CHO cells, HEK cells and BHK cells.

The term "a host cell", as used herein, represent any cell, including hybrid cells, in which heterologous DNA can be expressed. Typical host cells includes, but are not limited to insect cells, yeast cells, mammalian cells, including human cells, such as BHK, CHO, HEK, and COS cells. In practicing the present invention, the host cells being cultivated are preferably mammalian cells, more preferably an established mammalian cell line, including, without limitation, CHO (e.g., ATCC CCL 61), COS-1 (e.g., ATCC CRL 1650), baby hamster kidney (BHK) and HEK293 (e.g., ATCC CRL 1573; Graham et al., *J. Gen. Virol.* 36:59-72, 1977) cell lines. A preferred BHK cell line is the $tk^-$ ts13 BHK cell line (Waechter and Baserga, *Proc. Natl. Acad. Sci. LISA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A $tk^-$ ts13 BHK cell line is also available from the ATCC under accession number CRL 1632. Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci. USA* 77:4216-4220, 1980). Also useful are 3T3 cells, Namalwa cells, myelomas and fusions of myelomas with other cells.

In a further aspect, the invention provides a transgenic animal containing and expressing the polynucleotide construct.

In a further aspect, the invention provides a transgenic plant containing and expressing the polynucleotide construct.

In a further aspect, the invention relates to a method for producing the chimeric molecules of a ficolin-associated polypeptide of the invention, the method comprising cultivating a cell comprising the polynucleotide construct in an appropriate growth medium under conditions allowing expression of the polynucleotide construct and recovering the resulting polypeptide from the culture medium.

As used herein the term "appropriate growth medium" means a medium containing nutrients and other components required for the growth of cells and the expression of the nucleic acid sequence encoding the chimeric molecules of a ficolin-associated polypeptide of the invention.

In a further aspect, the invention relates to a method for producing the chimeric molecules of a ficolin-associated polypeptide, the method comprising recovering the polypeptide from milk produced by the transgenic animal.

In a further aspect, the invention relates to a method for producing the chimeric molecules of a ficolin-associated polypeptide, the method comprising cultivating a cell of a transgenic plant comprising the polynucleotide construct, and recovering the polypeptide from the resulting plant.

In the present context, the term "treatment" is meant to include both prevention of an expected condition involving inappropriate complement activation, such as inflammation and reperfusion injury and regulation of an already occurring condition, such as myocardial infarction and stroke with the purpose of inhibiting or minimising the tissue damage Prophylactic administration of the chimeric molecules of a ficolin-associated polypeptide according to the invention is thus included in the term "treatment".

The term "subject" as used herein is intended to mean any animal, in particular mammals, such as humans, and may, where appropriate, be used interchangeably with the term "patient".

The term "sequence identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or between polypeptides, as the case may be, as determined by the number of matches between strings of two or more nucleotide residues or two or more amino acid residues. "Identity" measures the percent of identical matches between the smaller of two or more sequences with gap alignments (if any) addressed by a particular mathematical model or computer program (i.e., "algorithms").

The term "similarity" is a related concept, but in contrast to "identity", refers to a sequence relationship that includes both identical matches and conservative substitution matches. If two polypeptide sequences have, for example, (fraction (10/20)) identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% ((fraction (15/20))). Therefore, in cases where there are conservative substitutions, the degree of similarity between two polypeptides will be higher than the percent identity between those two polypeptides.

Conservative modifications to the amino acid sequence of SEQ ID NO:1 (and the corresponding modifications to the encoding nucleotides) will produce ficolin-associated polypeptides having functional and chemical characteristics similar to those of naturally occurring FAP. In contrast, substantial modifications in the functional and/or chemical characteristics of a ficolin-associated polypeptide may be accomplished by selecting substitutions in the amino acid sequence of SEQ ID NO:1 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of a ficolin-associated polypeptide or a chimeric molecule of a ficolin-associated polypeptide, or to increase or decrease the affinity of a ficolin-associated polypeptide described herein.

Naturally occurring residues may be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human ficolin-associated polypeptide, or in the chimeric molecule of a ficolin-associated polypeptide that are homologous with non-human ficolin-associated polypeptides or into the non-homologous regions of the molecules.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine ('3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those that are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in SEQ ID NO:1 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a ficolin-associated polypeptide or a second modulator of complement activity to such similar polypeptides. With such a comparison, one can identify residues and portions of the molecules that are conserved among similar polypeptides. It will be appreciated that changes in areas of a ficolin-associated polypeptide or of a second modulator of complement activity that are not conserved relative to such similar polypeptides would be less likely to adversely affect the biological activity and/or structure of the ficolin-associated polypeptide or the second modulator of complement activity. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a ficolin-associated polypeptide or in a second modulator of complement activity that correspond to amino acid residues that are important for activity or structure in similar polypeptides. One skilled in the art may opt for chemically similar amino acid substitutions for such predicted important amino acid residues of ficolin-associated polypeptides or second modulators of complement activity and other polypeptides of the invention.

One skilled in the art can also analyze the three-dimensional structure and amino acid sequence in relation to that structure in similar polypeptides. In view of that information, one skilled in the art may predict the alignment of amino acid residues of a ficolin-associated polypeptide or of a second modulator of complement activity with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays as described herein. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol, 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins, which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3):377-87 (1997); Sippl et al., Structure, 4(1):15-9 (1996)), "profile analysis" (Bowie et al., Science, 253:164-170 (1991); Gribskov et al., Meth. Enzymol., 183:146-159 (1990); Gribskov et al., Proc. Nat. Acad. Sci., 84(13):4355-4358 (1987)), and "evolutionary linkage" (See Home, supra, and Brenner, supra).

Identity and similarity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, N.J., 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., Nucl. Acid. Res., 12:387 (1984); Genetics Computer Group, University of Wisconsin, Madison, Wis.), BLASTP, BLASTN, and FASTA (Altschul et al., J. Mol. Biol., 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in some embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., Proc. Natl. Acad. Sci USA, 89:10915-10919 (1992) for the BLOSUM 62 comparison matrix) is also used by the algorithm.

Preferred parameters for a polypeptide sequence comparison include the following:

Algorithm: Needleman et al., J. Mol. Biol, 48:443-453 (1970); Comparison matrix: BLOSUM 62 from Henikoff et al., Proc. Natl. Acad. Sci. USA, 89:10915-10919 (1992); Gap Penalty: 12, Gap Length Penalty: 4, Threshold of Similarity: 0.

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following: Algorithm: Needleman et al., J. Mol Biol., 48:443-453 (1970); Comparison matrix: matches=+10, mismatch=0, Gap Penalty: 50, Gap Length Penalty: 3.

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Preparation of Ficolin-Associated Polypeptides and Other Chimeric Polypeptides of the Invention The invention also relates to a method of preparing human Ficolin-associated polypeptides and other chimeric polypeptides of the invention as mentioned above. The Ficolin-associated polypeptides and other polypeptides of the invention described herein may be produced by means of recombinant nucleic acid techniques. In general, a cloned wild-type FAP nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete amino acid and nucleotide sequences for human FAP is given by SEQ ID NO:1 and SEQ ID NO:2.

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of FAP, one may introduce the alteration(s) of choice. Likewise, procedures for preparing a DNA construct using polymerase chain reaction using specific primers are well known to per-sons skilled in the art (cf. PCR Protocols, 1990, Academic Press, San Diego, Calif., USA).

The polypeptides of the present invention can also comprise non-naturally occurring amino acid residues. Non-naturally occurring amino acids include, without limitation, beta-alanine, desaminohistidine, trans-3-methylproline, 2,4-methanoproline, cis-4-hydroxyproline, trans-4-hydroxyproline, N-methylglycine, allo-threonine, methylthreonine, hydroxyethylcys-teine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, nor-valine, 2-azaphenylalanine, 3-azaphenylalanine, 4-azaphenylalanine, and 4-fluorophenylalanine. Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Polypeptides are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus oocytes* by microinjection of mutated mRNA and chemically aminoacylated suppressor tRNAs (Turcatti et al., J. Biol. Chem. 271:19991-8, 1996). Within a third method, *E. coli* cells are cul-tured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

The nucleic acid construct encoding the Ficolin-associated polypeptides and other polypeptides of the invention of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Labora-tory, Cold Spring Harbor, N.Y., 1989).

The nucleic acid construct encoding a Ficolin-associated polypeptide and the second modulator of complement activity, as well as chimeric molecules of the invention may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors. The DNA sequences encoding the human Ficolin-associated polypeptides and the second modulator of complement activity, as well as chimeric molecules of the invention and other polypeptides of the invention may also be prepared by polymerase chain reaction using specific primers, for instance as described in U.S. Pat. No. 4,683,202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of syn-thetic, genomic or cDNA origin (as appropriate), the fragments corresponding to various parts of the entire nucleic acid construct, in accordance with standard techniques.

The nucleic acid construct is preferably a DNA construct. DNA sequences for use in producing Ficolin-associated polypeptides, second modulators of complement activity, as well as chimeric molecules of the invention will typically encode a pre-pro polypeptide at the amino-terminus of FAP to obtain proper posttranslational processing and secretion from the host cell.

The DNA sequences encoding the human Ficolin-associated polypeptide and the second modulator of complement activity, as well as chimeric molecules of the invention are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the human Ficolin-associated polypeptide, the second modulator of complement activity, as well as chimeric molecules of the invention is operably linked to additional segments required for transcription of the DNA. In general, the expression vector is derived from plasmid or viral DNA, or may contain elements of both. The term, “operably linked” indicates that the segments are arranged so that they function in concert for their intended purposes, e.g. transcription initiates in a promoter and proceeds through the DNA sequence coding for the polypeptide.

Expression vectors for use in expressing Ficolin-associated polypeptide, the second modulator of complement activity, as well as chimeric molecules of the invention will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA encoding the human Ficolin-associated polypeptide, the second modulator of complement activity, as well as chimeric molecules of the invention in mammalian cells are the SV40 promoter (Subramani et al., Mol. Cell Biol. 1 (1981), 854-864), the MT-1 (metallothionein gene) promoter (Palmiter et al., Science 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

An example of a suitable promoter for use in insect cells is the polyhedrin promoter (U.S. Pat. No. 4,745,051; Vasuvedan et al., FEBS Lett. 311, (1992) 7-11), the P10 promoter (J. M. Vlak et al., J. Gen. Virology 69, 1988, pp. 765-776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652-654) promoters.

Examples of suitable promoters for use in filamentous fungus host cells are, for instance, the ADH3 promoter (McKnight et al., The EMBO J. 4 (1985), 2093-2099) or the tpiA promoter. Examples of other useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

The DNA sequences encoding the human Ficolin-associated polypeptide, the second modulator of complement activity, as well as chimeric molecules of the invention may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the FAP sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981) or the polyadenylation signal from the human FAP gene or the bovine FAP gene. The expression vectors may also include a noncoding viral leader sequence, such as the adenovirus 2 tripartite leader, located between the promoter and the RNA splice sites; and enhancer sequences, such as the SV40 enhancer.

To direct the human Ficolin-associated polypeptide, the second modulator of complement activity, as well as chimeric molecules of the invention into the secretory pathway of the host cells, a secretory signal sequence (also known as a leader sequence, prepro sequence or pre sequence) may be provided in the recombinant vector. The secretory signal sequence is joined to the DNA sequences encoding the human Ficolin-associated polypeptide, the second modulator of complement activity, or chimeric molecules of the invention in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed human Ficolin-associated polypeptide, the second modulator of complement activity, as well as chimeric molecules of the invention into the secretory pathway of the cell. The signal peptide may be naturally occurring signal peptide, or a functional part thereof, or it may be a synthetic peptide. Suitable signal peptides have been found to be the alpha-factor signal peptide (cf. U.S. Pat. No. 4,870,008), the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897), the yeast BAR1 signal peptide (cf. WO 87/02670), or the yeast aspartic protease 3 (YAP3) signal peptide (cf. M. Egel-Mitani et al., Yeast 6, 1990, pp. 127-137).

For efficient secretion in yeast, a sequence encoding a leader peptide may also be inserted downstream of the signal sequence and upstream of the DNA sequence encoding the human Ficolin-associated polypeptides, the second modulator of complement activity, as well as chimeric molecules of the invention. The function of the leader peptide is to allow the expressed peptide to be directed from the endoplasmic reticulum to the Golgi apparatus and further to a secretory vesicle for secretion into the culture medium (i.e. exportation of the human Ficolin-associated polypeptides, the second modulator of complement activity, as well as chimeric molecules of the invention across the cell wall or at least through the cellular membrane into the periplasmic space of the yeast cell). The leader peptide may be the yeast alpha-factor leader (the use of which is described in e.g. U.S. Pat. No. 4,546,082, U.S. Pat. No. 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral alpha-amylase, *A. niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran Manduca sexta adipokinetic hormone precursor signal peptide (cf. U.S. Pat. No. 5,023,328).

The procedures used to ligate the DNA sequences coding for the human Ficolin-associated polypeptides, the second modulator of complement activity, as well as chimeric molecules of the invention, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841-845.

Cloned DNA sequences are introduced into cultured mammalian cells by, for example, calcium phosphate-mediated transfection (Wigler et al., Cell 14:725-732, 1978; Corsaro and Pearson, Somatic Cell Genetics 7:603-616, 1981; Graham and Van der Eb, Virology 52d:456-467, 1973) or electroporation (Neumann et al., EMBO J. 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (Mammalian Cell Technology, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the human Ficolin-associated polypeptide of interest. Media generally include a carbon source, a nitrogen source, essential amino acids, essential sugars, vitamins, salts, phospholipids, protein and growth factors. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby in-creasing expression levels. Clones of stably transfected cells are then screened for expression of the human Ficolin-associated polypeptide of interest.

The host cell into which the DNA sequences encoding the human Ficolin-associated polypeptides, the second modulator of complement activity, as well as chimeric molecules of the invention is introduced may be any cell, which is capable of producing the posttranslational modified human polypeptides and includes yeast, fungi and higher eucaryotic cells.

Examples of mammalian cell lines for use in the present invention are the COS-1 (ATCC CRL 1650), baby hamster kidney (BHK) and 293 (ATCC CRL 1573; Graham et al., J. Gen. Virol. 36:59-72, 1977) cell lines. A preferred BHK cell line is the tk− ts13 BHK cell line (Waechter and Baserga, Proc. Natl. Acad. Sci. USA 79:1106-1110, 1982, incorporated herein by reference), hereinafter referred to as BHK 570 cells. The BHK 570 cell line has been deposited with the American Type Culture Collection, 12301 Parklawn Dr., Rockville, Md. 20852, under ATCC accession number CRL 10314. A tk− ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, Proc. Natl. Acad. Sci. USA 77:4216-4220, 1980).

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous poly-peptides there from are described, e.g. in U.S. Pat. No. 4,599,311, U.S. Pat. No. 4,931,373, U.S. Pat. Nos. 4,870,008, 5,037, 743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931, 373. The DNA sequences encoding the human Ficolin-associated polypeptides, the second modulator of complement activity, as well as chimeric molecules of the invention may be preceded by a signal sequence and optionally a leader sequence, e.g. as described above. Further examples of suitable yeast cells are strains of *Kluyveromyces*, such as *K. lactis, Hansenula*, e.g. *H. polymorpha*, or *Pichia*, e.g. *P. pastoris* (cf. Gleeson et al., J. Gen. Microbiol. 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, Gene 78: 147-156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. No. 4,745,051; U.S. Pat. No. 4,879,236; U.S. Pat. Nos. 5,155,037; 5,162,222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting expression of the human Ficolin-associated polypeptide after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The human Ficolin-associated polypeptide produced by the cells may then be recovered from the culture medium by conventional procedures including separating the host cells from the medium by centrifugation or filtration, precipitating the proteinaqueous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

Transgenic animal technology may be employed to produce the Ficolin-associated polypeptides and other polypeptides of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta lactoglobulin, a lactalbumin, and whey acidic protein. The beta lactoglobulin (BLG) promoter is preferred. In the case of the ovine beta lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non coding portion of the beta lactoglobulin gene (see Whitelaw et al., Biochem. J. 286: 31 39 (1992)). Similar fragments of promoter DNA from other species are also suitable.

Other regions of the beta lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836 840 (1988); Palmiter et al., Proc. Natl. Acad. Sci. USA 88: 478 482 (1991); Whitelaw et al., Transgenic Res. 1: 3 13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta lactoglobulin gene, is preferred. One such region is a DNA segment that provides for intron splicing and RNA polyadenylation from the 3' non coding region of the ovine beta lactoglobulin gene. When substituted for the natural 3' non coding sequences of a gene, this ovine beta lactoglobulin segment can both enhance and stabilize expression levels of the protein or polypeptide of interest. Within other embodiments, the region surrounding the initiation ATG of the FAP sequence is replaced with corresponding sequences from a milk specific protein gene. Such replacement provides a putative tissue specific initiation environment to enhance expression. It is convenient to replace the entire FAP pre pro and 5' non coding sequences with those of, for example, the BLG gene, although smaller regions may be replaced.

For expression of Ficolin-associated polypeptides, the second modulator of complement activity, as well as chimeric molecules of the invention in transgenic animals, a DNA segment encoding FAP is operably linked to additional DNA segments required for its expression to produce expression units. Such additional segments include the above mentioned promoter, as well as sequences that provide for termination of transcription and polyadenylation of mRNA. The expression units will further include a DNA segment encoding a secretory signal sequence operably linked to the segment encoding modified FAP. The secretory signal sequence may be a native FAP secretory signal sequence or may be that of another protein, such as a milk protein (see, for example, von Heijne, Nucl. Acids Res. 14: 4683 4690 (1986); and Meade et al., U.S. Pat. No. 4,873,316, which are incorporated herein by reference).

Construction of expression units for use in transgenic animals is conveniently carried out by inserting a FAP sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a FAP variant; thereby creating a gene fusion that includes the expression control sequences of the milk protein gene. In any event, cloning of the expression units in plasmids or other vectors facilitates the amplification of the FAP sequence. Amplification is conveniently carried out in bacterial (e.g. *E. coli*) host cells, thus the vectors will typically include an origin of replication and a selectable marker functional in bacterial host cells. The expression unit is then introduced into fertilized eggs (including early stage embryos) of the chosen host species. Introduction of heterologous DNA can be accomplished by one of several routes, including microinjection (e.g. U.S. Pat. No. 4,873,191), retroviral infection (Jaenisch, Science 240: 1468 1474 (1988)) or site directed integration using embryonic stem (ES) cells (reviewed by Bradley et al., Bio/Technology 10: 534 539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., Bio/Technology 6: 179 183 (1988); Wall et al., Biol. Reprod. 32: 645 651 (1985); Buhler et al., Bio/Technology 8: 140 143 (1990); Ebert et al., Bio/Technology 9: 835 838 (1991); Krimpenfort et al., Bio/Technology 9: 844 847 (1991); Wall et al., J. Cell. Biochem. 49: 113 120 (1992); U.S. Pat. No. 4,873,191; U.S. Pat. No. 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380 7384 (1980); Gordon and Ruddle, Science 214: 1244 1246 (1981); Palmiter and Brinster, Cell 41: 343 345 (1985); Brinster et al., Proc. Natl. Acad. Sci. USA 82: 4438 4442 (1985); and Hogan et al. (ibid.)). These techniques were subsequently adapted for use with larger animals, including livestock species (see, e.g., WO 88/00239, WO 90/05188, and WO 92/11757; and Simons et al., Bio/Technology 6: 179 183 (1988)). To summarise, in the most efficient route used to date in the generation of transgenic mice or livestock, several hundred linear molecules of the DNA of interest are injected into one of the pro nuclei of a fertilized egg according to established techniques. Injection of DNA into the cytoplasm of a zygote can also be employed.

Production in transgenic plants may also be employed. Expression may be generalised or directed to a particular organ, such as a tuber (see, Hiatt, Nature 344:469 479 (1990); Edelbaum et al., J. Interferon Res. 12:449 453 (1992); Sijmons et al., Bio/Technology 8:217 221 (1990); and EP 0 255 378).

FAP purification

The Ficolin-associated polypeptides and other polypeptides of the invention may be recovered from cell culture medium or milk. The Ficolin-associated polypeptides and other polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-FAP antibody column. Additional purification may be achieved by conventional chemical purification means, such as high performance liquid chromatography. Other methods of purification, including barium citrate precipitation, are known in the art, and may be applied to the purification of the novel Ficolin-associated polypeptides and other polypeptides described herein (see, for example, Scopes, R., Protein Purification, Springer-Verlag, N.Y., 1982).

For therapeutic purposes it is preferred that the Ficolin-associated polypeptides and other polypeptides of the invention are substantially pure. Thus, in a preferred embodiment of the invention the polypeptides of the invention a purified to at least about 90 to 95% homogeneity, preferably to at least about 98% homogeneity. Purity may be assessed by e.g. gel electrophoresis and amino-terminal amino acid sequencing.

The term "isolated polypeptide" refers to a polypeptide of the present invention that (1) has been separated from at least about 50 percent of polynucleotides, lipids, carbohydrates or other materials (i.e., contaminants) with which it is naturally associated. Preferably, the isolated polypeptide is substantially free from any other contaminating polypeptides or other contaminants that are found in its natural environment, which would interfere with its therapeutic, diagnostic, prophylactic or research use.

The term "microorganism" as used herein refers to bacteria, fungi, archaea, protists; microscopic plants and animals (such as green algae or plankton), the planarian and amoeba. Included within this definition are pathogenic microorganisms.

Assays

A General Procedure for SDS-PAGE and Western Blotting:

Electrophoresis was performed on 10% or 4-12% (w/v) Bis-Tris Polyacrylamide-gels with discontinuous buffers using the NuPAGE® system (Invitrogen) as recommended by the manufacture. Western blotting was performed using polyvinylidene difluoride membranes (PVDF-HyBond, GE-healthcare, Hilleroed, Denmark, cat. no. RPN303F), 2 μg/ml of biotin labeled primary monoclonal antibody and secondary visualization by HRP conjugated streptavidin (P0397, Dako, Glostrup, Denmark) diluted to 1:1500 in PBS, 0.05% Tween20. The membranes were developed with 0.04% 3-amino-9-ethylcarbazole (Sigma-aldrich, Broenby, Denmark, cat. no. A5754-100G) in acetone and 0.015% $H_2O_2$ in 50 mM sodium acetate buffer pH 5.

Co-Immunoprecipitation:

Immunoprecipitation of mannose binding lectin (MBL) serum complexes: 1 ml of normal human serum was diluted 1:1 in TBS (10 mM Tris, 140 mM NaCl, pH 7.5) and incubated end over end for 1 hour at 4° C. with 5 μg of the MBL specific mouse monoclonal antibody Hyb 131-11 (Bioporto, Gentofte, Denmark).

Immunoprecipitation of Ficolin-2 serum complexes: 0.5 ml of normal human serum was diluted 1:1 in TBS (10 mM Tris, 140 mM NaCl, pH 7.5) and incubated end over end for 1 hour at 4° C. with 5 μg of the Ficolin-2 specific mouse monoclonal antibody Hyb 219 (Munthe-Fog L, et al.

Immunoprecipitation of Ficolin-3 serum complexes: 0.2 ml of normal human serum was diluted 1:1 in TBS (10 mM Tris, 140 mM NaCl, pH 7.5) and incubated end over end for 1 hour at 4° C. with 5 μg of the Ficolin-3 specific mouse monoclonal antibody Hyb 334 (Munthe-Fog L, et al.

Immune complex precipitation was conducted with sheep anti mouse IgG conjugated magnetic dynal beads (Dynal-Invitrogen, Cat. No. 112.02D): After incubation with serum and primary antibodies (as above) $5\times10^7$ sheep anti mouse conjugated magnetic dynal beads were added and incubated for 30 min 4° C. The beads were magnetically separated and washed for three times with TBS-tween-$Ca^2$ (10 mM Tris, 140 mM NaCl, 0.05% tween, 5 mM $CaCl_2$, pH 7.5) and finally boiled in SDS-loading buffer and analyzed by SDS-PAGE and western blotting with biotin labeled monoclonal antibody mAb-8B3 (reacting with an epitope on the heavy chain/A-chain shared by MASP-1 and -3).

Immunoaffinity purification of FAP: 10 mg of mAb-8B3 (reacting with an epitope on the heavy chain/A-chain shared by FAP, MASP-1 and -3) or 10 mg of rabbit polyclonal anti FAP antibodies were conjugated to CNBr activated sepharose as recommended by the manufacturer (GE-healthcare, Hilleroed, Denmark, cat. no. 17-0430-01) and packed onto a column.

Purification from serum: 150 ml of a pool of normal human serum was diluted 1:1 with TBS+0.5 M NaCl+10 mM EDTA (10 mM Tris, 640 mM NaCl, 10 mM EDTA, pH 7.5) and loaded on the columns described above. The columns were washed with 1 l of TBS+0.5 M NaCl+10 mM EDTA and 1 ml fractions were eluted with 1 M Glycine-HCl, pH 2.5 and analyzed by SDS-PAGE and western blotting with biotin labeled monoclonal antibody mAb-8B3.

Purification of recombinant FAP: 2-3 l of culture supernatant (from CHO serum free medium/Gibco-Invitrogen, cat. no. 12651-014) from Chinese hamster ovarian cells (CHO cells) expressing recombinant FAP (rFAP) was loaded on the antibody columns described above. The columns were washed with 1.5 l of TBS+0.5 M NaCl+10 mM EDTA and 1 ml fractions were eluted with 1 M Glycine-HCl, pH 2.5. The eluted fractions were analyzed by SDS-PAGE and coomassie staining.

Recombinant expression of FAP: Full-length cDNA inserted into the pcDNA5/FRT vector (Invitrogen, cat. no. V6010-20) was ordered from Genscript (Genscript, N.J., USA) and co-transfected with the pOG44 vector (Invitrogen, cat. no. V6005-20) into the CHO Flp-In cell line (Invitrogen, cat. no. R758-07) and selected and cloned as recommended by the manufacturer (Invitrogen). The cells were grown in Freestyle CHO serum free medium (Invitrogen, cat. no. 12651-014) and culture supernatants were harvested and analyzed. Production of mono- and polyclonal antibodies: A peptide construct (ordered from Genscript, N.J., USA) of the FAP specific 17 C-terminal residues were coupled onto the toxoid form of tetanus and diphtheria using the cysteine coupling method with m-Maleimidobenzoyl-N-hydroxysuccinimide ester as recommended by the manufacturer (Thermo Fisher Scientific/Pierce, Illinois, USA).

Six mice and two rabbits were each immunized three times (with 14 days intervals) with 25 μg antigen adsorbed onto $Al(OH)_3$ and Freunds incomplete adjuvant. The polyclonal antibody titers were assessed using ELISA with the different FAP peptides coupled to a protein carrier.

Polyclonal rabbit antiserum (≈10 ml) was harvested 14 days after the first, second and third immunization.

Two mice were used for production of monoclonal antibodies. Four days prior to the fusion the mice received an intravenous injection of 25 μg antigen. The fusion was conducted as described elsewhere (Kohler, G. and C. Milstein. 1975. Continuous cultures of fused cells secreting antibody of predefined specificity. *Nature* 256:495-497).

Clones were selected by differential ELISA screening against peptides coupled to different protein carriers.

Functional complement assays: Ficolin-3 and MBL homozygous defect sera were used to investigate the function of FAP.

Ficolin-3 assay: Maxisorp plates (NUNC, Roskilde, Denmark, cat. no. 439454) were coated with acetylated bovine serum albumin at 5 μg/ml for 12 hours at 4° C. in coating buffer (15 mM $Na_2CO_3$, 35 mM $NaHCO_3$, pH 9.5). After blocking/washing four times in barbital/tween buffer (4 mM barbital, 145 mM NaCl, 2 mM $CaCl_2$, 1 mM $MgCl_2$, pH 7.4+0.05% Tween), recombinant human Ficolin-3 was added at 500 ng/ml I barbital/tween buffer and incubated for 1.5 hours at 20° C. with shaking. After washing the plates twice in barbital/tween buffer, recombinant FAP, human MASP-1, -2 or -3 as serum free medium culture supernatants were added in serial dilutions in the 1st dimension on separate plates and incubated for 1 hour at 20° C. with shaking. After washing the plates twice in barbital/tween buffer, Ficolin-3 or MASP-2 deficient serum were added in serial dilutions in the 2nd dimension on the plates and incubated for 30 min at 37° C. After washing the plates four times in barbital/tween buffer the deposition of complement factor C4 was measured by incubation for 1 hour at 20° C. with polyclonal rabbit antibodies to human C4c (Dako, Glostrup, Denmark cat. no Q0369) diluted at 1:2000, followed by four washing steps and incubation with horseradish peroxidase conjugated swine anti rabbit antibodies (Dako, Glostrup, Denmark cat. no P0399) for 45 min at 20° C. The signal was obtained by the plates were developed with 100 W/well of Ortho-phenylene-diamine (OPD) (0.4 mg/ml) dissolved in citrate buffer (35 mM citric acid, 65 mM $Na_2PO_4$, pH 5) with 0.12‰ (v/v) $H_2O_2$. The enzyme reaction was stopped with 1 M $H_2SO_4$ and optical density (OD) levels were measured at 490 nm-650 nm using a V-max Kinetic-reader (Molecular Devices).

Mannose-Binding Lectin assay: Maxisorp plates (NUNC, Roskilde, Denmark, cat. no. 439454) were coated with mannan (Sigma-aldrich, Broenby, Denmark, cat. no. M7504-1G) at 10 μg/ml for 12 hours at 4° C. in coating buffer (15 mM $Na_2CO_3$, 35 mM $NaHCO_3$, pH 9.5). After blocking/washing four times in barbital/tween buffer (4 mM barbital, 145 mM NaCl, 2 mM $CaCl_2$, 1 mM $MgCl_2$, pH 7.4+0.05% Tween) recombinant human Mannose-Binding Lectin was added at 0.5 μg/ml I barbital/tween buffer and incubated for 1.5 hours at 20° C. with shaking. After washing the plates twice in barbital/tween buffer, recombinant FAP, human MASP-1, -2 or -3 as serum free medium culture supernatants were added in serial dilutions in the 1st dimension on separate plates and incubated for 1 hour at 20° C. with shaking. After washing the plates twice in barbital/tween buffer, MBL or MASP-2 deficient serum were added in serial dilutions in the 2nd dimension on the plates and incubated for 45 min at 37° C. After washing the plates four times in barbital/tween buffer the deposition of complement factor C4 was measured by incubation for 1 hour at 20° C. with polyclonal rabbit antibodies to human C4c (Dako, Glostrup, Denmark cat. no Q0369) diluted at 1:2000, followed by four washing steps and incubation with horseradish peroxidase conjugated swine anti rabbit antibodies (Dako, Glostrup, Denmark cat. no P0399) for 45 min at 20° C. The signal was obtained by the plates were developed with 100 μl/well of Ortho-phenylene-diamine (OPD) (0.4 mg/ml) dissolved in citrate buffer (35 mM citric acid, 65 mM $Na_2PO_4$, pH 5) with 0.12 Too (v/v) $H_2O_2$. The enzyme reaction was stopped with 1 M $H_2SO_4$ and optical density (OD) levels were measured at 490 nm-650 nm using a V-max Kinetic-reader (Molecular Devices).

Genotyping assay: Different genotyping assays may be conducted where the genotype is determined in individuals using biological assays. Different kind of assays could be used such as:

- Hybridization-based methods
  - Dynamic allele-specific hybridization
  - Molecular beacons
  - SNP microarrays
- Enzyme-based methods
  - Restriction fragment length polymorphism
  - PCR-based methods
  - Flap endonuclease
  - Primer extension
  - 5'-nuclease
  - Oligonucleotide ligase assay
- Other post-amplification methods based on physical properties of DNA
  - Single strand conformation polymorphism
  - Temperature gradient gel electrophoresis
  - Denaturing high performance liquid chromatography
  - High-Resolution Melting of the entire amplicon
  - SNPlex
- Sequencing Administration and Pharmaceutical Compositions Combination Treatments The ficolin-associated polypeptide as defined in the present specification may be administered simultaneously or sequentially with one or more proteins selected from Ficolin-1, 2, 3, and mannose-binding lectin (MBL). The factors may be supplied in single-dosage form wherein the single-dosage form contains both compounds, or in the form of a kit-of-parts comprising a preparation of a ficolin-associated polypeptide as a first unit dosage form and a preparation of the one or more other compound as a second unit dosage form. Whenever a first or second or third, etc., unit dose is mentioned throughout this specification this does not indicate the preferred order of administration, but is merely done for convenience purposes.

By "simultaneous" dosing of a preparation of a ficolin-associated polypeptide and a preparation of one or more other compound is meant administration of the compounds in single-dosage form, or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

Another object of the present invention is to provide a pharmaceutical formulation comprising a ficolin-associated polypeptide which is present in a serum/plasma concentration from 0 mg/ml to 1 mg/ml, and wherein the formulation has a pH from 2.0 to 10.0. The formulation may further comprise a buffer system, preservative(s), tonicity agent(s), chelating agent(s), stabilizers and surfactants. In some embodiments of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In other embodiments the pharmaceutical formulation is a freeze-dried formulation, whereto the physician or the patient adds solvents and/or diluents prior to use.

In other embodiments the pharmaceutical formulation is a dried formulation (e.g. freeze-dried or spray-dried) ready for use without any prior dissolution.

In a further aspect the invention relates to a pharmaceutical formulation comprising an aqueous solution of a ficolin-associated polypeptide, and a buffer, wherein the ficolin-associated polypeptide is present in a serum/plasma concentration from 0-1 mg/ml or above, and wherein the formulation has a pH from about 2.0 to about 10.0.

In a other embodiments of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy,* $19^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In some embodiments the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In some embodiments the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In some embodiments, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy,* $19^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy,* $19^{th}$ edition, 1995.

In a further embodiment of the invention the formulation further comprises a stabilizer. The use of a stabilizer in pharmaceutical compositions is well-known to the skilled person. For convenience reference is made to Remington: *The Science and Practice of Pharmacy,* $19^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In some embodiments, amino acids to use in preparing the compositions of the invention are those carrying a charged side chain, such as arginine, lysine, aspartic acid, and glutamic acid. Any stereoisomer (i.e., L, D, or DL isomer) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In some embodiments the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^{\alpha}$-acylated derivatives of lysine, arginine or histidine, or side-chain acylated derivatives of lysine or arginine, $N^{\alpha}$-acylated derivatives of dipeptides comprising any combination of lysine, arginine or histidine and a neutral or acidic amino acid, $N^{\alpha}$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy,* 19th edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a ficolin-associated polypeptide according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

In some embodiments, the composition according to the invention is suitable for intraocular, intravenous, intraarterial, subcutaneous, intratracheal, or inhalational administration. Topical administration may be a particular advantage in the treatment of conditions associated with local inflammation, such as in the treatment of inflammation associated with burn or other conditions associated with the skin. Accordingly, in some embodiments administration is by topical administration.

In some embodiments, the disease to be treated is a disease that involves local inflammation. In some particular embodiments, eye droplets may be used in conditions associated with the eye, such as keratitis, such as diffuse lamellar keratitis (DLK).

In some embodiments, the disease to be treated is a drusen-associated disease. For example, in some embodiments, there is provided a method of treating (such as reducing, delaying, eliminating, or preventing) formation of drusen, inflammation, loss of photoreceptors cells, visual acuity or visual field, and/or choroidal neovascularization (CNV) in the eye of an individual, comprising administering to the individual an effective amount of a composition comprising a chimeric molecule according to the invention.

In some embodiments, the disease to be treated does not involve the classical complement pathway.

In some embodiments, the disease to be treated is related to macular degeneration (such as age-related macular degeneration or AMD).

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the ficolin-associated polypeptide, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block copolymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the ficolin-associated polypeptide, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the ficolin-associated polypeptide in the form of a nasal or pulmonal spray. As a still further option, the pharmaceutical compositions containing the ficolin-associated polypeptide of the invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In some embodiments of the invention the pharmaceutical formulation comprising the ficolin-associated polypeptide is stable for more than 6 weeks of usage and for more than 3 years of storage. In other embodiments of the invention the pharmaceutical formulation comprising the ficolin-associated polypeptide is stable for more than 4 weeks of usage and for more than 3 years of storage. In a further embodiment of the invention the pharmaceutical formulation comprising the ficolin-associated polypeptide is stable for more than 4 weeks of usage and for more than two years of storage. In an even further embodiment of the invention the pharmaceutical formulation comprising the ficolin-associated polypeptide is stable for more than 2 weeks of usage and for more than two years of storage.

The methods described herein may also be useful for treatment of certain renal diseases, such as membranoproliferative glomerulonephritis type II (MPGN II), hemolytic-uremic syndrome (HUS), lupus nephritis.

The methods described herein may also be useful for treatment of cardiovascular diseases. In some embodiments, the chimeric molecule according to the present invention is used for the treatment of ischemia reperfusion (including for example renal ischemia reperfusion and intestinal ischemia reperfusion).

Also provided are methods of treating organ transplant rejections. In some embodiments, there is provided methods of delaying onset of acute vascular rejection (such as antibody-mediated rejection of heart transplant), or for improving organ transplant survival in an individual by administration of a chimeric molecule according to the present invention.

In some embodiments, there is provided a method of improving organ transplant survival in an individual, the method comprises perfusing the organ to be transplanted to an individual with a composition comprising a chimeric molecule according to the present invention. In some embodiments, there is provided a method of improving survival of an organ transplant donor, comprising administering to the organ transplant donor an effective amount of a composition comprising a chimeric molecule according to the present invention.

Specific embodiments of the invention: As described above the present invention relates to chimeric molecules of a ficolin-associated polypeptide comprising a ficolin-associated polypeptide and a second modulator of complement activity.

In some embodiments the second modulator of complement activity is an inhibitor of complement activation.

In some embodiments the inhibitor of complement activation is selected from the list consisting of Factor H (FH), GAS6, Protein S, C1-inhibitor (C1-inh), complement component 4 binding protein (C4bp), Factor I (FI), CR1, DAF (CD55), CD59, CR2, or a functional fragment thereof.

In some embodiments the inhibitor of complement activation is an inhibitory synthetic peptide, such as compstatin with a sequence of ICVVQDWGHHRCT (SEQ ID NO: 58), wherein Thr-13 is a C-terminal amide and C2 and C12 form a disulfide bridge.

In some embodiments the inhibitor of complement activation is a microbial evasion protein, such as any one selected from the list consisting of Extracellular fibrinogen-binding protein (Efb), Staphylococcal superantigen-like protein-7 (SSL-7), *Staphylococcus* complement inhibitor (SCIN), Complement C2 receptor trispanning protein (CRIT), and Chemotaxis inhibitory protein of *Staphylococcus aureus* (CHIPS).

In some embodiments the inhibitor of complement activation is a microbial evasion protein selected from table 1 derived from J D Lambris, D Ricklin, B V Geisbrecht "Complement evasion by human pathogens"—Nature Reviews Microbiology, February 2008, Vol. 6, page 132 the content of which is hereby incorporated by reference.

TABLE 1

| Microbial complement-targeting proteins |
|---|
| Bacteria |
| *Actinobacillus* spp. |
| Omp100 Outer membrane protein 100 |
| *Bordetella* spp. |
| FHA Filamentous hemagglutinin |
| *Borrelia* spp. |
| CRASP Complement regulator-acquiring surface proteins |
| Erp OspE/F-related proteins |
| CD59-like protein |
| *Escherichia* spp. |
| OmpA Outer membrane protein A |
| StcE Secreted protease of C1 esterase inhibitor |
| TraT TraT outer membrane protein |
| *Moraxella* spp. |
| UspA1/2 Ubiquitous surface protein A1/A2 |
| *Neisseria* spp. |
| LOS Lipooligosaccharide |
| GNA1870 Genome-derived neisserial antigen 1870 |
| Por Outer membrane porins |
| Type IV pili |

TABLE 1-continued

| Microbial complement-targeting proteins |
|---|
| *Porphyromonas* spp. |
| prtH prtH protease |
| *Pseudomonas* spp. |
| PaE *Pseudomonas* elastase |
| PaAP *Pseudomonas* alkaline protease |
| Tuf Elongation factor |
| *Serratia* spp. |
| n/a 56 kDa protease |
| *Staphylococcus* spp. |
| CHIPS Chemotaxis inhibitory protein of *S. aureus* |
| Efb Extracellular fibrinogen-binding protein |
| Ehp a Efb-homologous protein |
| SAK Staphylokinase |
| Sbi *S. aureus* IgG-binding protein |
| SCIN Staphylococcal complement inhibitor |
| SpA *S. aureus* protein A |
| SSL-7 Staphylococcal superantigen-like protein 7 |
| *Streptococcus* spp. |
| Bac-Protein |
| Fba Fibronectin-binding protein |
| Hic b Factor H-binding inhibitor of complement |
| IdeS IgG-degrading Enzyme of *S. pyrogenes* |
| M b Surface proteins M family (Arp, Sir, etc.) |
| PLY Pneumolysin |
| PspA Pneumococcal surface protein A |
| PspC c Pneumococcal surface protein C |
| scpA/B Streptococcal C5a peptidase |
| SIC Streptococcal inhibitor of complement |
| SPE B Streptococcal pyrogenic exotoxin B |
| SpG *Streptococcus* protein G |
| *Yersinia* spp. |
| YadA *Yersinia* adhesin A |
| Viruses: |
| Herpes viruses |
| gC1/2 Transmembrane glycoproteins C1, C2 (HSV) C3b |
| gE + gI Glycoproteins E + I (HSV) |
| gp34, 68 Glycoproteins 34, 68 (HCMV) |
| gpI + gpIV Glycoproteins I + IV (VZV) |
| KCP d Kaposi's sarkoma-associated complement control protein (KSHV) |
| Retroviruses |
| gp41 Envelope glycoprotein 41 (HIV) |
| gp120 Envelope glycoprotein 120 (HIV) |
| Tat Transactivator of transcription (HIV) |
| Poxviruses |
| IMP Cowpox control inflammation modulatory protein (Cowpox Virus) |
| MOPICE Monkeypox inhibitor of complement enzymes (monkeypox virus) |
| SPICE Smallpox inhibitor of complement enzymes (variola virus) |
| VCP Vaccinia virus complement control protein (vaccinia virus) |
| Filoviruses |
| NS1 Non-structural protein 1 (West Nile virus) |
| Fungi: |
| *Candida albicans* |
| CRASP-1 Complement regulator-acquiring surface protein 1 |
| Gpm1p Phosphoglycerate mutase |
| Parasites: |
| *Echinococcus* spp. |
| Hydatid cyst wall |
| *Ixodes* spp. |
| IRAC *Ixodes ricinus* anti-complement protein |
| ISAC *Ixodes scapularis* anti-complement protein |

TABLE 1-continued

| Microbial complement-targeting proteins |
| --- |
| *Onchocerca* spp. |
| mf Microfilariae |
| *Ornithodoros* spp. |
| OmCI *Ornithodoros moubata* complement inhibitor |
| *Schistosoma* spp. |
| CRIT Complement C2 receptor trispanning |
| m28 28 kDa membrane serine protease |
| Pmy e Paramyosin (Schistosome complement inhibitor protein 1 (SCIP-1)) |
| *Trypanosoma* spp. |
| CRIT Complement C2 receptor trispanning |
| T-DAF *Trypanosoma* decay-accelerating factor |

In some embodiments the inhibitor of complement activation is Factor H, or a functional fragment thereof. In some embodiments the Factor H, or a functional fragment thereof comprises at least the first four SCR domains of Factor H.

In some embodiments the second modulator of complement activity is an immunoglobulin molecule or part thereof. In some embodiments the immunoglobulin molecule or part thereof is selected from the Fc component of human IgG1, IgG2, IgG3, and IgG4.

In some embodiments the ficolin-associated polypeptide is capable of associating with mannose-binding lectin (MBL).

In some embodiments the ficolin-associated polypeptide is capable of associating with any one of ficolin-1, ficolin-2, or ficolin-3.

In some embodiments the ficolin-associated polypeptide is capable of associating with any one of C1q, lung surfactant proteins SP-A and/or SP-D, and intracellular collagen-like defence molecules, such as CLL-11.

In some embodiments the ficolin-associated polypeptide is capable of associating with a specific acceptor protein, such as a specific receptor.

In some embodiments the ficolin-associated polypeptide comprises the amino acid sequence 20-297 of SEQ NO:3, or a functional variant thereof.

In some embodiments the ficolin-associated polypeptide comprises the amino acid sequence 20-380 of SEQ NO:1 or a functional variant thereof.

In some embodiments the ficolin-associated polypeptide comprises the amino acid sequence 16-296 of SEQ ID NO:9 or a functional variant thereof.

In some embodiments the ficolin-associated polypeptide has a molecular mass of about 40 kDa under non-reducing conditions on an SDS-PAGE.

In some embodiments the ficolin-associated polypeptide is N-linked glycosylated at one or two amino acids corresponding to a position selected from 49 and 178 of SEQ NO:1.

In some embodiments the ficolin-associated polypeptide is a recombinant protein.

In some embodiments the ficolin-associated polypeptide is in homodimer form.

In some embodiments the ficolin-associated polypeptide consists of the amino acid sequence 20-380 of SEQ ID NO 1.

In some embodiments the ficolin-associated polypeptide comprises the amino acid sequence of SEQ ID NO:4 or variants or immunologic fragments thereof.

In some embodiments the chimeric molecule according to the present invention mediates phagocytosis of dying or dead cells, such as apoptotic cells, and/or cellular debris.

In some embodiments the chimeric molecule according to the present invention mediates phagocytosis of a microorganism.

In some embodiments the ficolin-associated polypeptide has activity similar to other proteins with sequence homology, such as the engulfment adapter protein (GULP).

In some embodiments the ficolin-associated polypeptide and the second modulator of complement activity are directly or indirectly fused to each other in the form of a fusion protein.

In some embodiments the ficolin-associated polypeptide and the second modulator of complement activity are linked via a chemical crosslinker.

In some embodiments the ficolin-associated polypeptide and the second modulator of complement activity are non-covalently linked.

In some embodiments the host cell according the present invention is a eukaryotic cell.

In some embodiments the host cell according the present invention is of mammalian origin.

In some embodiments the host cell according to the present invention is selected from the group consisting of CHO cells, HEK cells and BHK cells.

In some embodiments the chimeric molecule according to the present invention is for the treatment of any indications associated with inflammation, apoptosis and/or autoimmunity.

In some embodiments the chimeric molecule according to the present invention is for the treatment of any autoimmune conditions such as Addison's disease, autoimmune hemolytic anemia, autoimmune thyroiditis, Crohn's disease, Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, psoriasis, various allergies.

In some embodiments the chimeric molecule according to the present invention is for the treatment of any inflammatory disorder selected from the group consisting of appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitis, hepatitis, Crohn's disease, enteritis, Whipple's disease, allergy, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumotransmicroscopicsilicovolcanoconiosis, alvealitis, bronchiolitis, pharyngitis, pleurisy, sinusitis, influenza, respiratory syncytial virus infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, ankylosing spondylitis, Berger's disease, Reiter's syndrome and Hodgkin's disease, keratitis, Type 2 diabetes, cystic fibrosis, myocardial infarction, reperfusion injury, stroke, dermatomyositis, metabolic syndrome, systemic inflammatory response syndrome, sepsis, multiple organ failure, disseminated intravascular coagulation, anaphylactic shock. Vascular complication and nephropathy associated with type 1 and/or type 2 diabetes, meningitis, bacterial septicaemia, complicated malaria, atypic haemolytic uremic syndrome, haemolytic uremic syndrome, age related macular degeneration, paroxysmal nocturnal hemoglobinuria, snake venom bite, burn injury, and complications to organ transplantations.

In some embodiments the chimeric molecule according to the present invention is for the treatment of any inflammatory disorder selected from the group consisting of organ ischemia, reperfusion injury, organ necrosis, vasulitis, endocarditis, atherosclerosis, thrombophlebitis, pericarditis, myocarditis, myocardial ischemia, periarteritis nodosa, rheumatic fever, congestive heart failure, adult respiratory distress syndrome, cerebral infarction, cerebral embolism. Vascular complications and nephropathy associated with type 1 and/or type 2 diabetes.

In some embodiments the chimeric molecule according to the present invention is for the treatment of any indications associated with coagulation, thrombotic or coagulopathic related diseases.

In some embodiments the chimeric molecule according to the present invention is for the treatment of an indication associated with coagulation, thrombotic or coagulopathic related diseases or disorders including inflammatory response and chronic thromboembolic diseases or disorders associated with fibrin formation including vascular disorders such as thrombosis, such as deep venous thrombosis, arterial thrombosis, post surgical thrombosis, coronary artery bypass graft (CABG), percutaneous transdermal coronary angioplastry (PTCA), platelet deposition stroke, tumor growth, tumor metastasis, angiogenesis, thrombolysis, atherosclerosis, restenosis, such as arteriosclerosis and/or restenosis following angioplastry, acute and chronic indications such as inflammation, sepsis, septic chock, septicemia, hypotension, adult respiratory distress syndrome (ARDS), systemic inflammatory response syndrome (SIRS), disseminated intravascular coagulopathy (DIC), pulmonary embolism, pathological platelet deposition, myocardial infarction, or the prophylactic treatment of mammals with atherosclerotic vessels at risk for thrombosis, venoocclusive disease following peripheral blood progenitor cell (PBPC) transplantation, hemolytic uremic syndrome (HUS), and thrombotic thrombocytopenic purpura (TTP) and rheumatic fever.

In some embodiments the chimeric molecule according to the present invention is for the treatment of an indication associated with coagulation, thrombotic or coagulopathic related diseases or disorders including inflammatory response and chronic thromboembolic diseases or disorders associated with fibrin formation including vascular disorders such as thrombosis, such as deep venous thrombosis, arterial thrombosis, post surgical thrombosis, coronary artery bypass graft (CABG), percutaneous transdermal coronary angioplastry (PTCA), platelet deposition stroke, tumor growth, tumor metastasis, angiogenesis, thrombolysis, atherosclerosis, restenosis, such as arteriosclerosis and/or restenosis following angioplastry, acute and chronic indications such as inflammation, pathological platelet deposition, myocardial infarction, or the prophylactic treatment of mammals with atherosclerotic vessels at risk for thrombosis, venoocclusive disease following peripheral blood progenitor cell (PBPC) transplantation, hemolytic uremic syndrome (HUS), and thrombotic thrombocytopenic purpura (TTP) and rheumatic fever.

In some embodiments the chimeric molecule according to the present invention is for preventing the occurrence of thromboembolic complications in identified high risk patients, such as those undergoing surgery or those with congestive heart failure.

In some embodiments the chimeric molecule according to the present invention is for the treatment of a medical condition associated with the heart.

In some embodiments the chimeric molecule according to the present invention is for the treatment of a medical condition associated with a deficiency in a ficolin-associated polypeptide.

Modulators of Complement Activity:

As discussed above the second modulator of complement activity used in the chimeric molecule of a ficolin-associated polypeptide may by any compound that directly or indirectly influences complement activity.

Natural complement inhibitors and regulatory proteins prevent the activation of the complement system, and include: (i) complement receptor 1 (CR1 or CD35) and DAF (decay accelerating factor or CD55), which compete with factor B for binding with C3b and block the alternative pathway, as well as similarly block the classical pathway C4b from interacting with C2, (ii) factor I, a plasma protease that cleaves C3b and C4b into their inactive forms to block formation of the convertases, and (iii) factor H which can compete with factor B, displace Bb from the convertase, act as a cofactor for factor I, and bind C3b that is already bound to cells. CD59 is a complement regulatory protein that inhibits MAC (C5b-9).

In some embodiments the modulator of complement activity used according to the present invention is Factor H. Factor H is a human plasma complement regulator that acts as a significant co-factor for Factor I in the cleavage and down-regulation of activated C4 and C3 and further downstream complement activation (Zipfel P F. Complement factor H: physiology and pathophysiology. Semin Thromb Hemost 2001; 27:191-9). Factor H thus works in at the central part of the complement system when initiation and activation have already occurred. In some embodiments, the Factor H is a wildtype Factor H, such as wildtype human Factor H. In some embodiments, the Factor H is a variant of wildtype Factor H.

In some embodiments the modulator of complement activity used according to the present invention is Protein S. This gene encodes a vitamin K-dependent plasma protein that functions as a cofactor for the anticoagulant protease, activated protein C (APC) to inhibit blood coagulation. It is found in plasma in both a free, functionally active form and also in an inactive form complexed with C4b-binding protein and helps to prevent coagulation and stimulating fibrinolysis. Mutations in this gene result in autosomal dominant hereditary thrombophilia. In some embodiments, the Protein S is a wildtype Protein S, such as wildtype human Protein S. In some embodiments, the Protein S is a variant of wildtype Protein S.

The amino acid sequences of human Protein S (SEQ ID NO:52) is one suitable example of a sequence that could be used as a modulator of complement activity of a chimeric protein according to the invention. Amino acid sequence of an exemplary human MAP-1/Protein S chimeric protein is illustrated by SEQ ID NO:56, and human Protein S/MAP1 chimeric protein by SEQ ID NO:57. For example, a Protein S variant may have an amino acid sequence that is at least about 70% identical to the amino acid sequence of a naturally occurring human Protein S (e.g., SEQ ID NO:52), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring Protein S (e.g., SEQ ID NO:52). In some embodiment, a variant of Protein S (or a fragment thereof) retains all the complement inhibition activity of Protein S (or a fragment thereof). In some embodiments, the variant of Protein S (or a fragment thereof) retains at least about 50%, for example, at least about any of 60%, 70%, 80%, 90%, or 95% of the complement inhibition activity of Protein S (or a fragment thereof).

In some embodiments the modulator of complement activity used according to the present invention is GAS6. This gene product is a gamma-carboxyglutamic acid (Gla)-containing protein thought to be involved in the stimulation of cell proliferation, and may play a role in thrombosis by amplifying platelet. It is a ligand for tyrosine-protein kinase receptors AXL, TYRO3 and MER whose signaling is implicated in cell growth and survival, cell adhesion and cell migration. Alternatively spliced transcript variants encoding different isoforms have been found for this gene. Transcript variant 1 is the predominant transcript and encodes the longest isoform. Transcript variant 2 is missing several 5'-exons and contains a different 5' UTR compared to transcript variant 1. This results in an isoform 2 with a shorter N-terminus, but retaining the two LamG domains at the C-terminus. Transcript variant 3 is missing several 5'-exons and contains a distinct 5' UTR compared to transcript variant 1. This results in an isoform 3 with a shorter N-terminus, but retaining the two LamG domains at the C-terminus. In some embodiments, the GAS6 is a wildtype GAS6, such as wildtype human GAS6. In some embodiments, the GAS6 is a variant of wildtype GAS6.

The amino acid sequences of human GAS6 (SEQ ID NO:46, SEQ ID NO:48, or SEQ ID NO:50) are suitable examples of sequences that could be used as a modulator of complement activity of a chimeric protein according to the invention. Amino acid sequence of an exemplary human MAP-1/GAS6 chimeric protein is illustrated by SEQ ID NO:54, and human GAS6/MAP1 chimeric protein by SEQ ID NO:55. For example, a GAS6 variant may have an amino acid sequence that is at least about 70% identical to the amino acid sequence of a naturally occurring human GAS6 (e.g., SEQ ID NO:46, SEQ ID NO:48, or SEQ ID NO:50), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring GAS6 (e.g., SEQ ID NO:46, SEQ ID NO:48, or SEQ ID NO:50). In some embodiment, a variant of GAS6 (or a fragment thereof) retains all the complement inhibition activity of GAS6 (or a fragment thereof). In some embodiments, the variant of GAS6 (or a fragment thereof) retains at least about 50%, for example, at least about any of 60%, 70%, 80%, 90%, or 95% of the complement inhibition activity of GAS6 (or a fragment thereof).

In some embodiments the complement inhibitor compound is an inhibitor of C5, C5a, or C5b. In some embodiments, the compound is a specific inhibitor of C5, C5a, or C5b. In other embodiments, the complement inhibitor compound is a polypeptide or a small molecule compound that inhibits C5, C5a, or C5b. In yet other embodiments, the inhibitor is an antibody that binds specifically to C5. In yet other embodiments, the inhibitor is a human monoclonal antibody against complement component C5, including eculizumab, pexelizumab or another anti-C5 antibody.

In yet a further embodiment the complement inhibitor compound is an inhibitor of C3 or C3 convertase. In some embodiments, the compound is a specific inhibitor of C3 or C3 convertase. In yet other embodiments, the complement inhibitor compound is a polypeptide, antibody or a small molecule compound that inhibits C3 or C3 convertase.

In yet a further embodiment the complement inhibitor compound is a potentiator of factor H. In some embodiments, the compound is a specific fragment of Factor H delivered to the joint. In yet other embodiments, the complement inhibitor compound is a polypeptide, antibody or a small molecule compound that potentiates Factor H. In yet other embodiments, the complement inhibitor consists in part of a monoclonal antibody specific for Factor H that promotes binding to the cartilage. In yet other embodiments, the monoclonal antibody is an isolated human monoclonal antibody.

In another embodiment, the complement inhibitor compound is an inhibitor of the membrane attack complex.

In another embodiment, the complement inhibitor compound is an inhibitor of proteases involved in the complement system. In some embodiments, the complement inhibitor is C1-INH. In yet other embodiments, the complement inhibitor is C1-INH purified from plasma or produced recombinantly in transgenic animals. In some embodiments, the C1-INH is recombinant human C1 inhibitor or functional equivalent thereof. In another embodiment, the complement inhibitor is a soluble complement regulator. In some embodiments, the complement inhibitor is soluble CR1 (sCR1), or analogues thereof. In other embodiments, the complement inhibitor compound is a CR2-Factor H fusion protein or a CR2-Crry fusion protein.

In other embodiments, the complement inhibitor compound is a small molecule. In yet other embodiments, the small molecule inhibits C5a or C3a. In other embodiments, the complement inhibitor compound is a compound that prevents cleavage of C2, C3, C4, or C5.

In other embodiments, the complement inhibitor compound is a Vaccinia complement control protein (Vaccinia CCP).

In other embodiments, the complement inhibitor compound is a decay-accelerating factor (DAF), a soluble decay-accelerating factor (sDAF), a membrane cofactor protein (MCP), a soluble membrane cofactor protein (sMCP), a fusion protein comprising sMCP fused to DAF (sMCP-DAF), CD59, a soluble CD59 protein (sCD59), or a fusion protein comprising DAF and CD59 (DAF-CD59). In yet other embodiments, the compound is an MCP-DAF fusion protein. In still other embodiments, the protein is CAB-2.

In other embodiments, the complement inhibitor compound is a variant or mutant C5a protein.

In other embodiments, the complement inhibitor compound is an antibody or functional fragment thereof that specifically binds C5, C3, C5a, C3a, C4a, C6, C7, C8, C9, factor B factor D, properdin (factor P), CD20, CD38, C5 receptor (C5R) or C5a receptor (CSaR).

In yet other embodiments, the antibody that specifically binds the C5 receptor is neutrazumab.

In yet other embodiments, the antibody that specifically binds C5 is eculizumab. In yet other embodiments, the antibody that binds CD38 is HuMax-CD38.

In yet other embodiments, the complement inhibitor compound is eculizumab.

In other embodiments, the complement inhibitor compound is a CSaR antagonist selected from the group consisting of N Me-FKPdChaWdR and F-(OpdChaWR) (Phe-[Orn-Pro-D-cyclohexylalanine-Trp-Arg]) CSaR.

In other embodiments, the complement inhibitor compound is an RNA aptamer. In yet other embodiments, the aptamer selectively binds and inhibits C5. In other embodiments, the complement inhibitor compound is a C3 inhibitor peptide or a functional analog thereof.

In other embodiments, the complement inhibitor compound is BCX-1470, FUT-175, K-76, recombinant human mannose-binding lectin (rhMBL), APT070, TNX-234, TNX-558, TA106, complement component 4 binding protein (C4bp), Factor H, Factor I, carboxypeptidase N, vitronectin, clusterin, JSM-7717, JPE-1375, or OmCI protein.

In other embodiments, the complement inhibitor compound inhibits C5, C3, C5a, C3a, C4a, C6, C7, C8, C9, factor B factor D, properdin (factor p), CD20, CD38, C5 receptor (C5R), C5a receptor (C5aR), C1q, C1, C1 r, or C1s. In another embodiment, the method further comprises administering to the subject a further therapeutic treatment. In various embodiments, the further therapeutic treatment comprises administration of an active agent, such as an antiinflammatory agent, an analgesic, or a steroid. In other embodiments, the further therapeutic treatment is a physical therapy, exercise or a local heat treatment. In one embodiment, when the further therapeutic treatment is an active agent, the antiinflammatory agent is a non-steroidal anti-inflammatory agent or a cyclooxygenase-2 selective inhibitor, the analgesic is a non-opioid analgesic, or the steroid is a corticosteroid drug. In some embodiments the second modulator of complement activity of the chimeric molecule is Factor H (FH), or a functional fragment thereof.

In some embodiments, the chimeric molecule comprises one, two, or more (such as any of three, four, five, or more) Factor H portions. These Factor H portions may be the same or different, for example in terms of amino acid sequences, structures, and/or functions. For example, in some embodiments, the chimeric molecule (such as a fusion protein) comprises: 1) a ficolin-associated polypeptide, and 2) one, two or more Factor H portions comprising a FH or a fragment thereof.

In some embodiments, the Factor H portion comprises a full length Factor H. In some embodiments, the Factor H portion comprises a fragment of Factor H. In some embodiments, the Factor H portion comprises at least the first four N-terminal short consensus repeat (SCR) domains of Factor H. In some embodiments, the Factor H portion comprises at least the first five N-terminal SCR domains of Factor H. In some embodiments, the Factor H portion lacks a heparin binding site. In some embodiments, the Factor H portion comprises a Factor H or a fragment thereof having a polymorphism that is protective against age-related macular degeneration.

In some embodiments, the Factor H portion comprises at least the first 5, 6, 7, 8, 9, 10, 11, 12, 13, 14, or more N-terminal SCR domains of Factor H.

In some embodiments, the Factor H portion comprises amino acids 21 to 320 of SEQ ID NO:20.

In some embodiments, the polynucleotide encoding a fusion protein comprising a ficolin-associated polypeptide and a Factor H portion also comprises a sequence encoding a signal peptide operably linked at the 5' end of the sequence encoding the fusion protein. In some embodiments, a linker sequence is used for linking the ficolin-associated polypeptide and the Factor H portion.

In some embodiments, the disease to be treated is a disease that is associated with Factor H deficiencies (including for example decrease in level of Factor H, decrease in activity of Factor H, or lacking wild type or protective Factor H). In some embodiments, the disease to be treated is not a disease that is associated with Factor H deficiencies.

The terms "Factor H portion", "Factor H", or just "FH" refers to human Factor H according to SEQ ID NO: 20 or a functional fragment thereof.

The Factor H portion of the chimeric molecule described herein comprises Factor H or a fragment thereof. Complement factor H (FH) is a single polypeptide chain plasma glycoprotein. The protein is composed of 20 repetitive SCR domains of approximately 60 amino acids, arranged in a continuous fashion like a string of 20 beads. Factor H binds to C3b, accelerates the decay of the alternative pathway C3-convertase (C3Bb), and acts as a cofactor for the proteolytic inactivation of C3b. In the presence of factor H, C3b proteolysis results in the cleavage of C3b. Factor H has at least three distinct binding domains for C3b, which are located within SCR 1-4, SCR 5-8, and SCR 19-20. Each site of factor H binds to a distinct region within the C3b protein: the N-terminal sites bind to native C3b; the second site, located in the middle region of factor H, binds to the C3c fragment and the sited located within SCR19 and 20 binds to the C3d region. In addition, factor H also contains binding sites for heparin, which are located within SCR 7, SCR 5-12, and SCR 20 of factor H and overlap with that of the C3b binding site. Structural and functional analyses have shown that the domains for the complement inhibitory activity of Factor H are located within the first four N-terminal SCR domains.

SEQ ID NO:20 represents the full-length human Factor H protein sequence. Amino acids 1-18 correspond to the leader peptide, amino acids 21-80 correspond to SCR 1, amino acids 85-141 correspond to SCR 2, amino acids 146-205 correspond to SCR 3, amino acids 210-262 correspond to SCR4, amino acids 267-320 correspond to SCR5. It is understood that species and strain variations exist for the disclosed peptides, polypeptides, and proteins, and that the Factor H or a fragment thereof encompasses all species and strain variations.

The Factor H portion described herein refers to any portion of a Factor H protein having some or all the complement inhibitory activity of the FH protein, and includes, but is not limited to, full-length Factor H proteins, biologically active fragments of Factor H proteins, a Factor H fragment comprising SCR1-4, or any homologue or variant of a naturally occurring Factor H or fragment thereof, as described in detail below. In some embodiments, the Factor H portion has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In some embodiments, the Factor H portion comprises the first four N-terminal SCR domains of Factor H. In some embodiments, the construct comprises the first five N-terminal SCR domains of Factor H. In some embodiments, the construct comprises the first six N-terminal SCR domains of Factor H. In some embodiments, the Factor H portion comprises (and in some embodiments consists of or consisting essentially of) at least the first four N-terminal SCR domains of Factor H, including for example, at least any of the first 5, 6, 7, 8, 9, 10, 11, 12, 13, 14, or more N-terminal SCR domains of Factor H.

In some embodiments, the Factor H is a wildtype Factor H, such as wildtype human Factor H. In some embodiments, the Factor H is a variant of wildtype Factor H.

In some embodiments, the Factor H portion lacks a heparin binding site. This can be achieved, for example, by mutation of the heparin binding site on Factor H, or by selecting Factor H fragments that do not contain a heparin binding site. In some embodiments, the Factor H portion comprises a Factor H or a fragment thereof having a polymorphism that is protective to age-related macular degeneration. Hageman et al., Proc. Natl. Acad Sci. USA 102(20):7227.

A homologue or variant of a Factor H protein or a fragment thereof includes proteins which differ from a naturally occurring Factor H (or Factor H fragment) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a Factor H homologue or variant may have an amino acid sequence that is at least about 70% identical to the amino acid sequence of a naturally occurring human Factor H (e.g., SEQ ID NO:20), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring Factor H (e.g., SEQ ID NO:20). In some embodiment, a homologue or variant of Factor H (or a fragment thereof) retains all the complement inhibition activity of Factor H (or a fragment thereof). In some embodiments, the homologue or variant of Factor H (or a fragment thereof) retains at least about 50%, for example, at least about any of 60%, 70%, 80%, 90%, or 95% of the complement inhibition activity of Factor H (or a fragment thereof).

In some embodiments, the Factor H portion comprises at least the first four N-terminal SCR domains of a human Factor H, such as a Factor H portion having an amino acid sequence containing at least amino acids 21 through 262 of the human Factor H (SEQ ID NO:20). In some embodiments, the Factor H portion comprises at least the first four N-terminal SCR domains of human Factor H having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 262 of the human Factor H (SEQ ID NO:20).

In some embodiments, the Factor H portion comprises at least the first five N-terminal SCR domains of a human Factor H, such as a Factor H portion having an amino acid sequence containing at least amino acids 21 through 320 of the human Factor H (SEQ ID NO:20). In some embodiments, the Factor H portion comprises at least the first five N-terminal SCR domains of human Factor H having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 320 of the human Factor H (SEQ ID NO:20). In some embodiments, the Factor H portion comprises a full length or a fragment of factor-H like 1 molecule (FHL-1), a protein encoded by an alternatively spliced transcript of the factor H gene. The mature FHL-1 contains 431 amino acids. The first 427 amino acids organize seven SCR domains and are identical to the N-terminal SCR domains of Factor H. The remaining four amino acid residues Ser-Phe-Thr-Leu (SFTL) at the C-terminus are specific to FHL-1. FHL-1 has been characterized functionally and shown to have factor H complement regulatory activity. The term "Factor H portion" also encompasses full length or fragments of factor H related molecules, including, but are not limited to, proteins encoded by the FHR1, FHR2, FHR3, FHR4, FHR5 genes. These factor H related proteins are disclosed, for example, in de Cordoba et al., Molecular Immunology 2004, 41: 355-367.

In some embodiments the second modulator of complement activity of the chimeric molecule is C4bp, or a functional fragment or portion thereof.

In some embodiments, the chimeric molecule comprises one, two, or more (such as any of three, four, five, or more) C4bp portions. In some embodiments, the chimeric molecule comprises either the alfa chain or the beta chain or combination of both. These C4bp portions may be the same or different, for example in terms of amino acid sequences, structures, and/or functions. For example, in some embodiments, the chimeric molecule (such as a fusion protein) comprises: 1) a ficolin-associated polypeptide, and 2) one, two or more C4bp portions comprising a C4bp or a fragment thereof.

In some embodiments, the C4bp portion comprises a full length C4bp. In some embodiments, the C4bp portion comprises a fragment of C4bp. In some embodiments, the C4bp portion comprises at least the first three N-terminal short consensus repeat (SCR) domains of C4bp alfa chain and/or the second SCR domain of C4bp beta chain. In some embodiments, the C4bp portion comprises a C4bp or a fragment thereof having a polymorphism that is protective against age-related macular degeneration.

In some embodiments, the C4bp portion comprises at least the first 3, 4, 5, 6, 7, 8 N-terminal SCR domains of C4bp alfa.

In some embodiments, the C4bp portion comprises at least the first 1, 2, 3 SCR domains of C4bp beta.

In some embodiments, the C4bp alfa portion comprises amino acids 21 to 597 of SEQ ID NO:21.

In some embodiments, the C4bp beta portion comprises amino acids 21 to 252 of SEQ ID NO:22.

In some embodiments, the polynucleotide encoding a fusion protein comprising a ficolin-associated polypeptide and a C4bp portion also comprises a sequence encoding a signal peptide operably linked at the 5' end of the sequence encoding the fusion protein. In some embodiments, a linker sequence is used for linking the ficolin-associated polypeptide and the C4bp portion.

In some embodiments, the disease to be treated is a disease that is associated with C4bp deficiencies (including for example decrease in level of C4bp, decrease in activity of C4bp, or lacking wild type or protective C4bp). In some embodiments, the disease to be treated is not a disease that is associated with C4bp deficiencies.

The terms "C4bp portion", "C4 binding protein", or just "C4bp" refers to human C4bp according to SEQ ID NO: 21 and SEQ ID NO: 22 or a functional fragment thereof.

The C4bp portion of the chimeric molecule described herein comprises C4bp or a fragment thereof. Complement C4 binding protein (C4bp) is a single polypeptide chain plasma glycoprotein. The protein is composed of seven identical alfa-chains and one beta chain linked by their C-terminal parts in a central core. It inhibits the action of C4.

It splits C4 convertase and is a cofactor for factor I which cleaves C4b. C4BP binds necrotic cells and DNA, to clean up after swelling. C4bp protein has at least two distinct binding domains for C4b, which are located within alfa SCR 1-3 and beta SCR 2.

SEQ ID NO:21 represents the full-length alfa chain of human C4bp protein sequence. Amino acids 1-20 correspond to the leader peptide, amino acids 49-110 correspond to SCR 1, amino acids 111-172 correspond to SCR 2, amino acids 173-236 correspond to SCR 3, amino acids 237-296 correspond to SCR4, amino acids 297-362 correspond to SCR5, amino acids 363-424 correspond to SCR6, amino acids 425-482 correspond to SCR7, amino acids 483-540 correspond to SCR8. It is understood that species and strain variations exist for the disclosed peptides, polypeptides, and proteins, and that the C4bp alfa chain or a fragment thereof encompasses all species and strain variations.

SEQ ID NO:22 represents the full-length beta chain of human C4bp protein sequence. Amino acids 1-20 correspond to the leader peptide, amino acids 21-78 correspond to SCR 1, amino acids 79-136 correspond to SCR 2, amino acids 137-193 correspond to SCR 3. It is understood that species and strain variations exist for the disclosed peptides, polypeptides, and proteins, and that the C4bp beta chain or a fragment thereof encompasses all species and strain variations.

The C4bp portion described herein refers to any portion of a C4bp protein having some or all the complement inhibitory activity of the C4bp protein, and includes, but is not limited to, full-length C4bp proteins, biologically active fragments of C4bp proteins, a C4bp fragment comprising SCR1-3, or any homologue or variant of a naturally occurring C4bp or fragment thereof, as described in detail below. In some embodiments, the C4bp portion has one or more of the following properties: (1) binding to C4, (2) binding to C3b/C4b, (3) accelerate the degradation of the C4bC2a complex by dissociating the complement fragment C2a.

In some embodiments the second modulator of complement activity of the chimeric molecule is Factor I (FI), or a functional fragment or portion thereof.

In some embodiments, the chimeric molecule comprises one, two, or more (such as any of three, four, five, or more) FI portions. These FI portions may be the same or different, for example in terms of amino acid sequences, structures, and/or functions. For example, in some embodiments, the chimeric molecule (such as a fusion protein) comprises: 1) a ficolin-associated polypeptide, and 2) one, two or more FI portions comprising a FI or a fragment thereof.

In some embodiments, the FI portion comprises a full length FI. In some embodiments, the FI portion comprises a fragment of FI. In some embodiments, the FI portion comprises at least the SP domain. In some embodiments, the FI portion comprises the FIMAC, SRCR, LDLRa1, LDLRb1 domains. In some embodiments, the FI portion comprises a FI or a fragment thereof having a polymorphism that is protective against age-related macular degeneration.

In some embodiments, the FI portion comprises amino acids 21 to 583 of SEQ ID NO:23.

In some embodiments, the polynucleotide encoding a fusion protein comprising a ficolin-associated polypeptide and a FI portion also comprises a sequence encoding a signal peptide operably linked at the 5' end of the sequence encoding the fusion protein. In some embodiments, a linker sequence is used for linking the ficolin-associated polypeptide and the FI portion.

In some embodiments, the disease to be treated is a disease that is associated with FI deficiencies (including for example decrease in level of FI, decrease in activity of FI, or lacking wild type or protective FI). In some embodiments, the disease to be treated is not a disease that is associated with FI deficiencies.

The terms "FI portion" or just "FI" refers to human Factor I according to SEQ ID NO: 23 or a functional fragment thereof.

The FI portion of the chimeric molecule described herein comprises FI or a fragment thereof. Factor I binding protein (FI) is a single polypeptide chain plasma glycoprotein. FI has restricted specificity limited to cleavage of arginyl bounds in its natural protein substrates C3b and C4b. Components such as FH, CR1, MCP or C4bp are required as cofactors. FI is synthesized as a single polypeptide chain with an N-terminal heavy (317 amino acids) chain and a C-terminal light chain (244 amino acids). The FI heavy chain has four domains: a FIMAC domain, a Scavenger Receptor Cysteine Rich (SRCR) domain and two LDL-receptor Class A domains; the precise biological function of the heavy chain is not known, but it is likely to play a key role in recognising the FI cleavage substrates (C3b and C4b) and the cofactor proteins needed for cleavage of C3b (FH, CR1, MCP) and C4b (C4BP). The LDL-receptor domains are likely to contain one Calcium-binding site each. The FI light chain is the serine protease (SP) domain containing the catalytic triad responsible for specific cleavage of C3b and C4b.

SEQ ID NO:23 represents the full-length of human FI protein sequence. Amino acids 1-18 correspond to the leader peptide, amino acids 55-108 correspond to the FIMAC domain, amino acids 114-212 correspond to the Scavenger Receptor Cysteine Rich (SRCR) domain, amino acids 213-257 correspond to the LDL-receptor Class A1 domains, amino acids 258-294 correspond to the LDL-receptor Class A2 domains, amino acids 340-574 correspond to peptidase domain.

The FI portion described herein refers to any portion of a FI protein having some or all the complement inhibitory activity of the FI protein, and includes, but is not limited to, full-length FI proteins, biologically active fragments of FI proteins, a FI fragment comprising at least the serine protease domain, or any homologue or variant of a naturally occurring FI or fragment thereof, as described in detail below. In some embodiments, the FI portion has one or more of the following properties: (1) cleavage of C3b (2) cleavage of C4b.

In some embodiments the second modulator of complement activity of the chimeric molecule is C1-inhibitor (C1-inh), or a functional fragment or portion thereof.

In some embodiments, the chimeric molecule comprises one, two, or more (such as any of three, four, five, or more) C1-inh portions. These C1-inh portions may be the same or different, for example in terms of amino acid sequences, structures, and/or functions. For example, in some embodiments, the chimeric molecule (such as a fusion protein) comprises: 1) a ficolin-associated polypeptide, and 2) one, two or more C1-inh portions comprising a C1-inh or a fragment thereof.

In some embodiments, the C1-inh portion comprises a full length C1-inh. In some embodiments, the C1-inh portion comprises a fragment of C1-inh. In some embodiments, the C1-inh portion comprises at least part of the serpin domain. In some embodiments, the C1-inh portion comprises a C1-inh or a fragment thereof having a polymorphism that is protective against age-related macular degeneration.

In some embodiments, the C1-inh portion comprises amino acids 21 to 500 of SEQ ID NO:24.

In some embodiments, the polynucleotide encoding a fusion protein comprising a ficolin-associated polypeptide and a C1-inh portion also comprises a sequence encoding a signal peptide operably linked at the 5' end of the sequence encoding the fusion protein. In some embodiments, a linker sequence is used for linking the ficolin-associated polypeptide and the C1-inh portion.

In some embodiments, the disease to be treated is a disease that is associated with C1-inh deficiencies (including for example decrease in level of C1-inh, decrease in activity of C1-inh, or lacking wild type or protective C1-inh). In some embodiments, the disease to be treated is not a disease that is associated with C1-inh deficiencies.

The terms "C1-inh portion" or just "C1-inh" refers to human C1-inhibitor according to SEQ ID NO: 24 or a functional fragment thereof.

The C1-inh portion of the chimeric molecule described herein comprises C1-inh or a fragment thereof. Complement C1 inhibitor protein (C1-inh) is a serine protease inhibitor (serpin) protein, the main function of which is the inhibition of the complement system to prevent spontaneous activation. The C-terminal serpin domain is similar to other serpins, and this part of C1-inh provides the inhibitory activity of C1-inh. The N-terminal domain (also some times referred to as the N-terminal tail) is not essential for C1-inh to inhibit proteinases. This domain has no similarity to other proteins. C1-inh is highly glycosylated, bearing both N- and O-glycans. N-terminal domain is especially heavily glycosylated. C1-inh is an acute phase protein, it circulates in blood. C1-inh irreversibly binds to and inactivates C1r and C1s proteinases in the C1 complex of classical pathway of complement. MASP-1 and MASP-2 proteinases in MBL complexes of the lectin pathway are also inactivated. This way, C1-inh prevents the proteolytic cleavage of later complement components C4 and C2 by C1 and MBL. Although named after its complement inhibitory activity, C1-inh also inhibits proteinases of the fibrinolytic, clotting, and kinin pathways. Most notably, C1-inh is the most important physiological inhibitor of plasma kallikrein, fXIa and fXIIa.

SEQ ID NO:24 represents the full-length of human C1-inh protein sequence. Amino acids 1-22 correspond to the leader peptide, amino acids 23-500 correspond to the serpin domain. It is understood that species and strain variations exist for the disclosed peptides, polypeptides, and proteins, and that the C1-inh or a fragment thereof encompasses all species and strain variations.

The C1-inh portion described herein refers to any portion of a C1-inh protein having some or all the complement inhibitory activity of the C1-inh protein, and includes, but is not limited to, full-length C1-inh proteins, biologically active fragments of C1-inh proteins, a C1-inh fragment comprising SCR1-3, or any homologue or variant of a naturally occurring C1-inh or fragment thereof, as described in detail below. In some embodiments, the C1-inh portion has one or more of the following properties: (1) binding to C1r and C1s, (2) inhibits activity of MASP-1 and MASP-2 proteinases, (3) inhibits proteinases of the fibrinolytic, clotting, and kinin pathways, (4) inhibitor of plasma kallikrein, Factor XIa and Factor XIIa.

In other embodiments the second modulator of complement activity is a homing domain that facilitates the transport and/or uptake at a particular site of complement activity, such as a site of inflammation.

Accordingly, in some embodiments, the second modulator of complement activity is a targeting molecule or targeting moiety which increases the targeting efficiency of the chimeric molecule. For example, the second modulator of complement activity may be a ligand (such as an amino acid sequence) that has the capability to bind or otherwise attach to an endothelial cell of a blood vessel (referred to as "vascular endothelial targeting amino acid ligand"). Exemplary vascular endothelial targeting ligands include, but are not limited to, VEGF, FGF, integrin, fibronectin, I-CAM, PDGF, or an antibody to a molecule expressed on the surface of a vascular endothelial cell.

In some embodiments, the chimeric molecule of a ficolin-associated polypeptide is conjugated (such as fused) to a ligand for intercellular adhesion molecules. For example, the second modulator of complement activity may be one or more carbohydrate moieties that bind to an intercellular adhesion molecule. The carbohydrate moiety facilitates localization of the chimeric molecule to the site of injury. The carbohydrate moiety can be attached to the chimeric molecule by means of an extracellular event such as a chemical or enzymatic attachment, or can be the result of an intracellular processing event achieved by the expression of appropriate enzymes. In some embodiments, the carbohydrate moiety binds to a particular class of adhesion molecules such as integrins or selectins, including E-selectin, L-selectin or P-selectin. In some embodiments, the carbohydrate moiety comprises an N-linked carbohydrate, for example the complex type, including fucosylated and sialylated carbohydrates. In some embodiments, the carbohydrate moiety is related to the Lewis X antigen, for example the sialylated Lewis X antigen.

For treatment of eye diseases such as AMD, the second modulator of complement activity may be an antibody that recognizes a neoepitope of the drusen. Other targeting molecules such as small targeting peptide can also be used. Other modifications of the chimeric molecule include, for example, glycosylation, acetylation, phosphorylation, amidation, derivatization by known protectinglblocking groups, and the like.

The second modulator of complement activity may be an immunologically active domain, such as an antibody epitope or other tag, to facilitate targeting of the polypeptide. Other amino acid sequences that may be included in the chimeric molecule include functional domains, such as active sites from enzymes such as a hydrolase, glycosylation domains, and cellular targeting signals.

Domain for Increasing the Circulatory Half-Life:

In some embodiments the chimeric molecule according to the invention is further modified with a domain for increasing the circulatory half-life of the chimeric molecule as compared to the ficolin-associated polypeptide, which domain is a hydrophilic substituent.

The term "hydrophilic substituent", as used herein means a molecule that is capable of conjugation to an attachment point of the peptide and which is water-soluble. The terms "hydrophilic" and "hydrophobic" are generally defined in terms of a partition coefficient P, which is the ratio of the equilibrium concentration of a compound in an organic phase to that in an aqueous phase. A hydrophilic compound has a log P value less than 1.0, typically less than about −0.5, where P is the partition coefficient of the compound between octanol and water, while hydrophobic compounds will generally have a log P greater than about 3.0, typically greater than about 5.0.

The polymer molecule is a molecule formed by covalent linkage of two or more monomers wherein none of the monomers is an amino acid residue. Preferred polymers are polymer molecules selected from the group consisting of polyalkylene oxides, including polyalkylene glycol (PAG), such as polyethylene glycol (PEG) and polypropylene glycol (PPG), branched PEGs, polyvinyl alcohol (PVA), polycarboxylate, poly-vinylpyrolidone, polyethylene-co-maleic acid anhydride, polystyrene-co-maleic acid anhydride, and dextran, including carboxymethyl-dextran, PEG being particular preferred. The term "attachment group" is intended to indicate a functional group of the peptide capable of attaching a polymer molecule. Useful attachment groups are, for example, amine, hydroxyl, carboxyl, aldehyde, ketone, sulfhydryl, succinimidyl, maleimide, vinylsulfone, oxime or halo acetate.

The term "PAO" as used herein refers to any polyalkylene oxide, including polyalkylene glycol (PAG), such as polyethylene glycol (PEG) and polypropylene glycol (PPG), branched PEGs and methoxypolyethylene glycol (mPEG) with a molecular weight from about 200 to about 100.000 Daltons.

The polymer molecule to be coupled to the ficolin-associated polypeptide may be any suitable molecule such as natural or synthetic homo-polymer or hetero-polymer, typically with a molecular weight in the range of about 300-100.000 Da, such as about 500-20.000 Da, or about 500-15.000 Da, or 2-15 kDa, or 3-15 kDa, or about 10 kDa.

When the term "about" is used herein in connection with a certain molecular weight the word "about" indicates an approximate average molecular weight distribution in a given polymer preparation.

Examples of homo-polymers include a polyalcohol (i.e., poly-OH), a polyamine (i.e, and a polycarboxylic acid (i.e., poly-COOH). A hetero-polymer is a polymer comprising different coupling groups such as hydroxyl group and amine group.

Examples of suitable polymer molecules include polymer molecule selected from the group consisting of polyalkylene oxide, including polyalkylene glycol (PAG), such as polyethylene glycol (PEG) and polypropylene glycol (PPG), branched PEGs, polyvinyl alcohol (PVA), polycarboxylate, poly-vinylpyrolidone, polyethylene-co-maleic acid anhydride, polystyrene-co-maleic acid anhydride, dextran, including carboxymethyl-dextran, or any other polymer suitable for reducing immunicenicity and/or increasing functional in vivo half-life and/or serum half-life. Generally, polyalkyleneglycol-derived polymers are biocompatible, non-toxic, non-antigenic, and non-immunogenic, have various water solubility properties, and are easily secreted from living organism.

PEG is the preferred polymer molecule, since it has only a few reactive groups capable of cross-linking compared to e.g. polysaccharides such as dextran. In particular, monofunctional PEG, e.g., methoxypolyethylene glycol (mPEG) is of interest since its coupling chemistry is relatively simple (only one reactive group is available for conjugating with attachment groups the peptide).

To effect covalent attachment of the polymer molecule(s) to a ficolin-associated polypeptide, the hydroxyl end groups of the polymer molecule must be provided in activated form, i.e. with reactive functional groups (examples of which includes primary amino groups, hydrazide (HZ), thiol (SH), succinate (SUC), succinimidyl succinate (SS), succinimidyl succinamide (SSA), succinimidyl proprionate (SPA), succinimidyl 3-mercaptopropionate (SSPA), Norleucine (NOR), succinimidyl carboxymethylate (SCM), succimidyl butanoate (SBA), succinimidyl carbonate (SC), succinimidyl glutarate (SG), acetaldehyde diethyl acetal (ACET), succinimidy carboxymethylate (SCM), benzotriazole carbonate (BTC), N-hydroxysuccinimide (NHS), aldehyde (ALD), trichlorophenyl carbonate (TCP) nitrophenylcarbonate (NPC), maleimide (MAL) vinylsulfone (VS), carbonylimidazole (CDI), isocyanate (NCO), iodine (IODO), expoxide (EPDX), iodoacetamide (IA), succinimidyl glutarate (SG) and tresylate (TRES).

Suitable activated polymer molecules are commercially available, e.g. from Nektar, formerly known as Shearwater Polymers, Inc., Huntsville, Ala., USA, or from PolyMASC Pharmaceuticals plc, UK or from Enzon pharmaceuticals. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference).

Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, SCM-PEG, BTC-PEG, EPDX-PEG, NCO-PEG, NPC-PEG, CDI-PEG, ALD-PEG, TRES-PEG, VS-PEG, IODO-PEG, IA-PEG, ACET-PEG and MAL-PEG, and branched PEGs such as PEG2-NHS and those disclosed in U.S. Pat. No. 5,672,662, U.S. Pat. No. 5,932,462 and U.S. Pat. No. 5,643,575 both which are incorporated herein by reference. Furthermore the following publications, incorporated herein by reference, disclose useful polymer molecules and/or PEGylation chemistries: U.S. Pat. No. 4,179,337, U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, US 94/17039, WO 94/18247, WO 94,28024, WO 95/00162, WO 95/11924, WO 95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, US 305, 382, 657, EP 605 963, EP 510 356, EP 400 472, EP 183 503 and EP 154 316 and Roberts et al. *Adv. Drug Delivery Revl.* 54: 459-476 (2002) and references described herein. The conjugation between a ficolin-associated polypeptide and the activated polymer is conducted by conventional method. Conventional methods are known to those skilled in the art.

It will be understood that the polymer conjugation is designed so as to produce the optimal molecule with respect to the number of polymer molecules attached, the size and form of such molecules (e.g. whether they are linear or branched), and the attachment site(s) on ficolin-associated polypeptides. The molecular weight of the polymer to be used may e.g., be chosen on the basis of the desired effect to be achieved.

The hydrophilic substituent may be attached to an amino group of the ficolin-associated polypeptide moiety by means of a carboxyl group of the hydrophilic substituent which forms an amide bond with an amino group of the amino acid to which it is attached. As an alternative, the hydrophilic substituent may be attached to said amino acid in such a way that an amino group of the hydrophilic substituent forms an amide bond with a carboxyl group of the amino acid. As a further option, the hydrophilic substituent may be linked to the ficolin-associated polypeptide via an ester bond. Formally, the ester can be formed either by reaction between a carboxyl group of the ficolin-associated polypeptide and a hydroxyl group of the substituent-to-be or by reaction between a hydroxyl group of the ficolin-associated polypeptide and a carboxyl group of the substituent-to-be. As a further alternative, the hydrophilic substituent can be an alkyl group which is introduced into a primary amino group of the ficolin-associated polypeptide.

In one embodiment of the invention the hydrophilic substituent comprises $H(OCH_2CH_2)_nO$— wherein n>4 with a molecular weight from about 200 to about 100.000 daltons.

In one embodiment of the invention the hydrophilic substituent comprises $CH_3O$—$(CH_2CH_2O)_n$—$CH_2CH_2$—O— wherein n>4 with a molecular weight from about 200 to about 100.000 Daltons.

In one embodiment of the invention the hydrophilic substituent is polyethylen glycol (PEG) with a molecular weight from about 200 to about 5000 Daltons.

In one embodiment of the invention the hydrophilic substituent is polyethylen glycol (PEG) with a molecular weight from about 5000 to about 20.000 Daltons.

In one embodiment of the invention the hydrophilic substituent is polyethylen glycol (PEG) with a molecular weight from about 20.000 to about 100.000 Daltons.

In one embodiment of the invention the hydrophilic substituent comprises is a methoxy-PEG (mPEG) with a molecular weight from about 200 to about 5000 Daltons.

In one embodiment of the invention the hydrophilic substituent is methoxy-polyethylen glycol (mPEG) with a molecular weight from about 5000 to about 20.000 Daltons.

In one embodiment of the invention the hydrophilic substituent is methoxy-polyethylen glycol (mPEG) with a molecular weight from about 20.000 to about 100.000 daltons.

In one embodiment of the invention the hydrophilic substituent is attached to an amino acid residue in such a way that a carboxyl group of the hydrophilic substituent forms an amide bond with an amino group of the amino acid residue.

In one embodiment of the invention the hydrophilic substituent is attached to a Lys residue.

In one embodiment of the invention the hydrophilic substituent is attached to an amino acid residue in such a way that an amino group of the hydrophilic substituent forms an amide bond with a carboxyl group of the amino acid residue.

In some embodiments the chimeric molecule according to the invention is further modified with a domain for increasing the circulatory half-life of the chimeric molecule as compared to the ficolin-associated polypeptide, which domain is a lipophilic substituent.

The term "lipophilic substituent" is characterised by comprising 4-40 carbon atoms and having a solubility in water at 20° C. in the range from about 0.1 mg/100 ml water to about 250 mg/100 ml water, such as in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml.

In one embodiment of the invention the lipophilic substituent comprises from 4 to 40 carbon atoms.

In one embodiment of the invention the lipophilic substituent comprises from 8 to 25 carbon atoms.

In one embodiment of the invention the lipophilic substituent comprises from 12 to 20 carbon atoms.

In one embodiment of the invention the lipophilic substituent is attached to an amino acid residue in such a way that a carboxyl group of the lipophilic substituent forms an amide bond with an amino group of the amino acid residue.

In one embodiment of the invention the lipophilic substituent is attached to a Lys residue.

In one embodiment of the invention the lipophilic substituent is attached to an amino acid residue in such a way that an amino group of the lipophilic substituent forms an amide bond with a carboxyl group of the amino acid residue.

In one embodiment of the invention the lipophilic substituent is attached to the ficolin-associated polypeptide by means of a spacer.

In one embodiment of the invention the spacer is an unbranched alkane α,ω-dicarboxylic acid group having from 1 to 7 methylene groups, such as two methylene groups which spacer forms a bridge between an amino group of the ficolin-associated polypeptide and an amino group of the lipophilic substituent.

In one embodiment of the invention the spacer is an amino acid residue except a Cys residue, or a dipeptide. Examples of suitable spacers include β-alanine, gamma-aminobutyric acid (GABA), γ-glutamic acid, succinic acid, Lys, Glu or Asp, or a dipeptide such as Gly-Lys. When the spacer is succinic acid, one carboxyl group thereof may form an amide bond with an amino group of the amino acid residue, and the other carboxyl group thereof may form an amide bond with an amino group of the lipophilic substituent. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the ε-amino group of Lys and the lipophilic substituent. In one embodiment, such a further spacer is succinic acid which forms an amide bond with the ε-amino group of Lys and with an amino group present in the lipophilic substituent. In another embodiment such a further spacer is Glu or Asp which forms an amide bond with the ε-amino group of Lys and another amide bond with a carboxyl group present in the lipophilic substituent, that is, the lipophilic substituent is a $N^ε$-acylated lysine residue.

In one embodiment of the invention the spacer is selected from the list consisting of β-alanine, gamma-aminobutyric acid (GABA), γ-glutamic acid, Lys, Asp, Glu, a dipeptide containing Asp, a dipeptide containing Glu, or a dipeptide containing Lys. In one embodiment of the invention the spacer is β-alanine. In one embodiment of the invention the spacer is gamma-aminobutyric acid (GABA). In one embodiment of the invention the spacer is γ-glutamic acid.

In one embodiment of the invention a carboxyl group of the ficolin-associated polypeptide forms an amide bond with an amino group of a spacer, and the carboxyl group of the amino acid or dipeptide spacer forms an amide bond with an amino group of the lipophilic substituent.

In one embodiment of the invention an amino group of the ficolin-associated polypeptide forms an amide bond with a carboxylic group of a spacer, and an amino group of the spacer forms an amide bond with a carboxyl group of the lipophilic substituent.

In one embodiment of the invention the lipophilic substituent comprises a partially or completely hydrogenated cyclopentanophenathrene skeleton.

In one embodiment of the invention the lipophilic substituent is an straight-chain or branched alkyl group. In one embodiment of the invention the lipophilic substituent is the acyl group of a straight-chain or branched fatty acid.

In one embodiment of the invention the acyl group of a lipophilic substituent is selected from the group comprising $CH_3(CH_2)_nCO$—, wherein n is 4 to 38, such as $CH_3(CH_2)_6CO$—, $CH_3(CH_2)_8CO$—, $CH_3(CH_2)_{10}CO$—, $CH_3(CH_2)_{12}CO$—, $CH_3(CH_2)_{14}CO$—, $CH_3(CH_2)_{16}CO$—, $CH_3(CH_2)_{18}CO$—, $CH_3(CH_2)_{20}CO$— and $CH_3(CH_2)_{22}CO$—.

In one embodiment of the invention the lipophilic substituent is an acyl group of a straight-chain or branched alkane α,ω-dicarboxylic acid.

In one embodiment of the invention the acyl group of the lipophilic substituent is selected from the group comprising $HOOC(CH_2)_mCO$—, wherein m is 4 to 38, such as $HOOC(CH_2)_{14}CO$—, $HOOC(CH_2)_{16}CO$—, $HOOC(CH_2)_{18}CO$—, $HOOC(CH_2)_{20}CO$— and $HOOC(CH_2)_{22}CO$—.

In one embodiment of the invention the lipophilic substituent is a group of the formula $CH_3(CH_2)_p((CH_2)_qCOOH)CHNH$—$CO(CH_2)_2CO$—, wherein p and q are integers and p+q is an integer of from 8 to 40, such as from 12 to 35.

In one embodiment of the invention the lipophlic substituent is a group of the formula $CH_3(CH_2)_rCO$—$NHCH(COOH)(CH_2)_2CO$—, wherein r is an integer of from 10 to 24.

In one embodiment of the invention the lipophilic substituent is a group of the formula $CH_3(CH_2)_sCO$—$NHCH((CH_2)_2COOH)CO$—, wherein s is an integer of from 8 to 24.

In one embodiment of the invention the lipophilic substituent is a group of the formula $COOH(CH_2)_tCO$— wherein t is an integer of from 8 to 24.

In one embodiment of the invention the lipophilic substituent is a group of the formula —$NHCH(COOH)(CH_2)_4NH$—$CO(CH_2)_uCH_3$, wherein u is an integer of from 8 to 18.

In one embodiment of the invention the lipophilic substituent is a group of the formula —$NHCH(COOH)(CH_2)_4NH$—$COCH((CH_2)_2COOH)NH$—$CO(CH_2)_wCH_3$, wherein w is an integer of from 10 to 16.

In one embodiment of the invention the lipophilic substituent is a group of the formula —$NHCH(COOH)(CH_2)_4NH$—$CO(CH_2)_2CH(COOH)NH$—$CO(CH_2)_xCH_3$, wherein x is an integer of from 10 to 16.

In one embodiment of the invention the lipophilic substituent is a group of the formula —$NHCH(COOH)(CH_2)_4NH$—$CO(CH_2)_2CH(COOH)NHCO(CH_2)_yCH_3$, wherein y is zero or an integer of from 1 to 22.

In one embodiment of the invention the lipophilic substituent is N-Lithocholoyl.

In one embodiment of the invention the lipophilic substituent is N-Choloyl.

In one embodiment of the invention the chimeric molecule of a ficolin-associated polypeptide has one lipophilic substituent. In one embodiment of the invention the chimeric molecule of a ficolin-associated polypeptide has two lipophilic substituents. In one embodiment of the invention the chimeric molecule of a ficolin-associated polypeptide has three lipophilic substituents. In one embodiment of the invention the chimeric molecule of a ficolin-associated polypeptide has four lipophilic substituents.

Example 1

Detection of Alternative Transcription of the MASP1 Gene

Methods: In order to detect the three transcript variants of MASP1: MASP1, MASP3 and FAP, specific primers for each variant were design. PCR was set up with a common forward primer in exon 6 (5'-gcacccagagccacagtg-3' SEQ ID NO: 59) and specific reverse primers: MASP1 in exon 12 (5'-gccttccagtgtgtgggc-3' SEQ ID NO: 60), MASP3 in exon 11 (5-gccttccagagtgtggtca-3' SEQ ID NO: 61) and FAP in exon 8a (5'-cgatctggagagcgaactc-3' SEQ ID NO: 62) (FIG. 1). PCR amplifications were carried out in 20-μl volumes containing: 50 ng liver cDNA (Clontech), 0.25 μM of each primer, 2.5 mM MgCl2, 0.2 mM dNTP, 50 mM KCl, 10 mM Tris-HCl, pH 8.4, and 0.4 units of Platinum Taq DNA polymerase (Invitrogen). The PCR reactions were performed at the following cycling parameters: 10 min94° C., 30 or 40 cycles (30 sec94° C., 50 sec58° C., 90 sec72° C.), 10 min72° C. Samples were analysed on 2% agarose gels.

Results: Alternative transcription of the MASP1 gene was detected in liver cDNA. The MASP1, MASP3, and FAP transcripts were amplified using a common forward primer located in exon 6 and specific reverse primers located in exon 12 (MASP1), exon 11 (MASP3), and exon 8a (FAP). MASP1 generates a fragment of 500 bp, MASP3 generates a fragment of 506 bp and FAP generates a fragment of 309 bp.

Tissue Expression of the FAP Fragment

Methods: Commercially available human tissue cDNA panels (Clontech) were investigated for MASP1, MASP3, and FAP expression with the same PCR assays as described above. Samples were analysed on 2% agarose gels.

Results: The tissue distributions of the MASP1, MASP3, and FAP genes were investigated in cDNA panels from Clontech (FIG. 2). MASP1, MASP3, and FAP transcripts were amplified using a common forward primer and specific reverse primers. GADPH was used as reference gene. All three genes were highly expressed in the liver, and additionally, FAP was strongly expressed in heart tissue (marked with black arrows). Minor expression of the FAP gene was detected in brain, colon, prostate, skeletal muscle, and small intestine (marked with white arrows).

DNA Sequencing of the FAPexon8a of 100 Individuals.

Methods: Direct sequencing of the exon 8a including the intron-exon boundary of the MASP1/MASP3/FAP gene spanning from position +44,083 to +44,431 relative to the translation ATG start site, was performed on genomic DNA templates from 100 healthy Caucasian individuals. The fragment was amplified by using a single primer set (forward: 5'-ctgttcttcacactggctg-3' SEQ ID NO: 63, reverse: 5'-ctgctgagatcatgttgttc-3' SEQ ID NO: 64), where the forward primers contained a 5'-T7 sequence (5'-ttatacgactcacta-3' SEQ ID NO: 65). PCR amplifications were carried out in 20-μl volumes containing: 50 ng genomic DNA, 0.25 μM of each primer, 2.5 mM MgCl2, 0.2 mM dNTP, 50 mM KCl, 10 mM Tris-HCl, pH 8.4, and 0.4 units of Platinum Taq DNA polymerase (Invitrogen). The PCR reactions were performed at the following cycling parameters: 2 min94° C., 15 cycles(30 sec94° C., 60 sec64° C., 60 sec72° C.), 15 cycles(30 sec94° C., 60 sec58° C., 60 sec72° C.), 5 min72° C. and were sequenced in the forward direction using the ABI BigDye cycle sequencing terminator kit (Applied Biosystems, Foster City, Calif.) according to the protocol using 5'-biotinylated sequence primers. Sequence reactions were purified on the PyroMark Vacuum Prep Workstation (Biotage) using streptavidin beads (GenoVision). Sequence analysis was performed on an ABI Prism 3100 Genetic Analyser (Applied Biosystems). The resulting DNA sequences were aligned using BioEdit software, and DNA polymorphisms were confirmed visually from sequence electropherograms.

Results: All sequences were aligned using BioEdit software. No genetic variations in the 100 healthy individuals were observed in the exon 8a or the exon-intron regions.

Example 2

Immunoprecipitation.

Specific immunoprecipitation of MAP-1 from serum was performed with the MAP-1 specific mAb 20C4 (raised against the 17 MAP-1 specific C-terminal peptide) or mAb 8B3, a monoclonal antibody reacting against the common heavy chain of MASP-1/3 used as control precipitation antibody. A total of 10 μg of anti MAP-1 or MASP-1/3 antibody was allowed to bind to sheep anti mouse or rabbit IgG Dynabeads (M-280, cat. 112.02D/112.04D, Dynal/Invitrogen). After a washing step the beads were applied to a pool of normal human serum (diluted 1:1 in TBS) and incubated end over end for 1 hour at 4° C. After final washing steps and magnetic separation the beads were boiled in SDS loading buffer and subjected to SDS-PAGE and western blotting probed with antibodies to MAP-1, MBL, and Ficolin-3.

The same precipitation procedure as described above was performed with mAbs to MBL (Hyb 131-11, Bioporto, Denmark), Ficolin-2 (FCN219) and Ficolin-3 (FCN334). To compensate for differences in serum concentrations of MBL, Ficolin-2 and -3 were precipitated from 1 ml, 300 μl and 100 μl serum, respectively. Samples were analyzed by SDS-PAGE and western blotting probed with pAb against MAP-1.

Immunohistochemistry.

CHO cells expressing rMAP-1 were grown in culture flasks in RPMI+10%. Cells were harvested at 80-90% confluence the cells were harvested and fixed for 24 h in 4% formaldehyde-PBS and subsequently embedded in paraffin. Six different human liver tissues and samples from two different myocardial tissues, two skeleton muscle tissues and two samples obtained from human aorta were also fixed and paraffin embedded as described above. Sections of 5 μm slices were obtained with a Leitz Wetzlar microtome and placed on glass slides and stored at 4° C. until assayed. Pre-treatments and analyses were performed as described previously. Primary antibodies were the MAP-1 specific monoclonal antibodies mAb 12B11 or affinity purified, monospecific rabbit anti-MAP-1 all diluted to 5 μg/ml. Isotype antibody controls were applied to the tissues at the same concentration. Secondary antibody was EnVision™ antibody (HRP-anti mouse or HRP-anti rabbit, Dako, Glostrup, Denmark). Analysis of staining patterns was conducted under a Leica DMLB2 microscope.

SDS-PAGE and Western Blotting.

Electrophoresis was performed on 10% or 4-12% (w/v) Bis-Tris Polyacrylamide-gels with discontinuous buffers using the NuPAGE® system (Invitrogen) essentially as described by the manufacturer. Western blotting was performed using polyvinylidene difluoride membranes (PVDF-HyBond, Amersham Bioscience), 2 μg/ml of primary mAbs and secondary visualization by HRP conjugated streptavidin (P0397, Dako) diluted to 1:1500 or HRP-Rabbit anti mouse IgG (P0260, Dako) diluted to 1:1000 in PBS, 0.05% Tween20. The membranes were developed with 3-amino-9-ethylcarbazole (Sigma) (0.04% in acetone) and 0.015% $H_2O_2$ in 50 mM sodium acetate buffer pH 5.

Complement Activation Assay.

The influence of MAP-1 on the MBL and Ficolin-3 mediated complement factor C4 deposition was assessed essentially as described previously. Briefly, mannan (MBL ligand) (Sigma-Aldrich M7504) or acetylated bovine serum albumin (Ficolin-3 ligand) was immobilized to Maxisorp ELISA plates (Nunc, Denmark) at 10 μg/ml. After washing with, rMBL or rFicolin-3 (0.4 μg/ml) was added and incubated for 1.5 hour. rMAP-1 or rMASP-2 was applied for 1 hour in two-fold serial dilutions in the first dimension followed by incubation for 45 min at 37° C. with serial dilutions of serum deficient of MBL or Ficolin-3 in the second dimension. The C4 deposition was measured using a pAb to C4c (Q0369, Dako, Glostrup/Denmark).

In addition we assessed the displacement of MASP-2 with MAP-1 using a pure system. rMASP-2 was pre-incubated for 45 min at 20° C. in serial dilutions in the first dimension on an rMBL/mannan matrix as described above followed by incubation with dilutions of rMAP-1 in the second dimension for 45 min at 20° C. Purified C4 (from Quidel, Calif., USA) was added at a concentration of 1 μg/ml and incubated for 45 min at 37° C. Detection was conducted as above.

Results.

MAP-1 Co-Precipitates with Ficolin-2, Ficolin-3 and MBL

To investigate a possible association of MAP-1 with MBL and Ficolin-3 we precipitated serum complexes using both anti MAP-1 mAb20C4 and a mAb against the common heavy chain of MASP-1 and MASP-3 (mAb8B3). The precipitates were subsequently analyzed by western blotting probed with antibodies to MAP-1, MBL, and Ficolin-3, respectively. We observed pronounced Ficolin-3 co-precipitation bands, but weaker bands were also seen with MBL (FIG. 24A). The samples wee not probed with antibodies against Ficolin-2 since they did not work in western blot. We then reversed the immunoprecipitation using mAbs against MBL, Ficolin-2 and Ficolin-3 to precipitate 1 ml, 300 μl and 100 μl serum, respectively, which was perform to adjust for differences in the serum concentration of MBL (2 μg/ml), Ficolin-2 (5 μg/ml) and Ficolin-3 (20 μg/ml), respectively. The samples were subsequently analyzed by western blotting probed with antibodies to MAP-1. Distinct MAP-1 bands were observed in the precipitates from Ficolin-2 and -3 and a much weaker band was apparent in the MBL precipitate, where immunoprecipitated rMAP-1 and serum MAP-1 served as controls (FIG. 24B).

MAP-1 Inhibits Complement Activity of the Lectin Pathway.

Serum deficient of MBL and Ficolin-3 in combination with rMBL and rFicolin-3 were used to reconstitute for MBL and Ficolin-3 complement C4 activation activity. Mannan and acetylated BSA served as ligands for MBL and Ficolin-3, respectively. Both rMBL and rFicolin-3 were able to initiate C4 deposition in MBL and Ficolin-3 deficient sera, respectively (FIG. 25A (A) and FIG. 25B (D)). Application of rMASP-2 resulted in a strong positive dose dependent enhancement of the C4 deposition via both the Ficolin-3 and MBL activation pathways (FIG. 25A (B) and FIG. 25B (E)), whereas application of rMAP-1 resulted in a pronounced dose dependent inhibition of the C4 deposition via both pathways (FIG. 25A (C) and FIG. 25A (F)). In addition we addressed a possible displacement of MASP-2 with MAP-1 using a system of pure components comprising only of rMBL, rMASP-2, rMAP-1 and purified C4. rMASP-2 was pre-incubated with mannan/rMBL complexes in serial dilutions. Thereafter, rMAP-1 was added in varying concentrations followed by addition of purified C4. Application of rMAP-1 to the system clearly resulted in a dose dependent inhibition of C4 deposition (FIG. 26).

Example 3

Chimeric molecules composed of MAP-1 and other complement inhibitory proteins are generated according to the following exemplary standard procedures. The MAP-1 protein (complete) is conjugated to following human proteins: Factor I, Factor H, C4bp and C1inh using standard methods for covalent coupling, such as:

1) 1-Ethyl-3-[3-dimethylaminopropyl]carbodiimide hydrochloride (EDC, a zero-length crosslinker) is used to couple the MAP-1 protein to other conjugates via a carboxyl to primary amines group coupling as described by the manufacturer (Pierce, CAS nr. 25952-53-8).

2) Isuccinimidyl suberate (DSS) (with an 8-carbon spacer arm) is used to couple the MAP-1 protein to other conjugates via amine to amines group coupling as described by the manufacturer (Pierce, CAS nr. 68528-80-3).

3) EMCS ([N-e-Maleimidocaproyloxy]succinimide ester) (with a 9.4 å spacer arm) is used to couple the MAP-1 protein to other conjugates via sulfhydryl to amino group coupling as described by the manufacturer (Pierce, product nr. 22308).

Example 4

The following list are examples of constructs of the present invention made in accordance with the teaching herein. The constructs all have the basic formula of MAP-1-linker-complement modulator or complement modulator-linker-MAP-1. The contructs may also be generated without any linker. Notations in parenthesis indicate details within a particular section of the composition. For example, "(complete)" means that the entire mature protein sequence with the amino acid sequence 20-380 of native human FAP (SEQ ID NO: 1) is used in the construct. It is understood that this list is not limiting and only provides examples of some of the constructs disclosed in the present application.

MAP-1 (complete)-(Gly4Ser)3(SEQ ID NO: 69)-DAF
MAP-1 (complete)-(Gly4Ser)3(SEQ ID NO: 69)-Factor H
MAP-1 (complete)-(Gly4Ser)3(SEQ ID NO: 69)-human CD59
MAP-1 (complete)-(Gly4Ser)3(SEQ ID NO: 69)-MCP
MAP-1 (complete)-(Gly4Ser)3(SEQ ID NO: 69)-R1
MAP-1 (complete)-(Gly4Ser)3(SEQ ID NO: 69)-Crry
MAP-1 (complete)-(Gly4Ser)3(SEQ ID NO: 69)-mouse CD59
MAP-1 (complete)-(Gly4Ser)3(SEQ ID NO: 69)-human IgG1 Fc
MAP-1 (complete)-(Gly4Ser)3(SEQ ID NO: 69)-human IgM Fc
MAP-1 (complete)-(Gly4Ser)3(SEQ ID NO: 69)-murine IgG3 Fc
MAP-1 (complete)-(Gly4Ser)3(SEQ ID NO: 69)-murine IgM Fc
MAP-1 (complete)-(Gly4Ser)3(SEQ ID NO: 69)-Factor I
MAP-1 (complete)-(Gly4Ser)3(SEQ ID NO: 69)-C4bp
MAP-1 (complete)-(Gly4Ser)3(SEQ ID NO: 69)-C1inh
MAP-1 (complete)-(Gly3Ser)4(SEQ ID NO: 70)-DAF
MAP-1 (complete)-(Gly3Ser)4(SEQ ID NO: 70)-Factor H
MAP-1 (complete)-(Gly3Ser)4(SEQ ID NO: 70)-human CD59
MAP-1 (complete)-(Gly3Ser)4(SEQ ID NO: 70)-MCP
MAP-1 (complete)-(Gly3Ser)4(SEQ ID NO: 70)-CR1
MAP-1 (complete)-(Gly3Ser)4(SEQ ID NO: 70)-Crry
MAP-1 (complete)-(Gly3Ser)4(SEQ ID NO: 70)-mouse CD59
MAP-1 (complete)-(Gly3Ser)4(SEQ ID NO: 70)-human IgG1 Fc
MAP-1 (complete)-(Gly3Ser)4(SEQ ID NO: 70)-human IgM Fc
MAP-1 (complete)-(Gly3Ser)4(SEQ ID NO: 70)-murine IgG3 Fc
MAP-1 (complete)-(Gly3Ser)4(SEQ ID NO: 70)-murine IgM Fc
MAP-1 (complete)-(Gly3Ser)4(SEQ ID NO: 70)-Factor I
MAP-1 (complete)-(Gly3Ser)4(SEQ ID NO: 70)-C4bp
MAP-1 (complete)-(Gly3Ser)4(SEQ ID NO: 70)-C1inh
MAP-1 (complete)-(Gly4Ser)3(SEQ ID NO: 69)-DAF (SCRs 2-4)
MAP-1 (complete)-(Gly3Ser)4(SEQ ID NO: 70)-DAF (SCRs 2-4)
MAP-1 (complete)-(Gly4Ser)3(SEQ ID NO: 69)-CR1 (LP-SCR1-4-SCR8-11-SCR15-18)
MAP-1 (complete)-(Gly4Ser)3(SEQ ID NO: 69)-Crry (5 N-terminal SCRs)
MAP-1 (complete)-VSVFPLE (SEQ ID NO: 66)-DAF
MAP-1 (complete)-VSVFPLE (SEQ ID NO: 66)-Factor H
MAP-1 (complete)-VSVFPLE (SEQ ID NO: 66)-human CD59
MAP-1 (complete)-VSVFPLE (SEQ ID NO: 66)-MCP
MAP-1 (complete)-VSVFPLE (SEQ ID NO: 66)-CR1
MAP-1 (complete)-VSVFPLE (SEQ ID NO: 66)-Crry
MAP-1 (complete)-VSVFPLE (SEQ ID NO: 66)-mouse CD59
MAP-1 (complete)-VSVFPLE (SEQ ID NO: 66)-human IgG1 Fc
MAP-1 (complete)-VSVFPLE (SEQ ID NO: 66)-human IgM Fc
MAP-1 (complete)-VSVFPLE (SEQ ID NO: 66)-murine IgG3 Fc
MAP-1 (complete)-VSVFPLE (SEQ ID NO: 66)-murine IgM Fc
MAP-1 (complete)-VSVFPLE (SEQ ID NO: 66)-Factor I
MAP-1 (complete)-VSVFPLE (SEQ ID NO: 66)-C4bp
MAP-1 (complete)-VSVFPLE (SEQ ID NO: 66)-C1inh

Example 5

Exemplary specific sequences of MAP-1 chimeric molecules, which may be produced as fusion proteins:

Human fusion proteins containing a ficolin-associated polypeptide portion and a second modulator of complement activity may be made by recombinant DNA cloning and gene expression method.

Amino acid sequence of an exemplary human MAP-1/FH chimeric protein (SEQ ID NO:25) and an exemplary polynucleotide sequence encoding the human MAP-1/FH chimeric protein (SEQ ID NO:26). The construct is illustrated in FIG. 27.

Amino acid sequence of an exemplary human FH/MAP-1 chimeric protein (SEQ ID NO:27) and an exemplary polynucleotide sequence encoding the human FH/MAP-1 chimeric protein (SEQ ID NO:28). The construct is illustrated in FIG. 27. The amino acid sequences of human MAP-1 (SEQ ID NO:29-31) are all suitable examples of sequences that could be used as the MAP-1 portion of a chimeric protein according to the invention. The amino acid sequences of human FH (SEQ ID NO:32-36) are all suitable examples of sequences that could be used as a FH portion of a chimeric protein according to the invention.

In the following examples the FH portion may be replaced by any one of C4bp, FI, or C1-inh:

The amino acid sequences of human C4bp (SEQ ID NO:37-40) are all suitable examples of sequences that could be used as a C4bp portion of a chimeric protein according to the invention. The construct is illustrated in FIG. 28.

The amino acid sequences of human FI (SEQ ID NO:41-44) are all suitable examples of sequences that could be used as a FI portion of a chimeric protein according to the invention. The construct is illustrated in FIG. 29.

The amino acid sequences of human C1-inh (SEQ ID NO:45) are all suitable examples of sequences that could be used as a C1-inh portion of a chimeric protein according to the invention. The construct is illustrated in FIG. 30.

Example 6

Detailed Exemplary Procedure for the Production of MAP-1/FH Fusion Protein:

Construction of Expression Vectors

The pEDdC vector, which carries a cloning sequence for insertion of the target gene followed by the selectable and amplifiable marker (dhfr), will be used for expression of the fusion gene.

Two sets of primers are designed for each gene to be linked. These primers contain restriction enzyme sequences adaptable with the expression vector. The primers are developed in order to amplify the two fusion protein, MAP-1 and FH. MAP-1 and FH will have identical restriction enzyme sequences in the region to be linked. Optional linker sequence may be incorporated.

In order to be able to obtain the protein expression in cell culture supernatant, a construct containing optional signal peptide may be incorporated. For cytoplasmic expression of chimeric protein, the construct does not contain the signal peptide. In this way, the fusion protein would be expressed and accumulated in the cytoplasmic area of the host cell rather than that of the supernatant.

Fusion Gene Construction

Cloning of MAP-1/FH is performed briefly as follows. The MAP-1 and FH genes are amplified from human liver cDNA and run at agarose gel. The gene is then cut out of the gel, purified, and digested with respective restriction enzymes. The products are purified and the two genes ligated. After ligation, the gene construct is purified and inserted into the pED vector and characterized. The pEDdC/MAP-1/FH vector is transformed into *Escherichia coli* bacteria and plated on selective LB medium (containing 100 μg/mL ampicillin) and grown overnight at 37° C. Bacterial colonies are screened for the presence of both gene by colony PCR. Positive colonies are picked, streaked, and cultured in LB. Plasmids are purified and sequenced in order to confirm the sequence.

Transfection and MAP-1/FH Expression

The pEDdC/MAP-1/FH construct is transfected into the Chinese hamster ovary (CHO) DG44 cell line. This CHO clone is a double deletion mutant that contains no copies of the hamster dhfr gene. Untransfected cells are grown in IMDM supplemented by 10% dFBS, 100 units/ml penicillin, 0.1 mg/ml streptomycin, 2 mM L-glutamine, 10 mM hypoxanthine, and 1.6 mM thymidine (HT-supplement) in a 37° C. humidified atmosphere containing 5% $CO_2$. Cells are passaged using 0.05% trypsin in PBS. Stable transfections are performed using the LipofectAMINE PLUS reagent kit. Transfection is performed by seeding $8\times10^5$ cells in 6-cm culture wells on day 0. On day 1, cell medium is replaced and the cells transfected according to the manufacturer's protocol, adding 60 μl of LipofectAMINE, 0.2 μg of $pSV_2neo$, and 20 μg of the pEDdC/MAP-1/FH vector. On day 3, cells are transferred to 25 $cm^2$ flasks, and on day 5, cells are transferred to a medium containing 0.5 mg/ml G418 and lacking hypoxanthine and thymidine. G418-resistant clones are usual obtained after 12 days. Selection and gene amplification with MTX are initiated by cultivating cells in cell medium containing 0.5 mg/ml G418, 50 nM MTX, which lacked hypoxanthine and thymidine. When cells regain normal growth rate and morphology, the concentration of MTX is gradually increased to 200 nM.

Example 7

Chimeric Proteins of rMAP-1 and Factor H.

Purification of Proteins

Factor H from human plasma was purified essentially as described by Laine et al. J Immunol 2007; 178:3831-6 with the modification that the monoclonal anti human Factor H antibody Hyb 268-01 (Bioporto A/S, Gentofte, Denmark) was coupled to the purification matrix and used to affinity purify plasma Factor H.

Recombinant, full-length, non-tagged MBL/Ficolin associated protein-1 (rMAP-1) was expressed in CHO DG 44 cells in serum-free medium (SFM) (CHO CD-1, Lonza) and RPMI 1640 with 10% fetal calf serum (FCS) and purified as described previously Skjoedt M O, et al. Serum concentration and interaction properties of MBL/ficolin associated protein-1. Immunobiology doi:101016/jimbio201009011.

Recombinant, full-length, non-tagged mannose-binding lectin (rMBL) was expressed in CHO DG 44 cells in serum-free medium (SFM) (CHO CD-1, Lonza) and purified by affinity chromatography on a mannan-agarose column as described previously Skjoedt M O, et al. J Biol Chem 2010; 285:8234-43.

SDS-PAGE 4-12% Bis-Tris SDS-PAGE and coomassie staining was used to determine the molecular composition and purity of the proteins mentioned above. The conditions were according to the instructions from the manufacturer (Invitrogen).

Protein Coupling rMAP-1 and Factor H was covalently linked by glutaraldehyde coupling according to the recommendations by Carter J M. Conjugation of Peptides to Carrier Proteins via Glutaraldehyde The Protein Protocols Handbook, Part VII, 679-687, DOI: 101007/978-1-60327-259-9_117: Springer, 1996. The conjugated product is named rMAP-1/Factor H hybrid molecule.

Complement Activation Assays

The MBL dependent complement activation was analyzed with the purified proteins described above. The methods and reagents used in these assays have previously been described (Skjoedt M O, et al. J Biol Chem 2010; 285:8234-43, and Palarasah Y, et al. J Clin Microbiol; 48:908-14), except for the inclusion of plasma Factor H and rMAP-1/Factor H hybrid molecule described here.

Results and Discussion

Protein Analysis

Analysis of the purified recombinant MAP-1 revealed an expected non-reduced molecular mass of ≈45 kDa (FIG. 31). No dysfunctional disulfide bridge formation was observed. Analysis of the purified plasma Factor H revealed an expected molecular mass of ≈150 kDa (FIG. 31). A high purity was observed for both rMAP-1 and Factor H.

Analysis of the purified recombinant MBL revealed an expected reduced molecular mass of ≈30 kDa. A high purity was observed for rMBL (FIG. 32). Analysis non-reduced pattern of rMBL revealed a disulfide bridge mediated oligomerization comparable with native serum derived MBL (FIG. 32).

Complement Deposition Assays

A simple scheme illustrates the composition of the assays employed in the following (FIG. 33).

Initially the rMAP-1/Factor H hybrid molecule was introduced to the MBL dependent complement assay to investigate if this chimeric protein is able to inhibit the activation and deposition of complement factor C3. FIG. 34 illustrates a clear dose dependent inhibition mediated by the chimeric protein of the MBL dependent C3 activation.

To further investigate if rMAP-1 and Factor H binds to rMBL under the conditions employed here, we measured the association with specific monoclonal antibodies to MAP-1 and Factor H, respectively. FIG. 35A shows the binding of rMAP-1 to rMBL bound to mannan. The rMAP-1/Factor H hybrid molecule shows a reduced binding to rMBL compared with the non-conjugated rMAP-1, suggesting that a part of the rMAP-1 linked to Factor H is conformational changed. FIG. 35B shows the binding of Factor H to rMBL. As expected only the Factor H in the rMAP-1/Factor H hybrid form is able to bind to the MBL/mannan complex.

The purified plasma Factor H shows no effect on the C3 deposition (FIG. 36A) or the C9/Terminal complement complex formation (FIG. 36B) in the MBL assay. In contrast to this the purified rMAP-1 showed a significant inhibition of the C3 deposition (FIG. 37A) and the C9/Terminal complement complex formation (FIG. 37B). When non-conjugated purified rMAP-1 and Factor H are applied together in the assays, the deposition patterns are equivalent to the results obtained with rMAP-1 alone (FIG. 38A-B). These data show that Factor H does not play a role unless it is covalently attached to rMAP-1. When the rMAP-1/Factor H hybrid molecule is employed in the complement activation assays a pronounced dose-dependent inhibition of both the C3 deposition (FIG. 39A) and the C9/Terminal complement complex formation (FIG. 39B). This is in spite of the fact that a large proportion of the rMAP-1 presumably is not able to bind to rMBL due to misfolding after the glutaraldehyde coupling (see FIG. 35A). A combined MAP-1/Factor H hybrid molecule might thus be a potent regulator of adverse in vivo inflammation caused by complement activation and could perhaps also operate at levels where lectin pathway related proteins have been shown to play a role (apoptosis, necrosis, thrombosis and coagulation).

SEQ ID NO: 1. The complete 380 amino acid sequences for human FAP. (Two potential glycosylation sites identified at amino acid position 49 and 178 are highlighted):

MRWLLLYYALCFSLSKASAHTVELNNMFGQIQSPGYPDSYPSDSEVTWNI

TVPDGFRIKLYFMHFNLESSYLCEYDYVKVETEDQVLATFCGRETTDTEQ

TPGQEVVLSPGSFMSITFRSDFSNEERFTGFDAHYMAVDVDECKEREDEE

LSCDHYCHNYIGGYYCSCRFGYILHTDNRTCRVECSDNLFTQRTGVITSP

DFPNPYPKSSECLYTIELEEGFMVNLQFEDIFDIEDHPEVPCPYDYIKIK

VGPKVLGPFCGEKAPEPISTQSHSVLILFHSDNSGENRGWRLSYRAAGNE

CPELQPPVHGKIEPSQAKYFFKDQVLVSCDTGYKVLKDNVEMDTFQIECL

KDGTWSNKIPTCKKNEIDLESELKSEQVTE

SEQ ID NO: 2. The complete cDNA nucleotide sequences for human FAP:

atgaggtggctgcttctctattatgctctgtgcttctccctgtcaaaggc ttcagcccacaccgtggagctaaacaatatgtttggccagatccagtcgc ctggttatccagactcctatcccagtgattcagaggtgacttggaatatc actgtcccagatgggtttcggatcaagctttacttcatgcacttcaactt -continued ggaatcctcctacctttgtgaatatgactatgtgaaggtagaaactgagg accaggtgctggcaaccttctgtggcagggagaccacagacacagagcag actcccggccaggaggtggtcctctcccctggctccttcatgtccatcac tttccggtcagatttctccaatgaggagcgtttcacaggctttgatgccc actacatggctgtggatgtggacgagtgcaaggagagggaggacgaggag ctgtcctgtgaccactactgccacaactacattggcggctactactgctc ctgccgcttcggctacatcctccacacagacaacaggacctgccgagtgg agtgcagtgacaacctcttcactcaaaggactggggtgatcaccagccct gacttcccaaacccttaccccaagagctctgaatgcctgtataccatcga gctggaggagggtttcatggtcaacctgcagtttgaggacatatttgaca ttgaggaccatcctgaggtgccctgcccctatgactacatcaagatcaaa gttggtccaaaagttttggggcctttctgtggagagaaagccccagaacc catcagcacccagagccacagtgtcctgatcctgttccatagtgacaact cgggagagaaccggggctggaggctctcatacagggctgcaggaaatgag tgcccagagctacagcctcctgtccatgggaaaatcgagccctcccaagc caagtatttcttcaaagaccaagtgctcgtcagctgtgacacaggctaca aagtgctgaaggataatgtggagatggacacattccagattgagtgtctg aaggatgggacgtggagtaacaagattcccacctgtaaaaaaaatgaaat cgatctggagagcgaactcaagtcagagcaagtgacagagtga SEQ NO: 3. Minimum sequence of a ficolin-associated polypeptide comprising the CUB1-EGF-CUB2 domains including a signal peptide of amino acids 1-19. The sequence corresponds to exon 2 to exon 6:

MRWLLLYYALCFSLSKASAHTVELNNMFGQIQSPGYPDSYPSDSEVTWNI

TVPDGFRIKLYFMHENLESSYLCEYDYVKVETEDQVLATFCGRETTDTEQ

TPGQEVVLSPGSFMSITERSDFSNEERFTGFDAHYMAVDVDECKEREDEE

LSCDHYCHNYIGGYYCSCRFGYILHTDNRTCRVECSDNLFTQRTGVITSP

DFPNPYPKSSECLYTIELEEGFMVNLQFEDIFDIEDHPEVPCPYDYIKIK

VGPKVLGPFCGEKAPEPISTQSHSVLILFHSDNSGENRGWRLSYRAA

SEQ ID NO: 4. Unique terminal 17 amino acids of FAP:

KNEIDLESELKSEQVTE

SEQ ID NO: 5 Protein sequence of human MASP-1:

MRWLLLYYALCFSLSKASAHTVELNNMFGQIQSPGYPDSYPSDSEVTWNI

TVPDGFRIKLYFMHENLESSYLCEYDYVKVETEDQVLATFCGRETTDTEQ

TPGQEVVLSPGSFMSITERSDFSNEERFTGFDAHYMAVDVDECKEREDEE

LSCDHYCHNYIGGYYCSCRFGYILHTDNRTCRVECSDNLFTQRTGVITSP

DFPNPYPKSSECLYTIELEEGFMVNLQFEDIFDIEDHPEVPCPYDYIKIK

VGPKVLGPFCGEKAPEPISTQSHSVLILFHSDNSGENRGWRLSYRAAGNE

CPELQPPVHGKIEPSQAKYFFKDQVLVSCDTGYKVLKDNVEMDTFQIECL

KDGTWSNKIPTCKIVDCRAPGELEHGLIITSTRNNLTTYKSEIKYSCQEP

YYKMLNNNTGIYTCSAQGVWMNKVLGRSLPTCLPVCGLPKESRKLMARIE

NGRPAQKGTTPWIAMLSHLNGQPFCGGSLLGSSWIVTAAHCLHQSLDPED

PTLRDSDLLSPSDFKIILGKHWRLRSDENEQHLGVKHTTLHPQYDPNTFE

-continued

NDVALVELLESPVLNAFVMPICLPEGPQQEGAMVIVSGWGKQFLQRFPET

LMEIEIPIVDHSTCQKAYAPLKKKVTRDMICAGEKEGGKDACAGDSGGPM

VTLNRERGQWYLVGTVSWGDDCGKKDRYGVYSYIHHNKDWIQRVTGVRN

SEQ ID NO: 6 cDNA sequence of human MASP-1:
GAAGTCAGCCACACAGGATAAAGGAGGGAAGGGAAGGAGCAGATCTTTTC

GGTAGGAAGACAGATTTTGTTGTCAGGTTCCTGGGAGTGCAAGAGCAAGT

CAAAGGAGAGAGAGAGGAGAGAGGAAAAGCCAGAGGGAGAGAGGGGGAGA

GGGGATCTGTTGCAGGCAGGGGAAGGCGTGACCTGAATGGAGAATGCCAG

CCAATTCCAGAGACACACAGGGACCTCAGAACAAAGATAAGGCATCACGG

ACACCACACCGGGCACGAGCTCACAGGCAAGTCAAGCTGGGAGGACCAAG

GCCGGGCAGCCGGGAGCACCCAAGGCAGGAAAATGAGGTGGCTGCTTCTC

TATTATGCTCTGTGCTTCTCCCTGTCAAAGGCTTCAGCCCACACCGTGGA

GCTAAACAATATGTTTGGCCAGATCCAGTCGCCTGGTTATCCAGACTCCT

ATCCCAGTGATTCAGAGGTGACTTGGAATATCACTGTCCCAGATGGGTTT

CGGATCAAGCTTTACTTCATGCACTTCAACTTGGAATCCTCCTACCTTTG

TGAATATGACTATGTGAAGGTAGAAACTGAGGACCAGGTGCTGGCAACCT

TCTGTGGCAGGGAGACCACAGACACAGAGCAGACTCCCGGCCAGGAGGTG

GTCCTCTCCCCTGGCTCCTTCATGTCCATCACTTTCCGGTCAGATTTCTC

CAATGAGGAGCGTTTCACAGGCTTTGATGCCCACTACATGGCTGTGGATG

TGGACGAGTGCAAGGAGAGGGAGGACGAGGAGCTGTCCTGTGACCACTAC

TGCCACAACTACATTGGCGGCTACTACTGCTCCTGCCGCTTCGGCTACAT

CCTCCACACAGACAACAGGACCTGCCGAGTGGAGTGCAGTGACAACCTCT

TCACTCAAAGGACTGGGGTGATCACCAGCCCTGACTTCCCAAACCCTTAC

CCCAAGAGCTCTGAATGCCTGTATACCATCGAGCTGGAGGAGGGTTTCAT

GGTCAACCTGCAGTTTGAGGACATATTTGACATTGAGGACCATCCTGAGG

TGCCCTGCCCCTATGACTACATCAAGATCAAAGTTGGTCCAAAAGTTTTG

GGGCCTTTCTGTGGAGAGAAAGCCCCAGAACCCATCAGCACCCAGAGCCA

CAGTGTCCTGATCCTGTTCCATAGTGACAACTCGGGAGAGAACCGGGGCT

GGAGGCTCTCATACAGGGCTGCAGGAAATGAGTGCCCAGAGCTACAGCCT

CCTGTCCATGGGAAAATCGAGCCCTCCCAAGCCAAGTATTTCTTCAAAGA

CCAAGTGCTCGTCAGCTGTGACACAGGCTACAAAGTGCTGAAGGATAATG

TGGAGATGGACACATTCCAGATTGAGTGTCTGAAGGATGGGACGTGGAGT

AACAAGATTCCCACCTGTAAAATTGTAGACTGTAGAGCCCCAGGAGAGCT

GGAACACGGGCTGATCACCTTCTCTACAAGGAACAACCTCACCACATACA

AGTCTGAGATCAAATACTCCTGTCAGGAGCCCTATTACAAGATGCTCAAC

AATAACACAGGTATATATACCTGTTCTGCCCAAGGAGTCTGGATGAATAA

AGTATTGGGGAGAAGCCTACCCACCTGCCTTCCAGTGTGTGGGCTCCCCA

AGTTCTCCCGGAAGCTGATGGCCAGGATCTTCAATGGACGCCCAGCCCAG

AAAGGCACCACTCCCTGGATTGCCATGCTGTCACACCTGAATGGGCAGCC

CTTCTGCGGAGGCTCCCTTCTAGGCTCCAGCTGGATCGTGACCGCCGCAC

ACTGCCTCCACCAGTCACTCGATCCGGAAGATCCGACCCTACGTGATTCA

-continued

GACTTGCTCAGCCCTTCTGACTTCAAAATCATCCTGGGCAAGCATTGGAG

GCTCCGGTCAGATGAAAATGAACAGCATCTCGGCGTCAAACACACCACTC

TCCACCCCCAGTATGATCCCAACACATTCGAGAATGACGTGGCTCTGGTG

GAGCTGTTGGAGAGCCCAGTGCTGAATGCCTTCGTGATGCCCATCTGTCT

GCCTGAGGGACCCCAGCAGGAAGGAGCCATGGTCATCGTCAGCGGCTGGG

GGAAGCAGTTCTTGCAAAGGTTCCCAGAGACCCTGATGGAGATTGAAATC

CCGATTGTTGACCACAGCACCTGCCAGAAGGCTTATGCCCCGCTGAAGAA

GAAAGTGACCAGGGACATGATCTGTGCTGGGGAGAAGGAAGGGGGAAAGG

ACGCCTGTGCGGGTGACTCTGGAGGCCCCATGGTGACCCTGAATAGAGAA

AGAGGCCAGTGGTACCTGGTGGGCACTGTGTCCTGGGGTGATGACTGTGG

GAAGAAGGACCGCTACGGAGTATACTCTTACATCCACCACAACAAGGACT

GGATCCAGAGGGTCACCGGAGTGAGGAACTGAATTTGGCTCCTCAGCCCC

AGCACCACCAGCTGTGGGCAGTCAGTAGCAGAGGACGATCCTCCGATGAA

AGCAGCCATTTCTCCTTTCCTTCCTCCCATCCCCCCTCCTTCGGCCTATC

CATTACTGGGCAATAGAGCAGGTATCTTCACCCCCTTTTCACTCTCTTTA

AAGAGATGGAGCAAGAGAGTGGTCAGAACACAGGCCGAATCCAGGCTCTA

TCACTTACTAGTTTGCAGTGCTGGGCAGGTGACTTCATCTCTTCGAACTT

CAGTTTCTTCATAAGATGGAAATGCTATACCTTACCTACCTCGTAAAAGT

CTGATGAGGAAAAGATTAACTAATAGATGCATAGCACTTAACAGAGTGCA

TAGCATACACTGTTTTCAATAAATGCACCTTAGCAGAAGGTCGATGTGTC

TACCAGGCAGACGAAGCTCTCTTACAAACCCCTGCCTGGGTCTTAGCATT

GATCAGTGACACACCTCTCCCCTCAACCTTGACCATCTCCATCTGCCCTT

AAATGCTGTATGCTTTTTTGCCACCGTGCAACTTGCCCAACATCAATCTT

CACCCTCATCCCTAAAAAAGTAAAACAGACAAGGTTCTGAGTCCTGTGGT

ATGTCCCCTAGCAAATGTAACTAGGAACATGCACTAGATGACAGATTGCG

GGAGGGCCTGAGAGAAGCAGGGACAGGAGGGAGCCTGGGGATTGTGGTTT

GGGAAGGCAGACACCTGGTTCTAGAACTAGCTCTGCCCTTAGCCCCCTGT

ATGACCCTATGCAAGTCCTCCTCCCTCATCTCAAAGGGTCCTCAAAGCTC

TGACGATCTAAGATACAATGAAGCCATTTTCCCCCTGATAAGATGAGGTA

AAGCCAATGTAACCAAAAGGCAAAAATTACAATCGGTTCAAAGGAACTTT

GATGCAGACAAAATGCTGCTGCTGCTGCTCCTGAAATACCCACCCCTTTC

CACTACGGGTGGGTTCCCAAGGACATGGGACAGGCAAAGTGTGAGCCAAA

GGATCCTTCCTTATTCCTAAGCAGAGCATCTGCTCTGGGCCCTGGCCTCC

TTCCCTTCTTGGGAAACTGGGCTGCATGAGGTGGGCCCTGGTAGTTTGTA

CCCCAGGCCCCTATACTCTTCCTTCCTATGTCCACAGCTGACCCCAAGCA

GCCGTTCCCCGACTCCTCACCCCTGAGCCTCACCCTGAACTCCCTCATCT

TGCAAGGCCATAAGTGTTTTCCAAGCAAAATGCCTCTCCCATCCTCTCTC

AGGAAGCTTCTAGAGACTTTATGCCCTCCAGAGCTCCAAGATATAAGCCC

TCCAAGGGATCAGAAGCTCCAAGTTCCTGTCTTCTGTTTTATAGAAATTG

ATCTTCCCTGGGGGACTTTAACTCTTGACCTGTATGCAGCTGTTGGAGTA

-continued

ATTCCAGGTCTCTTGAAAAAAAAGAGGAAGATAATGGAGAATGAGAACAT

ATATATATATATATTAAGCCCCAGGCTGAATACTCAGGGACAGCAATTCA

CAGCCTGCCTCTGGTTCTATAAACAAGTCATTCTACCTCTTTGTGCCCTG

CTGTTTATTCTGTAAGGGGAAGGTGGCAATGGGACCCAGCTCCATCAGAC

ACTTGTCAAGCTAGCAGAAACTCCATTTTCAATGCCAAAGAAGAACTGTA

ATGCTGTTTTGGAATCATCCCAAGGCATCCCAAGACACCATATCTTCCCA

TTTCAAGCACTGCCTGGGCACACCCCAACATCCCAGGCTGTGGTGGCTCC

TGTGGGAACTACCTAGATGAAGAGAGTATCATTTATACCTTCTAGGAGCT

CCTATTGGGAGACATGAAACATATGTAATTGACTACCATGTAATAGAACA

AACCCTGCCAAGTGCTGCTTTGGAAAGTCATGGAGGTAAAAGAAAGACCA

TTC

SEQ ID NO: 7 Protein sequence of human MASP-3:

MRWLLLYYALCFSLSKASAHTVELNNMFGQIQSPGYPDSYPSDSEVTWNI

TVPDGFRIKLYFMHFNLESSYLCEYDYVKVETEDQVLATFCGRETTDTEQ

TPGQEVVLSPGSFMSIITRSDFSNEERFTGFDAHYMAVDVDECKEREDEE

LSCDHYCHNYIGGYYCSCRFGYILHTDNRTCRVECSDNLFTQRTGVITSP

DFPNPYPKSSECLYTIELEEGFMVNLQFEDIFDIEDHPEVPCPYDYIKIK

VGPKVLGPFCGEKAPEPISTQSHSVLILFHSDNSGENRGWRLSYRAAGNE

CPELQPPVHGKIEPSQAKYFFKDQVLVSCDTGYKVLKDNVEMDTFQIECL

KDGTWSNKIPTCKIVDCRAPGELEHGLIITSTRNNLTTYKSEIKYSCQEP

YYKMLNNNTGIYTCSAQGVWMNKVLGRSLPTCLPECGQPSRSLPSLVKRI

IGGRNAEPGLFPWQALIVVEDTSRVPNDKWFGSGALLSASWILTAAHVLR

SQRRDTTVIPVSKEHVTVYLGLHDVRDKSGAVNSSAARVVLHPDFNIQNY

NHDIALVQLQEPVPLGPHVMPVCLPRLEPEGPAPHMLGLVAGWGISNPNV

TVDEIISSGTRTLSDVLQYVKLPVVPHAECKTSYESRSGNYSVTENMFCA

GYYEGGKDTCLGDSGGAFVIFDDLSQRWVVQGLVSWGGPEECGSKQVYGV

YTKVSNYVDWVWEQMGLPQSVVEPQVER

SEQ ID NO: 8 cDNA sequence of human MASP-3:

GAAGTCAGCCACACAGGATAAAGGAGGGAAGGGAAGGAGCAGATCTTTTC

GGTAGGAAGACAGATTTTGTTGTCAGGTTCCTGGGAGTGCAAGAGCAAGT

CAAAGGAGAGAGAGAGGAGAGAGGAAAAGCCAGAGGGAGAGAGGGGGAGA

GGGGATCTGTTGCAGGCAGGGGAAGGCGTGACCTGAATGGAGAATGCCAG

CCAATTCCAGAGACACACAGGGACCTCAGAACAAAGATAAGGCATCACGG

ACACCACACCGGGCACGAGCTCACAGGCAAGTCAAGCTGGGAGGACCAAG

GCCGGGCAGCCGGGAGCACCCAAGGCAGGAAAATGAGGTGGCTGCTTCTC

TATTATGCTCTGTGCTTCTCCCTGTCAAAGGCTTCAGCCCACACCGTGGA

GCTAAACAATATGTTTGGCCAGATCCAGTCGCCTGGTTATCCAGACTCCT

ATCCCAGTGATTCAGAGGTGACTTGGAATATCACTGTCCCAGATGGGTTT

CGGATCAAGCTTTACTTCATGCACTTCAACTTGGAATCCTCCTACCTTTG

TGAATATGACTATGTGAAGGTAGAAACTGAGGACCAGGTGCTGGCAACCT

TCTGTGGCAGGGAGACCACAGACACAGAGCAGACTCCCGGCCAGGAGGTG

GTCCTCTCCCCTGGCTCCTTCATGTCCATCACTTTCCGGTCAGATTTCTC

-continued

CAATGAGGAGCGTTTCACAGGCTTTGATGCCCACTACATGGCTGTGGATG

TGGACGAGTGCAAGGAGAGGGAGGACGAGGAGCTGTCCTGTGACCACTAC

TGCCACAACTACATTGGCGGCTACTACTGCTCCTGCCGCTTCGGCTACAT

CCTCCACACAGACAACAGGACCTGCCGAGTGGAGTGCAGTGACAACCTCT

TCACTCAAAGGACTGGGGTGATCACCAGCCCTGACTTCCCAAACCCTTAC

CCCAAGAGCTCTGAATGCCTGTATACCATCGAGCTGGAGGAGGGTTTCAT

GGTCAACCTGCAGTTTGAGGACATATTTGACATTGAGGACCATCCTGAGG

TGCCCTGCCCCTATGACTACATCAAGATCAAAGTTGGTCCAAAAGTTTTG

GGGCCTTTCTGTGGAGAGAAAGCCCCAGAACCCATCAGCACCCAGAGCCA

CAGTGTCCTGATCCTGTTCCATAGTGACAACTCGGGAGAGAACCGGGGCT

GGAGGCTCTCATACAGGGCTGCAGGAAATGAGTGCCCAGAGCTACAGCCT

CCTGTCCATGGGAAAATCGAGCCCTCCCAAGCCAAGTATTTCTTCAAAGA

CCAAGTGCTCGTCAGCTGTGACACAGGCTACAAAGTGCTGAAGGATAATG

TGGAGATGGACACATTCCAGATTGAGTGTCTGAAGGATGGGACGTGGAGT

AACAAGATTCCCACCTGTAAAATTGTAGACTGTAGAGCCCCAGGAGAGCT

GGAACACGGGCTGATCACCTTCTCTACAAGGAACAACCTCACCACATACA

AGTCTGAGATCAAATACTCCTGTCAGGAGCCCTATTACAAGATGCTCAAC

AATAACACAGGTATATATACCTGTTCTGCCCAAGGAGTCTGGATGAATAA

AGTATTGGGGAGAAGCCTACCCACCTGCCTTCCAGAGTGTGGTCAGCCCT

CCCGCTCCCTGCCAAGCCTGGTCAAGAGGATCATTGGGGGCCGAAATGCT

GAGCCTGGCCTCTTCCCGTGGCAGGCCCTGATAGTGGTGGAGGACACTTC

GAGAGTGCCAAATGACAAGTGGTTTGGGAGTGGGGCCCTGCTCTCTGCGT

CCTGGATCCTCACAGCAGCTCATGTGCTGCGCTCCCAGCGTAGAGACACC

ACGGTGATACCAGTCTCCAAGGAGCATGTCACCGTCTACCTGGGCTTGCA

TGATGTGCGAGACAAATCGGGGGCAGTCAACAGCTCAGCTGCCCGAGTGG

TGCTCCACCCAGACTTCAACATCCAAAACTACAACCACGATATAGCTCTG

GTGCAGCTGCAGGAGCCTGTGCCCCTGGGACCCCACGTTATGCCTGTCTG

CCTGCCAAGGCTTGAGCCTGAAGGCCCGGCCCCCCACATGCTGGGCCTGG

TGGCCGGCTGGGGCATCTCCAATCCCAATGTGACAGTGGATGAGATCATC

AGCAGTGGCACACGGACCTTGTCAGATGTCCTGCAGTATGTCAAGTTACC

CGTGGTGCCTCACGCTGAGTGCAAAACTAGCTATGAGTCCCGCTCGGGCA

ATTACAGCGTCACGGAGAACATGTTCTGTGCTGGCTACTACGAGGGCGGC

AAAGACACGTGCCTTGGAGATAGCGGTGGGGCCTTTGTCATCTTTGATGA

CTTGAGCCAGCGCTGGGTGGTGCAAGGCCTGGTGTCCTGGGGGGGACCTG

AAGAATGCGGCAGCAAGCAGGTCTATGGAGTCTACACAAAGGTCTCCAAT

TACGTGGACTGGGTGTGGGAGCAGATGGGCTTACCACAAAGTGTTGTGGA

GCCCCAGGTGGAACGGTGAGCTGACTTACTTCCTCGGGGCCTGCCTCCCC

TGAGCGAAGCTACACCGCACTTCCGACAGCACACTCCACATTACTTATCA

GACCATATGGAATGGAACACACTGACCTAGCGGTGGCTTCTCCTACCGAG

ACAGCCCCCAGGACCCTGAGAGGCAGAGTGTGGTATAGGGAAAAGGCTCC

-continued

AGGCAGGAGACCTGTGTTCCTGAGCTTGTCCAAGTCTCTTTCCCTGTCTG

GGCCTCACTCTACCGAGTAATACAATGCAGGAGCTCAACCAAGGCCTCTG

TGCCAATCCCAGCACTCCTTTCCAGGCCATGCTTCTTACCCCAGTGGCCT

TTATTCACTCCTGACCACTTATCAAACCCATCGGTCCTACTGTTGGTATA

ACTGAGCTTGGACCTGACTATTAGAAAATGGTTTCTAACATTGAACTGAA

TGCCGCATCTGTATATTTTCCTGCTCTGCCTTCTGGGACTAGCCTTGGCC

TAATCCTTCCTCTAGGAGAAGAGCATTCAGGTTTTGGGAGATGGCTCATA

GCCAAGCCCCTCTCTCTTAGTGTGATCCCTTGGAGCACCTTCATGCCTGG

GGTTTCTCTCCCAAAAGCTTCTTGCAGTCTAAGCCTTATCCCTTATGTTC

CCCATTAAAGGAATTTCAAAAGACATGGAGAAAGTTGGGAAGGTTTGTGC

TGACTGCTGGGAGCAGAATAGCCGTGGGAGGCCCACCAAGCCCTTAAATT

CCCATTGTCAACTCAGAACACATTTGGGCCCATATGCCACCCTGGAACAC

CAGCTGACACCATGGGCGTCCACACCTGCTGCTCCAGACAAGCACAAAGC

AATCTTTCAGCCTTGAAATGTATTATCTGAAAGGCTACCTGAAGCCCAGG

CCCGAATATGGGGACTTAGTCGATTACCTGGAAAAAGAAAAGACCCACAC

TGTGTCCTGCTGTGCTTTTGGGCAGGAAAATGGAAGAAAGAGTGGGGTGG

GCACATTAGAAGTCACCCAAATCCTGCCAGGCTGCCTGGCATCCCTGGGG

CATGAGCTGGGCGGAGAATCCACCCCGCAGGATGTTCAGAGGGACCCACT

CCTTCATTTTTCAGAGTCAAAGGAATCAGAGGCTCACCCATGGCAGGCAG

TGAAAAGAGCCAGGAGTCCTGGGTTCTAGTCCCTGCTCTGCCCCCAACTG

GCTGTATAACCTTTGAAAAATCATTTTCTTTGTCTGAGTCTCTGGTTCTC

CGTCAGCAACAGGCTGGCATAAGGTCCCCTGCAGGTTCCTTCTAGCTGGA

GCACTCAGAGCTTCCCTGACTGCTAGCAGCCTCTCTGGCCCTCACAGGGC

TGATTGTTCTCCTTCTCCCTGGAGCTCTCTCTCCTGAAAATCTCCATCAG

AGCAAGGCAGCCAGAGAAGCCCCTGAGAGGGAATGATTGGGAAGTGTCCA

CTTTCTCAACCGGCTCATCAAACACACTCCTTTGTCTATGAATGGCACAT

GTAAATGATGTTATATTTTGTATCTTTTATATCATATGCTTCACCATTCT

GTAAAGGGCCTCTGCATTGTTGCTCCCATCAGGGGTCTCAAGTGGAAATA

AACCCTCGTGGATAACCAAAAAAAAAAAAAAAAAAA

SEQ ID NO: 9 Protein sequence of human MASP-2:
MRLLTLLGLLCGSVATPLGPKWPEPVFGRLASPGFPGEYANDQERRWTLT

APPGYRLRLYFTHEDLELSHLCEYDFVKLSSGAKVLATLCGQESTDTERA

PGKDTFYSLGSSLDIITRSDYSNEKPFTGFEAFYAAEDIDECQVAPGEAP

TCDHHCHNHLGGFYCSCRAGYVLHRNKRTCSALCSGQVFTQRSGELSSPE

YPRPYPKLSSCTYSISLEEGFSVILDFVESFDVETHPETLCPYDFLKIQT

DREEHGPFCGKTLPHRIETKSNTVTITFVTDESGDHTGWKIHYTSTAQPC

PYPMAPPNGHVSPVQAKYILKDSFSIFCETGYELLQGHLPLKSFTAVCQK

DGSWDRPMPACSIVDCGPPDDLPSGRVEYITGPGVTTYKAVIQYSCEETF

YTMKVNDGKYVCEADGFWTSSKGEKSLPVCEPVCGLSARTTGGRIYGGQK

AKPGDFPWQVLILGGTTAAGALLYDNWVLTAAHAVYEQKHDASALDIRMG

TLKRLSPHYTQAWSEAVFIHEGYTHDAGFDNDIALIKLNNKVVINSNITP

-continued

ICLPRKEAESFMRTDDIGTASGWGLTQRGFLARNLMYVDIPIVDHQKCTA

AYEKPPYPRGSVTANMLCAGLESGGKDSCRGDSGGALVFLDSETERWFVG

GIVSWGSMNCGEAGQYGVYTKVINYIPWIENIISDF

SEQ ID NO: 10 cDNA sequence of human MASP-2:
GGCCAGCTGGACGGGCACACCATGAGGCTGCTGACCCTCCTGGGCCTTCT

GTGTGGCTCGGTGGCCACCCCCTTGGGCCCGAAGTGGCCTGAACCTGTGT

TCGGGCGCCTGGCATCCCCCGGCTTTCCAGGGGAGTATGCCAATGACCAG

GAGCGGCGCTGGACCCTGACTGCACCCCCCGGCTACCGCCTGCGCCTCTA

CTTCACCCACTTCGACCTGGAGCTCTCCCACCTCTGCGAGTACGACTTCG

TCAAGCTGAGCTCGGGGGCCAAGGTGCTGGCCACGCTGTGCGGGCAGGAG

AGCACAGACACGGAGCGGGCCCCTGGCAAGGACACTTTCTACTCGCTGGG

CTCCAGCCTGGACATTACCTTCCGCTCCGACTACTCCAACGAGAAGCCGT

TCACGGGGTTCGAGGCCTTCTATGCAGCCGAGGACATTGACGAGTGCCAG

GTGGCCCCGGGAGAGGCGCCCACCTGCGACCACCACTGCCACAACCACCT

GGGCGGTTTCTACTGCTCCTGCCGCGCAGGCTACGTCCTGCACCGTAACA

AGCGCACCTGCTCAGCCCTGTGCTCCGGCCAGGTCTTCACCCAGAGGTCT

GGGGAGCTCAGCAGCCCTGAATACCCACGGCCGTATCCCAAACTCTCCAG

TTGCACTTACAGCATCAGCCTGGAGGAGGGGTTCAGTGTCATTCTGGACT

TTGTGGAGTCCTTCGATGTGGAGACACACCCTGAAACCCTGTGTCCCTAC

GACTTTCTCAAGATTCAAACAGACAGAGAAGAACATGGCCCATTCTGTGG

GAAGACATTGCCCCACAGGATTGAAACAAAAAGCAACACGGTGACCATCA

CCTTTGTCACAGATGAATCAGGAGACCACACAGGCTGGAAGATCCACTAC

ACGAGCACAGCGCAGCCTTGCCCTTATCCGATGGCGCCACCTAATGGCCA

CGTTTCACCTGTGCAAGCCAAATACATCCTGAAAGACAGCTTCTCCATCT

TTTGCGAGACTGGCTATGAGCTTCTGCAAGGTCACTTGCCCCTGAAATCC

TTTACTGCAGTTTGTCAGAAAGATGGATCTTGGGACCGGCCAATGCCCGC

GTGCAGCATTGTTGACTGTGGCCCTCCTGATGATCTACCCAGTGGCCGAG

TGGAGTACATCACAGGTCCTGGAGTGACCACCTACAAAGCTGTGATTCAG

TACAGCTGTGAAGAGACCTTCTACACAATGAAAGTGAATGATGGTAAATA

TGTGTGTGAGGCTGATGGATTCTGGACGAGCTCCAAAGGAGAAAAATCAC

TCCCAGTCTGTGAGCCTGTTTGTGGACTATCAGCCCGCACAACAGGAGGG

CGTATATATGGAGGGCAAAAGGCAAAACCTGGTGATTTTCCTTGGCAAGT

CCTGATATTAGGTGGAACCACAGCAGCAGGTGCACTTTTATATGACAACT

GGGTCCTAACAGCTGCTCATGCCGTCTATGAGCAAAAACATGATGCATCC

GCCCTGGACATTCGAATGGGCACCCTGAAAAGACTATCACCTCATTATAC

ACAAGCCTGGTCTGAAGCTGTTTTTATACATGAAGGTTATACTCATGATG

CTGGCTTTGACAATGACATAGCACTGATTAAATTGAATAACAAAGTTGTA

ATCAATAGCAACATCACGCCTATTTGTCTGCCAAGAAAAGAAGCTGAATC

CTTTATGAGGACAGATGACATTGGAACTGCATCTGGATGGGGATTAACCC

AAAGGGGTTTTCTTGCTAGAAATCTAATGTATGTCGACATACCGATTGTT

GACCATCAAAAATGTACTGCTGCATATGAAAAGCCACCCTATCCAAGGGG

-continued

AAGTGTAACTGCTAACATGCTTTGTGCTGGCTTAGAAAGTGGGGGCAAGG

ACAGCTGCAGAGGTGACAGCGGAGGGGCACTGGTGTTTCTAGATAGTGAA

ACAGAGAGGTGGTTTGTGGGAGGAATAGTGTCCTGGGGTTCCATGAATTG

TGGGGAAGCAGGTCAGTATGGAGTCTACACAAAAGTTATTAACTATATTC

CCTGGATCGAGAACATAATTAGTGATTTTTAACTTGCGTGTCTGCAGTCA

AGGATTCTTCATTTTTAGAAATGCCTGTGAAGACCTTGGCAGCGACGTGG

CTCGAGAAGCATTCATCATTACTGTGGACATGGCAGTTGTTGCTCCACCC

AAAAAAACAGACTCCAGGTGAGGCTGCTGTCATTTCTCCACTTGCCAGTT

TAATTCCAGCCTTACCCATTGACTCAAGGGGACATAAACCACGAGAGTGA

CAGTCATCTTTGCCCACCCAGTGTAATGTCACTGCTCAAATTACATTTCA

TTACCTTAAAAAGCCAGTCTCTTTTCATACTGGCTGTTGGCATTTCTGTA

AACTGCCTGTCCATGCTCTTTGTTTTTAAACTTGTTCTTATTGAAAAAAA

AAAAAAAAAA

SEQ ID NO: 11 Protein sequence of human sMAP (MAp19):
MRLLTLLGLLCGSVATPLGPKWPEPVFGRLASPGFPGEYANDQERRWTLT

APPGYRLRLYFTHFDLELSHLCEYDEVKLSSGAKVLATLCGQESTDTERA

-continued

PGKDTFYSLGSSLDITFRSDYSNEKPFTGFEAFYAAEDIDECQVAPGEAP

TCDHHCHNHLGGFYCSCRAGYVLHRNKRTCSEQSL

SEQ ID NO: 12 cDNA sequence of human sMAP (MAp19):
GGCCAGCTGGACGGGCACACCATGAGGCTGCTGACCCTCCTGGGCCTTCT

GTGTGGCTCGGTGGCCACCCCCTTGGGCCCGAAGTGGCCTGAACCTGTGT

TCGGGCGCCTGGCATCCCCCGGCTTTCCAGGGGAGTATGCCAATGACCAG

GAGCGGCGCTGGACCCTGACTGCACCCCCCGGCTACCGCCTGCGCCTCTA

CTTCACCCACTTCGACCTGGAGCTCTCCCACCTCTGCGAGTACGACTTCG

TCAAGCTGAGCTCGGGGGCCAAGGTGCTGGCCACGCTGTGCGGGCAGGAG

AGCACAGACACGGAGCGGGCCCCTGGCAAGGACACTTTCTACTCGCTGGG

CTCCAGCCTGGACATTACCTTCCGCTCCGACTACTCCAACGAGAAGCCGT

TCACGGGGTTCGAGGCCTTCTATGCAGCCGAGGACATTGACGAGTGCCAG

GTGGCCCCGGGAGAGGCGCCCACCTGCGACCACCACTGCCACAACCACCT

GGGCGGTTTCTACTGCTCCTGCCGCGCAGGCTACGTCCTGCACCGTAACA

AGCGCACCTGCTCAGAGCAGAGCCTCTAGCCTCCCCTGGAGCTCCGGCCT

GCCCAGCAGGTCAGAAGCCAGAGCCAGCCTGCTGGCCTCAGCTCCGGGTT

GGGCTGAGATGGCTGTGCCCCAACTCCCATTCACCCACCATGGACCCAAT

AATAAACCTGGCCCCACCCCAAAAAAAAAAAAAAAAAA

DNA Primers:

SEQ ID NO: 13:
5'-gcacccagagccacagtg-3'

SEQ ID NO: 14:
5'-gccttccagtgtgtgggc-3'

SEQ ID NO: 15:
5-gccttccagagtgtggtca-3'

SEQ ID NO: 16:
5'-cgatctggagagcgaactc-3'

SEQ ID NO: 17:
5'-ctgttcttcacactggctg-3'

SEQ ID NO: 18:
5'-ctgctgagatcatgttgttc-3'

SEQ ID NO: 19:
5'-TTATACGACTCACTA-3'

SEQ ID NO: 20 (Amino acid sequence of human Factor H):
MRLLAKTICLMLWATCVAEDCNELPPRRNTEILTGSWSDQTYPEGTQATYKCRPGYRSLGNVIMVCRKGEWVALNPLRKCQKR PCGHPGDTPFGTFTLTGGNVFEYGVKAVYTCNEGYQLLGEINYRECDTDGWTNDIPICEVVKCLPVTAPENGKIVSSAMEPDR EYHFGQAVREVCNSGYKIEGDEEMHCSDDGFWSKEKPKCVEISCKSPDVINGSPISQKIIYKENERFQYKCNMGYEYSERGDA VCTESGWRPLPSCEEKSCDNPYIPNGDYSPLRIKHRTGDEITYQCRNGFYPATRGNTAKCTSTGWIPAPRCTLKPCDYPDIKH GGLYHENMRRPYFPVAVGKYYSYYCDEHFETPSGSYWDHIHCTQDGWSPAVPCLRKCYFPYLENGYNQNHGRKFVQGKSIDVA CHPGYALPKAQTTVTCMENGWSPTPRCIRVKTCSKSSIDTENGFISESQYTYALKEKAKYQCKLGYVTADGETSGSTRCGKDG WSAQPTCIKSCDTPVFMNARTKNDFTWFKLNDTLDYECHDGYESNTGSTTGSTVCGYNGWSDLPICYERECELPKIDVHLVPD RKKDQYKVGEVLKFSCKPGETIVGPNSVQCYHEGLSPDLPICKEQVQSCGPPPELLNGNVKEKTKEEYGHSEVVEYYCNPRFL MKGPNKTQCVDGEWTTLPVCIVEESTCGDIPELEHGWAQLSSPPYYYGDSVEFNCSESFTMIGHRSITCIHGVWTQLPQCVAT DKLKKCKSSNLIILEEHLKNKKEEDHNSNTRYRCRGKEGWIHTVCINGRWDPEVNCSMAQTQLCPPPPQIPNSHNMTTTLNYR -continued DGEKVSVLCQENYLTQEGEEITCKDGRWQSIPLCVEKTPCSQPPQTEHGTINSSRSSQESYAHGTKLSYTCEGGFRISEENET TCYMGKWSSPPQCEGLPCKSPPEISHGVVAHMSDSYQYGEEVTYKCFEGEGIDGPATAKCLGEKWSHPPSCIKTDCLSLPSFE NAIPMGEKKDVYKAGEQVTYTCATYYKMDGASNVTCINSRWTGRPTCRDTSCVNPPTVQNAYIVSRQMSKYPSGERVRYQCRS PYEMFGDEEVMCLNGNWTEPPQCKDSTGKCGPPPPIDNGDITSFPLSVYAPASSVEYQCQNLYQLEGNKRITCRNGQWSEPPK

CLHPCVISREIMENYNTALRWTAKQKLYSRTGESVEFVCKRGYRLSSRSHTLRTTCWDGKLEYPTCAKR

SEQ ID NO: 21 (Amino acid sequence of human C4bp alfa):
MHPPKTPSGALHRKRKMAAWPFSRLWKVSDPILFQMTLTAALLPAVLGNCGPPPTLSFAAPMDITLTETRFKTGTTLKYTCLP GYVRSHSTQTLTCNSDGEWVYNTFCIYKRCRHPGELRNGQVEIKTDLSEGSQIEFSCSEGFFLIGSTTSRCEVQDRGVGWSHP LPQCEIVKCKPPPDIRNGRHSGEENFYAYGFSVTYSCDPRFSLLGHASISCTVENETIGVWRPSPPTCEKTTCRKPDVSHGEM VSGFGPIYNYKDTIVEKCQKGFVLRGSSVIHCDADSKWNPSPPACEPNSCINLPDIPHASWETYPRPTKEDVYVVGTVLRYRC HPGYKPTTDEPTTVICQKNLRWTPYQGCEALCCPEPKLNNGEITQHRKSRPANHCVYFYGDEISFSCHETSRFSATCQGDGTW SPRTPSCGDICNEPPKTAHGHYKQSSSYSFFKEEIIYECDKGYILVGQAKLSCSYSHWSAPAPQCKALCRKPELVNGRLSVDK DQYVEPENVTIQCDSGYGVVGPQSITCSGNRTWYPEVPKCEWETPEGCEQVLTGKRLMQCLPNPEDVKMALEVYKLSLETEQL

ELQRDSARQSTLDKEL

SEQ ID NO: 22 (Amino acid sequence of human C4bp beta):
METWCACCLMVAWRVSASDAEHCPELPPVDNSIEVAKEVEGQILGTYVCIKGYHLVGKKTLECNASKEWDNTTTECRLGHCPD PVLVNGEFSSSGPVNVSDKITFMCNDHYILKGSNRSQCLEDHTWAPPFPICKSRDCDPPGNPVHGYFEGNNFTLGSTTSYYCE DRYYLVGVQEQQCVDGEWSSALPVCKLTQEAPKPECEKALLAFQESKNLCEAMENFMQQLKESGMTMEELKYSLELKKAELKA

KLL

SEQ ID NO: 23 (Amino acid sequence of human FI):
MKLLHVELLFLCFHLRECKVTYTSQEDLVEKKCLAKKYTHLSCDKVECQPWQRCIEGTCVCKLPYQCPKNGTAVCATNRRSFP TYCQQKSLECLHPGTKELNNGTCTAEGKESVSLKHGNTDSEGIVEVKLVDQDKTMFICKSSWSMREANVACLDLGFQQGADTQ RRFKLSDLSINSTECLHVHCRGLETSLAECTFTKRRTMGYQDFADVVCYTQKADSPMDDFFQCVNGKYISQMKACDGINDCGD QSDELCCKACQGKGFHCKSGVCIPSQYQCNGEVDCTTGEDEVGCAGFASVAQEETEILTADMDAERRRIKSLLPKLSCGVKNR MHIRRKRIVGGKRAQLGDLPWQVAIKDASGTTCGGIYIGGCWILTAAHCLRASKTHRYQIWTTVVDWTHPDLKRIVIEYVDRI IFHENYNAGTYQND'ALIEMKKDGNKKDCELPRSIPACVPWSPYLFQPNDTCIVSGWGREKDNERVESLQWGEVKLISNCSKF YGNRFYEKEMECAGTYDGSIDACKGDSGGPLVCMDANNVTYVWGVVSWGENCGKPEFPGVYTKVANYEDWISYHVGRPFISQY

NV

SEQ ID NO: 24 (Amino acid sequence of human C1-inh):
MASRLTLLTLLLLLLAGDRASSNPNATSSSSQDPESLQDRGEGKVATTVISKMLFVEPILEVSSLPTTNSTTNSATKITANTT DEPTTQPTTEPTTQPTIQPTQPTTQLPTDSPTQPTTGSFCPGPVTLCSDLESHSTEAVLGDALVDFSLKLYHAFSAMKKVETN MAFSPFSIASLLTQVLLGAGENTKTNLESILSYPKDFTCVHQALKGFTTKGVTSVSQIFHSPDLAIRDTFVNASRTLYSSSPR VLSNNSDANLELINTWVAKNTNNKISRLLDSLPSDTRLVLLNAIYLSAKWKTTFDPKKTAMEPFHFKNSVIKVPMMNSKKYPV AHFIDQTLKAKVGQLQLSHNLSLVILVPQNLKHRLEDMEQALSPSVFKAIMEKLEMSKFQPTLLTLPRIKVTTSQDMLSIMEK LEFFDFSYDLNLCGLTEDPDLQVSAMQHQTVLELTETGVEAAAASAISVARTLLVFEVQQPFLFVLWDQQHKFPVFMGRVYDP

RA

SEQ ID NO: 25 (Amino acid sequence of human MAP1/FH):
HTVELNNMFGQIQSPGYPDSYPSDSEVTWNITVPDGFRIKLYFMHFNLESSYLCEYDYVKVETEDQVLATFCGRETTDT

EQTPGQEVVLSPGSFMSITFRSDFSNEERFTGFDAHYMAVDVDECKEREDEELSCDHYCHNYIGGYYCSCRFGYILHTD

NRTCRVECSDNLFTQRTGVITSPDFPNPYPKSSECLYTIELEEGFMVNLQFEDIFDIEDHPEVPCPYDYIKIKVGPKVL

GPFCGEKAPEPISTQSHSVLILFHSDNSGENRGWRLSYRAAGNECPELQPPVHGKIEPSQAKYFFKDQVLVSCDTGYKV

LKDNVEMDTFQIECLKDGTWSNKIPTCKKNEIDLESELKSEQVTEGGGGSGGGGSCVAEDCNELPPRRNTEILTGSWSD

QTYPEGTQAIYKCRPGYRSLGNVIMVCRKGEWVALNPLRKCQKRPCGHPGDTPFGTFTLTGGNVFEYGVKAVYTCNEGY

-continued

QLLGEINYRECDTDGWTNDIPICEVVKCLPVTAPENGKIVSSAMEPDREYHFGQAVRFVCNSGYKIEGDEEMHCSDDGF

WSKEKPKCVEISCKSPDVINGSPISQKIIYKENERFQYKCNMGYEYSERGDAVCTESGWRPLPSCEEKSCDNPYIPNGD

YSPLRIKHRTGDEITYQCRNGFYPATRGNTAKCTSTGWIPAPRCTLKP

SEQ ID NO: 26 (Nucleic acid sequence of human MAP-1/FH):
CACACCGTGGAGCTAAACAATATGTTTGGCCAGATCCAGTCGCCTGGTTATCCAGACTCCTATCCCAGTGATTCAGAGG

TGACTTGGAATATCACTGTCCCAGATGGGTTTCGGATCAAGCTTTACTTCATGCACTTCAACTTGGAATCCTCCTACCT

TTGTGAATATGACTATGTGAAGGTAGAAACTGAGGACCAGGTGCTGGCAACCTTCTGTGGCAGGGAGACCACAGACACA

GAGCAGACTCCCGGCCAGGAGGTGGTCCTCTCCCCTGGCTCCTTCATGTCCATCACTTTCCGGTCAGATTTCTCCAATG

AGGAGCGTTTCACAGGCTTTGATGCCCACTACATGGCTGTGGATGTGGACGAGTGCAAGGAGAGGGAGGACGAGGAGCT

GTCCTGTGACCACTACTGCCACAACTACATTGGCGGCTACTACTGCTCCTGCCGCTTCGGCTACATCCTCCACACAGAC

AACAGGACCTGCCGAGTGGAGTGCAGTGACAACCTCTTCACTCAAAGGACTGGGGTGATCACCAGCCCTGACTTCCCAA

ACCCTTACCCCAAGAGCTCTGAATGCCTGTATACCATCGAGCTGGAGGAGGGTTTCATGGTCAACCTGCAGTTTGAGGA

CATATTTGACATTGAGGACCATCCTGAGGTGCCCTGCCCCTATGACTACATCAAGATCAAAGTTGGTCCAAAAGTTTTG

GGGCCTTTCTGTGGAGAGAAAGCCCCAGAACCCATCAGCACCCAGAGCCACAGTGTCCTGATCCTGTTCCATAGTGACA

ACTCGGGAGAGAACCGGGGCTGGAGGCTCTCATACAGGGCTGCAGGAAATGAGTGCCCAGAGCTACAGCCTCCTGTCCA

TGGGAAAATCGAGCCCTCCCAAGCCAAGTATTTCTTCAAAGACCAAGTGCTCGTCAGCTGTGACACAGGCTACAAAGTG

CTGAAGGATAATGTGGAGATGGACACATTCCAGATTGAGTGTCTGAAGGATGGGACGTGGAGTAACAAGATTCCCACCT

GTAAAAAAAATGAAATCGATCTGGAGAGCGAACTCAAGTCAGAGCAAGTGACAGAGGGCGGAGGTGGGTCGGGTGGCGG

CGGATCTTGTGTAGCAGAAGATTGCAATGAACTTCCTCCAAGAAGAAATACAGAAATTCTGACAGGTTCCTGGTCTGAC

CAAACATATCCAGAAGGCACCCAGGCTATCTATAAATGCCGCCCTGGATATAGATCTCTTGGAAATGTAATAATGGTAT

GCAGGAAGGGAGAATGGGTTGCTCTTAATCCATTAAGGAAATGTCAGAAAAGGCCCTGTGGACATCCTGGAGATACTCC

TTTTGGTACTTTTACCCTTACAGGAGGAAATGTGTTTGAATATGGTGTAAAAGCTGTGTATACATGTAATGAGGGGTAT

CAATTGCTAGGTGAGATTAATTACCGTGAATGTGACACAGATGGATGGACCAATGATATTCCTATATGTGAAGTTGTGA

AGTGTTTACCAGTGACAGCACCAGAGAATGGAAAAATTGTCAGTAGTGCAATGGAACCAGATCGGGAATACCATTTTGG

ACAAGCAGTACGGTTTGTATGTAACTCAGGCTACAAGATTGAAGGAGATGAAGAAATGCATTGTTCAGACGATGGTTTT

TGGAGTAAAGAGAAACCAAAGTGTGTGGAAATTTCATGCAAATCCCCAGATGTTATAAATGGATCTCCTATATCTCAGA

AGATTATTTATAAGGAGAATGAACGATTTCAATATAAATGTAACATGGGTTATGAATACAGTGAAAGAGGAGATGCTGT

ATGCACTGAATCTGGATGGCGTCCGTTGCCTTCATGTGAAGAAAAATCATGTGATAATCCTTATATTCCAAATGGTGAC

TACTCACCTTTAAGGATTAAACACAGAACTGGAGATGAAATCACGTACCAGTGTAGAAATGGTTTTTATCCTGCAACCC

GGGGAAATACAGCAAAATGCACAAGTACTGGCTGGATACCTGCTCCGAGATGTACCT

SEQ ID NO: 27 (Amino acid sequence of human FH/MAP-1):
CVAEDCNELPPRRNTEILTGSWSDQTYPEGTQAIYKCRPGYRSLGNVIMVCRKGEWVALNPLRKCQKRPCGHPGDTPFG

TFTLTGGNVFEYGVKAVYTCNEGYQLLGEINYRECDTDGWTNDIPICEVVKCLPVTAPENGKIVSSAMEPDREYHFGQA

VRFVCNSGYKIEGDEEMHCSDDGFWSKEKPKCVEISCKSPDVINGSPISQKIIYKENERFQYKCNMGYEYSERGDAVCT

ESGWRPLPSCEEKSCDNPYIPNGDYSPLRIKHRTGDEITYQCRNGFYPATRGNTAKCTSTGWIPAPRCTLKPGGGGSGG

GGSHTVELNNMFGQIQSPGYPDSYPSDSEVTWNITVPDGFRIKLYFMHFNLESSYLCEYDYVKVETEDQVLATFCGRET

TDTEQTPGQEVVLSPGSFMSITFRSDFSNEERFTGFDAHYMAVDVDECKEREDEELSCDHYCHNYIGGYYCSCRFGYIL

HTDNRTCRVECSDNLFTQRTGVITSPDFPNPYPKSSECLYTIELEEGFMVNLQFEDIFDIEDHPEVPCPYDYIKIKVGP

KVLGPFCGEKAPEPISTQSHSVLILFHSDNSGENRGWRLSYRAAGNECPELQPPVHGKIEPSQAKYFFKDQVLVSCDTG

YKVLKDNVEMDTFQIECLKDGTWSNKIPTCKKNEIDLESELKSEQVTE

-continued

SEQ ID NO: 28 (Nucleic acid sequence of human FH/MAP-1):
TGTGTAGCAGAAGATTGCAATGAACTTCCTCCAAGAAGAAATACAGAAATTCTGACAGGTTCCTGGTCTGACCAAACAT

ATCCAGAAGGCACCCAGGCTATCTATAAATGCCGCCCTGGATATAGATCTCTTGGAAATGTAATAATGGTATGCAGGAA

GGGAGAATGGGTTGCTCTTAATCCATTAAGGAAATGTCAGAAAAGGCCCTGTGGACATCCTGGAGATACTCCTTTTGGT

ACTTTTACCCTTACAGGAGGAAATGTGTTTGAATATGGTGTAAAAGCTGTGTATACATGTAATGAGGGGTATCAATTGC

TAGGTGAGATTAATTACCGTGAATGTGACACAGATGGATGGACCAATGATATTCCTATATGTGAAGTTGTGAAGTGTTT

ACCAGTGACAGCACCAGAGAATGGAAAAATTGTCAGTAGTGCAATGGAACCAGATCGGGAATACCATTTTGGACAAGCA

GTACGGTTTGTATGTAACTCAGGCTACAAGATTGAAGGAGATGAAGAAATGCATTGTTCAGACGATGGTTTTTGGAGTA

AAGAGAAACCAAAGTGTGTGGAAATTTCATGCAAATCCCCAGATGTTATAAATGGATCTCCTATATCTCAGAAGATTAT

TTATAAGGAGAATGAACGATTTCAATATAAATGTAACATGGGTTATGAATACAGTGAAAGAGGAGATGCTGTATGCACT

GAATCTGGATGGCGTCCGTTGCCTTCATGTGAAGAAAAATCATGTGATAATCCTTATATTCCAAATGGTGACTACTCAC

CTTTAAGGATTAAACACAGAACTGGAGATGAAATCACGTACCAGTGTAGAAATGGTTTTTATCCTGCAACCCGGGGAAA

TACAGCAAAATGCACAAGTACTGGCTGGATACCTGCTCCGAGATGTACCTGGCGGAGGTGGGTCGGGTGGCGGCGGATC

TCACACCGTGGAGCTAAACAATATGTTTGGCCAGATCCAGTCGCCTGGTTATCCAGACTCCTATCCCAGTGATTCAGAG

GTGACTTGGAATATCACTGTCCCAGATGGGTTTCGGATCAAGCTTTACTTCATGCACTTCAACTTGGAATCCTCCTACC

TTTGTGAATATGACTATGTGAAGGTAGAAACTGAGGACCAGGTGCTGGCAACCTTCTGTGGCAGGGAGACCACAGACAC

AGAGCAGACTCCCGGCCAGGAGGTGGTCCTCTCCCCTGGCTCCTTCATGTCCATCACTTTCCGGTCAGATTTCTCCAAT

GAGGAGCGTTTCACAGGCTTTGATGCCCACTACATGGCTGTGGATGTGGACGAGTGCAAGGAGAGGGAGGACGAGGAGC

TGTCCTGTGACCACTACTGCCACAACTACATTGGCGGCTACTACTGCTCCTGCCGCTTCGGCTACATCCTCCACACAGA

CAACAGGACCTGCCGAGTGGAGTGCAGTGACAACCTCTTCACTCAAAGGACTGGGGTGATCACCAGCCCTGACTTCCCA

AACCCTTACCCCAAGAGCTCTGAATGCCTGTATACCATCGAGCTGGAGGAGGGTTTCATGGTCAACCTGCAGTTTGAGG

ACATATTTGACATTGAGGACCATCCTGAGGTGCCCTGCCCCTATGACTACATCAAGATCAAAGTTGGTCCAAAAGTTTT

GGGGCCTTTCTGTGGAGAGAAAGCCCCAGAACCCATCAGCACCCAGAGCCACAGTGTCCTGATCCTGTTCCATAGTGAC

AACTCGGGAGAGAACCGGGGCTGGAGGCTCTCATACAGGGCTGCAGGAAATGAGTGCCCAGAGCTACAGCCTCCTGTCC

ATGGGAAAATCGAGCCCTCCCAAGCCAAGTATTTCTTCAAAGACCAAGTGCTCGTCAGCTGTGACACAGGCTACAAAGT

GCTGAAGGATAATGTGGAGATGGACACATTCCAGATTGAGTGTCTGAAGGATGGGACGTGGAGTAACAAGATTCCCACC

TGTAAAAAAAATGAAATCGATCTGGAGAGCGAACTCAAGTCAGAGCAAGTGACAGAG

SEQ ID NO: 29 (Amino acid sequence of human MAP-1: CUB1, EGF; CUB2, CCP1, without unique 17 amino acids):
MRWLLLYYALCFSLSKASAHTVELNNMFGQIQSPGYPDSYPSDSEVTWNITVPDGFRIKLYFMHFNLESSYLCEYDYVK

VETEDQVLATFCGRETTDTEQTPGQEVVLSPGSFMSITFRSDFSNEERFTGFDAHYMAVDVDECKEREDEELSCDHYCH

NYIGGYYCSCRFGYILHTDNRTCRVECSDNLFTQRTGVITSPDFPNPYPKSSECLYTIELEEGFMVNLQFEDIFDIEDH

PEVPCPYDYIKIKVGPKVLGPFCGEKAPEPISTQSHSVLILFHSDNSGENRGWRLSYRAAGNECPELQPPVHGKIEPSQ

AKYFFKDQVLVSCDTGYKVLKDNVEMDTFQIECLKDGTWSNKIPTCK

SEQ ID NO: 30 (Amino acid sequence of human MAP-1: CUB1, EGF, CUB2):
WLLLYYALCFSLSKASAHTVELNNMFGQIQSPGYPDSYPSDSEVTWNITVPDGFRIKLYFMHFNLESSYLCEYDYVKVE

TEDQVLATFCGRETTDTEQTPGQEVVLSPGSFMSITFRSDFSNEERFTGFDAHYMAVDVDECKEREDEELSCDHYCHNY

IGGYYCSCRFGYILHTDNRTCRVECSDNLFTQRTGVITSPDFPNPYPKSSECLYTIELEEGFMVNLQFEDIFDIEDHPE

VPCPYDYIKIKVGPKVLGPFCGEKAPEPISTQSHSVLILFHSDNSGENRGWRLSYRAA

SEQ ID NO: 31 (Amino acid sequence of human MAP-1: CUB2, CCP1):
VECSDNLFTQRTGVITSPDFPNPYPKSSECLYTIELEEGFMVNLQFEDIFDIEDHPEVPCPYDYIKIKVGPKVLGPFCG
EKAPEPISTQSHSVLILFHSDNSGENRGWRLSYRAAGNECPELQPPVHGKIEPSQAKYFFKDQVLVSCDTGYKVLKDNV
EMDTFQIECLKDGTWSNKIPTCKKNEIDLESELKSEQVTE -continued SEQ ID NO: 32 (Amino acid sequence of human FH, SCR1-4):
MRLLAKIICLMLWAICVAEDCNELPPRRNTEILTGSWSDQTYPEGTQAIYKCRPGYRSLGNVIMVCRKGEWVALNPLRK

CQKRPCGHPGDTPFGTFTLTGGNVFEYGVKAVYTCNEGYQLLGEINYRECDTDGWTNDIPICEVVKCLPVTAPENGKIV

SSAMEPDREYHFGQAVRFVCNSGYKIEGDEEMHCSDDGFWSKEKPKCVEISCKSPDVINGSPISQKIIYKENERFQYKC

NMGYEYSERGDAVCTESGWRPLPSCEE

SEQ ID NO: 33 (Amino acid sequence of human FH, SCR 7-20):
RKCYFPYLENGYNQNHGRKFVQGKSIDVACHPGYALPKAQTTVTCMENGWSPTPRCIRVKTCSKSSIDIENGFISESQY

TYALKEKAKYQCKLGYVTADGETSGSIRCGKDGWSAQPTCIKSCDIPVFMNARTKNDFTWFKLNDTLDYECHDGYESNT

GSTTGSIVCGYNGWSDLPICYERECELPKIDVHLVPDRKKDQYKVGEVLKFSCKPGFTIVGPNSVQCYHFGLSPDLPIC

KEQVQSCGPPPELLNGNVKEKTKEEYGHSEVVEYYCNPRFLMKGPNKIQCVDGEWTTLPVCIVEESTCGDIPELEHGWA

QLSSPPYYYGDSVEFNCSESFTMIGHRSITCIHGVWTQLPQCVAIDKLKKCKSSNLIILEEHLKNKKEFDHNSNIRYRC

RGKEGWIHTVCINGRWDPEVNCSMAQIQLCPPPPQIPNSHNMTTTLNYRDGEKVSVLCQENYLIQEGEEITCKDGRWQS

IPLCVEKIPCSQPPQIEHGTINSSRSSQESYAHGTKLSYTCEGGFRISEENETTCYMGKWSSPPQCEGLPCKSPPEISH

GVVAHMSDSYQYGEEVTYKCFEGFGIDGPAIAKCLGEKWSHPPSCIKTDCLSLPSFENAIPMGEKKDVYKAGEQVTYTC

ATYYKMDGASNVTCINSRWTGRPTCRDTSCVNPPTVQNAYIVSRQMSKYPSGERVRYQCRSPYEMFGDEEVMCLNGNWT

EPPQCKDSTGKCGPPPPIDNGDITSFPLSVYAPASSVEYQCQNLYQLEGNKRITCRNGQWSEPPKCLHPCVISREIMEN

YNIALRWTAKQKLYSRTGESVEFVCKRGYRLSSRSHTLATTCWDGKLEYPTCAKR

SEQ ID NO: 34 (Amino acid sequence of human FH, SCR 7-14):
KTCSKSSIDIENGFISESQYTYALKEKAKYQCKLGYVTADGETSGSIRCGKDGWSAQPTCIKSCDIPVFMNARTKNDFT

WFKLNDTLDYECHDGYESNTGSTTGSIVCGYNGWSDLPICYERECELPKIDVHLVPDRKKDQYKVGEVLKFSCKPGFTI

VGPNSVQCYHFGLSPDLPICKEQVQSCGPPPELLNGNVKEKTKEEYGHSEVVEYYCNPRFLMKGPNKIQCVDGEWTTLP

VCIVEESTCGDIPELEHGWAQLSSPPYYYGDSVEFNCSESFTMIGHRSITCIHGVWTQLPQCVAIDKLKKCKSSNLIIL

EEHLKNKKEFDHNSNIRYRCRGKEGWIHTVCINGRWDPEVNCSMAQIQLCPPPPQIPNSHNMTTTLNYRDGEKVSVLCQ

ENYLIQEGEEITCKDGRWQSIPLCVEKIPCSQPPQIEHGTINSSRSSQESYAHGTKLSYTCEGGFRISEENETTCYMGK

WSSPPQCEG

SEQ ID NO: 35 (Amino acid sequence of human FH, SCR 12-14):
ESTCGDIPELEHGWAQLSSPPYYYGDSVEFNCSESFTMIGHRSITCIHGVWTQLPQCVAIDKLKKCKSSNLIILEEHLK
NKKEFDHNSNIRYRCRGKEGWIHTVCINGRWDPEVNCSMAQIQLCPPPPQIPNSHNMTTTLNYRDGEKVSVLCQENYLI
QEGEEITCKDGRWQSIPLCVEK SEQ ID NO: 36 (Amino acid sequence of human FH, SCR 19-20):
TGKCGPPPPIDNGDITSFPLSVYAPASSVEYQCQNLYQLEGNKRITCRNGQWSEPPKCLHPCVISREIMENYNIALRWT
AKQKLYSRTGESVEFVCKRGYRLSSRSHTLRTTCWDGKLEYPTCAKR SEQ ID NO: 37 (Amino acid sequence of human C4bp, alfa chain, SCR 1-3):
NCGPPPTLSFAAPMDITLTETRFKTGTTLKYTCLPGYVRSHSTQTLTCNSDGEWVYNTFCIYKRCRHPGELRNGQVEIK
TDLSFGSQIEFSCSEGFFLIGSTTSRCEVQDRGVGWSHPLPQCEIVKCKPPPDIRNGRHSGEENFYAYGFSVTYSCDPR
FSLLGHASISCTVENETIGVWRPSPPTCEK SEQ ID NO: 38 (Amino acid sequence of human C4bp, alfa chain, SCR 1-3 + beta chain, SCR 2):
NCGPPPTLSFAAPMDITLTETRFKTGTTLKYTCLPGYVRSHSTQTLTCNSDGEWVYNTFCIYKRCRHPGELRNGQVEIK

TDLSFGSQIEFSCSEGFFLIGSTTSRCEVQDRGVGWSHPLPQCEIVKCKPPPDIRNGRHSGEENFYAYGFSVTYSCDPR

FSLLGHASISCTVENETIGVWRPSPPTCEKGHCPDPVLVNGEFSSSGPVNVSDKITFMCNDHYILKGSNRSQCLEDHTW

APPFPICKS

SEQ ID NO: 39 (Amino acid sequence of human C4bp, alfa chain, SCR 1-3 + beta chain, SCR 1-2):
NCGPPPTLSFAAPMDITLTETRFKTGTTLKYTCLPGYVRSHSTQTLTCNSDGEWVYNTFCIYKRCRHPGELRNGQVEIK

TDLSFGSQIEFSCSEGFFLIGSTTSRCEVQDRGVGWSHPLPQCEIVKCKPPPDIRNGRHSGEENFYAYGFSVTYSCDPR

FSLLGHASISCTVENETIGVWRPSPPTCEKEHCPELPPVDNSIFVAKEVEGQILGTYVCIKGYHLVGKKTLFCNASKEW

DNTTTECRLGHCPDPVLVNGEFSSSGPVNVSDKITFMCNDHYILKGSNRSQCLEDHTWAPPFPICKS

-continued

SEQ ID NO: 40 (Amino acid sequence of human C4bp, alfa chain, SCR 1-8 + beta chain, SCR 1-3):
NCGPPPTLSFAAPMDITLTETRFKTGTTLKYTCLPGYVRSHSTQTLTCNSDGEWVYNTFCIYKRCRHPGELRNGQVEIK

TDLSFGSQIEFSCSEGFFLIGSTTSRCEVQDRGVGWSHPLPQCEIVKCKPPPDIRNGRHSGEENFYAYGFSVTYSCDPR

FSLLGHASISCTVENETIGVWRPSPPTCEKITCRKPDVSHGEMVSGFGPIYNYKDTIVFKCQKGFVLRGSSVIHCDADS

KWNPSPPACEPNSCINLPDIPHASWETYPRPTKEDVYVVGTVLRYRCHPGYKPTTDEPTTVICQKNLRWTPYQGCEALC

CPEPKLNNGEITQHRKSRPANHCVYFYGDEISFSCHETSRFSAICQGDGTWSPRTPSCGDICNFPPKIAHGHYKQSSSY

SFFKEEIIYECDKGYILVGQAKLSCSYSHWSAPAPQCKALCRKPELVNGRLSVDKDQYVEPENVTIQCDSGYGVVGPQS

ITCSGNRTWYPEVPKCEWEHCPELPPVDNSIFVAKEVEGQILGTYVCIKGYHLVGKKTLFCNASKEWDNTTTECRLGHC

PDPVLVNGEFSSSGPVNVSDKITFMCNDHYILKGSNRSQCLEDHTWAPPFPICKSRDCDPPGNPVHGYFEGNNFTLGST

ISYYCEDRYYLVGVQEQQCVDGEWSSALPVCKL

SEQ ID NO: 41(Amino acid sequence of human FI, SRCR, LDLRa1, LDLRb1, SP):
KFSVSLKHGNTDSEGIVEVKLVDQDKTMFICKSSWSMREANVACLDLGFQQGADTQRRFKLSDLSINSTECLHVHCRGL

ETSLAECTFTKRRTMGYQDFADVVCYTQKADSPMDDFFQCVNGKYISQMKACDGINDCGDQSDELCCKACQGKGFHCKS

GVCIPSQYQCNGEVDCITGEDEVGCAGFASVAQEETEILTADMDAERRRIKSLLPKLSCGVKNRMHIRRKRIVGGKRAQ

LGDLPWQVAIKDASGITCGGIYIGGCWILTAAHCLRASKTHRYQIWTTVVDWIHPDLKRIVIEYVDRIIFHENYNAGTY

QNDIALIEMKKDGNKKDCELPRSIPACVPWSPYLFQPNDTCIVSGWGREKDNERVFSLQWGEVKLISNCSKFYGNRFYE

KEMECAGTYDGSIDACKGDSGGPLVCMDANNVTYVWGVVSWGENCGKPEFPGVYTKVANYFDWISYHVGRPFISQYNV

SEQ ID NO: 42 (Amino acid sequence of human FI, LDLRa1, LDLRb1, SP):
KADSPMDDFFQCVNGKYISQMKACDGINDCGDQSDELCCKACQGKGFHCKSGVCIPSQYQCNGEVDCITGEDEVGCAGF

ASVAQEETEILTADMDAERRRIKSLLPKLSCGVKNRMHIRRKRIVGGKRAQLGDLPWQVAIKDASGITCGGIYIGGCWI

LTAAHCLRASKTHRYQIWTTVVDWIHPDLKRIVIEYVDRIIFHENYNAGTYQNDIALIEMKKDGNKKDCELPRSIPACV

PWSPYLFQPNDTCIVSGWGREKDNERVFSLQWGEVKLISNCSKFYGNRFYEKEMECAGTYDGSIDACKGDSGGPLVCMD

ANNVTYVWGVVSWGENCGKPEFPGVYTKVANYFDWISYHVGRPFISQYNV

SEQ ID NO: 43 (Amino acid sequence of human FI, LDLRb1, SP):
KACQGKGFHCKSGVCIPSQYQCNGEVDCITGEDEVGCAGFASVAQEETEILTADMDAERRRIKSLLPKLSCGVKNRMHI

RRKRIVGGKRAQLGDLPWQVAIKDASGITCGGIYIGGCWILTAAHCLRASKTHRYQIWTTVVDWIHPDLKRIVIEYVDR

IIFHENYNAGTYQNDIALIEMKKDGNKKDCELPRSIPACVPWSPYLFQPNDTCIVSGWGREKDNERVFSLQWGEVKLIS

NCSKFYGNRFYEKEMECAGTYDGSIDACKGDSGGPLVCMDANNVTYVWGVVSWGENCGKPEFPGVYTKVANYFDWISYH

VGRPFISQYNV

SEQ ID NO: 44 (Amino acid sequence of human FI, SP):
VAQEETEILTADMDAERRRIKSLLPKLSCGVKNRMHIRRKRIVGGKRAQLGDLPWQVAIKDASGITCGGIYIGGCWILT

AAHCLRASKTHRYQIWTTVVDWIHPDLKRIVIEYVDRIIFHENYNAGTYQNDIALIEMKKDGNKKDCELPRSIPACVPW

SPYLFQPNDTCIVSGWGREKDNERVFSLQWGEVKLISNCSKFYGNRFYEKEMECAGTYDGSIDACKGDSGGPLVCMDAN

NVTYVWGVVSWGENCGKPEFPGVYTKVANYFDWISYHVGRPFISQYNV

SEQ ID NO: 45 (Amino acid sequence of human C1-inh, serpin domain):
HSTEAVLGDALVDFSLKLYHAFSAMKKVETNMAFSPFSIASLLTQVLLGAGENTKTNLESILSYPKDFTCVHQALKGFT

TKGVTSVSQIFHSPDLAIRDTFVNASRTLYSSSPRVLSNNSDANLELINTWVAKNTNNKISRLLDSLPSDTRLVLLNAI

YLSAKWKTTFDPKKTRMEPFHFKNSVIKVPMMNSKKYPVAHFIDQTLKAKVGQLQLSHNLSLVILVPQNLKHRLEDMEQ

ALSPSVFKAIMEKLEMSKFQPTLLTLPRIKVTTSQDMLSIMEKLEFFDFSYDLNLCGLTEDPDLQVSAMQHQTVLELTE

TGVEAAAASAISVARTLLVFEVQQPFLFVLWDQQHKFPVFMGRVYDPRA

Amino acid sequence of human GAS6 growth arrest-specific 6, transcript variant 1 (SEQ ID NO 46)
MAPSLSPGPAALRRAPQLLLLLLAAECALAALLPAREATQFLRPRQRRAFQVFEEAKQGHLERECVEELCSR

EEAREVFENDPETDYFYPRYLDCINKYGSPYTKNSGFATCVQNLPDQCTPNPCDRKGTQACQDLMGNFFC

-continued

LCKAGWGGRLCDKDVNECSQENGGCLQICHNKPGSFHCSCHSGFELSSDGRTCQDIDECADSEACGEA

RCKNLPGSYSCLCDEGFAYSSQEKACRDVDECLQGRCEQVCVNSPGSYTCHCDGRGGLKLSQDMDTCE

DILPCVPFSVAKSVKSLYLGRMFSGTPVIRLRFKRLQPTRLVAEFDFRTFDPEGILLFAGGHQDSTWIVLAL

RAGRLELQLRYNGVGRVTSSGPVINHGMWQTISVEELARNLVIKVNRDAVMKIAVAGDLFQPERGLYHLN

LTVGGIPFHEKDLVQPINPRLDGCMRSWNWLNGEDTTIQETVKVNTRMQCFSVTERGSFYPGSGFAFYSL

DYMRTPLDVGTESTWEVEVVAHIRPAADTGVLFALWAPDLRAVPLSVALVDYHSTKKLKKQLVVLAVEHT

ALALMEIKVCDGQEHVVTVSLRDGEATLEVDGTRGQSEVSAAQLQERLAVLERHLRSPVLTFAGGLPDVP

VTSAPVTAFYRGCMTLEVNRRLLDLDEAAYKHSDITAHSCPPVEPAAA

Nucleic acid sequence of human GAS6 growth arrest-specific 6, transcript variant 1
(SEQ ID NO 47)
gccacctgcgtgcaaaacctgcctgaccagtgcacgcccaacccctgcgataggaaggggacccaagcctgccaggacctcatgg gcaacttcttctgcctgtgtaaagctggctgggggggccggctctgcgacaaagatgtcaacgaatgcagccaggagaacggggg ctgcctccagatctgccacaacaagccgggtagcttccactgttcctgccacagcggcttcgagctctcctctgatggcaggacctgcc aagacatagacgagtgcgcagactcggaggcctgcggggaggcgcgctgcaagaacctgcccggctcctactcctgcctctgtgac gagggctttgcgtacagctcccaggagaaggcttgccgagatgtggacgagtgtctgcagggccgctgtgagcaggtctgcgtgaa ctccccagggagctacacctgccactgtgacgggcgtgggggcctcaagctgtcccaggacatggacacctgtgaggacatcttgc cgtgcgtgcccttcagcgtggccaagagtgtgaagtccttgtacctgggccggatgttcagtgggacccccgtgatccgactgcgctt caagaggctgcagcccaccaggctggtagctgagtttgacttccggacctttgaccccgagggcatcctcctctttgccggaggccac caggacagcacctggatcgtgctggccctgagagccggccggctggagctgcagctgcgctacaacggtgtcggccgtgtcaccag cagcggcccggtcatcaaccatggcatgtggcagacaatctctgttgaggagctggcgcggaatctggtcatcaaggtcaacaggg atgctgtcatgaaaatcgcggtggccggggacttgttccaaccggagcgaggactgtatcatctgaacctgaccgtgggaggtattc ccttccatgagaaggacctcgtgcagcctataaaccctcgtctggatggctgcatgaggagctggaactggctgaacggagaagac accaccatccaggaaacggtgaaagtgaacacgaggatgcagtgcttctcggtgacggagagaggctctttctaccccgggagcg gcttcgccttctacagcctggactacatgcggacccctctggacgtcgggactgaatcaacctgggaagtagaagtcgtggctcacat ccgcccagccgcagacacaggcgtgctgtttgcgctctgggcccccgacctccgtgccgtgcctctctctgtggcactggtagactatc actccacgaagaaactcaagaagcagctggtggtcctggccgtggagcatacggccttggccctaatggagatcaaggtctgcgac ggccaagagcacgtggtcaccgtctcgctgagggacggtgaggccaccctggaggtggacggcaccaggggccagagcgaggt gagcgccgcgcagctgcaggagaggctggccgtgctcgagaggcacctgcggagccccgtgctcacctttgctggcggcctgcca gatgtgccggtgacttcagcgccagtcaccgcgttctaccgcggctgcatgacactggaggtcaaccggaggctgctggacctgga cgaggcggcgtacaagcacagcgacatcacggcccactcctgcccccccgtggagcccgccgcagcctaggcccccacgggacgc ggcaggcttctcagtctctgtccgagacagccgggaggagcctgggggctcctcaccacgtggggccatgctgagagctgggctttc ctctgtgaccatcccggcctgtaacatatctgtaaatagtgagatggacttggggcctctgacgccgcgcactcagccgtgggcccgg gcgcggggaggccggcgcagcgcagagcgggctcgaagaaaataattctctattatttttattaccaagcgcttctttctgactctaa aatatggaaaataaaatatttacagaaagctttgtaaaaaaaaaaaaaaaaaa Amino acid sequence of human GAS6 growth arrest-specific 6, transcript variant 2
(SEQ ID NO 48)
MDTCEDILPCVPFSVAKSVKSLYLGRMFSGTPVIRLRFKRLQPTRLVAEFDFRTFDPEGILLFAGGHQDST

WIVLALRAGRLELQLRYNGVGRVTSSGPVINHGMWQTISVEELARNLVIKVNRDAVMKIAVAGDLFQPER

GLYHLNLTVGGIPFHEKDLVQPINPRLDGCMRSWNWLNGEDTTIQETVKVNTRMQCFSVTERGSFYPGS

GFAFYSLDYMRTPLDVGTESTWEVEVVAHIRPAADTGVLFALWAPDLRAVPLSVALVDYHSTKKLKKQLV

VLAVEHTALALMEIKVCDGQEHVVTVSLRDGEATLEVDGTRGQSEVSAAQLQERLAVLERHLRSPVLTFA

GGLPDVPVTSAPVTAFYRGCMTLEVNRRLLDLDEAAYKHSDITAHSCPPVEPAAA

-continued

Nucleic acid sequence of human GAS6 growth arrest-specific 6, transcript variant 2
(SEQ ID NO 49)
ttgattgaaaccagtaaatgcttctctttggggttggggttttagtttcaaatgcccccggggggttactttttacggccccgtgtcctgt agcaccgtcatttaaatggaacagcacagcgtgcaccgccgccccccacccctccaccaagcagggcccttcccagctctccacctg ctgggctgaagtcagccttcccagccgggccttgatcagaagcgtgcaccaacaccccgggagctgcccggtcaggggaggaggg cagggaaatggggccagggcgcgctggccccacagagtctggatgcgacctctgggtggtgccctggccagtccctgcagccgcct gccccagccccgtctgagatgccgctgtgctgcggttggccggtttttttttgcttgcagacatagacgagtgcgcagactcggaggc ctgcggggaggcgcgctgcaagaacctgcccggctcctactcctgcctctgtgacgagggctttgcgtacagctcccaggagaagg cttgccgagatgtggacgagtgtctgcagggccgctgtgagcaggtctgcgtgaactccccagggagctacacctgccactgtgacg ggcgtgggggcctcaagctgtcccaggacatggacacctgtgaggacatcttgccgtgcgtgcccttcagcgtggccaagagtgtg aagtccttgtacctgggccggatgttcagtgggacccccgtgatccgactgcgcttcaagaggctgcagcccaccaggctggtagct gagtttgacttccggacctttgaccccgagggcatcctcctctttgccggaggccaccaggacagcacctggatcgtgctggccctga gagccggccggctggagctgcagctgcgctacaacggtgtcggccgtgtcaccagcagcggcccggtcatcaaccatggcatgtgg cagacaatctctgttgaggagctggcgcggaatctggtcatcaaggtcaacagggatgctgtcatgaaaatcgcggtggccgggga cttgttccaaccggagcgaggactgtatcatctgaacctgaccgtgggaggtattcccttccatgagaaggacctcgtgcagcctata aaccctcgtctggatggctgcatgaggagctggaactggctgaacggagaagacaccaccatccaggaaacggtgaaagtgaac acgaggatgcagtgcttctcggtgacggagagaggctctttctaccccgggagcggcttcgccttctacagcctggactacatgcgg acccctctggacgtcgggactgaatcaacctgggaagtagaagtcgtggctcacatccgcccagccgcagacacaggcgtgctgttt gcgctctgggcccccgacctccgtgccgtgcctctctctgtggcactggtagactatcactccacgaagaaactcaagaagcagctgg tggtcctggccgtggagcatacggccttggccctaatggagatcaaggtctgcgacggccaagagcacgtggtcaccgtctcgctga gggacggtgaggccaccctggaggtggacggcaccaggggccagagcgaggtgagcgccgcgcagctgcaggagaggctggc cgtgctcgagaggcacctgcggagccccgtgctcacctttgctggcggcctgccagatgtgccggtgacttcagcgccagtcaccgc gttctaccgcggctgcatgacactggaggtcaaccggaggctgctggacctggacgaggcggcgtacaagcacagcgacatcacg gcccactcctgcccccccgtggagcccgccgcagcctaggcccccacgggacgcggcaggcttctcagtctctgtccgagacagccg ggaggagcctgggggctcctcaccacgtggggccatgctgagagctgggctttcctctgtgaccatcccggcctgtaacatatctgta aatagtgagatggacttggggcctctgacgccgcgcactcagccgtgggcccgggcgcggggaggccggcgcagcgcagagcgg gctcgaagaaaataattctctattatttttattaccaagcgcttctttctgactctaaaatatggaaaataaaatatttacagaaagcttt gtaaaaaaaaaaaaaaaaa Amino acid sequence of human GAS6 growth arrest-specific 6, transcript variant 3
(SEQ ID NO 50)
MFSGTPVIRLRFKRLQPTRLVAEFDFRTFDPEGILLFAGGHQDSTWIVLALRAGRLELQLRYNGVGRVTSS

GPVINHGMWQTISVEELARNLVIKVNRDAVMKIAVAGDLFQPERGLYHLNLTVGGIPFHEKDLVQPINPRL

DGCMRSWNWLNGEDTTIQETVKVNTRMQCFSVTERGSFYPGSGFAFYSLDYMRTPLDVGTESTWEVEV

VAHIRPAADTGVLFALWAPDLRAVPLSVALVDYHSTKKLKKQLVVLAVEHTALALMEIKVCDGQEHVVTV

SLRDGEATLEVDGTRGQSEVSAAQLQERLAVLERHLRSPVLTFAGGLPDVPVTSAPVTAFYRGCMTLEVN

RRLLDLDEAAYKHSDITAHSCPPVEPAAA

Nucleic acid sequence of human GAS6 growth arrest-specific 6, transcript variant 3
(SEQ ID NO 51)
cacaccgacctgtcacaccggtgcctgtcacaccactgcctgtcacactgacttgtcaccggtgtctgtcacaccgacctgtcacactg gtgcctgtcacactggtgcctgtcacaccgacctgtcacaccggtgcctgtcacaccgacctgtcacactgacctgtcacaccggtag gaatgcagtacccacatgtggacgtttctgggcagggcggctcttgtctttcctcttcagcctgggcctgtgcctgggggttgatgaga gtgagcatttatttaaaaagcaaaaccacaggtggaaagagtcaccaggacagcttctcggagtcgcagacctgggatgcagccgt ggggctcttgggtctgggctgcgacgttcagggcttccagccagccctcgccttgaggttctttgcctcgctgcctcatgtactcatgca gagggtgtcggacccctgcgagatgtccagctcaccctggctgcccacggtgggcagggcaggcctggctcagccccagcccctcc -continued atcttccaggggtgtcagctcacaccggctttggttctgtccccccttcgggcagcgtggagaaaccacagcccagaacagggaacttt ccaggacagccatcttcaaggcatccatatctatttcataatagtgtatactttttaatgattctctgtaatttttgtatgcttgaaatatttc ataatttaaaaataaagggtcaagggaaatgagcagggaaggagatgacggggacccccgagaagccctgtgggaagcggctg ctgcaagcccgcccttcacctgggagtcccagtggggcaggtgtgacagcctctggggtctcagcagctagaggcggggtggccac tcccgaggcacaggagggacagtggacccgctgcgcggccggggcgtggggctcaggggagcaggagtgaaggccacatcccc gaccggcgtggccccccgtccgtggcaggacatcttgccgtgcgtgcccttcagcgtggccaagagtgtgaagtccttgtacctgggc cggatgttcagtgggacccccgtgatccgactgcgcttcaagaggctgcagcccaccaggctggtagctgagtttgacttccggacct ttgaccccgagggcatcctcctctttgccggaggccaccaggacagcacctggatcgtgctggccctgagagccggccggctggag ctgcagctgcgctacaacggtgtcggccgtgtcaccagcagcggcccggtcatcaaccatggcatgtggcagacaatctctgttgag gagctggcgcggaatctggtcatcaaggtcaacagggatgctgtcatgaaaatcgcggtggccggggacttgttccaaccggagc gaggactgtatcatctgaacctgaccgtgggaggtattcccttccatgagaaggacctcgtgcagcctataaaccctcgtctggatgg ctgcatgaggagctggaactggctgaacggagaagacaccaccatccaggaaacggtgaaagtgaacacgaggatgcagtgctt ctcggtgacggagagaggctctttctaccccgggagcggcttcgccttctacagcctggactacatgcggacccctctggacgtcgg gactgaatcaacctgggaagtagaagtcgtggctcacatccgcccagccgcagacacaggcgtgctgtttgcgctctgggcccccg acctccgtgccgtgcctctctctgtggcactggtagactatcactccacgaagaaactcaagaagcagctggtggtcctggccgtgga gcatacggccttggccctaatggagatcaaggtctgcgacggccaagagcacgtggtcaccgtctcgctgagggacggtgaggcc accctggaggtggacggcaccaggggccagagcgaggtgagcgccgcgcagctgcaggagaggctggccgtgctcgagaggca cctgcggagccccgtgctcacctttgctggcggcctgccagatgtgccggtgacttcagcgccagtcaccgcgttctaccgcggctgc atgacactggaggtcaaccggaggctgctggacctggacgaggcggcgtacaagcacagcgacatcacggcccactcctgccccc ccgtggagcccgccgcagcctaggcccccacgggacgcggcaggcttctcagtctctgtccgagacagccgggaggagcctgggg gctcctcaccacgtggggccatgctgagagctgggctttcctctgtgaccatcccggcctgtaacatatctgtaaatagtgagatgga cttggggcctctgacgccgcgcactcagccgtgggcccgggcgcggggaggccggcgcagcgcagagcgggctcgaagaaaata attctctattatttttattaccaagcgcttctttctgactctaaaatatggaaaataaaatatttacagaaagctttgtaaaaaaaaaaaa aaaaaa Amino acid sequence of human Protein S (PROS1)(alpha) (SEQ ID NO 52)
MRVLGGRCGALLACLLLVLPVSEANFLSKQQASQVLVRKRRANSLLEETKQGNLERECIEELCNKEEAREV

FENDPETDYFYPKYLVCLRSFQTGLFTAARQSTNAYPDLRSCVNAIPDQCSPLPCNEDGYMSCKDGKASFT

CTCKPGWQGEKCEFDINECKDPSNINGGCSQICDNTPGSYHCSCKNGFVMLSNKKDCKDVDECSLKPSI

CGTAVCKNIPGDFECECPEGYRYNLKSKSCEDIDECSENMCAQLCVNYPGGYTCYCDGKKGFKLAQDQK

SCEVVSVCLPLNLDTKYELLYLAEQFAGVVLYLKFRLPEISRFSAEFDFRTYDSEGVILYAESIDHSAWLLIA

LRGGKIEVQLKNEHTSKITTGGDVINNGLWNMVSVEELEHSISIKIAKEAVMDINKPGPLFKPENGLLETK

VYFAGFPRKVESELIKPINPRLDGCIRSWNLMKQGASGIKEIIQEKQNKHCLVTVEKGSYYPGSGIAQFHI

DYNNVSSAEGWHVNVTLNIRPSTGTGVMLALVSGNNTVPFAVSLVDSTSEKSQDILLSVENTVIYRIQAL

SLCSDQQSHLEFRVNRNNLELSTPLKIETISHEDLQRQLAVLDKAMKAKVATYLGGLPDVPFSATPVNAFY

NGCMEVNINGVQLDLDEAISKHNDIRAHSCPSVWKKTKNS

Nucleic acid sequence of human Protein S (PROS1)(alpha) (SEQ ID NO 53)
tttggaaacgtcacactgtggaggaaaagcagcaactagggagctggtgaagaaggatgtctcagcagtgtttactaggcctccaa cactagagcccatcccccagctccgaaaagcttcctggaaatgtccttgttatcacttcccctctcgggctgggcgctgggagcgggc ggtctcctccgccccccggctgttccgccgaggctcgctgggtcgctggcgccgccgcgcagcacggctcagaccgaggcgcacagg ctcgcagctccgcggcgcctagcgctccggtccccgccgcgacgcgccaccgtccctgccggcgcctccgcgcgcttcgaaatgagg gtcctgggtgggcgctgcggggcgctgctggcgtgtctcctcctagtgcttcccgtctcagaggcaaactttttgtcaaagcaacagg -continued cttcacaagtcctggttaggaagcgtcgtgcaaattctttacttgaagaaaccaaacagggtaatcttgaaagagaatgcatcgaag aactgtgcaataaagaagaagccagggaggtctttgaaaatgacccggaaacggattatttttatccaaaatacttagtttgtcttcg ctcttttcaaactgggttattcactgctgcacgtcagtcaactaatgcttatcctgacctaagaagctgtgtcaatgccattccagacca gtgtagtcctctgccatgcaatgaagatggatatatgagctgcaaagatggaaaagcttcttttacttgcacttgtaaaccaggttggc aaggagaaaagtgtgaatttgacataaatgaatgcaaagatccctcaaatataaatggaggttgcagtcaaatttgtgataatacac ctggaagttaccactgttcctgtaaaaatggttttgttatgctttcaaataagaaagattgtaaagatgtggatgaatgctctttgaagc caagcatttgtggcacagctgtgtgcaagaacatcccaggagattttgaatgtgaatgccccgaaggctacagatataatctcaaat caaagtcttgtgaagatatagatgaatgctctgagaacatgtgtgctcagctttgtgtcaattaccctggaggttacacttgctattgtg atgggaagaaaggattcaaacttgcccaagatcagaagagttgtgaggttgtttcagtgtgccttcccttgaaccttgacacaaagta tgaattactttacttggcggagcagtttgcaggggttgttttatatttaaaatttcgtttgccagaaatcagcagattttcagcagaattt gatttccggacatatgattcagaaggcgtgatactgtacgcagaatctatcgatcactcagcgtggctcctgattgcacttcgtggtgg aaagattgaagttcagcttaagaatgaacatacatccaaaatcacaactggaggtgatgttattaataatggtctatggaatatggtg tctgtggaagaattagaacatagtattagcattaaaatagctaaagaagctgtgatggatataaataaacctggaccccUttaagc cggaaaatggattgctggaaaccaaagtatactttgcaggattccctcggaaagtggaaagtgaactcattaaaccgattaaccctc gtctagatggatgtatacgaagctggaatttgatgaagcaaggagcttctggaataaaggaaattattcaagaaaaacaaaataag cattgcctggttactgtggagaagggctcctactatcctggttctggaattgctcaatttcacatagattataataatgtatccagtgctg agggttggcatgtaaatgtgaccttgaatattcgtccatccacgggcactggtgttatgcttgccttggtttctggtaacaacacagtgc cctttgctgtgtccttggtggactccacctctgaaaaatcacaggatattctgttatctgttgaaaatactgtaatatatcggatacaggc cctaagtctatgttccgatcaacaatctcatctggaatttagagtcaacagaaacaatctggagttgtcgacaccacttaaaatagaa accatctcccatgaagaccttcaaagacaacttgccgtcttggacaaagcaatgaaagcaaaagtggccacatacctgggtggcctt ccagatgttccattcagtgccacaccagtgaatgccttttataatggctgcatggaagtgaatattaatggtgtacagttggatctgga tgaagccatttctaaacataatgatattagagctcactcatgtccatcagtttggaaaaagacaaagaattcttaaggcatcttttctct gcttataatacctttttccttgtgtgtaattatacttatgtttcaataacagctgaagggttttatttacaatgtgcagtctttgattattttgtg gtcctttcctgggatttttaaaaggtcctttgtcaaggaaaaaaattctgttgtgatataaatcacagtaaagaaattcttacttctcttgc tatctaagaatagtgaaaaataacaattttaaatttgaatttttttcctacaaatgacagtttcaatttttgtttgtaaaactaaattttaat tttatcatcatgaactagtgtctaaatacctatgtttttttcagaaagcaaggaagtaaactcaaacaaaagtgcgtgtaattaaatact attaatcataggcagatactattttgtttatgtttttgtttttttcctgatgaaggcagaagagatggtggtctattaaatatgaattgaat ggagggtcctaatgccttatttcaaaacaattcctcaggggggaacagctttggcttcatctttctcttgtgtggcttcacatttaaaccag tatctttattgaattagaaaacaagtgggacatattttcctgagagcagcacaggaatcttcttcttggcagctgcagtctgtcaggat gagatatcagattaggttggataggtggggaaatctgaagtgggtacatttttttaaattttgctgtgtgggtcacacaaggtctacatt acaaaagacagaattcagggatggaaaggagaatgaacaaatgtgggagttcatagttttccttgaatccaacttttaattaccaga gtaagttgccaaaatgtgattgttgaagtacaaaaggaactatgaaaaccagaacaaattttaacaaaaggacaaccacagaggg atatagtgaatatcgtatcattgtaatcaaagaagtaaggaggtaagattgccacgtgcctgctggtactgtgatgcatttcaagtgg cagttttatcacgtttgaatctaccattcatagccagatgtgtatcagatgtttcactgacagtttttaacaataaattcttttcactgtattt tatatcacttataataaatcggtgtataattttaaaatgcatgtgaatatctttattatatcaactgtttgaataaaacaaaattacataat agacatttaactcttcaaaaaaaaaaaaaaaa Amino acid sequence of human MAP-1/GAS6 transcript variant 1 (SEQ ID NO 54)
HTVELNNMFGQIQSPGYPDSYPSDSEVTWNITVPDGFRIKLYFMHFNLESSYLCEYDYVKVETEDQVLATF

CGRETTDTEQTPGQEVVLSPGSFMSITFRSDFSNEERFTGFDAHYMAVDVDECKEREDEELSCDHYCHN

YIGGYYCSCRFGYILHTDNRTCRVECSDNLFTQRTGVITSPDFPNPYPKSSECLYTIELEEGFMVNLQFEDI

FDIEDHPEVPCPYDYIKIKVGPKVLGPFCGEKAPEPISTQSHSVLILFHSDNSGENRGWRLSYRAAGNECP

-continued

ELQPPVHGKIEPSQAKYFFKDQVLVSCDTGYKVLKDNVEMDTFQIECLKDGTWSNKIPTCKKNEIDLESEL

KSEQVTEGGGGSGGGGSALLPAREATQFLRPRQRRAFQVFEEAKQGHLERECVEELCSREEAREVFEND

PETDYFYPRYLDCINKYGSPYTKNSGFATCVQNLPDQCTPNPCDRKGTQACQDLMGNFFCLCKAGWGGR

LCDKDVNECSQENGGCLQICHNKPGSFHCSCHSGFELSSDGRTCQDIDECADSEACGEARCKNLPGSY

SCLCDEGFAYSSQEKACRDVDECLQGRCEQVCVNSPGSYTCHCDGRGGLKLSQDMDTCEDILPCVPFSV

AKSVKSLYLGRMFSGTPVIRLRFKRLQPTRLVAEFDFRTFDPEGILLFAGGHQDSTWIVLALRAGRLELQLR

YNGVGRVTSSGPVINHGMWQTISVEELARNLVIKVNRDAVMKIAVAGDLFQPERGLYHLNLTVGGIPFHE

KDLVQPINPRLDGCMRSWNWLNGEDTTIQETVKVNTRMQCFSVTERGSFYPGSGFAFYSLDYMRTPLDV

GTESTWEVEVVAHIRPAADTGVLFALWAPDLRAVPLSVALVDYHSTKKLKKQLVVLAVEHTALALMEIKVC

DGQEHVVTVSLRDGEATLEVDGTRGQSEVSAAQLQERLAVLERHLRSPVLTFAGGLPDVPVTSAPVTAFY

RGCMTLEVNRRLLDLDEAAYKHSDITAHSCPPVEPAAA

Amino acid sequence of human GAS6 transcript variant 1/MAP1 (SEQ ID NO 55)
ALLPAREATQFLRPRQRRAFQVFEEAKQGHLERECVEELCSREEAREVFENDPETDYFYPRYLDCINKYGS

PYTKNSGFATCVQNLPDQCTPNPCDRKGTQACQDLMGNFFCLCKAGWGGRLCDKDVNECSQENGGCL

QICHNKPGSFHCSCHSGFELSSDGRTCQDIDECADSEACGEARCKNLPGSYSCLCDEGFAYSSQEKACR

DVDECLQGRCEQVCVNSPGSYTCHCDGRGGLKLSQDMDTCEDILPCVPFSVAKSVKSLYLGRMFSGTPV

IRLRFKRLQPTRLVAEFDFRTFDPEGILLFAGGHQDSTWIVLALRAGRLELQLRYNGVGRVTSSGPVINHG

MWQTISVEELARNLVIKVNRDAVMKIAVAGDLFQPERGLYHLNLTVGGIPFHEKDLVQPINPRLDGCMRS

WNWLNGEDTTIQETVKVNTRMQCFSVTERGSFYPGSGFAFYSLDYMRTPLDVGTESTWEVEVVAHIRPA

ADTGVLFALWAPDLRAVPLSVALVDYHSTKKLKKQLVVLAVEHTALALMEIKVCDGQEHVVTVSLRDGEA

TLEVDGTRGQSEVSAAQLQERLAVLERHLRSPVLTFAGGLPDVPVTSAPVTAFYRGCMTLEVNRRLLDLDE

AAYKHSDITAHSCPPVEPAAAGGGGSGGGGSHTVELNNMFGQIQSPGYPDSYPSDSEVTWNITVPDGFR

IKLYFMHFNLESSYLCEYDYVKVETEDQVLATFCGRETTDTEQTPGQEVVLSPGSFMSITFRSDFSNEERFT

GFDAHYMAVDVDECKEREDEELSCDHYCHNYIGGYYCSCRFGYILHTDNRTCRVECSDNLFTQRTGVITS

PDFPNPYPKSSECLYTIELEEGFMVNLQFEDIFDIEDHPEVPCPYDYIKIKVGPKVLGPFCGEKAPEPISTQS

HSVLILFHSDNSGENRGWRLSYRAAGNECPELQPPVHGKIEPSQAKYFFKDQVLVSCDTGYKVLKDNVE

MDTFQIECLKDGTWSNKIPTCKKNEIDLESELKSEQVTE

Amino acid sequence of human MAP-1/Protein S (SEQ ID NO 56)
HTVELNNMFGQIQSPGYPDSYPSDSEVTWNITVPDGFRIKLYFMHFNLESSYLCEYDYVKVETEDQVLATF

CGRETTDTEQTPGQEVVLSPGSFMSITFRSDFSNEERFTGFDAHYMAVDVDECKEREDEELSCDHYCHN

YIGGYYCSCRFGYILHTDNRTCRVECSDNLFTQRTGVITSPDFPNPYPKSSECLYTIELEEGFMVNLQFEDI

FDIEDHPEVPCPYDYIKIKVGPKVLGPFCGEKAPEPISTQSHSVLILFHSDNSGENRGWRLSYRAAGNECP

ELQPPVHGKIEPSQAKYFFKDQVLVSCDTGYKVLKDNVEMDTFQIECLKDGTWSNKIPTCKKNEIDLESEL

KSEQVTEGGGGSGGGGSGSGGGGSNFLSKQQASQVLVRKRRANSLLEETKQGNLERECIEELCNKEEA

REVFENDPETDYFYPKYLVCLRSFQTGLFTAARQSTNAYPDLRSCVNAIPDQCSPLPCNEDGYMSCKDGK

ASFTCTCKPGWQGEKCEFDINECKDPSNINGGCSQICDNTPGSYHCSCKNGFVMLSNKKDCKDVDECS

LKPSICGTAVCKNIPGDFECECPEGYRYNLKSKSCEDIDECSENMCAQLCVNYPGGYTCYCDGKKGFKLA

QDQKSCEVVSVCLPLNLDTKYELLYLAEQFAGVVLYLKFRLPEISRFSAEFDFRTYDSEGVILYAESIDHSA

WLLIALRGGKIEVQLKNEHTSKITTGGDVINNGLWNMVSVEELEHSISIKIAKEAVMDINKPGPLFKPENG

LLETKVYFAGFPRKVESELIKPINPRLDGCIRSWNLMKQGASGIKEIIQEKQNKHCLVTVEKGSYYPGSGIA

QFHIDYNNVSSAEGWHVNVTLNIRPSTGTGVMLALVSGNNTVPFAVSLVDSTSEKSQDILLSVENTVIYRI

-continued

QALSLCSDQQSHLEFRVNRNNLELSTPLKIETISHEDLQRQLAVLDKAMKAKVATYLGGLPDVPFSATPVN

AFYNGCMEVNINGVQLDLDEAISKHNDIRAHSCPSVWKKTKNS

Amino acid sequence of human Protein S/MAP1 (SEQ ID NO 57)
NFLSKQQASQVLVRKRRANSLLEETKQGNLERECIEELCNKEEAREVFENDPETDYFYPKYLVCLRSFQTG

LFTAARQSTNAYPDLRSCVNAIPDQCSPLPCNEDGYMSCKDGKASFTCTCKPGWQGEKCEFDINECKDP

SNINGGCSQICDNTPGSYHCSCKNGFVMLSNKKDCKDVDECSLKPSICGTAVCKNIPGDFECECPEGYR

YNLKSKSCEDIDECSENMCAQLCVNYPGGYTCYCDGKKGFKLAQDQKSCEVVSVCLPLNLDTKYELLYLA

EQFAGVVLYLKFRLPEISRFSAEFDFRTYDSEGVILYAESIDHSAWLLIALRGGKIEVQLKNEHTSKITTGG

DVINNGLWNMVSVEELEHSISIKIAKEAVMDINKPGPLFKPENGLLETKVYFAGFPRKVESELIKPINPRLD

GCIRSWNLMKQGASGIKEIIQEKQNKHCLVTVEKGSYYPGSGIAQFHIDYNNVSSAEGWHVNVTLNIRPS

TGTGVMLALVSGNNTVPFAVSLVDSTSEKSQDILLSVENTVIYRIQALSLCSDQQSHLEFRVNRNNLELST

PLKIETISHEDLQRQLAVLDKAMKAKVATYLGGLPDVPFSATPVNAFYNGCMEVNINGVQLDLDEAISKHN

DIRAHSCPSVWKKTKNSGSGGGGSHTVELNNMFGQIQSPGYPDSYPSDSEVTWNITVPDGFRIKLYFMH

FNLESSYLCEYDYVKVETEDQVLATFCGRETTDTEQTPGQEVVLSPGSFMSITFRSDFSNEERFTGFDAHY

MAVDVDECKEREDEELSCDHYCHNYIGGYYCSCRFGYILHTDNRTCRVECSDNLFTQRTGVITSPDFPNP

YPKSSECLYTIELEEGFMVNLQFEDIFDIEDHPEVPCPYDYIKIKVGPKVLGPFCGEKAPEPISTQSHSVLILF

HSDNSGENRGWRLSYRAAGNECPELQPPVHGKIEPSQAKYFFKDQVLVSCDTGYKVLKDNVEMDTFQIE

CLKDGTWSNKIPTCKKNEIDLESELKSEQVTE

The invention claimed is:

1. A chimeric molecule of a ficolin-associated polypeptide comprising:

a) a human ficolin-associated polypeptide comprising the amino acid sequence set forth in SEQ ID NO: 1 or a variant thereof having at least 80% sequence identity to the amino acid sequence set forth in SEQ ID NO: 1; and b) an immunoglobulin molecule or part thereof.

2. The chimeric molecule according to claim 1, wherein said ficolin-associated polypeptide comprises the amino acid sequence of residues 20-297 of SEQ NO:3, or a functional variant thereof having at least 80% sequence identity to the amino acid sequence of residues 20-297 of SEQ ID NO: 3.

3. The chimeric molecule according to claim 1, wherein said ficolin-associated polypeptide comprises the amino acid sequence of residues 20-380 of SEQ NO:1 or a functional variant thereof having at least 80% sequence identity to the amino acid sequence of residues 20-380 of SEQ ID NO: 1.

4. The chimeric molecule according to claim 1, wherein said ficolin-associated polypeptide is in homodimer form.

5. The chimeric molecule according to claim 1, wherein said ficolin-associated polypeptide consist of the amino acid sequence of residues 20-380 of SEQ ID NO 1.

6. The chimeric molecule according to claim 1, wherein said ficolin-associated polypeptide comprises the amino acid sequence of SEQ ID NO:4 or variants or immunologic fragments thereof having at least 80% sequence identity to the amino acid sequence of SEQ ID NO: 4.

7. The chimeric molecule according to claim 1, wherein said ficolin-associated polypeptide and said immunoglobulin molecule or part thereof are directly or indirectly fused to each other in the form of a fusion protein.

8. A composition comprising the chimeric molecule as defined in claim 1.

9. The chimeric molecule of claim 1, wherein said immunoglobulin molecule or part thereof consists of the Fc component of human IgG1, IgG2, IgG3, or IgG4.

10. The chimeric molecule of claim 1, wherein said chimeric molecule directly or indirectly modulate complement activation when administered to a subject compared to complement activation in an appropriate control subject.

* * * * *